(12) United States Patent
Chun et al.

(10) Patent No.: US 9,902,803 B2
(45) Date of Patent: *Feb. 27, 2018

(54) EPOXY COMPOUND HAVING ALKOXY SILYL GROUP, COMPOSITION COMPRISING SAME, CURED PRODUCT, USE THEREOF AND METHOD FOR PREPARING EPOXY COMPOUND HAVING ALKOXY SILYL GROUP

(71) Applicant: KOREA INSTITUTE OF INDUSTRIAL TECHNOLOGY, Cheonan (KR)

(72) Inventors: Hyun-Aee Chun, Seongnam (KR); Yun-Ju Kim, Seoul (KR); Su-Jin Park, Ansan (KR); Sook-Yeon Park, Gunpo (KR); Sung-Hwan Park, Gunpo (KR); Sang-Yong Tak, Busan (KR)

(73) Assignee: KOREA INSTITUTE OF INDUSTRIAL TECHNOLOGY, Cheonan (KR)

(*) Notice: Subject to any disclaimer, the term of this patent is extended or adjusted under 35 U.S.C. 154(b) by 504 days.

This patent is subject to a terminal disclaimer.

(21) Appl. No.: 14/384,669

(22) PCT Filed: Mar. 14, 2013

(86) PCT No.: PCT/KR2013/002062
§ 371 (c)(1),
(2) Date: Sep. 11, 2014

(87) PCT Pub. No.: WO2013/137663
PCT Pub. Date: Sep. 19, 2013

(65) Prior Publication Data
US 2015/0105493 A1    Apr. 16, 2015

(30) Foreign Application Priority Data

Mar. 14, 2012 (KR) .................. 10-2012-0026130
Mar. 14, 2012 (KR) .................. 10-2012-0026131
(Continued)

(51) Int. Cl.
*C08G 59/32* (2006.01)
*C08G 59/04* (2006.01)
(Continued)

(52) U.S. Cl.
CPC ....... *C08G 59/3281* (2013.01); *C07D 303/36* (2013.01); *C07F 7/1836* (2013.01);
(Continued)

(58) Field of Classification Search
CPC .. C08G 59/3281; C08G 59/04; C08G 59/306; C09D 163/00; C08K 3/36; C08K 7/14;
(Continued)

(56) References Cited

U.S. PATENT DOCUMENTS 3,935,346 A    1/1976  Stengle et al.
4,220,513 A    9/1980  Green et al.
(Continued)

FOREIGN PATENT DOCUMENTS

CN    1293685 A    2/2001
CN    1303382 A    7/2001
(Continued)

OTHER PUBLICATIONS

Extended European Search Report for European Patent Application No. 13796871.5 dated Dec. 9, 2015.
(Continued)

*Primary Examiner* — Randy Gulakowski
*Assistant Examiner* — Ha S Nguyen

(57) ABSTRACT

The present invention relates to an alkoxysilylated epoxy compound, a composite of which exhibits good heat resis-
(Continued)

tance properties, low CTE and high glass transition temperature and not requiring a coupling agent, a composition including the same, a cured product formed of the composition, a use of the cured product, and a method of preparing the epoxy compound having alkoxysilyl group. An epoxy compound having an epoxy group and an alkoxysilyl group, a composition including the epoxy compound, a curing agent, a filler and/or a reaction catalyst, a cured product of the composition, and a use of the composition including an electronic part are provided. In a composite and/or cured product, the epoxy composition forms chemical bonds and exhibits improved heat resistance properties, decreased CTE, and increased glass transition temperature or Tg less. The cured product exhibits good flame retardant property by the introduction of the alkoxysilyl group.

19 Claims, 4 Drawing Sheets

(30) Foreign Application Priority Data

May 7, 2012 (KR) .................. 10-2012-0048282
Mar. 14, 2013 (KR) .................. 10-2013-0027308

(51) Int. Cl.
*C08G 59/30* (2006.01)
*C09D 163/00* (2006.01)
*C08K 7/14* (2006.01)
*C08K 3/36* (2006.01)
*C07F 7/18* (2006.01)
*C07D 303/36* (2006.01)
*C08L 63/00* (2006.01)

(52) U.S. Cl.
CPC ............ *C07F 7/1876* (2013.01); *C08G 59/04* (2013.01); *C08G 59/306* (2013.01); *C08K 3/36* (2013.01); *C08K 7/14* (2013.01); *C08L 63/00* (2013.01); *C09D 163/00* (2013.01)

(58) Field of Classification Search
CPC .... C07D 303/36; C07F 7/1876; C07F 7/1836; C08L 63/00
See application file for complete search history.

(56) References Cited

U.S. PATENT DOCUMENTS

| | | | |
|---|---|---|---|
| 4,292,151 A | 9/1981 | Inata et al. | |
| 4,789,711 A | 12/1988 | Monnier et al. | |
| 5,019,607 A * | 5/1991 | Coltrain ................. | C08G 18/58 523/435 |
| 5,248,710 A | 9/1993 | Shiobara et al. | |
| 5,266,612 A | 11/1993 | Kim et al. | |
| 5,300,588 A | 4/1994 | Shiobara et al. | |
| 5,336,786 A * | 8/1994 | Shiobara ............... | C07F 7/1836 549/215 |
| 5,478,871 A | 12/1995 | Takebe et al. | |
| 6,087,513 A | 7/2000 | Liao et al. | |
| 7,521,511 B2 | 4/2009 | Tanaka et al. | |
| 8,084,130 B2 | 12/2011 | Hamada et al. | |
| 2003/0078322 A1 | 4/2003 | Honda et al. | |
| 2004/0241331 A1 | 12/2004 | Durairaj et al. | |
| 2006/0205891 A1 | 9/2006 | Tanaka et al. | |
| 2006/0214153 A1 | 9/2006 | Ikezawa et al. | |
| 2007/0100043 A1 | 5/2007 | Shiono | |
| 2007/0282081 A1 | 12/2007 | Ichiroku | |
| 2008/0221238 A1 | 9/2008 | Su et al. | |
| 2008/0234409 A1 | 9/2008 | Akagi et al. | |
| 2011/0082321 A1 | 4/2011 | Sakurai et al. | |
| 2011/0098380 A1 | 4/2011 | Hearn et al. | |
| 2011/0143092 A1 | 6/2011 | Asai et al. | |
| 2011/0319589 A1 | 12/2011 | Takeyama et al. | |
| 2012/0041102 A1 | 2/2012 | Chun et al. | |
| 2012/0153512 A1 | 6/2012 | Sugimoto et al. | |
| 2012/0292487 A1 | 11/2012 | Yukawa et al. | |
| 2012/0295199 A1 | 11/2012 | Takeyama et al. | |
| 2012/0315765 A1 | 12/2012 | Nakajima et al. | |
| 2014/0100320 A1 | 4/2014 | Nagano et al. | |

FOREIGN PATENT DOCUMENTS

| | | |
|---|---|---|
| CN | 1784462 A | 7/2006 |
| CN | 101701058 A | 5/2010 |
| EP | 0 618 246 A2 | 10/1994 |
| EP | 1114834 A1 | 11/2001 |
| EP | 2 119 721 A1 | 11/2009 |
| EP | 2 767 535 A2 | 8/2014 |
| JP | 61-272244 A | 12/1986 |
| JP | 62-050312 A | 3/1987 |
| JP | S62-292826 A | 12/1987 |
| JP | S63-280720 A | 11/1988 |
| JP | 06-345847 A | 12/1994 |
| JP | 07-258240 A | 10/1995 |
| JP | 08-193091 A | 7/1996 |
| JP | 2003-055435 A | 2/2003 |
| JP | 2003-141933 A | 5/2003 |
| JP | 2006-012784 A | 1/2006 |
| JP | 2006-137800 A | 6/2006 |
| JP | 2007-126496 A | 5/2007 |
| JP | 2010-003897 A | 1/2010 |
| JP | 2010-065161 A | 3/2010 |
| JP | 2010-520952 A | 6/2010 |
| JP | 2010-229212 A | 10/2010 |
| JP | 2011-057755 A | 3/2011 |
| JP | 2011-208120 A | 10/2011 |
| JP | 2011-225740 A | 11/2011 |
| JP | 2012-246422 A | 12/2012 |
| JP | 2012-246425 A | 12/2012 |
| KR | 1993-0007997 A | 5/1993 |
| KR | 10-2005-0123140 A | 12/2005 |
| KR | 10-2006-0129517 A | 12/2006 |
| KR | 10-0929380 B1 | 12/2009 |
| KR | 10-2010-0126490 A | 12/2010 |
| WO | WO 99/62894 A2 | 12/1999 |
| WO | WO 2004/094499 A1 | 11/2004 |
| WO | WO 2008/041555 A1 | 4/2008 |
| WO | WO 2010/092947 A1 | 8/2010 |
| WO | WO 2011/093188 A1 | 8/2011 |
| WO | WO 2011/093236 A1 | 8/2011 |
| WO | WO 2011/102470 A1 | 8/2011 |
| WO | WO 2012/070637 A1 | 5/2012 |
| WO | WO 2013/180375 A1 | 12/2013 |

OTHER PUBLICATIONS

Tahseen Razzaq et al., "Investigating the Existence of Nonthermal/Specific Microwave Effects Using Silicon Carbide Heating Elements as Power Modulators", The Journal of Organic Chemistry, 2008, pp. 6321-6329, vol. 73, No. 16, American Chemical Society.
Zhang et al., "Characterization of siliconized diallyl bisphenol A type epoxy resin and study on its curing properties", Chemistry and Adhesion, Jun. 28, 2006, pp. 369-371 & 375, vol. 28, No. 6, Huaxue Yu Nianhe Bianji Weiyuanhui.
Lei Xue et al., "Precise Synthesis of Poly(silphenylenesiloxane)s with Epoxy Side Functional Groups by Tris(pentafluorophenyl)borane as a Catalyst", Polymer Journal, Mar. 5, 2007, pp. 379-388, vol. 39, No. 4, The Society of Polymer Science, Japan.
Nobuo Suzuki et al., "Concise Encyclopedia of Polymer Science and Engineering", Polymer Dictionary, 1994, pp. 455-456, Maruzen Inc., Japan.
Extended European Search Report for European Application No. 13813009.1 dated Feb. 12, 2016.
Tsung-Han Ho et al., "Modification of epoxy resin with siloxane containing phenol aralkyl epoxy resin for electronic encapsulation application" European Polymer Journal, 2001, pp. 267-274, vol. 37, Elsevier Science Ltd.

(56) References Cited

OTHER PUBLICATIONS

Barry Arkles, "Silane Coupling Agents: Connecting Across Boundaries", 2006, pp. 1-60, Gelest Inc., http://www.gelest.de/goods/pdf/couplingagents.pdf.
Chinese Office Action for CN Application No. 201280053687.4, dated May 20, 2015.
Chinese Office Action for Chinese Patent Application No. 201280052291.8 dated Oct. 28, 2015.
Chinese Office Action for Chinese Patent Application No. 201380046568.0 dated Nov. 2, 2015.
Extended European Search Report for European Patent Application No. 13772355.7 dated Oct. 16, 2015.
International Search Report for PCT/KR2013/002062 filed on Mar. 14, 2013.
Office Action from United States Patent Office for U.S. Appl. No. 14/390,340, dated Jul. 10, 2017.
Office Action from United States Patent Office for U.S. Appl. No. 14/404,942, dated Jul. 19, 2017.

* cited by examiner

EPOXY COMPOUND HAVING ALKOXY SILYL GROUP, COMPOSITION COMPRISING SAME, CURED PRODUCT, USE THEREOF AND METHOD FOR PREPARING EPOXY COMPOUND HAVING ALKOXY SILYL GROUP

TECHNICAL FIELD

The present invention relates to an epoxy compound having an alkoxysilyl group (hereinafter 'alkoxysilylated epoxy compound') exhibiting good heat resistance properties, a composition including the same, a cured product formed of the composition, a use of the cured product, and a method of preparing the epoxy compound having an alkoxysilyl group. More particularly, the present invention relates to an alkoxysilylated epoxy compound, a composite of which exhibits good heat resistance properties, in particular, exhibiting a low coefficient of thermal expansion (CTE) and a high increasing effect of glass transition temperature (including a transition temperature-less (Tg-less) compound, not having a glass transition temperature) and not requiring a separate coupling agent, a composition including the same, a cured product formed of the composition, a use of the cured product, and a method of preparing the epoxy compound having an alkoxysilyl group.

BACKGROUND ART

The coefficient of thermal expansion (CTE) of a polymer material—specifically, a cured product formed of an epoxy compound—is about 50 to 80 ppm/° C., a significantly high level, on the level of several to tens times the CTE of a inorganic material such as ceramic material or a metal (for example, the CTE of silicon is 3 to 5 ppm/° C., and the CTE of copper is 17 ppm/° C.). Thus, when the polymer material is used along with the inorganic material or the metal in a semiconductor, a display, or the like, the properties and processability of the polymer material are significantly limited due to the different CTEs of the polymer material and the inorganic material or the metal. In addition, during semiconductor packaging in which a silicon wafer and a polymer substrate are used side by side, or during a coating process in which a polymer film is coated with an inorganic shielding layer to impart gas barrier properties, product defects such as the generation of cracks in an inorganic layer, the warpage of a substrate, the peeling-off of a coating layer, the failure of a substrate, and the like, may be generated due to a large CTE-mismatch between constituent elements due to changes in processing and/or applied temperature conditions.

Because of the high CTE of the polymer material and the resultant dimensional change of the polymer material, the development of technologies such as next generation semiconductor substrates, printed circuit boards (PCBs), packaging, organic thin film transistors (OTFTs), and flexible display substrates may be limited. Particularly, at the current time, in the semiconductor and PCB fields, designers are facing challenges in the design of next generation parts requiring high degrees of integration, miniaturization, flexibility, performance, and the like, in securing processability and reliability in parts due to polymer materials having significantly high CTE as compared to metal/ceramic materials. In other words, due to the high thermal expansion properties of the polymer material at part processing temperatures, defects may be generated, processability may be limited, and the design of the parts and the securing of processability and reliability therein may be objects of concern. Accordingly, improved thermal expansion properties or dimensional stability of the polymer material are necessary in order to secure processability and reliability in electronic parts.

In general, in order to improve thermal expansion properties—i.e., to obtain a low CTE in a polymer material such as an epoxy compound, (1) a method of producing a composite of the epoxy compound with inorganic particles (an inorganic filler) and/or fibers and (2) a method of designing a novel epoxy compound having a decreased CTE have been used.

When the composite of the epoxy compound and the inorganic particles as the filler is formed in order to improve thermal expansion properties, a large amount of silica inorganic particles, having about 2 to 30 μm is required to be used to obtain a CTE decrease effect. However, due to the presence of the large amount of inorganic particles, the processability and physical properties of the parts may be deteriorated. That is, the presence of the large amount of inorganic particles may decrease fluidity, and voids may be generated during the filling of narrow spaces. In addition, the viscosity of the material may increase exponentially due to the addition of the inorganic particles. Further, the size of the inorganic particles tends to decrease due to semiconductor structure miniaturization. When a filler having a particle size of 1 μm or less is used, the decrease in fluidity (viscosity reduction) may be worsened. When inorganic particles having a large average particle diameter are used, the frequency of insufficient filling in the case of a composition including a resin and the inorganic particles may increase. While the CTE may largely decrease when a composition including an organic resin and a fiber as the filler is used, the CTE may remain high as compared to that of a silicon chip or the like.

As described above, the manufacturing of highly integrated and high performance electronic parts for next generation semiconductor substrates, PCBs, and the like may be limited due to the limitations in the technology of the combination of epoxy compounds. Thus, the development of a polymer composite having improved heat resistance properties—namely, a low CTE and a high glass transition temperature—is required to overcome the challenge of a lack of heat resistance properties due to a high CTE and processability of a common thermosetting polymer composite.

DISCLOSURE

Technical Problem

An embodiment of the present invention provides an alkoxysilylated epoxy compound, a composite of which exhibits good heat resistance properties, particularly low CTE and high glass transition temperature properties and a cured product of which exhibits good flame retardant property.

Another embodiment of the present invention provides an epoxy compound, a composite of which exhibits good heat resistance properties, particularly low CTE and high glass transition temperature properties and a cured product of which exhibits good flame retardant property.

Further another embodiment of the present invention provides a cured product of an epoxy composition in accordance with an exemplary embodiment, a composite of which exhibits good heat resistance properties, particularly low CTE and high glass transition temperature properties, while the cured product exhibits good flame retardant property.

In addition, another embodiment of the present invention provides a use of an epoxy composition in accordance with an exemplary embodiment.

Another embodiment of the present invention provides a method of preparing an epoxy compound having an alkoxysilyl group.

Technical Solution

According to the first embodiment of the present invention, there is provided an epoxy compound having an alkoxysilyl group having a structure selected from the group consisting of following Formulae AI to HI.

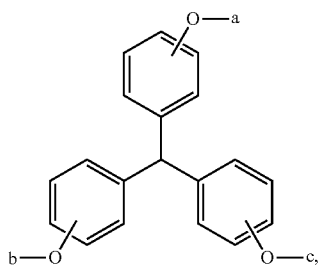
AI

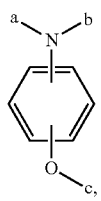
BI

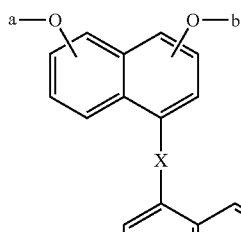
CI

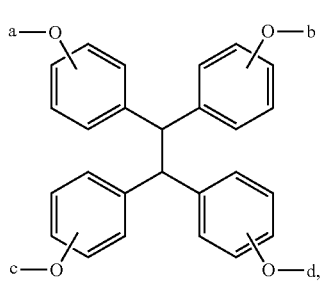
DI

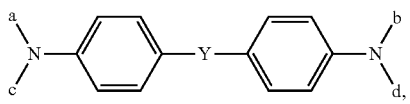
EI

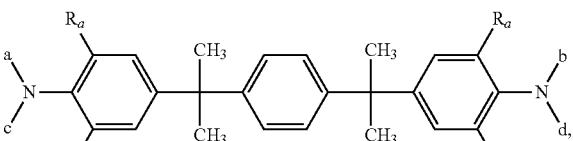
FI

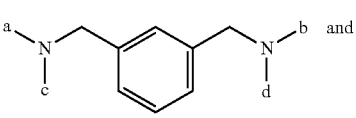
GI and

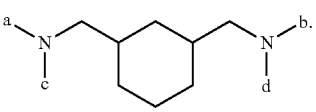
HI.

One or two of substituents a to c in Formula AI or BI have the form of Formula S1, one or two thereof have the form of Formula S2 or S3, and the remainder thereof may be hydrogen or $-(CH_2)_{z-2}CH=CH_2$ where z is an integer from 3 to 10.

One to three of substituents a to d in Formulae CI to HI have the form of Formula S1, one to three thereof have the form of Formula S2 or S3, and the remainder thereof may be hydrogen or $-(CH_2)_{z-2}CH=CH_2$ where z is an integer from 3 to 10.

A meta position of oxygen in Formula BI may be substituted with a linear or branched C1-C10 alkyl group.

X in Formula CI is a direct linkage, $-CH_2-$ or

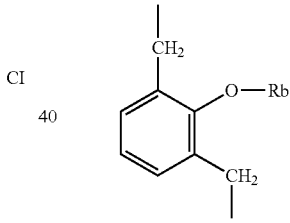

where Rb is H or a C1-C3 alkyl group.

Y in Formula EI is $-CH_2-$, $-C(CH_3)_2-$, $-C(CF_3)_2-$, $-S-$ or $-SO_2-$.

Ra in Formula FI is H or a C1-C3 alkyl group.

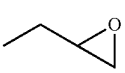 [Formula S1]

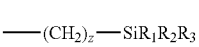 [Formula S2]

 [Formula S3]

In Formulae S2 and S3, at least one of $R_1$ to $R_3$ is an alkoxy group having 1 to 10 carbon atoms, the remainder thereof are alkyl groups having 1 to 10 carbon atoms, the alkyl group and the alkoxy group are a linear chain or a branched chain alkyl group or alkoxy group, and z is an integer from 3 to 10.

According to the second embodiment of the present invention, the epoxy compound having an alkoxysilyl group of the first embodiment, in which the epoxy compound having an alkoxysilyl group is selected from the group consisting of compounds of following Formula F, may be provided.
[Formula F]
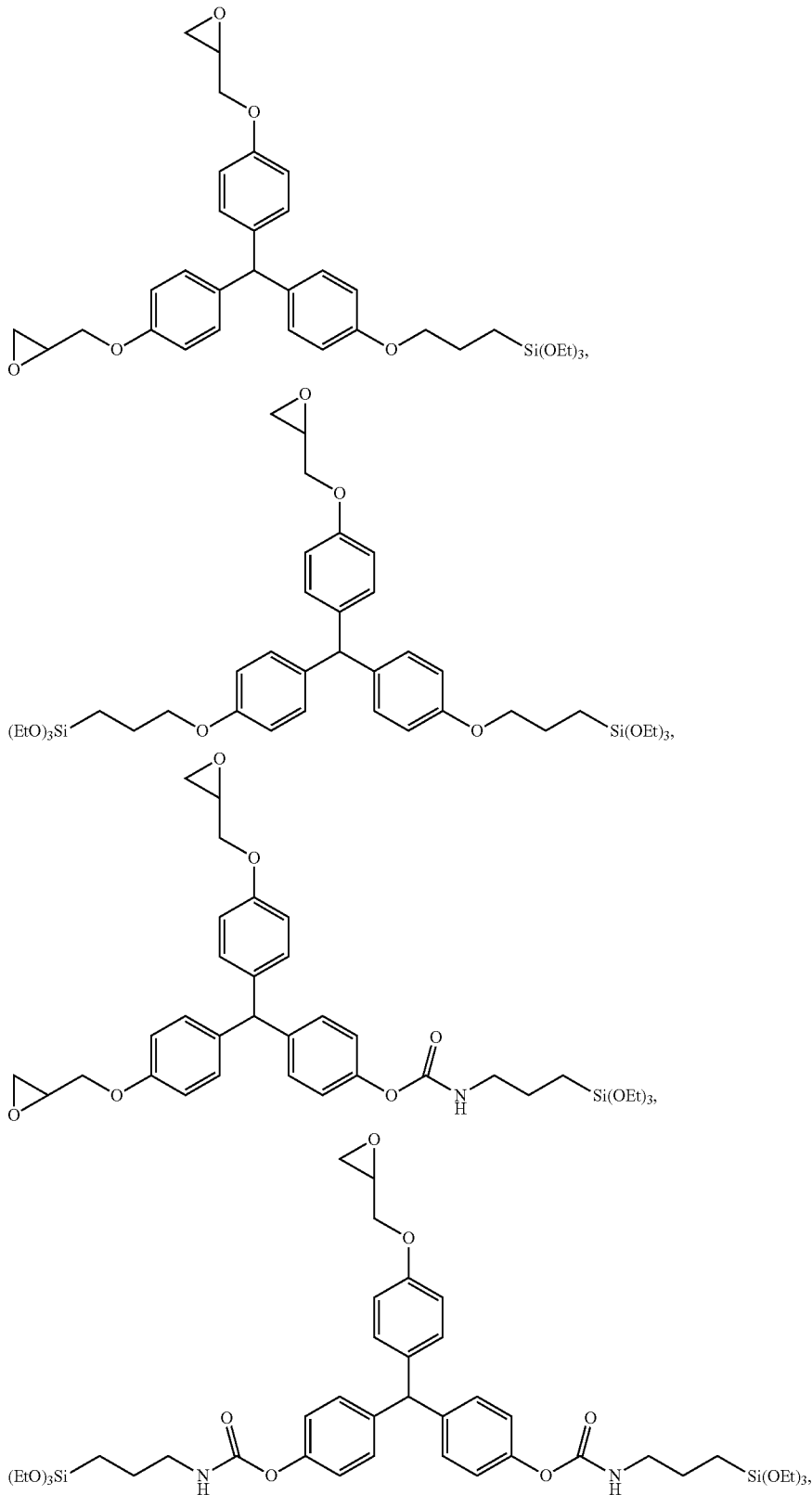

7
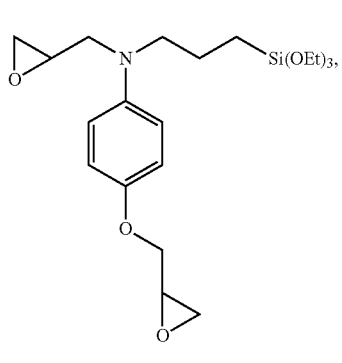
-continued
8
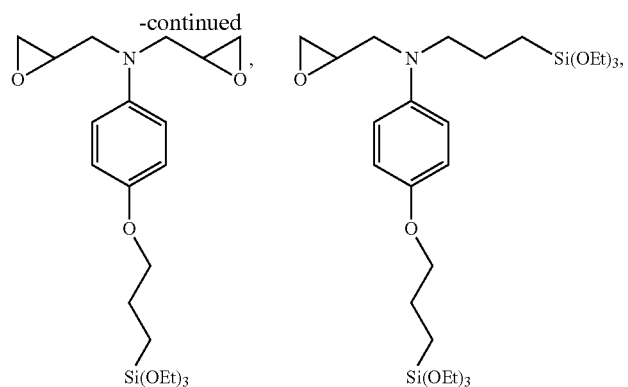
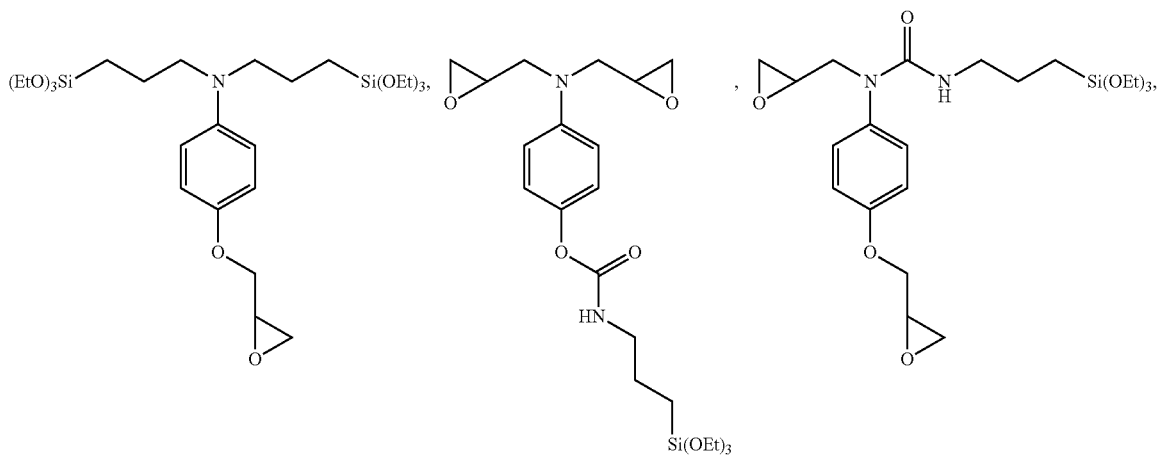
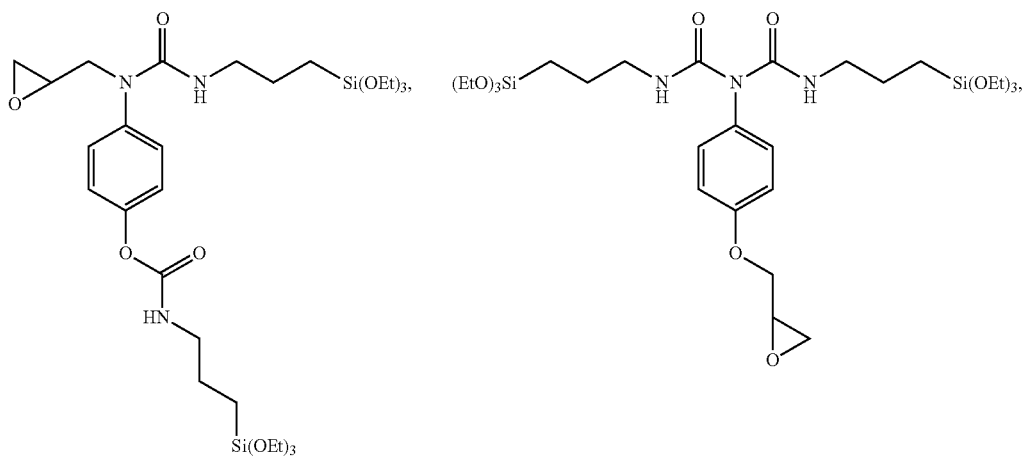
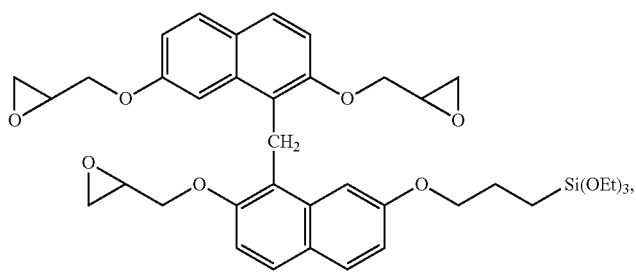

-continued
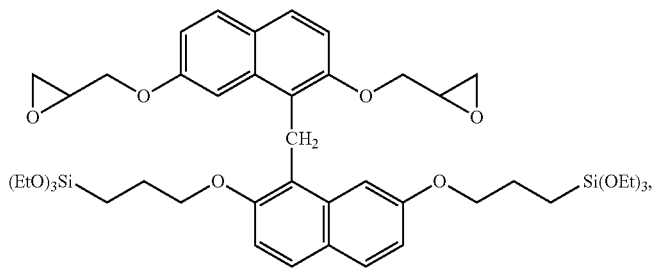
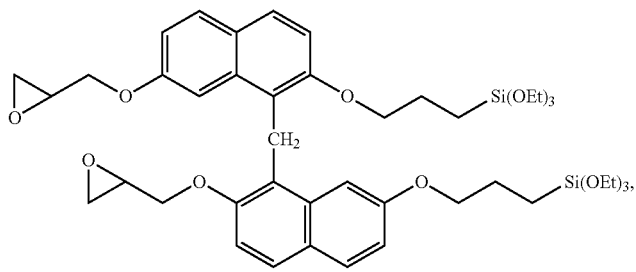
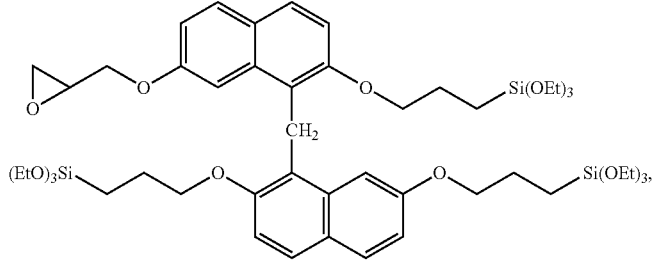
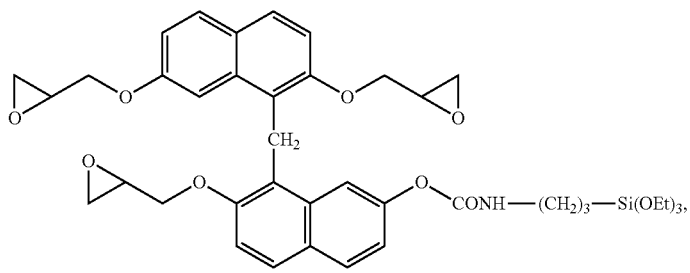
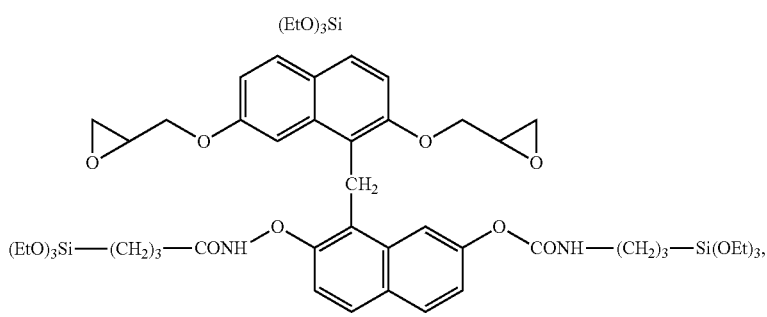
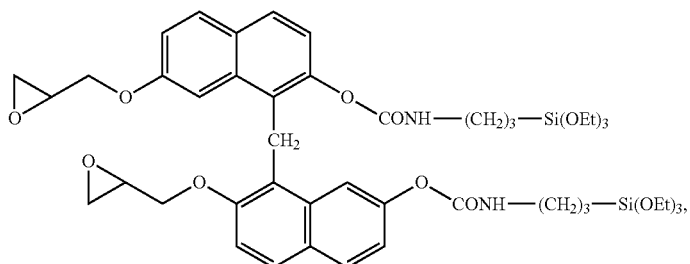

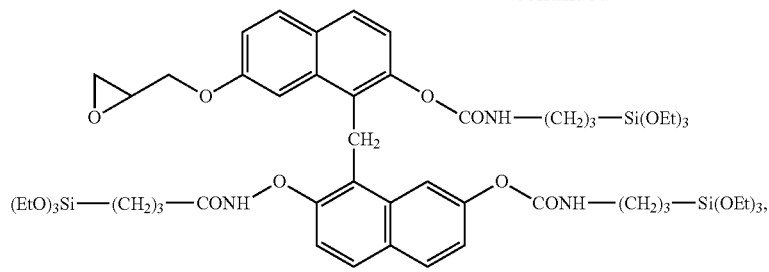
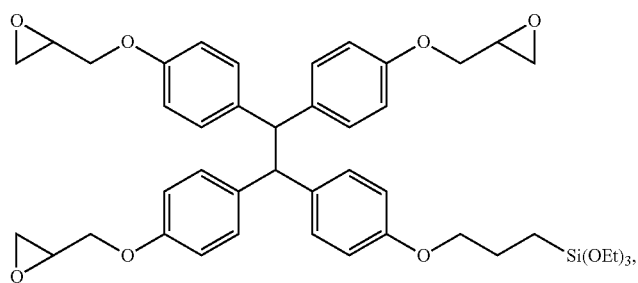
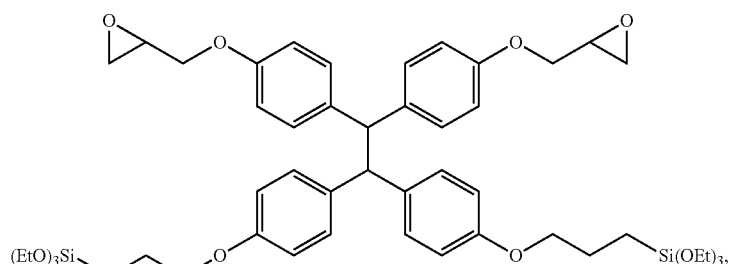

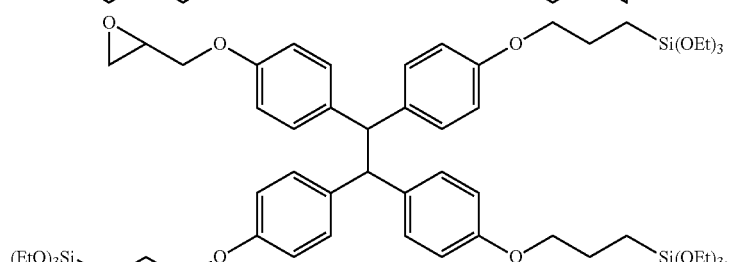
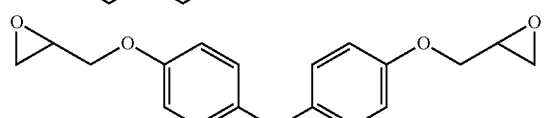
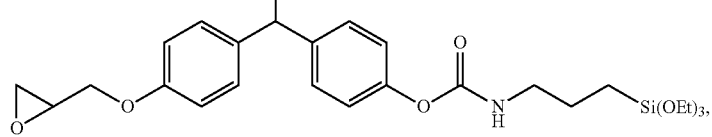

-continued
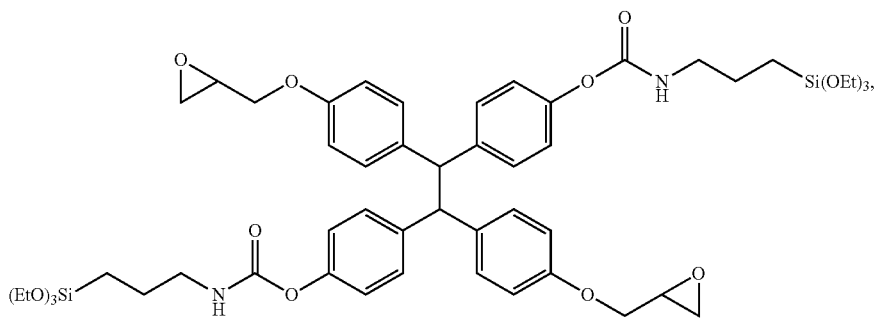
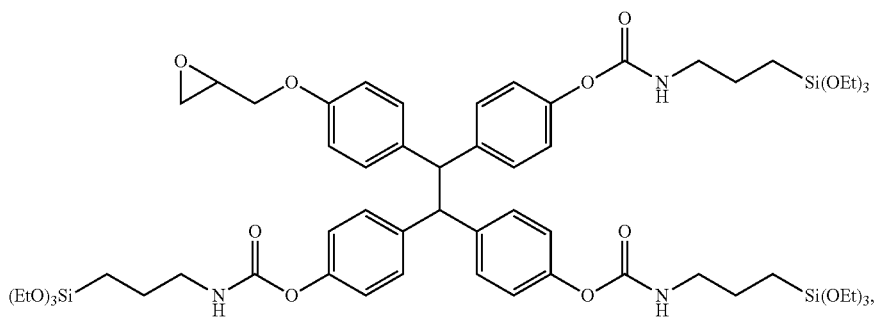
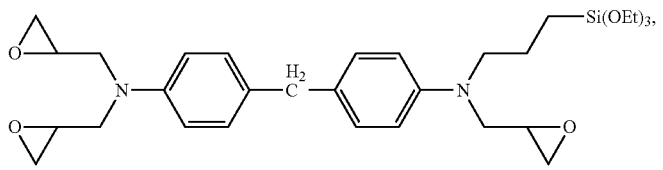
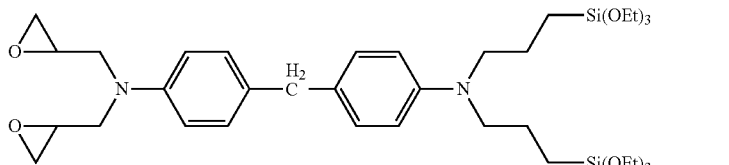
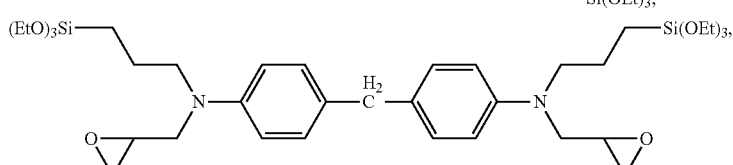
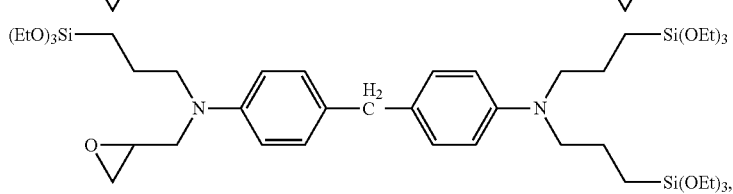

-continued
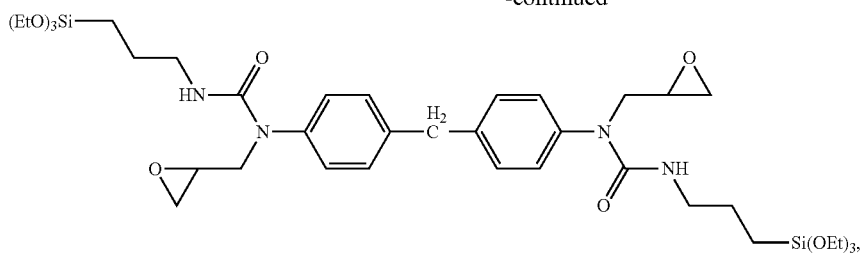
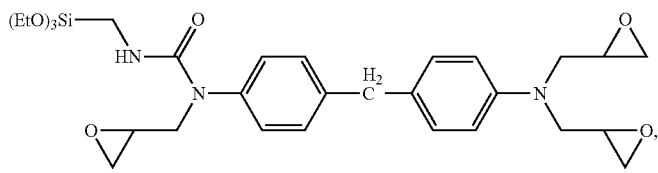
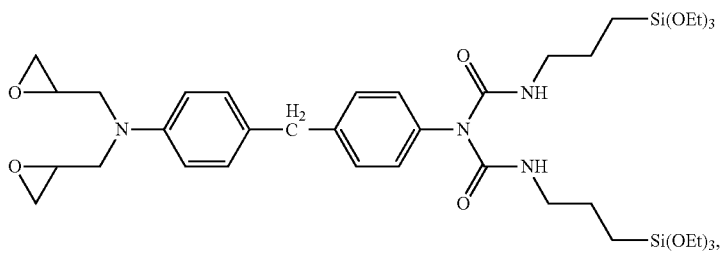
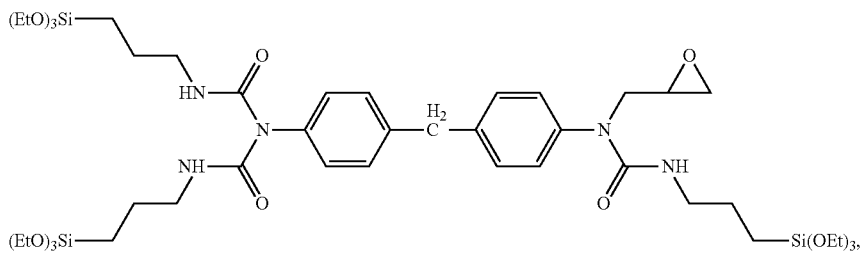
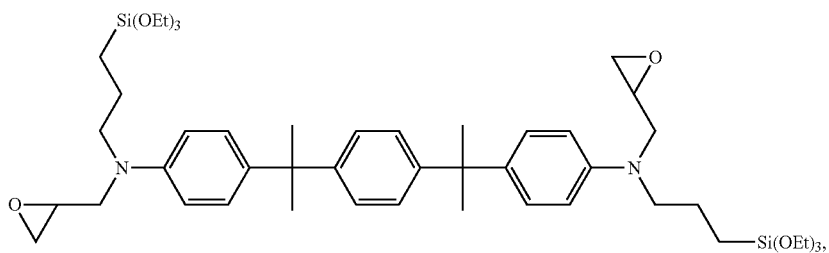
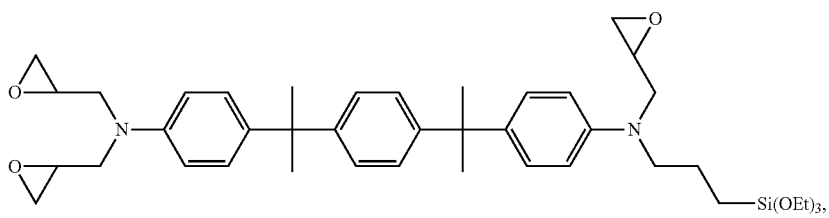
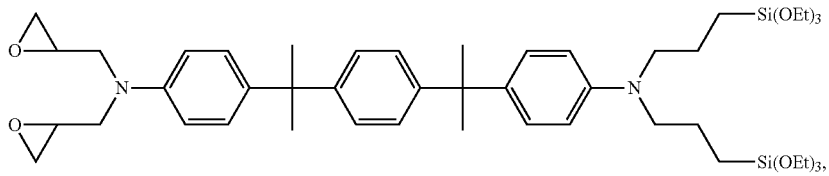

-continued
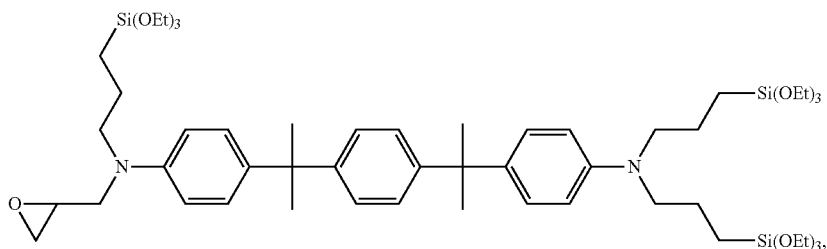
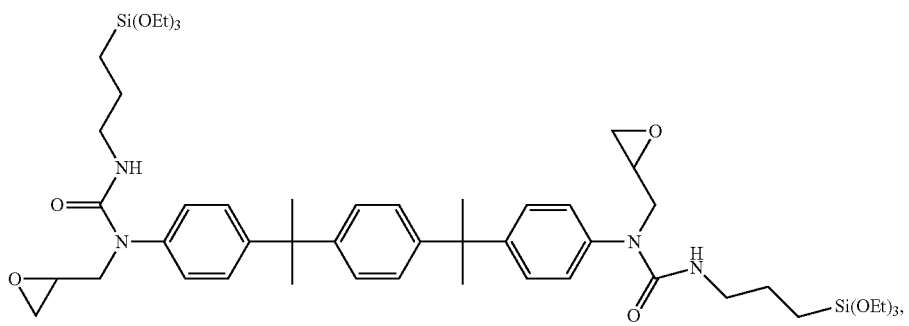
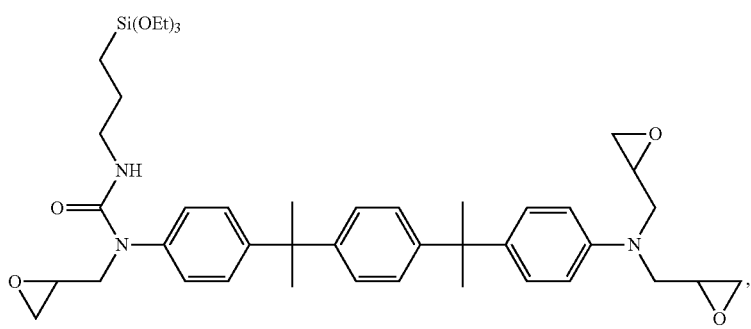
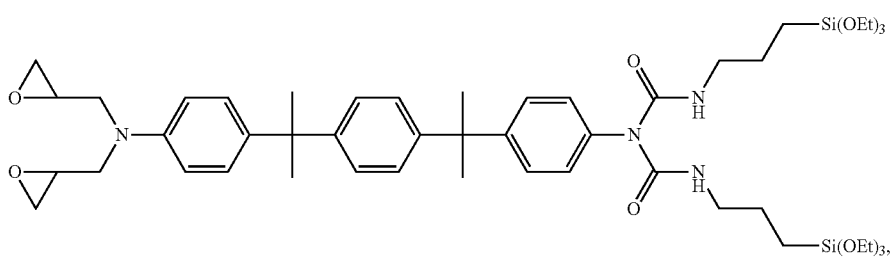
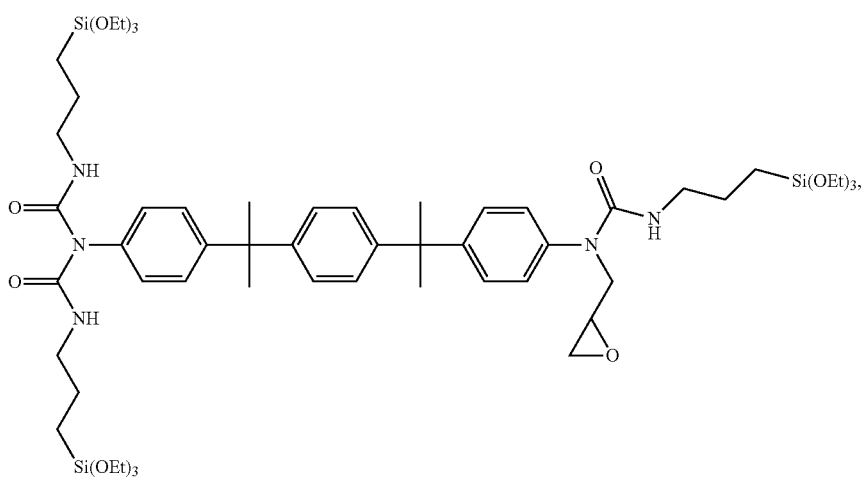

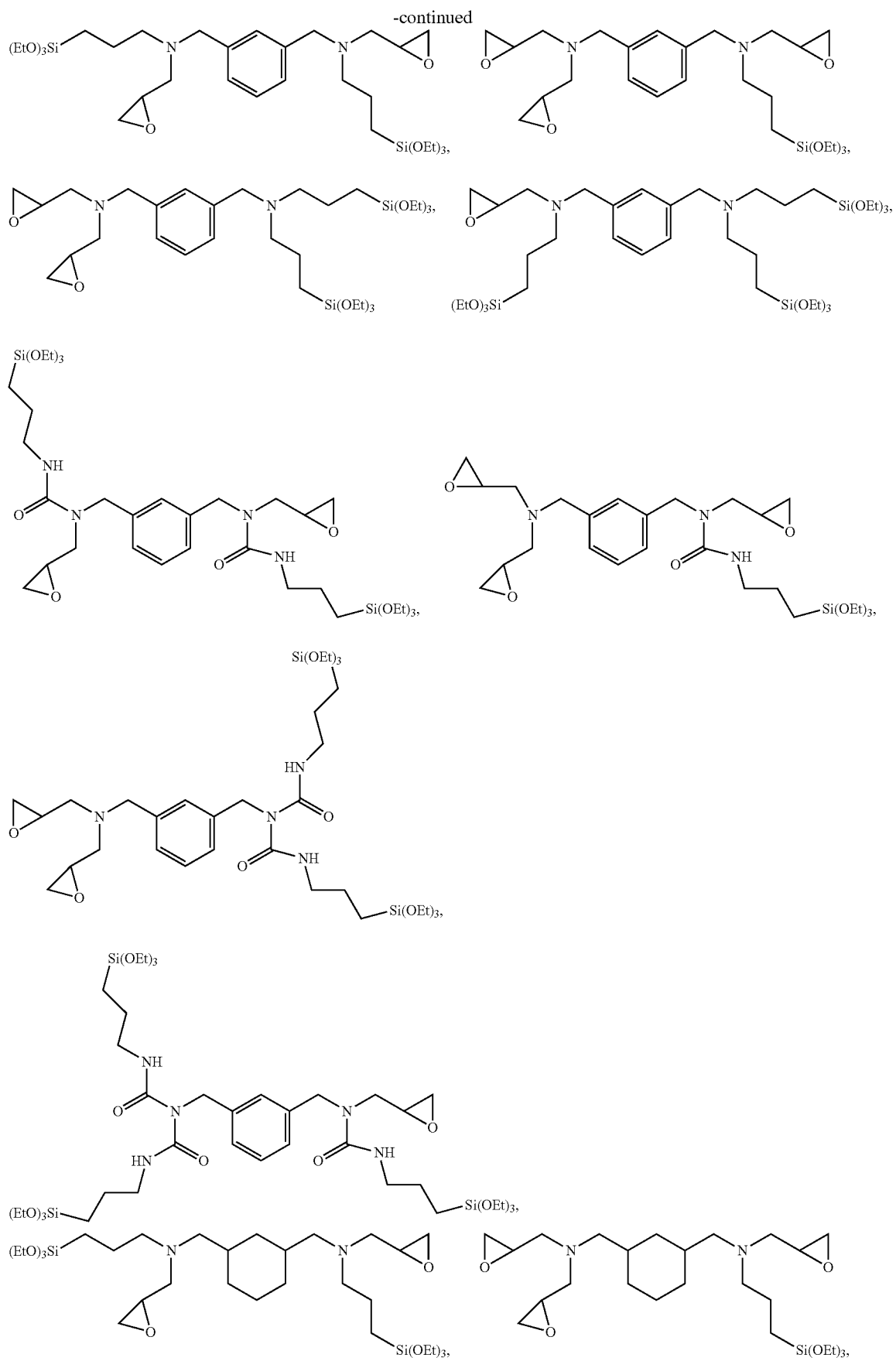

21
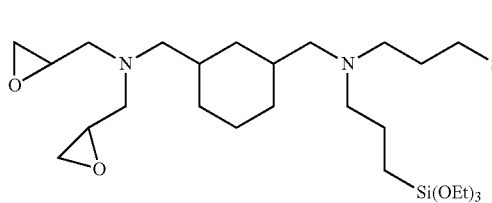
22
-continued
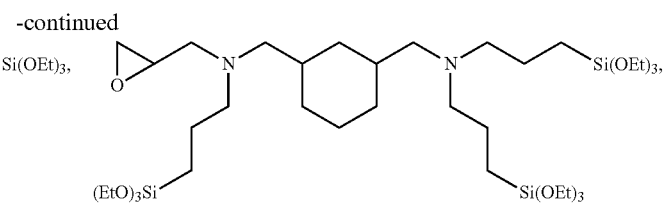
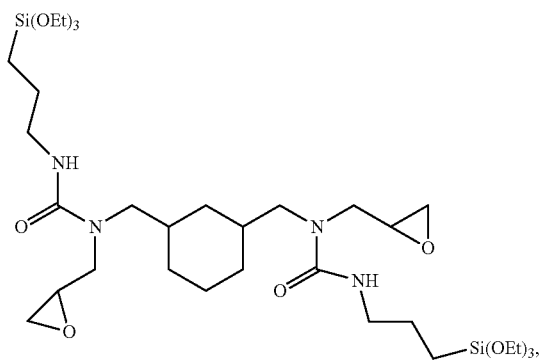
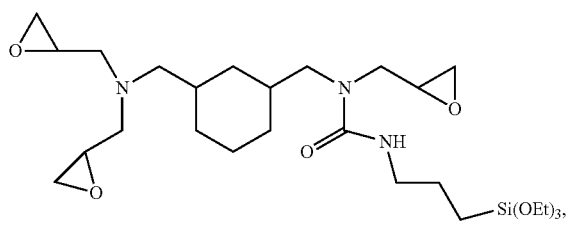
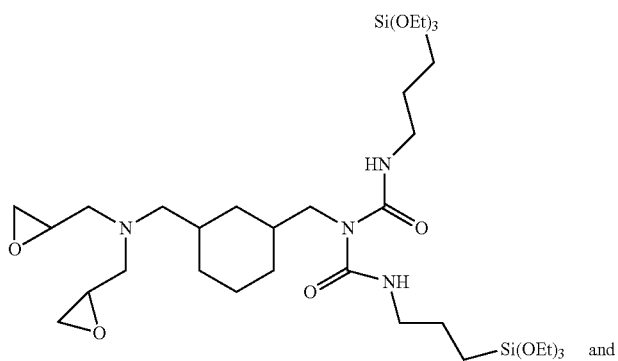
and
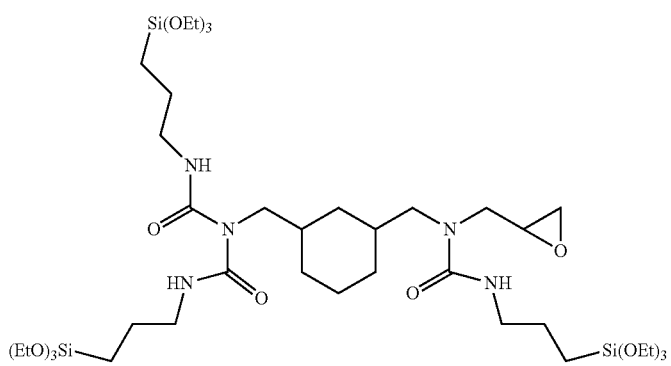

According to the third embodiment of the present invention, there is provided a polymer selected from the group consisting of compounds of following Formula P.
[Formula P]
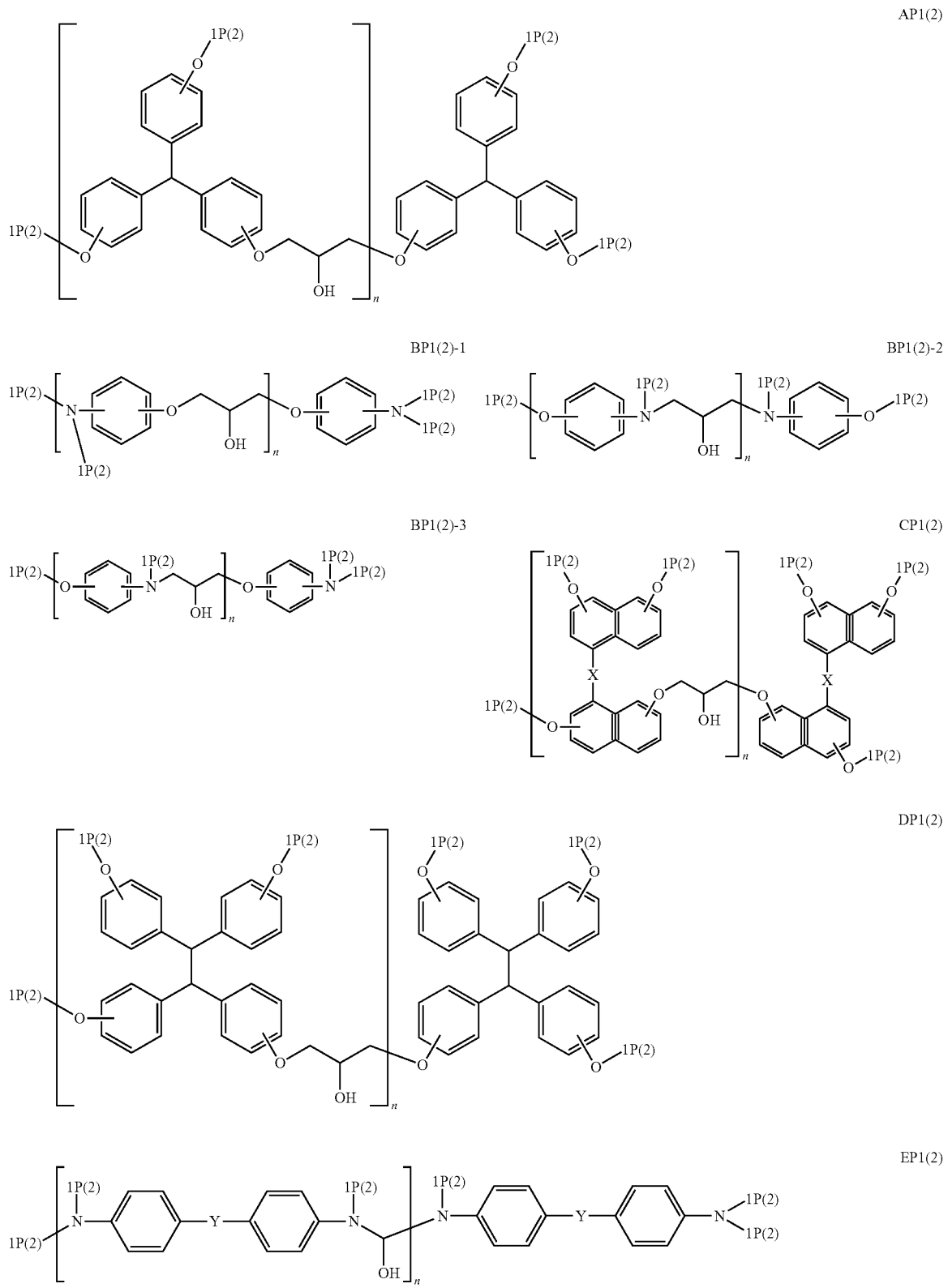

-continued

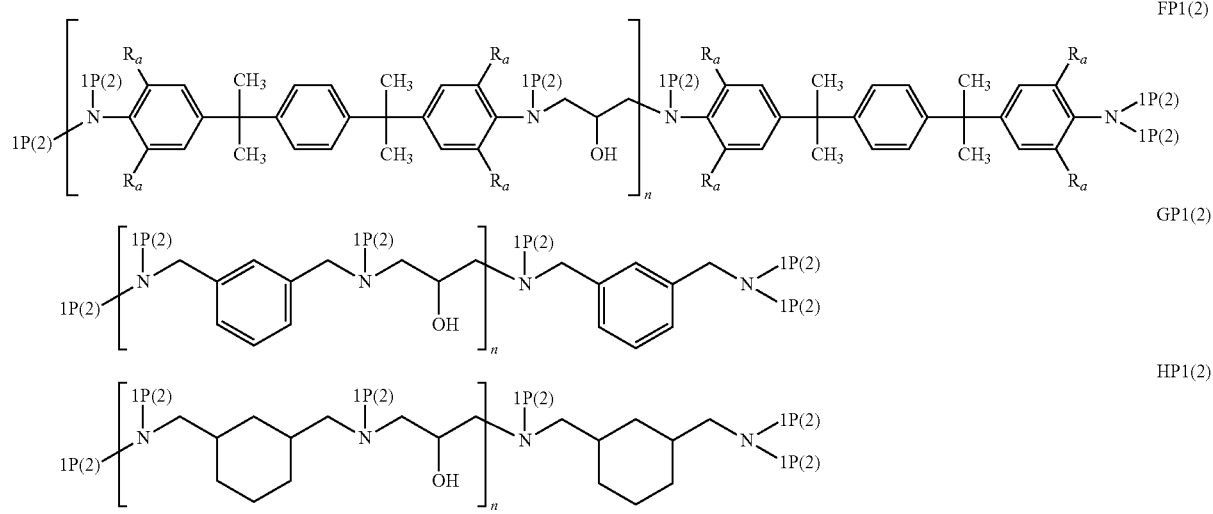

In the above compounds, Each of 1P(2) is independently selected from an epoxy group of following Formula S1, following Formula S2, —$(CH_2)_{z-2}CH=CH_2$ where z is an integer from 3 to 10, and hydrogen.

A meta position of oxygen in Formulae BP1(2)-1 to BP1(2)-3 may be substituted with a linear or branched C1-C10 alkyl group.

X in Formula CP1(2) is a direct linkage, —$CH_2$— or

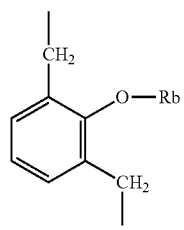

where Rb is H or a C1-C3 alkyl group.

Y in Formula EP1(2) is —$CH_2$—, —$C(CH_3)_2$—, —$C(CF_3)_2$—, —S— or —$SO_2$—.

Ra in Formula FP1(2) is H or a C1-C3 alkyl group.

n is an integer from 1 to 100.

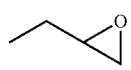

[Formula S1]

—$(CH_2)_z$—$SiR_1R_2R_3$   [Formula S2]

In Formula S2, at least one of $R_1$ to $R_3$ is an alkoxy group having 1 to 10 carbon atoms, the remainder thereof are alkyl groups having 1 to 10 carbon atoms, the alkyl group and the alkoxy group are a linear chain or a branched chain alkyl group or alkoxy group, and z is an integer from 3 to 10.

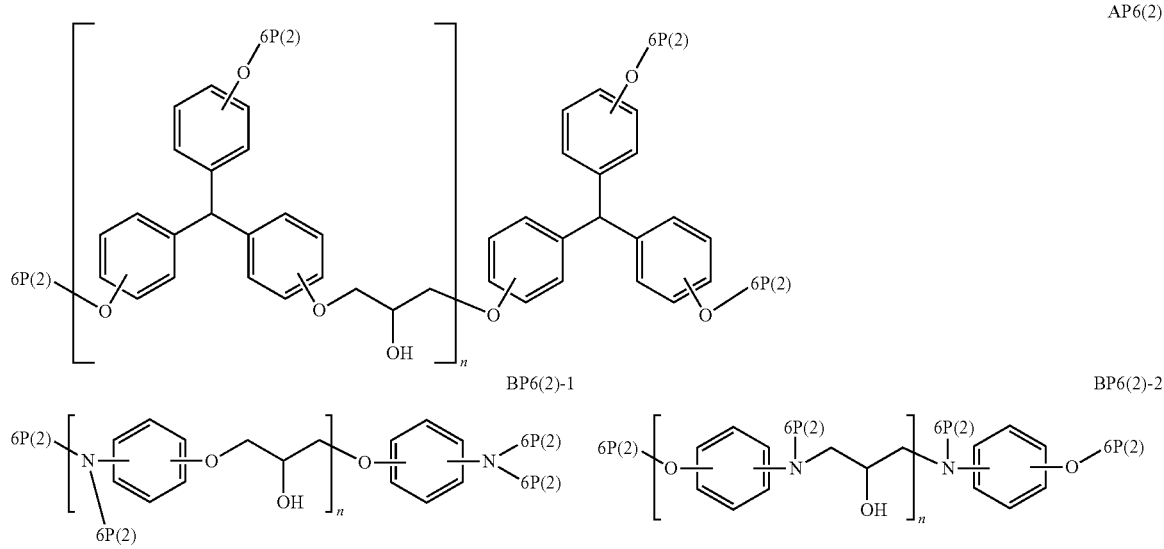

-continued
BP6(2)-3
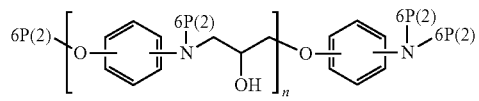
CP6(2)
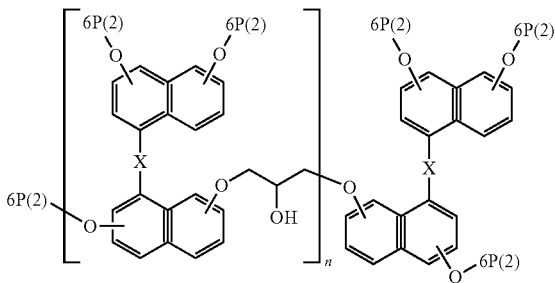
DP6(2)
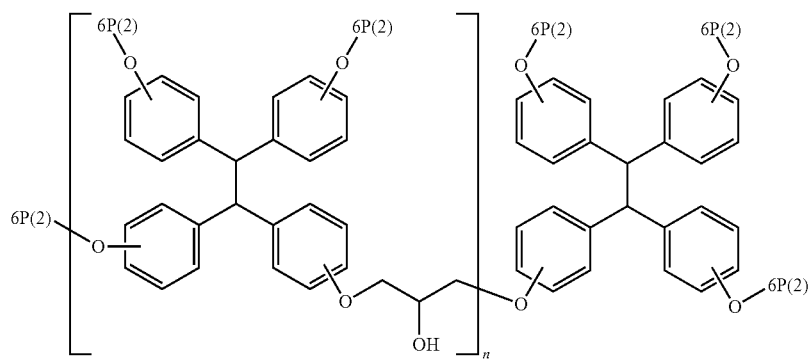
EP6(2)
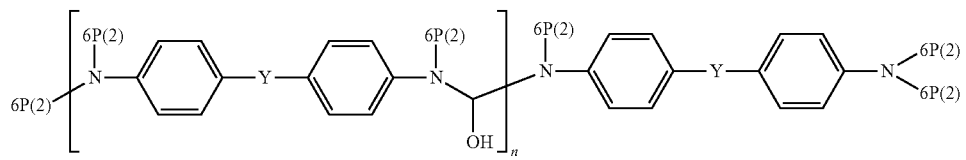
FP6(2)
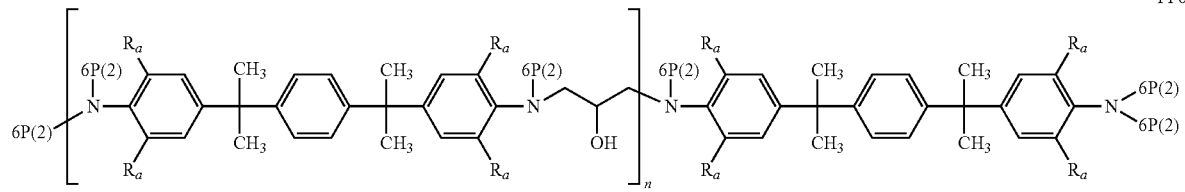
GP6(2)
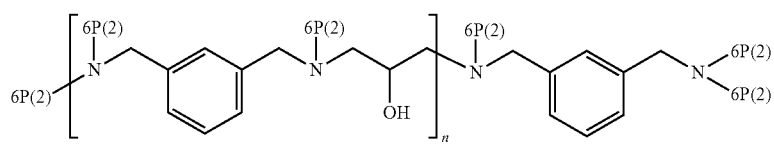
HP6(2)
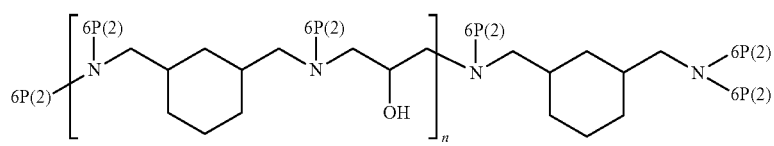

In the above compounds, each of 6P(2) is independently selected from the epoxy group of the above Formula S1, following Formula S3, and hydrogen.

A meta position of oxygen in Formulae BP6(2)-1 to BP(2)-3 may be substituted with a linear or branched C1-C10 alkyl group.

X in Formula CP6(2) is a direct linkage, —CH$_2$— or

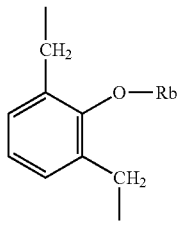

where Rb is H or a C1-C3 alkyl group.

Y in Formula EP6(2) is —CH$_2$—, —C(CH$_3$)$_2$—, —C(CF$_3$)$_2$—, —S— or —SO$_2$—.

Ra in Formula FP6(2) is H or a C1-C3 alkyl group.

n is an integer from 1 to 100.

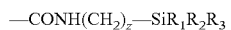  [Formula S3]

In Formula S3, at least one of R$_1$ to R$_3$ is an alkoxy group having 1 to 10 carbon atoms, the remainder thereof are alkyl groups having 1 to 10 carbon atoms, the alkyl group and the alkoxy group are a linear chain or a branched chain alkyl group or alkoxy group, and z is an integer from 3 to 10.

According to the fourth embodiment of the present invention, there is provided an epoxy composition including at least one epoxy compound having an alkoxysilyl group having a structure selected from the group consisting of following Formulae AI to HI.

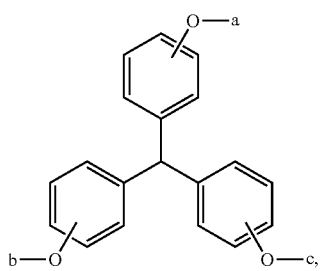
AI

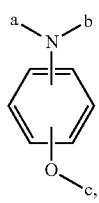
BI

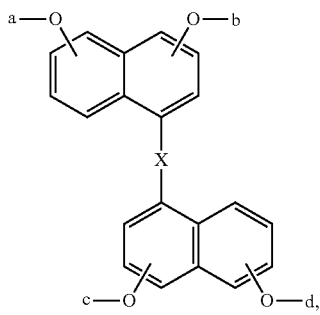
CI

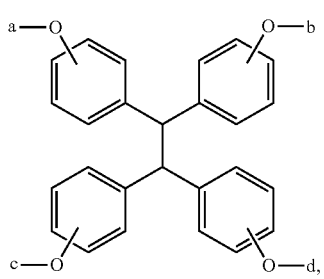
DI

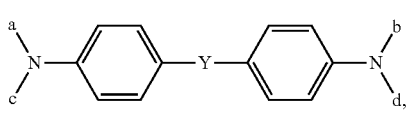
EI

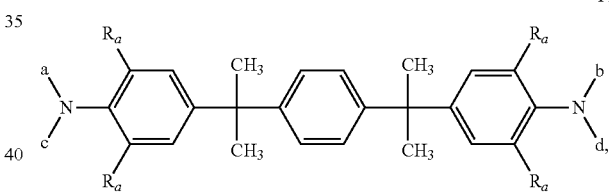
FI

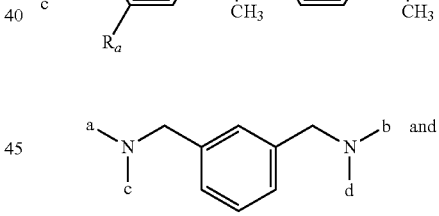
GI

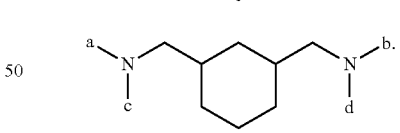
HI

One or two of substituents a to c in Formula AI or BI have the form of Formula S1, one or two thereof have the form of Formula S2 or S3, and the remainder thereof may be hydrogen or —(CH$_2$)$_{z-2}$CH=CH$_2$ where z is an integer from 3 to 10.

One to three of substituents a to d in Formulae CI to HI have the form of Formula S1, one to three thereof have the form of Formula S2 or S3, and the remainder thereof may be hydrogen or —(CH$_2$)$_{z-2}$CH=CH$_2$ where z is an integer from 3 to 10.

A meta position of oxygen in Formula BI may be substituted with a linear or branched C1-C10 alkyl group.

X in Formula CI is a direct linkage, —CH$_2$— or

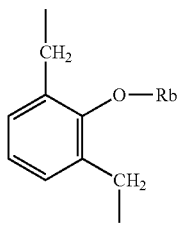

where Rb is H or a C1-C3 alkyl group.

Y in Formula EI is —CH$_2$—, —C(CH$_3$)$_2$—, —C(CF$_3$)$_2$—, —S— or —SO$_2$—.

Ra in Formula FI is H or a C1-C3 alkyl group.

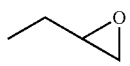 [Formula S1]

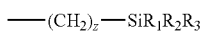 [Formula S2]

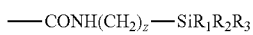 [Formula S3]

In Formulae S2 and S3, at least one of $R_1$ to $R_3$ is an alkoxy group having 1 to 10 carbon atoms, the remainder thereof are alkyl groups having 1 to 10 carbon atoms, the alkyl group and the alkoxy group are a linear chain or a branched chain alkyl group or alkoxy group, and z is an integer from 3 to 10.

According to the fifth embodiment of the present invention, the epoxy composition of the fourth embodiment, in which, at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound is further included, may be provided.

According to the sixth embodiment of the present invention, the epoxy composition of the fourth embodiment, in which the epoxy compound includes bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolak unit, as a core structure, may be provided.

According to the seventh embodiment of the present invention, the epoxy composition of the sixth embodiment, in which the epoxy compound includes the bisphenol A, the biphenyl, the naphthalene, or the fluorene as the core structure, may be provided.

According to the eighth embodiment of the present invention, the epoxy composition of the fifth embodiment, in which the epoxy composition includes 10 wt % to 100 wt % of the epoxy compound having an alkoxysilyl group and 0 wt % to 90 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on a total amount of the epoxy compound, may be provided.

According to the ninth embodiment of the present invention, the epoxy composition of the eighth embodiment, in which the epoxy composition includes 30 wt % to 100 wt % of the epoxy compound having an alkoxysilyl group and 0 wt % to 70 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on the total amount of the epoxy compound, may be provided.

According to the tenth embodiment of the present invention, the epoxy composition according to any one of the first to ninth embodiments, in which at least one kind of filler selected from the group consisting of inorganic particles and a fiber is included, may be provided.

According to the eleventh embodiment of the present invention, the epoxy composition of the tenth embodiment, in which the inorganic particle is at least one selected from the group consisting of a metal oxide selected from the group consisting of silica, zirconia, titania, alumina, silicon nitride and aluminum nitride, T-10 type silsesquioxane, ladder type silsesquioxane and cage type silsesquioxane, may be provided.

According to a twelfth embodiment of the present invention, the epoxy composition of the tenth embodiment, in which an amount of the inorganic particles is 5 wt % to 95 wt % based on a total solid content of the epoxy composition, may be provided.

According to the thirteenth embodiment of the present invention, the epoxy composition of the twelfth embodiment, in which an amount of the inorganic particles is 30 wt % to 95 wt % based on a total solid content of the epoxy composition, may be provided.

According to the fourteenth embodiment of the present invention, the epoxy composition of the twelfth embodiment, in which an amount of the inorganic particles is 5 wt % to 60 wt % based on a total solid content of the epoxy composition, may be provided.

According to the fifteenth embodiment of the present invention, the epoxy composition of the tenth embodiment, in which the fiber is at least one selected from the group consisting of a glass fiber selected from the group consisting of an E-glass fiber, a T-glass fiber, an S-glass fiber, an NE-glass fiber, a H-glass fiber and quartz, and an organic fiber selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber, may be provided.

According to the sixteenth embodiment of the present invention, the epoxy composition of the fifteenth embodiment, in which the fiber is the E-glass fiber, may be provided.

According to the seventeenth embodiment of the present invention, the epoxy composition of the fifteenth embodiment, in which the fiber is the T-glass fiber, may be provided.

According to the eighteenth embodiment of the present invention, the epoxy composition of the tenth embodiment, in which an amount of the fiber is 10 wt % to 90 wt % based on a total solid content of the epoxy composition, may be provided.

According to the nineteenth embodiment of the present invention, the epoxy composition of the tenth embodiment, in which the inorganic particles are further included in the case that the fiber is included therein, may be provided.

According to the twentieth embodiment of the present invention, the epoxy composition according to any one of the first to nineteenth embodiments, in which a curing agent is further included, may be provided.

According to the twenty-first embodiment of the present invention, the epoxy composition according to any one of the first to twentieth embodiments, in which an reaction catalyst for alkoxysilyl group is further included, may be provided.

According to the twenty-second embodiment of the present invention, the epoxy composition of the twenty-first embodiment, in which the reaction catalyst for alkoxysilyl group is at least one selected from the group consisting of at least one inorganic acid selected from the group consisting of nitric acid, sulfuric acid, hydrochloric acid, acetic acid and phosphoric acid, ammonia, KOH, NH$_4$OH, amine, a transition metal alkoxide, and a tin compound, may be provided.

According to the twenty-third embodiment of the present invention, the epoxy composition of the twenty-first embodiment, in which the reaction catalyst is used by 0.01 to 0.1 equivalents based on 1 equivalent of an alkoxysilyl group of the epoxy compound having an alkoxysilyl group, may be provided.

According to the twenty-fourth embodiment of the present invention, the epoxy composition of the twenty-first embodiment, in which water is further included, may be provided.

According to the twenty-fifth embodiment of the present invention, there is provided an electronic material including the epoxy composition according to any one of the first to twenty-fourth embodiments.

According to the twenty-sixth embodiment of the present invention, there is provided a substrate including the epoxy composition according to any one of the first to twenty-fourth embodiments.

According to the twenty-seventh embodiment of the present invention, there is provided a film including the epoxy composition according to any one of the first to twenty-fourth embodiments.

According to the twenty-eighth embodiment of the present invention, there is provided a laminate including a metal layer placed on a base layer formed by using the epoxy composition according to any one of the first to twenty-fourth embodiments.

According to the twenty-ninth embodiment of the present invention, there is provided a printed circuit board including the laminate of the twenty-eighth embodiment.

According to the thirtieth embodiment of the present invention, there is provided a semiconductor device including the printed circuit board of the twenty-ninth embodiment.

According to the thirty-first embodiment of the present invention, there is provided a semiconductor packaging material including the epoxy composition according to any one of the first to twenty-fourth embodiments.

According to the thirty-second embodiment of the present invention, there is provided a semiconductor device including the semiconductor packaging material according to any one of the thirty-first embodiment.

According to the thirty-third embodiment of the present invention, there is provided an adhesive including the epoxy composition according to any one of the first to twenty-fourth embodiments.

According to the thirty-fourth embodiment of the present invention, there is provided a paint composition including the epoxy composition according to any one of the first to twenty-fourth embodiments.

According to the thirty-fifth embodiment of the present invention, there is provided a composite material including the epoxy composition according to any one of the first to twenty-fourth embodiments.

According to the thirty-sixth embodiment of the present invention, there is provided a prepreg including the epoxy composition according to any one of the first to twenty-fourth embodiments.

According to the thirty-seventh embodiment of the present invention, there is provided a laminate including a metal layer placed on the prepreg of the thirty-sixth embodiment.

According to the thirty-eighth embodiment of the present invention, there is provided a cured product of the epoxy composition according to any one of the first to twenty-fourth embodiments.

According to the thirty-ninth embodiment of the present invention, the cured product of the thirty-eighth embodiment, in which the cured product has a coefficient of thermal expansion of 60 ppm/° C. or less, may be provided.

According to the fortieth embodiment of the present invention, the cured product of the thirty-eighth embodiment, in which the cured product has a glass transition temperature of 100° C. or over, or does not exhibit the glass transition temperature, may be provided.

According to the forty-first embodiment of the present invention, there is provided a method of preparing an epoxy compound having an alkoxysilyl group including a first step of preparing one Intermediate Product (11) of following Formulae A11 to H11 by reacting one starting material of following Formulae AS to HS with an alkenyl compound of following Formula M1 in the presence of a base, and an optional solvent, then by reacting with epichlorohydrin in situ, and a second step of preparing one target product of following Formulae AI to HI by reacting one of the above Intermediate Products (11) with an alkoxysilane of following Formula M2 in the presence of a metal catalyst and an optional solvent.

[Starting Material]

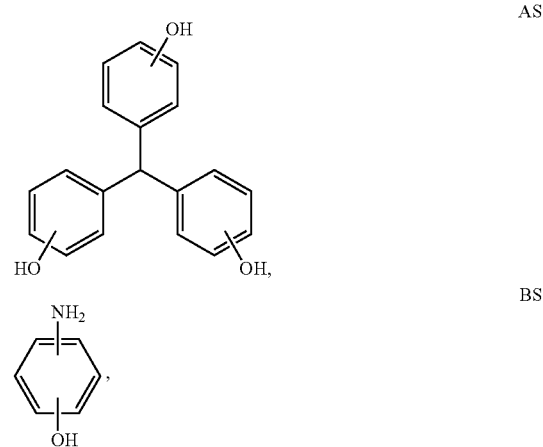

-continued

CS

[Structure: two naphthalene units each bearing two OH groups, connected through X]

DS

[Structure: tetra(hydroxyphenyl)methane-type, central carbon with four hydroxyphenyl groups]

ES $H_2N$—C$_6$H$_4$—Y—C$_6$H$_4$—$NH_2$,

FS $H_2N$—[substituted phenyl with $R_a$, $CH_3$]—C(CH$_3$)$_2$—C$_6$H$_4$—C(CH$_3$)$_2$—[substituted phenyl with $R_a$]—$NH_2$,

GS $H_2N$—CH$_2$—(m-phenylene)—CH$_2$—$NH_2$ and

HS $H_2N$—CH$_2$—(cyclohexane-1,3-diyl)—CH$_2$—$NH_2$

A meta position of oxygen in Formula BS above may be substituted with a linear or branched C1-C10 alkyl group.

X in Formula CS is a direct linkage, —CH$_2$— or

[Structure: 2,6-bis(methylene)phenol with O—Rb]

where Rb is H or a C1-C3 alkyl group.

Y in Formula ES is —CH$_2$—, —C(CH$_3$)$_2$—, —C(CF$_3$)$_2$—, —S— or —SO$_2$—.

Ra in Formula FS is H or a C1-C3 alkyl group.

X—(CH$_2$)$_{z-2}$—CH═CH$_2$   [Formula M1]

In Formula M1, X is a halide of Cl, Br or I, —O—SO$_2$—CH$_3$, —O—SO$_2$—CF$_3$, or —O—SO$_2$—C$_6$H$_4$—CH$_3$, and z is an integer from 3 to 10.

A11

[Structure: triphenylmethane with O—$e_1$, $f_1$—O, O—$g_1$ substituents]

B11

[Structure: triphenylamine with $e_1$—N, $f_1$, O—$g_1$]

C11

[Structure: two naphthalene units with $e_1$—O, O—$f_1$, $g_1$—O, O—$h_1$, connected via X]

D11

[Structure: tetra(aryl)methane core with $e_1$—O, O—$f_1$, g—O, O—$h_1$ substituents]

E11

$e_1$—N($g_1$)—C$_6$H$_4$—Y—C$_6$H$_4$—N($f_1$)($h_1$),

F11

$e_1$—N($g_1$)—[phenyl with Ra, CH$_3$]—C(CH$_3$)$_2$—C$_6$H$_4$—C(CH$_3$)$_2$—[phenyl with Ra]—N($f_1$)($h_1$),

G11

$e_1$—N($g_1$)—CH$_2$—(m-phenylene)—CH$_2$—N($f_1$)($h_1$) and

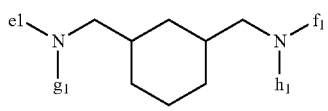
H11

One or two of substituents e1, f1, and g1 in Formula A11 or B11 have the form of Formula S1, and at least one thereof is —(CH$_2$)$_{z-2}$—CH=CH$_2$ where z is an integer from 3 to 10 and may be hydrogen when an unreacted site is present.

One to three of substituents e1, f1, g1, and h1 in Formulae C11 to H11 have the form of Formula S1, and at least one thereof is —(CH$_2$)$_{z-2}$—CH=CH$_2$ where z is an integer from 3 to 10 and may be hydrogen when an unreacted site is present.

A meta position of oxygen in Formula B11 above may be substituted with a linear or branched C1-C10 alkyl group.

X in Formula C11 is a direct linkage, —CH$_2$— or

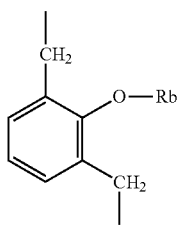

where Rb is H or a C1-C3 alkyl group.

Y in Formula E11 is —CH$_2$—, —C(CH$_3$)$_2$—, —C(CF$_3$)$_2$—, —S— or —SO$_2$—.

Ra in Formula F11 is H or a C1-C3 alkyl group.

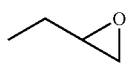
[Formula S1]

HSiR$_1$R$_2$R$_3$    [Formula M2]

In Formula M2, at least one of R$_1$ to R$_3$ is a C1-C10 alkoxy group, the remainder thereof are C1-C10 alkyl groups, and the alkoxy group and the alkyl group are a linear chain or a branched chain alkoxy group and alkyl group.

[Target Product]

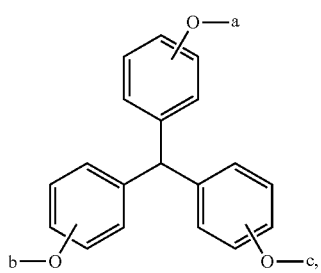
A1

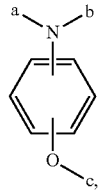
B1

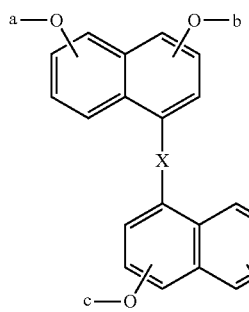
C1

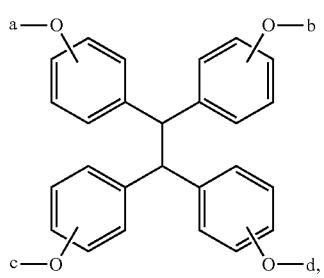
D1

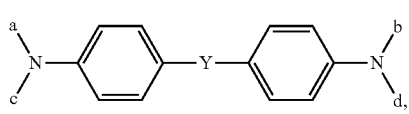
E1

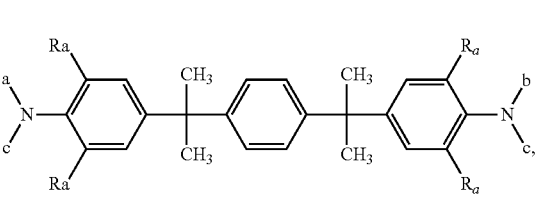
F1

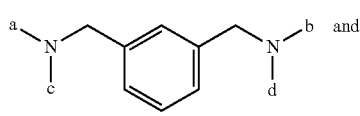
G1 and

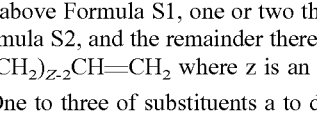
H1

One or two of substituents a to c in Formula AI or BI are the above Formula S1, one or two thereof have the form of Formula S2, and the remainder thereof may be hydrogen or —(CH$_2$)$_{z-2}$CH=CH$_2$ where z is an integer from 3 to 10.

One to three of substituents a to d in Formulae CI to HI are the above Formula S1, one to three thereof have the form of Formula S2, and the remainder thereof may be hydrogen or —(CH$_2$)$_{z-2}$CH=CH$_2$ where z is an integer from 3 to 10.

A meta position of oxygen in Formula BI may be substituted with a linear or branched C1-C10 alkyl group.

X in Formula CI is a direct linkage, —CH$_2$— or

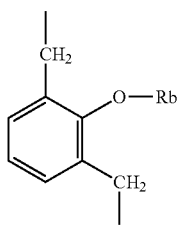

where Rb is H or a C1-C3 alkyl group.

Y in Formula EI is —CH$_2$—, —C(CH$_3$)$_2$—, —C(CF$_3$)$_2$—, —S— or —SO$_2$—.

Ra in Formula FI is H or a C1-C3 alkyl group.

—(CH$_2$)$_z$—SiR$_1$R$_2$R$_3$     [Formula S2]

In Formula S2, at least one of R$_1$ to R$_3$ is an alkoxy group having 1 to 10 carbon atoms, the remainder thereof are alkyl groups having 1 to 10 carbon atoms, the alkoxy group and the alkyl group are a linear chain or a branched chain alkoxy group or alkyl group, and z is an integer from 3 to 10.

According to the forty-second embodiment of the present invention, the method of preparing an epoxy compound having an alkoxysilyl group of the forty-first embodiment, in which 1 to 10 equivalents of the alkenyl compound of Formula M1 react with 1 equivalent of a hydroxyl group of the starting material, and subsequently, 1 to 10 equivalents of the epichlorohydrin react with 1 equivalent of the hydroxyl group of the starting material during the first step, may be provided.

According to the forty-third embodiment of the present invention, the method of preparing an epoxy compound having an alkoxysilyl group of the forty-first embodiment, in which the first step is performed at a temperature from room temperature to 100° C. for 1 to 120 hours, may be provided.

According to the forty-fourth embodiment of the present invention, the method of preparing an epoxy compound having an alkoxysilyl group of the forty-first embodiment, in which 1 to 5 equivalents of the alkoxysilane of Formula M2 react with 1 equivalent of the alkenyl group of the above Intermediate Product (11) during the second step, may be provided.

According to the forty-fifth embodiment of the present invention, the method of preparing an epoxy compound having an alkoxysilyl group of the forty-first embodiment, in which the second step is performed at a temperature from room temperature to 100° C. for 1 to 72 hours, may be provided.

According to the forty-sixth embodiment of the present invention, there is provided a method of preparing an epoxy compound having an alkoxysilyl group including a first step of preparing one Intermediate Product (21) of following Formulae A21 to H21 by reacting one starting material of following Formulae AS to HS with an alkenyl compound of following Formula M1 in the presence of a base and an optional solvent, a second step of preparing one Intermediate Product (22) of following Formulae A22 to H22 by reacting one of the above Intermediate Products (21) with a peroxide in the presence of an optional base and an optional solvent, a third step of preparing one Intermediate Product (23) of following Formulae A23 to H23 by reacting one of the above Intermediate Products (22) with the alkenyl compound of following Formula M1 in the presence of a base and an optional solvent, and a fourth step of preparing one target product among following Formulae AI to HI by reacting one of the above Intermediate Products (23) with the alkoxysilane of following Formula M2 in the presence of a metal catalyst and an optional solvent.

[Starting Material]

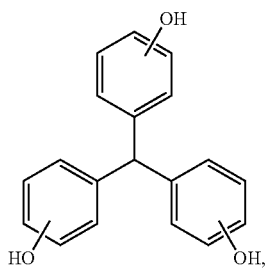
AS

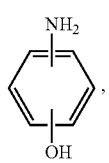
BS

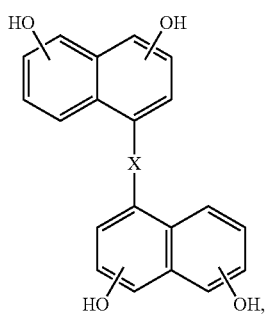
CS

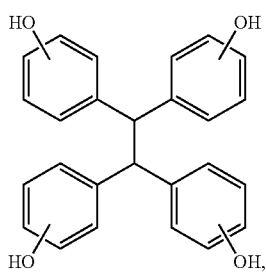
DS

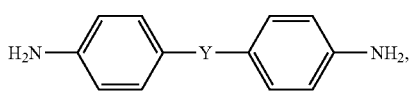
ES

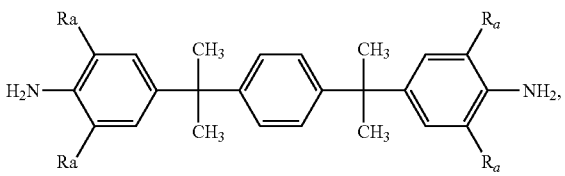
FS

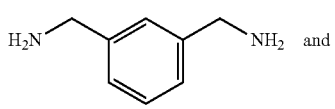
GS
and

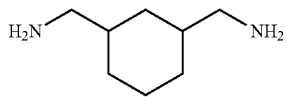

A meta position of oxygen in Formula BS above may be substituted with a linear or branched C1-C10 alkyl group.

X in Formula CS is a direct linkage, —CH$_2$— or

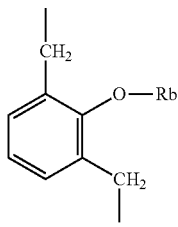

where Rb is H or a C1-C3 alkyl group.

Y in Formula ES is —CH$_2$—, —C(CH$_3$)$_2$—, —C(CF$_3$)$_2$—, —S— or —SO$_2$—.

Ra in Formula FS is H or a C1-C3 alkyl group.

 [Formula M1]

In Formula M1, X is a halide of Cl, Br or I, —O—SO$_2$—CH$_3$, —O—SO$_2$—CF$_3$, or —O—SO$_2$—C$_6$H$_4$—CH$_3$, and z is an integer from 3 to 10.

[Intermediate Product (21)]

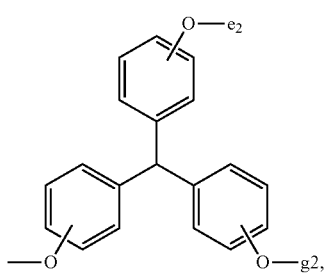 A21

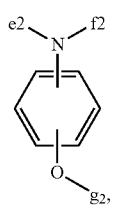 B21

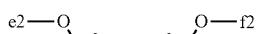

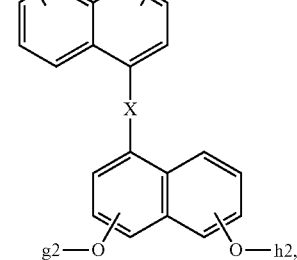 C21

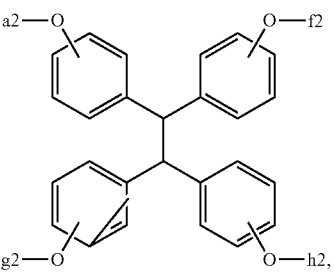 D21

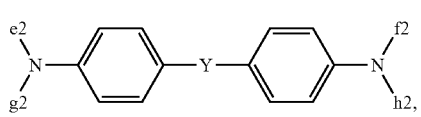 E21

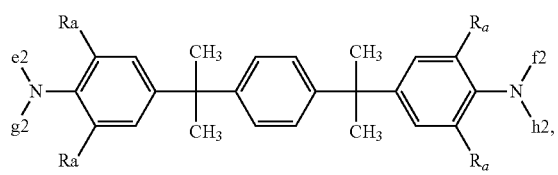 F21

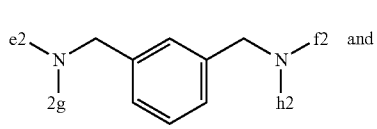 G21 and

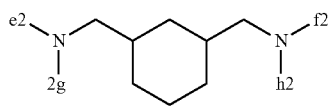 H21

One or two of substituents e2 to g2 in Formula A21 or B21 are —(CH$_2$)$_{z-2}$—CH=CH$_2$ where z is an integer from 3 to 10, and the remainder thereof are hydrogen.

One to three of substituents e2 to h2 in Formulae C21 to H21 are —(CH$_2$)$_{z-2}$—CH=CH$_2$ where z is an integer from 3 to 10, and the remainder thereof are hydrogen.

A meta position of oxygen in Formula B21 above may be substituted with a linear or branched C1-C10 alkyl group.

X in Formula C21 is a direct linkage, —CH$_2$— or

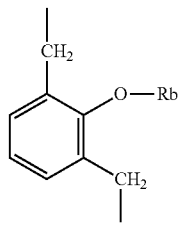

where Rb is H or a C1-C3 alkyl group.

Y in Formula E21 is —CH$_2$—, —C(CH$_3$)$_2$—, —C(CF$_3$)$_2$—, —S— or —SO$_2$—.

Ra in Formula F21 is H or a C1-C3 alkyl group.

[Intermediate Product (22)]

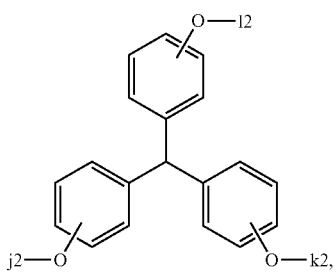
A22

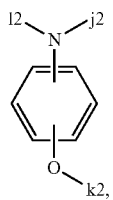
B22

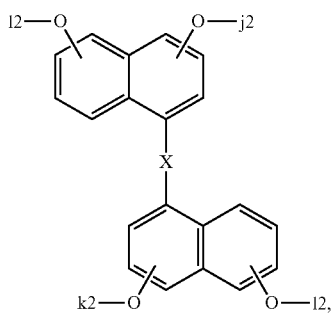
C22

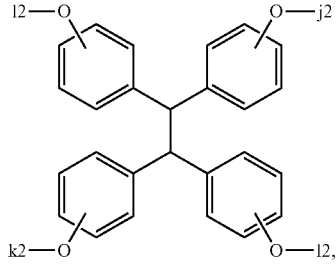
D22

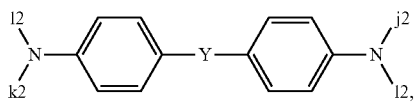
E22

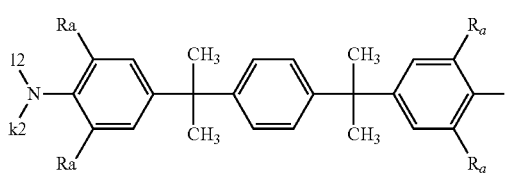
F22

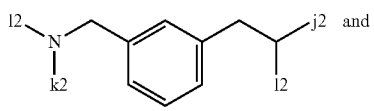 and
G22

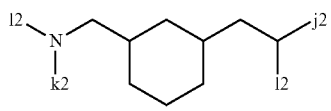
H22

One or two of substituents i2 to k2 in Formulae A22 to B22 have the form of Formula S1, and at least one thereof is hydrogen and may be —$(CH_2)_{z-2}$—CH=$CH_2$ where z is an integer from 3 to 10.

One to three of substituents i2 to l2 in Formulae C22 to H22 have the form of Formula S1, and at least one thereof is hydrogen and may be —$(CH_2)_{z-2}$—CH=$CH_2$ where z is an integer from 3 to 10.

A meta position of oxygen in Formula B22 above may be substituted with a linear or branched C1-C10 alkyl group.

X in Formula C22 is a direct linkage, —$CH_2$— or

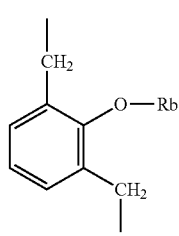

where Rb is H or a C1-C3 alkyl group.

Y in Formula E22 is —$CH_2$—, —C($CH_3$)—, —C($CF_3$)$_2$—, —S— or —$SO_2$—.

Ra in Formula F22 is H or a C1-C3 alkyl group.

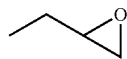 [Formula S1]

X—$(CH_2)_{z-2}$—CH=$CH_2$ [Formula M1]

In Formula M1, X is a halide of Cl, Br or I, —O—$SO_2$—$CH_3$, —O—$SO_2$—$CF_3$, or —O—$SO_2$—$C_6H_4$—$CH_3$, and z is an integer from 3 to 10.

[Intermediate Product (23)]

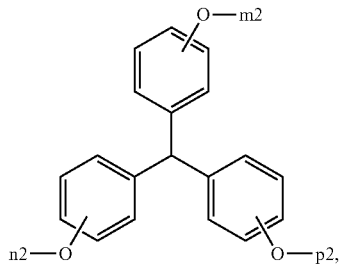
A23

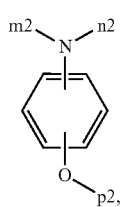
B23

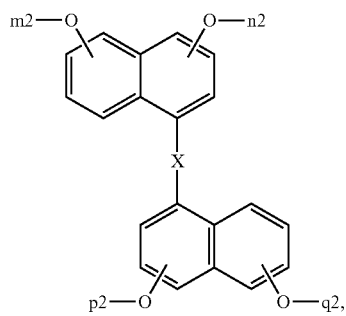

C23

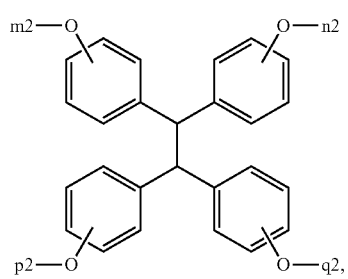

D23

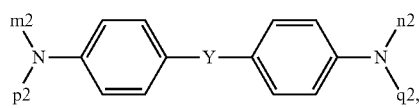

E23

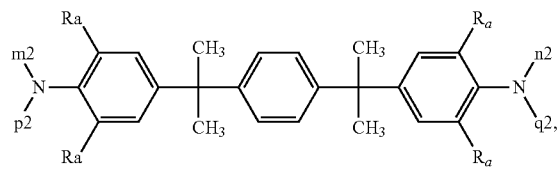

F23

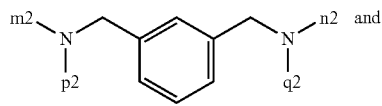

G23

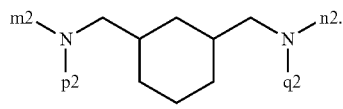

H23

One or two of substituents m2, n2, and p2 in Formula A23 or B23 are the above Formula S1, and at least one thereof is $-(CH_2)_{z-2}-CH=CH_2$ where z is an integer from 3 to 10 and may be hydrogen.

One to three of substituents m2, n2, p2, and q2 in Formulae C23 to H23 are the above Formula S1, and at least one thereof is $-(CH_2)_{z-2}-CH=CH_2$ where z is an integer from 3 to 10 and may be hydrogen.

A meta position of oxygen in Formula B23 above may be substituted with a linear or branched C1-C10 alkyl group.

X in Formula C23 is a direct linkage, $-CH_2-$ or

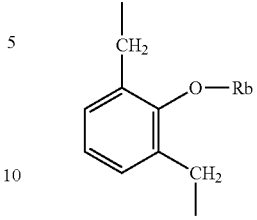

where Rb is H or a C1-C3 alkyl group.

Y in Formula E23 is $-CH_2-$, $-C(CH_3)_2-$, $-C(CF_3)_2-$, $-S-$ or $-SO_2-$.

Ra in Formula F23 is H or a C1-C3 alkyl group.

$$HSiR_1R_2R_3 \qquad [\text{Formula M2}]$$

In Formula M2, at least one of $R_1$ to $R_3$ is a C1-C10 alkoxy group, and the remainder thereof are linear or branched C1-C10 alkyl groups.

[Target Product]

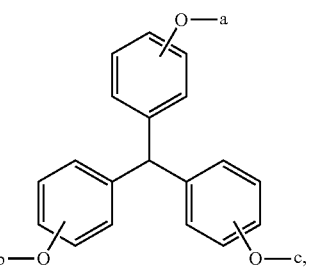

A1

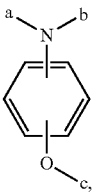

B1

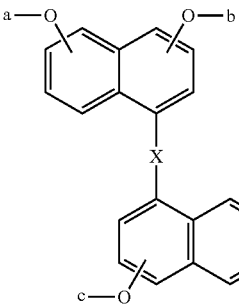

C1

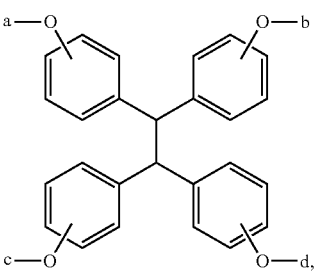

D1

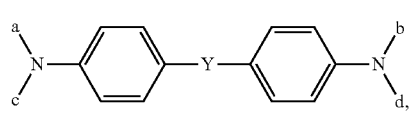

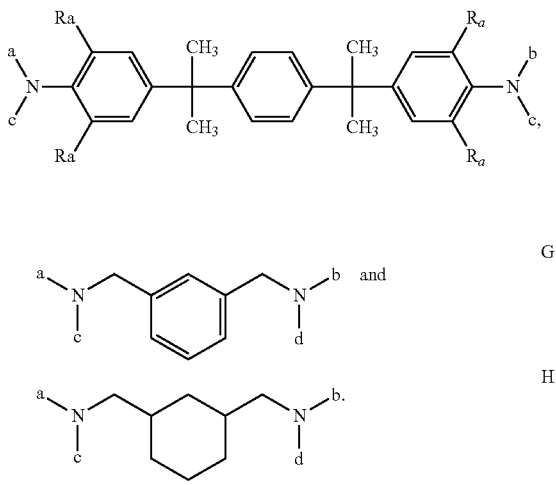

One or two of substituents a to c in Formula AI or BI are the above Formula S1, one or two thereof have the form of Formula S2, and the remainder thereof may be hydrogen or —(CH$_2$)$_{z-2}$CH═CH$_2$ where z is an integer from 3 to 10.

One to three of substituents a to d in Formulae CI to HI are the above Formula S1, one to three thereof have the form of Formula S2, and the remainder thereof may be hydrogen or —(CH$_2$)$_{z-2}$CH═CH$_2$ where z is an integer from 3 to 10.

A meta position of oxygen in Formula BI may be substituted with a linear or branched C1-C10 alkyl group.

X in Formula CI is a direct linkage, —CH$_2$— or

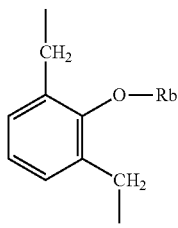

where Rb is H or a C1-C3 alkyl group.

Y in Formula EI is —CH$_2$—, —C(CH$_3$)$_2$—, —C(CF$_3$)$_2$—, —S— or —SO$_2$—.

Ra in Formula FI is H or a C1-C3 alkyl group.

—(CH$_2$)$_z$—SiR$_1$R$_2$R$_3$                    [Formula S2]

In Formulae S2, at least one of R$_1$ to R$_3$ is an alkoxy group having 1 to 10 carbon atoms, the remainder thereof are alkyl groups having 1 to 10 carbon atoms, z is an integer from 3 to 10, and the alkyl group and the alkoxy group are a linear chain or a branched chain alkyl group or alkoxy group.

According to the forty-seventh embodiment of the present invention, the method of preparing an epoxy compound having an alkoxysilyl group of the forty-sixth embodiment, in which 1 to 10 equivalents of an alkenyl group of the alkenyl compound of Formula M1 react with 1 equivalent of a hydroxyl group of the starting material during the first step, may be provided.

According to the forty-eighth embodiment of the present invention, the method of preparing an epoxy compound having an alkoxysilyl group of the forty-sixth embodiment, in which the first step is performed at a temperature from room temperature to 100° C. for 1 to 120 hours, may be provided.

According to the forty-ninth embodiment of the present invention, the method of preparing an epoxy compound having an alkoxysilyl group of the forty-sixth embodiment, in which 1 to 10 equivalents of a peroxide group of the peroxide react with 1 equivalent of the alkenyl group of the above Intermediate Product (21) during the second step, may be provided.

According to the fiftieth embodiment of the present invention, the method of preparing an epoxy compound having an alkoxysilyl group of the forty-sixth embodiment, in which the second step is performed at a temperature from room temperature to 100° C. for 1 to 120 hours, may be provided.

According to the fifty-first embodiment of the present invention, the method of preparing an epoxy compound having an alkoxysilyl group of the forty-sixth embodiment, in which 1 to 10 equivalents of the alkenyl compound of Formula M1 react with 1 equivalent of a hydroxyl group of the above Intermediate Product (22) during the third step, may be provided.

According to the fifty-second embodiment of the present invention, the method of preparing an epoxy compound having an alkoxysilyl group of the forty-sixth embodiment, in which the third step is performed at a temperature from room temperature to 100° C. for 1 to 120 hours, may be provided.

According to the fifty-third embodiment of the present invention, the method of preparing an epoxy compound having an alkoxysilyl group of the forty-sixth embodiment, in which 1 to 5 equivalents of alkoxysilane of Formula M2 react with 1 equivalent of the alkenyl group of the above Intermediate Product (23) during the fourth step, may be provided.

According to the fifty-fourth embodiment of the present invention, the method of preparing an epoxy compound having an alkoxysilyl group of the forty-sixth embodiment, in which, the fourth step is performed at a temperature from room temperature to 100° C. for 1 to 72 hours, may be provided.

According to the fifty-fifth embodiment of the present invention, there is provided a method of preparing an epoxy compound having an alkoxysilyl group including a first step of preparing one Intermediate Product (31) of following Formulae A31 to H31 by reacting one starting material of following Formulae AS to HS with an alkenyl compound of following Formula M1 in the presence of a base and an optional solvent, a second step of preparing one Intermediate Product (32) of following Formulae A32 to H32 by reacting the above Intermediate Product (31) with a peroxide in the presence of an optional base and an optional solvent, and a third step of preparing one target product following Formulae AI to HI by reacting the above Intermediate Product (32) with alkoxysilane of following Formula M2 in the presence of a metal catalyst and an optional solvent.

[Starting Material]

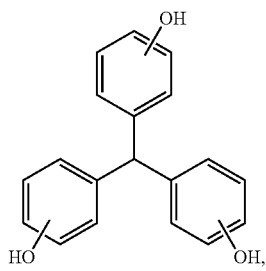
AS

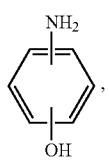
BS

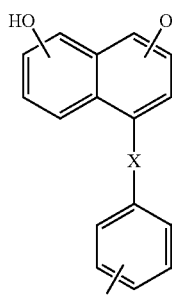
CS

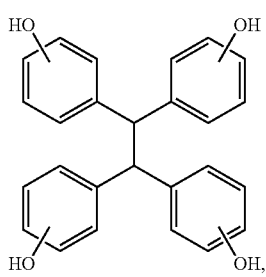
DS

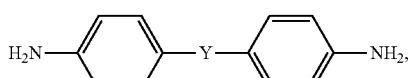
ES

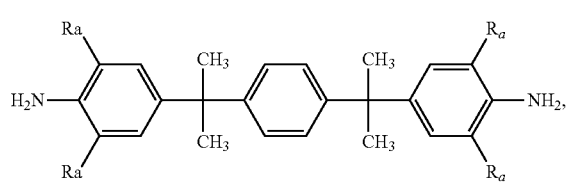
FS

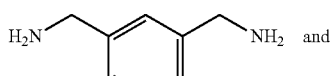
GS and

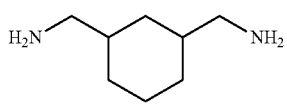
HS

A meta position of oxygen in Formula BS above may be substituted with a linear or branched C1-C10 alkyl group.

X in Formula CS is a direct linkage, —CH$_2$— or

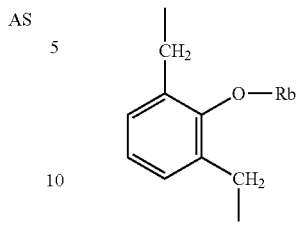

where Rb is H or a C1-C3 alkyl group.

Y in Formula ES is —CH$_2$—, —C(CH$_3$)$_2$—, —C(CF$_3$)$_2$—, —S— or —SO$_2$—.

Ra in Formula FS is H or a C1-C3 alkyl group.

$$X-(CH_2)_{z-2}-CH=CH_2 \quad \text{[Formula M1]}$$

In Formula M1, X is a halide of Cl, Br or I, —O—SO$_2$—CH$_3$, —O—SO$_2$—CF$_3$, or —O—SO$_2$—C$_6$H$_4$—CH$_3$, and z is an integer from 3 to 10.

[Intermediate Product (31)]

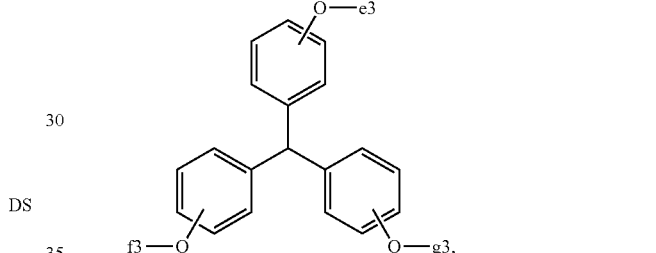
A31

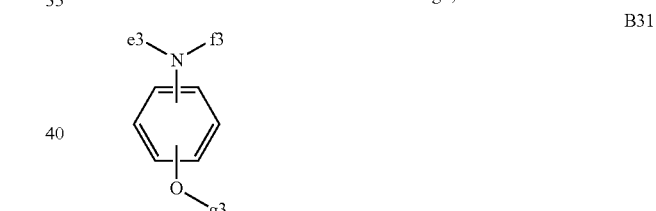
B31

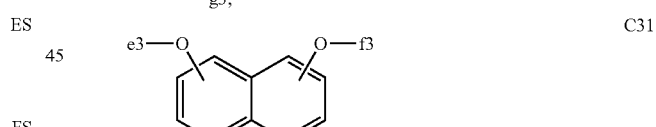
C31

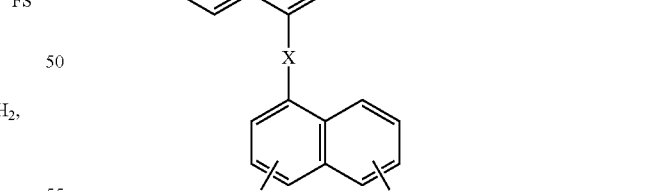

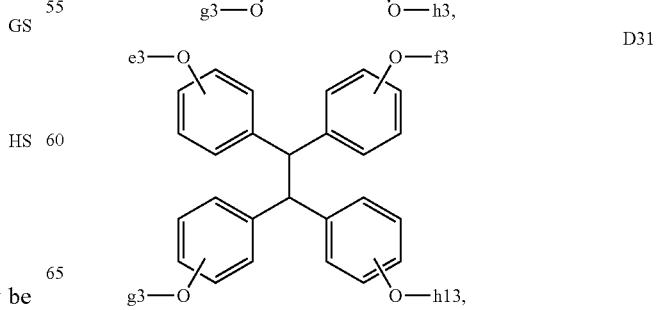
D31

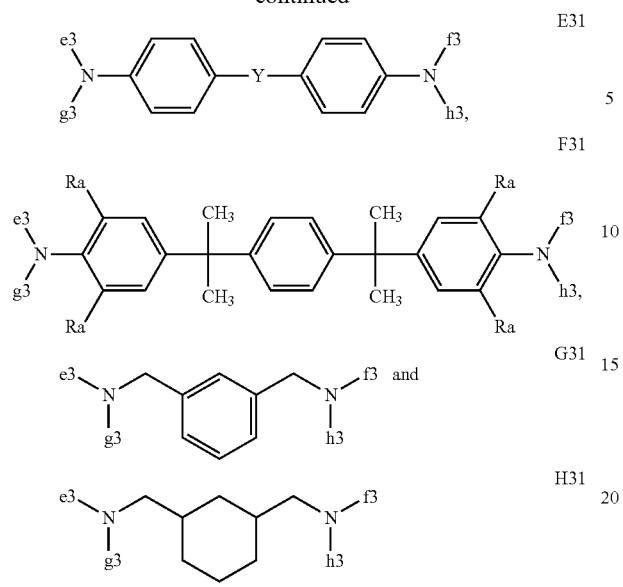

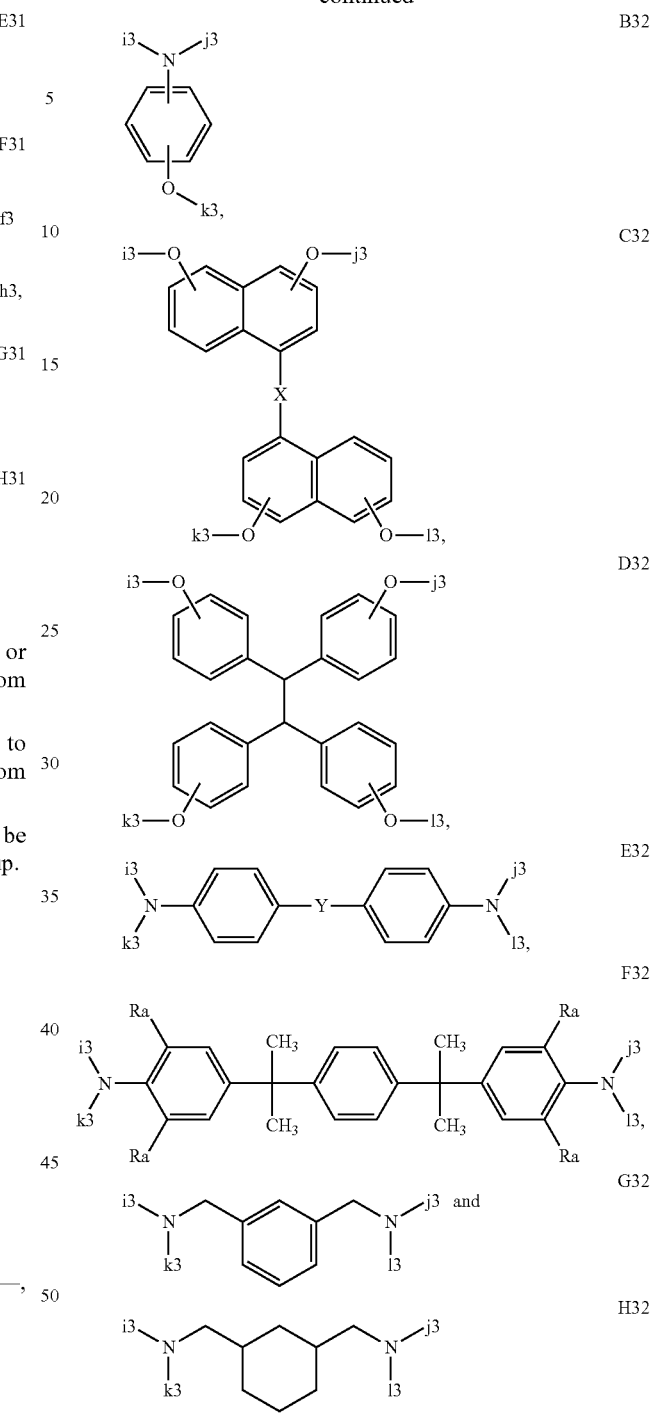

One or two of substituents e3 to g3 in Formula A31 or B31 are —(CH$_2$)$_{z-2}$—CH=CH$_2$ where z is an integer from 3 to 10, and the remainder thereof may be hydrogen.

One to three of substituents e3 to h3 in Formulae C31 to H31 are —(CH$_2$)$_{z-2}$—CH=CH$_2$ where z is an integer from 3 to 10, and the remainder thereof may be hydrogen.

A meta position of oxygen in Formula B31 above may be substituted with a linear or branched C1-C10 alkyl group.

X in Formula C31 is a direct linkage, —CH$_2$— or

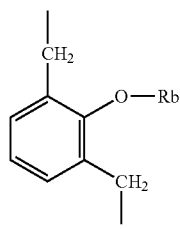

where Rb is H or a C1-C3 alkyl group.

Y in Formula E31 is —CH$_2$—, —C(CH$_3$)$_2$—, —C(CF$_3$)$_2$—, —S— or —SO$_2$—.

Ra in Formula F31 is H or a C1-C3 alkyl group.

[Intermediate Product (32)]

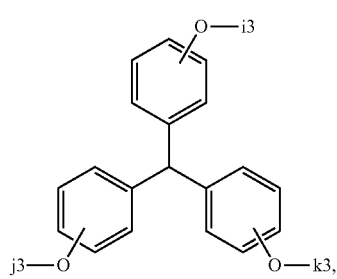

One or two of substituents i3 to k3 in Formulae A32 to B32 have the form of Formula S1, and at least one thereof is —(CH$_2$)$_{z-2}$—CH=CH$_2$ where z is an integer from 3 to 10 and may be hydrogen when an unreacted site is present.

One to three of substituents i3 to l3 in Formulae C32 to H32 have the form of Formula S1, and at least one thereof is —(CH$_2$)$_{z-2}$—CH=CH$_2$ where z is an integer from 3 to 10 and may be hydrogen when an unreacted site is present.

A meta position of oxygen in Formula B32 above may be substituted with a linear or branched C1-C10 alkyl group.

X in Formula C32 is a direct linkage, —CH$_2$— or

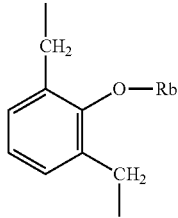

where Rb is H or a C1-C3 alkyl group.

Y in Formula E32 is —CH$_2$—, —C(CH$_3$)$_2$—, —C(CF$_3$)$_2$—, —S— or —SO$_2$—.

Ra in Formula F32 is H or a C1-C3 alkyl group.

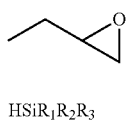

[Formula S1]

HSiR$_1$R$_2$R$_3$ [Formula M2]

In Formula M2, at least one of R$_1$ to R$_3$ is a C1-C10 alkoxy group, the remainder thereof are C1-C10 alkyl groups, and the alkoxy group and the alkyl group are a linear chain or a branched chain alkoxy group or alkyl group.

[Target Product]

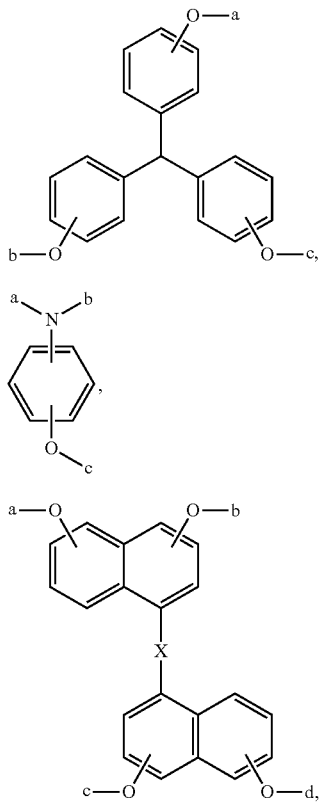

AI

BI

CI

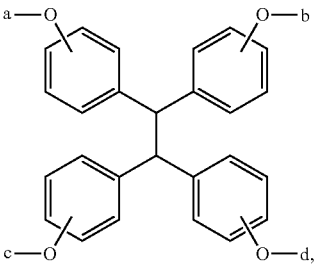

DI

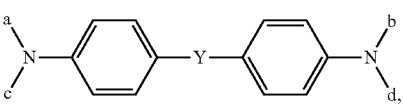

EI

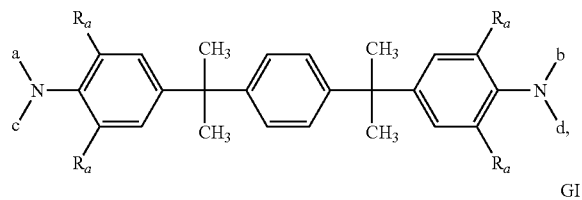

FI

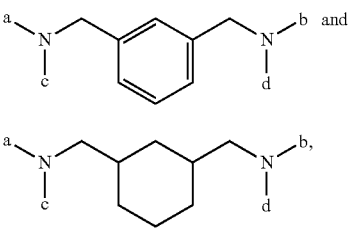

GI and

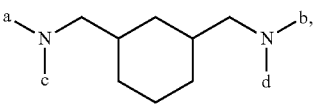

HI

One or two of substituents a to c in Formula AI or BI are the above Formula S1, one or two thereof have the form of Formula S1, and the remainder thereof may be hydrogen or —(CH$_2$)$_{z-2}$CH=CH$_2$ where z is an integer from 3 to 10.

One to three of substituents a to d in Formulae CI to HI are the above Formula S1, one to three thereof have the form of Formula S2, and the remainder thereof may be hydrogen or —(CH$_2$)$_{z-2}$CH=CH$_2$ where z is an integer from 3 to 10.

A meta position of oxygen in Formula BI may be substituted with a linear or branched C1-C10 alkyl group.

X in Formula CI is a direct linkage, —CH$_2$— or

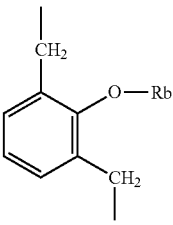

where Rb is H or a C1-C3 alkyl group.

Y in Formula EI is —CH$_2$—, —C(CH$_3$)$_2$—, —C(CF$_3$)$_2$—, —S— or —SO$_2$—.

Ra in Formula FI is H or a C1-C3 alkyl group.

—(CH$_2$)$_z$—SiR$_1$R$_2$R$_3$ [Formula S2]

In Formulae S2, at least one of R$_1$ to R$_3$ is an alkoxy group having 1 to 10 carbon atoms, the remainder thereof are alkyl groups having 1 to 10 carbon atoms, the alkyl group and the alkoxy group are a side chain or a branched chain alkyl group or alkoxy group, and z is an integer from 3 to 10.

According to the fifty-sixth embodiment of the present invention, the method of preparing an epoxy compound having an alkoxysilyl group of the fifty-fifth embodiment, in which, 1 to 10 equivalents of the an alkenyl group of the alkenyl compound of Formula M1 react with 1 equivalent of a hydroxyl group of the starting material during the first step, may be provided.

According to the fifty-seventh embodiment of the present invention, the method of preparing an epoxy compound having an alkoxysilyl group of the fifty-fifth embodiment, in which, the first step is performed at the temperature from room temperature to 100° C. for 1 to 120 hours, may be provided.

According to the fifty-eighth embodiment of the present invention, the method of preparing an epoxy compound having an alkoxysilyl group of the fifty-fifth embodiment, in which, 1 to 5 equivalents of a peroxide group of the peroxide react with 1 equivalent of the alkenyl group of the above Intermediate Product (31) during the second step, may be provided.

According to the fifty-ninth embodiment of the present invention, the method of preparing an epoxy compound having an alkoxysilyl group of the fifty-fifth embodiment, in which, the second step is performed at a temperature from room temperature to 100° C. for 1 to 120 hours, may be provided.

According to the sixtieth embodiment of the present invention, the method of preparing an epoxy compound having an alkoxysilyl group of the fifty-fifth embodiment, in which, 1 to 5 equivalents of alkoxysilane of Formula M2 react with 1 equivalent of the alkenyl group of the above Intermediate Product (32) during the third step, may be provided.

According to the sixty-first embodiment of the present invention, the method of preparing an epoxy compound having an alkoxysilyl group of the fifty-fifth embodiment, in which, the third step is performed at a temperature from room temperature to 120° C. for 1 to 72 hours, may be provided.

According to the sixty-second embodiment of the present invention, there is provided a method of preparing an epoxy compound having an alkoxysilyl group including a first step of preparing one Intermediate Product (41) of following Formulae A41 to H41 by reacting one starting material of following Formulae AS to HS with epichlorohydrin in the presence of a base and an optional solvent, a second step of preparing one Intermediate Product (42) of following Formulae A42 to H42 by reacting the above Intermediate Product (41) with an alkenyl compound of following Formula M1 in the presence of a base and an optional solvent, and a third step of preparing one target product of following Formulae AI to HI by reacting the above Intermediate Product (42) with alkoxysilane of following Formula M2 in the presence of a metal catalyst and an optional solvent.

[Starting Material]

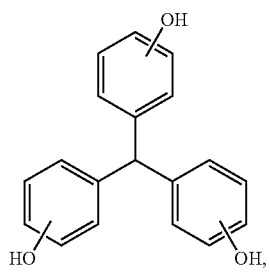
AS

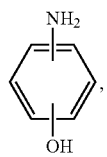
BS

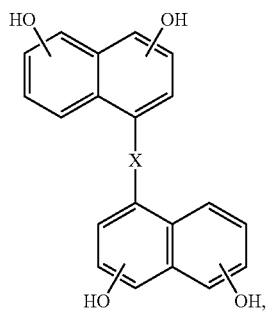
CS

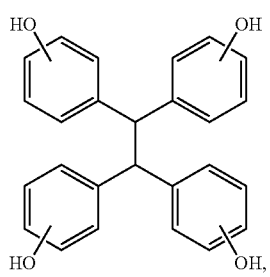
DS

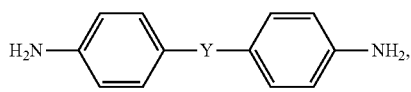
ES

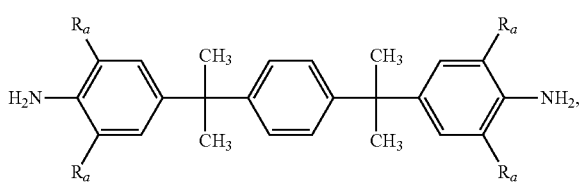
FS

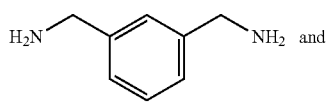
GS

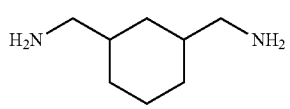
HS

A meta position of oxygen in Formula BS above may be substituted with a linear or branched C1-C10 alkyl group.

X in Formula CS is a direct linkage, —CH$_2$— or

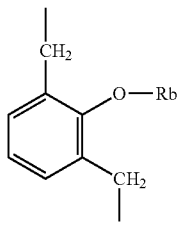

where Rb is H or a C1-C3 alkyl group.

Y in Formula ES is —CH$_2$—, —C(CH$_3$)$_2$—, —C(CF$_3$)$_2$—, —S— or —SO$_2$—.

Ra in Formula FS is H or a C1-C3 alkyl group.

[Intermediate Product (41)]

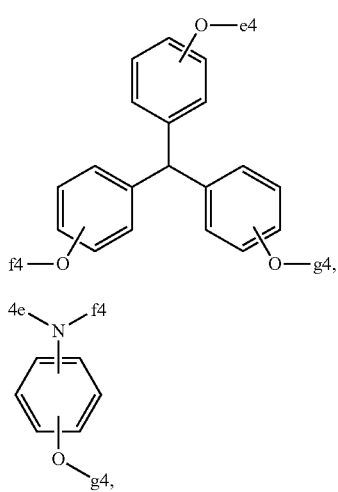

A41

B41

C41

D41

E41

-continued

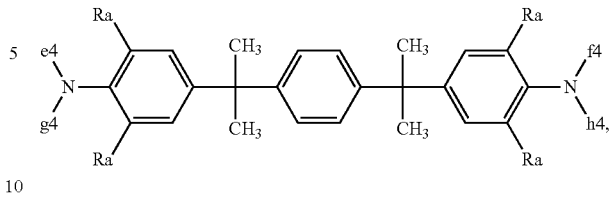

F41

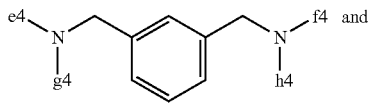

G41 and

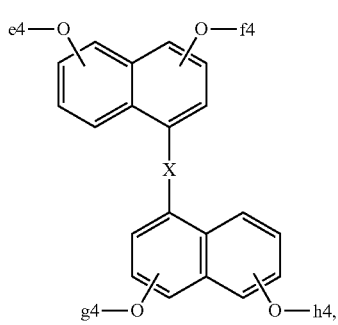

H41

One or two of substituents e4 to g4 in Formulae A41 to B41 have the form of Formula S1, and the remainder thereof are hydrogen.

One to three of substituents e4 to h4 in Formulae C41 to H41 have the form of Formula S1, and the remainder thereof are hydrogen.

A meta position of oxygen in Formula B41 above may be substituted with a linear or branched C1-C10 alkyl group.

X in Formula C41 is a direct linkage, —CH$_2$— or

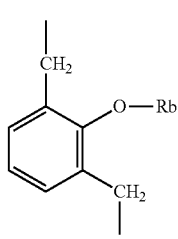

where Rb is H or a C1-C3 alkyl group.

Y in Formula E41 is —CH$_2$—, —C(CH$_3$)$_2$—, —C(CF$_3$)$_2$—, —S— or —SO$_2$—.

Ra in Formula F41 is H or a C1-C3 alkyl group.

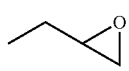

[Formula S1]

[Formula M1]

In Formula M1, X is a halide of Cl, Br or I, —O—SO$_2$—CH$_3$, —O—SO$_2$—CF$_3$, or —O—SO$_2$—C$_6$H$_4$—CH$_3$, and z is an integer from 3 to 10.

[Intermediate Product (42)]

A42 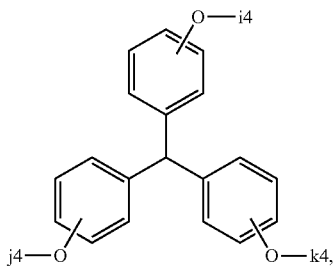

B42 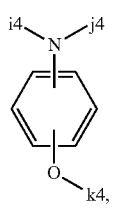

C42 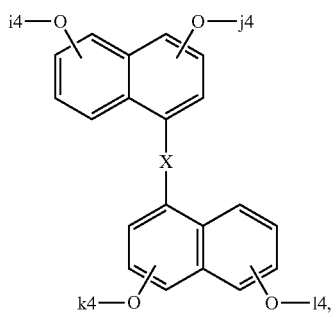

D42 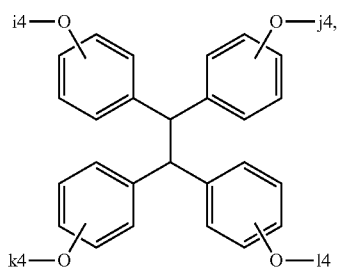

E42 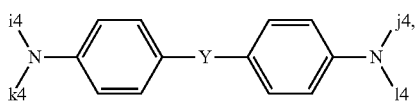

F42 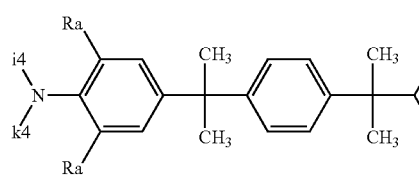

G42 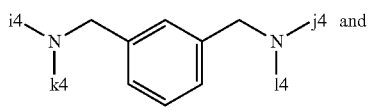

H42 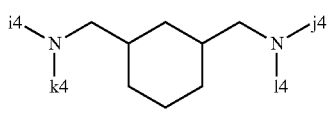

One or two of substituents i4 to k4 in Formula A42 or B42 are the above Formula S1, and at least one thereof is $-(CH_2)_{z-2}-CH=CH_2$ where z is an integer from 3 to 10 and may be hydrogen when an unreacted site is present.

One to three of substituents i4 to l4 in Formulae C42 to H42 are the above Formula S1, and at least one thereof is $-(CH_2)_{z-2}-CH=CH_2$ where z is an integer from 3 to 10 and may be hydrogen when an unreacted site is present.

A meta position of oxygen in Formula B42 above may be substituted with a linear or branched C1-C10 alkyl group, and X in Formula C42 is a direct linkage, $-CH_2-$ or

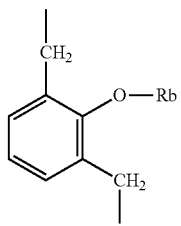

where Rb is H or a C1-C3 alkyl group.

Y in Formula E42 is $-CH_2-$, $-C(CH_3)_2-$, $-C(CF_3)_2-$, $-S-$ or $-SO_2-$.

Ra in Formula F42 is H or a C1-C3 alkyl group.

$$HSiR_1R_2R_3 \quad \text{[Formula M2]}$$

In Formula M2, at least one of $R_1$ to $R_3$ is a C1-C10 alkoxy group, the remainder thereof are linear or branched C1-C10 alkyl groups, and the alkoxy group and the alkyl group are a linear chain or a branched chain alkoxy group or alkyl group.

[Target Product]

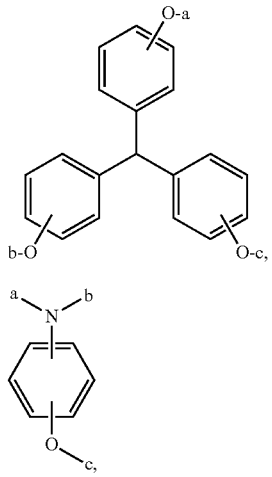

AI

BI

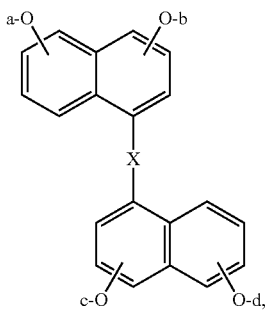

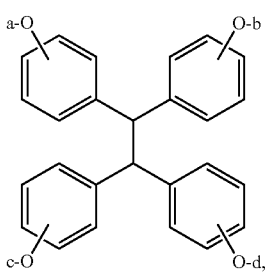

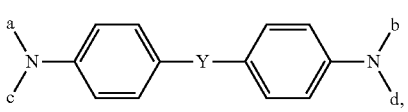

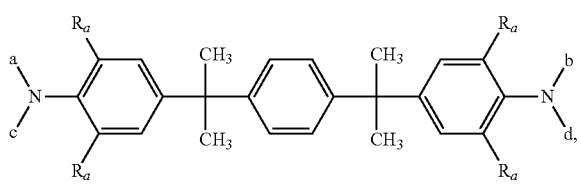

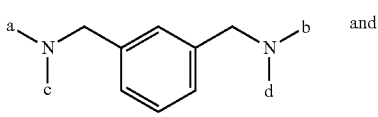

and

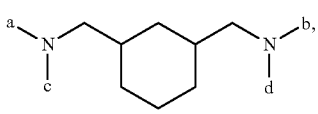

One or two of substituents a to c in Formula AI or BI are the above Formula S, one or two thereof have the form of Formula S2, and the remainder thereof may be hydrogen or —(CH$_2$)$_{z-2}$ CH=CH$_2$ where z is an integer from 3 to 10.

One to three of substituents a to d in Formulae CI to HI are the above Formula S1, one to three thereof have the form of Formula S2, and the remainder thereof may be hydrogen or —(CH$_2$)$_{z-2}$CH=CH$_2$ where z is an integer from 3 to 10.

A meta position of oxygen in Formula BI may be substituted with a linear or branched C1-C10 alkyl group.

X in Formula CI is a direct linkage, —CH$_2$— or

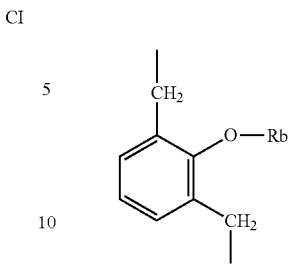

where Rb is H or a C1-C3 alkyl group.

Y in Formula EI is —CH$_2$—, —C(CH$_3$)$_2$—, —C(CF$_3$)$_2$—, —S— or —SO$_2$—.

Ra in Formula FI is H or a C1-C3 alkyl group.

—(CH$_2$)$_z$—SiR$_1$R$_2$R$_3$     [Formula S2]

In Formula S2, at least one of R$_1$ to R$_3$ is an alkoxy group having 1 to 10 carbon atoms, the remainder thereof are alkyl groups having 1 to 10 carbon atoms, the alkoxy group and the alkyl group are a side chain or a branched chain alkoxy group or alkyl group, and z is an integer from 3 to 10.

According to the sixty-third embodiment of the present invention, the method of preparing an epoxy compound having an alkoxysilyl group of the sixty-second embodiment, in which, 1 to 10 equivalents of a glycidyl group of the epichlorohydrin react with 1 equivalent of a hydroxyl group of the starting material during the first step, may be provided.

According to the sixty-fourth embodiment of the present invention, the method of preparing an epoxy compound having an alkoxysilyl group of the sixty-second embodiment, in which, the first step is performed at a temperature from room temperature to 100° C. for 1 to 120 hours, may be provided.

According to the sixty-fifth embodiment of the present invention, the method of preparing an epoxy compound having an alkoxysilyl group of the sixty-second embodiment, in which, 1 to 10 equivalents of an alkenyl group of the alkenyl group of Formula M1 react with 1 equivalent of a hydroxyl group of the above Intermediate Product (41) during the second step, may be provided.

According to the sixty-sixth embodiment of the present invention, the method of preparing an epoxy compound having an alkoxysilyl group of the sixty-second embodiment, in which, the second step is performed at a temperature from room temperature to 100° C. for 1 to 120 hours, may be provided.

According to the sixty-seventh embodiment of the present invention, the method of preparing an epoxy compound having an alkoxysilyl group of the sixty-second embodiment, in which, 1 to 5 equivalents of alkoxysilane of Formula M2 react with 1 equivalent of the alkenyl group of the above Intermediate Product (42) during the third step, may be provided.

According to the sixty-eighth embodiment of the present invention, the method of preparing an epoxy compound having an alkoxysilyl group of the sixty-second embodiment, in which, the third step is performed at a temperature from room temperature to 120° C. for 1 to 72 hours, may be provided.

According to the sixty-ninth embodiment of the present invention, there is provided a method of preparing an epoxy compound having an alkoxysilyl group including a first step of preparing one Intermediate Product (51) of following Formulae A51 to H51 by reacting one starting material of following Formulae AS to HS with an alkenyl compound of Formula M1 in the presence of a base and an optional solvent, a second step of preparing one Intermediate Product (52) of following Formulae A52 to H52 by reacting the above Intermediate Product (51) with the peroxide in the presence of a base and an optional solvent, and a third step of preparing one target product of following Formulae AI to HI by reacting the above Intermediate Product (52) with isocyanate-based alkoxysilane of following Formula M3 in the presence of an optional base and an optional solvent.

[Starting Material]

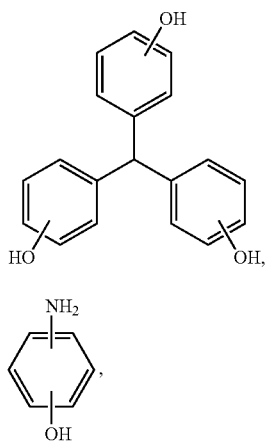

AS

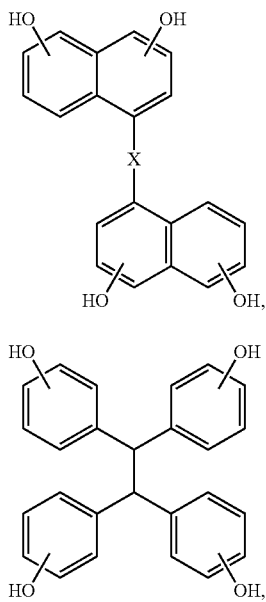

BS

CS

DS

ES

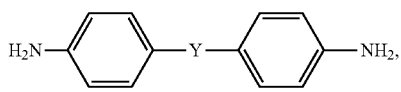

FS

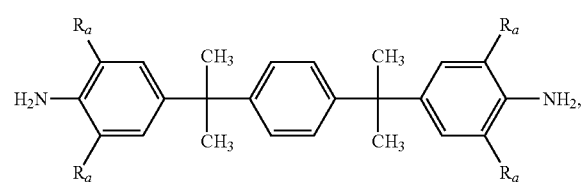

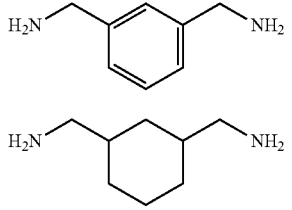

GS
and
HS

A meta position of oxygen in Formula BS above may be substituted with a linear or branched C1-C10 alkyl group.

X in Formula CS is a direct linkage, —$CH_2$— or

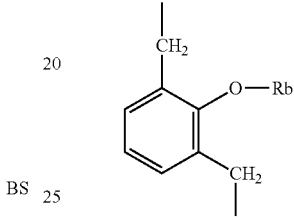

where Rb is H or a C1-C3 alkyl group.

Y in Formula ES is —$CH_2$—, —$C(CH_3)_2$—, —$C(CF_3)_2$—, —S— or —$SO_2$—.

Ra in Formula FS is H or a C1-C3 alkyl group.

[Intermediate Product (51)]

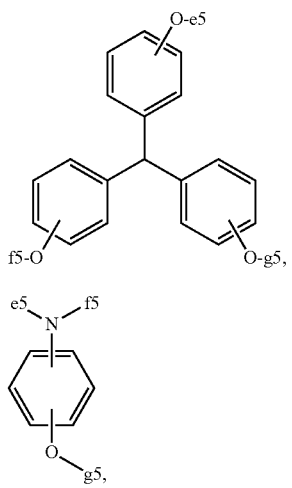

A51

B51

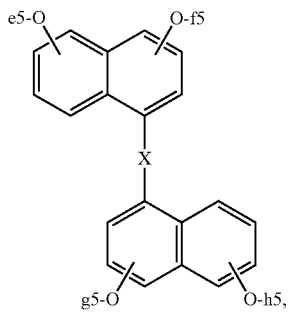

C51

-continued

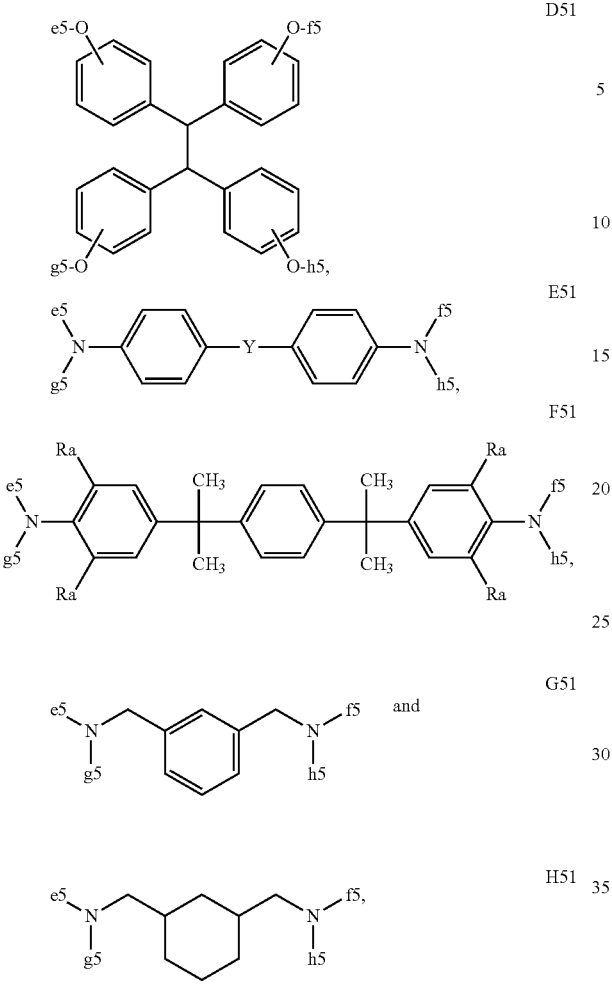

One or two of substituents e5 to g5 in Formula A51 or B51 are —(CH$_2$)$_{z-2}$—CH=CH$_2$ where z is an integer from 3 to 10, and the remainder thereof are hydrogen.

One to three of substituents e5 to h5 in Formulae C51 to H51 are —(CH$_2$)$_{z-2}$—CH=CH$_2$ where z is an integer from 3 to 10, and the remainder thereof are hydrogen.

A meta position of oxygen in Formula B51 above may be substituted with a linear or branched C1-C10 alkyl group.

X in Formula C51 is a direct linkage, —CH$_2$— or

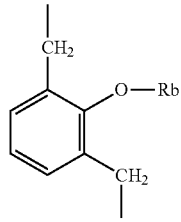

where Rb is H or a C1-C3 alkyl group.

Y in Formula E51 is —CH$_2$—, —C(CH$_3$)$_2$—, —C(CF$_3$)$_2$—, —S— or —SO$_2$—.

Ra in Formula F51 is H or a C1-C3 alkyl group.

[Intermediate Product (52)]

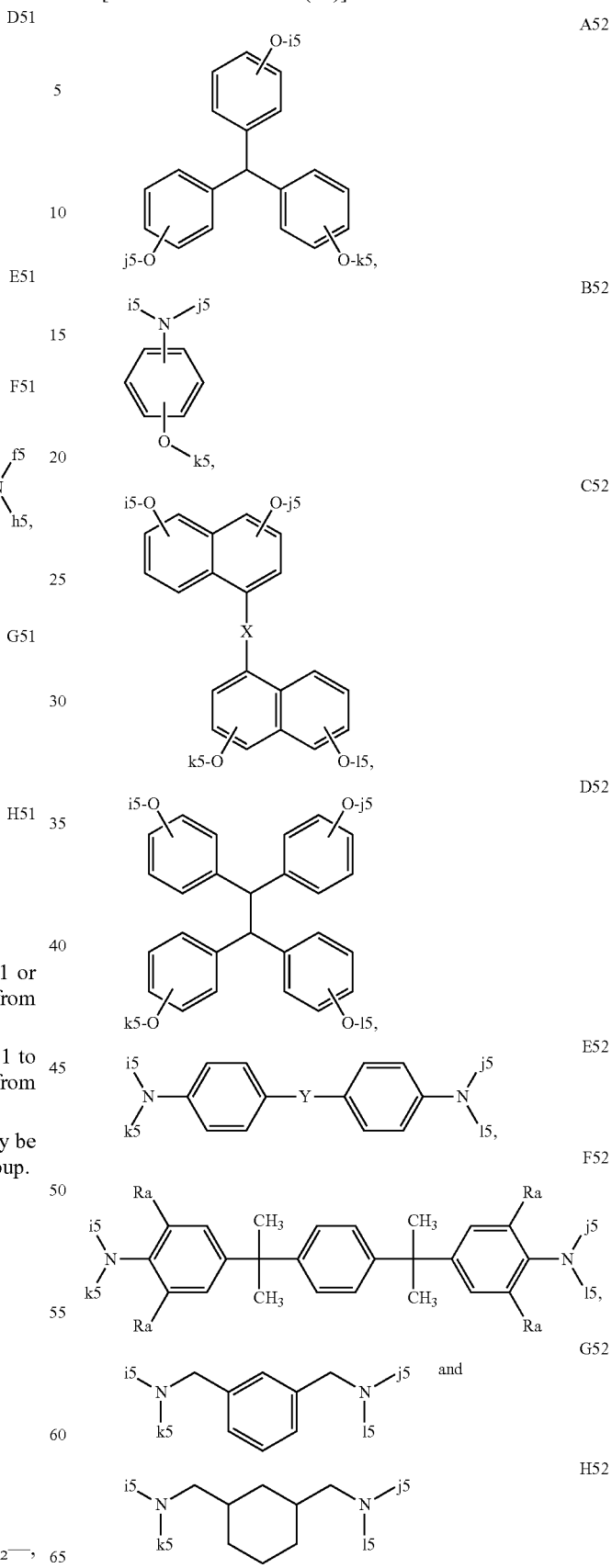

One or two of substituents i5 to k5 in Formulae A52 to B52 have the form of Formula S1, and at least one thereof is hydrogen and may be —(CH$_2$)$_{z-2}$—CH=CH$_2$ where z is an integer from 3 to 10 when an unreacted site is present.

One to three of substituents i5 to 15 in Formulae C52 to H52 have the form of Formula S1, and at least one thereof is hydrogen and may be —(CH$_2$)$_{z-2}$—CH=CH$_2$ where z is an integer from 3 to 10 when an unreacted site is present.

A meta position of oxygen in Formula B52 above may be substituted with a linear or branched C1-C10 alkyl group.

X in Formula C52 is a direct linkage, —CH$_2$— or

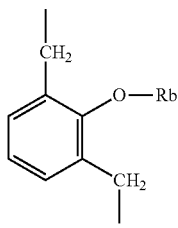

where Rb is H or a C1-C3 alkyl group.

Y in Formula E52 is —CH$_2$—, —C(CH$_3$)$_2$—, —C(CF$_3$)$_2$—, —S— or —SO$_2$—.

Ra in Formula F52 is H or a C1-C3 alkyl group.

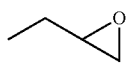 [Formula S1]

OCN—(CH$_2$)$_2$—SiR$_1$R$_2$R$_3$ [Formula M3]

In Formula M3, at least one of R$_1$ to R$_3$ is a C1-C10 alkoxy group, the remainder thereof are linear or branched C1-C10 alkyl groups, the alkoxy group and the alkyl group are a linear chain or a branched chain alkoxy group or alkyl group, and z is an integer from 3 to 100.

[Target Product]

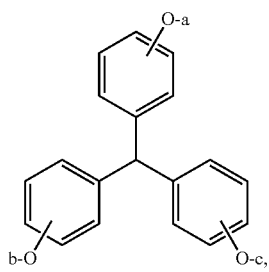 AI

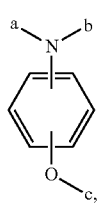 BI

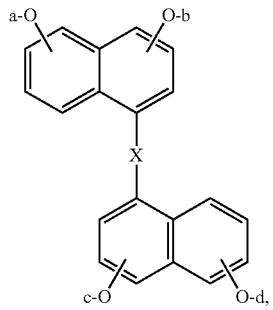 CI

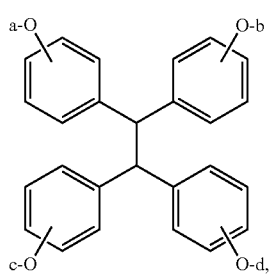 DI

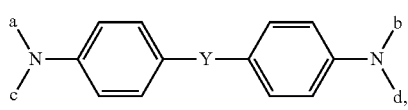 EI

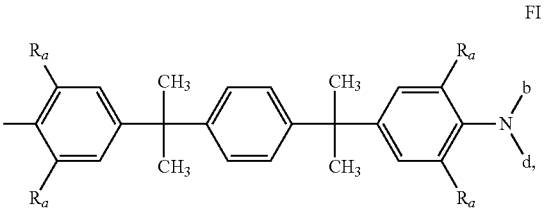 FI

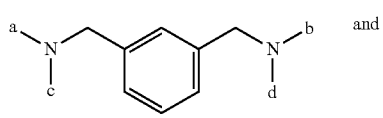 GI and

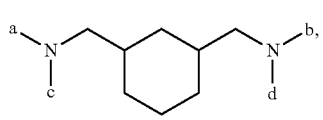 HI

One or two of substituents a to c in Formula AI or BI are the above Formula S1, one or two thereof are Formula S2 or S3, and the remainder thereof may be hydrogen or —(CH$_2$)$_{z-2}$CH=CH$_2$ where z is an integer from 3 to 10.

One to three of substituents a to d in Formulae CI to HI are the above Formula S1, one to three thereof have the form of Formula S3, and the remainder thereof may be hydrogen or —(CH$_2$)$_{z-2}$CH=CH$_2$ where z is an integer from 3 to 10.

A meta position of oxygen in Formula BI may be substituted with a linear or branched C1-C10 alkyl group.

X in Formula CI is a direct linkage, —CH$_2$— or

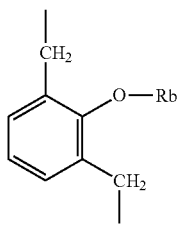

where Rb is H or a C1-C3 alkyl group.

Y in Formula EI is —CH$_2$—, —C(CH$_3$)$_2$—, —C(CF$_3$)$_2$—, —S— or —SO$_2$—.

Ra in Formula FI is H or a C1-C3 alkyl group.

—CONH(CH$_2$)$_z$—SiR$_1$R$_2$R$_3$     [Formula S3]

In Formula S3, at least one of R$_1$ to R$_3$ is an alkoxy group having 1 to 10 carbon atoms, the remainder thereof are alkyl groups having 1 to 10 carbon atoms, the alkoxy group and the alkyl group are a linear chain or a branched chain alkoxy group or alkyl group, and z is an integer from 3 to 10.

According to the seventieth embodiment of the present invention, the method of preparing an epoxy compound having an alkoxysilyl group of the sixty-ninth embodiment, in which, 1 to 10 equivalents of an alkenyl group of the alkenyl compound of Formula M1 react with 1 equivalent of a hydroxyl group of the starting material during the first step, may be provided.

According to the seventy-first embodiment of the present invention, the method of preparing an epoxy compound having an alkoxysilyl group of the sixty-ninth embodiment, in which, the first step is performed at a temperature from room temperature to 100° C. for 1 to 120 hours, may be provided.

According to the seventy-second embodiment of the present invention, the method of preparing an epoxy compound having an alkoxysilyl group of the sixty-ninth embodiment, in which, 1 to 10 equivalents of a peroxide group of the peroxide react with 1 equivalent of the alkenyl group of the above Intermediate Product (51) during the second step, may be provided.

According to the seventy-third embodiment of the present invention, the method of preparing an epoxy compound having an alkoxysilyl group of the sixty-ninth embodiment, in which, the second step is performed at a temperature from room temperature to 100° C. for 1 to 120 hours, may be provided.

According to the seventy-fourth embodiment of the present invention, the method of preparing an epoxy compound having an alkoxysilyl group of the sixty-ninth embodiment, in which, 1 to 5 equivalents of isocyanate-based alkoxysilane of Formula M3 react with 1 equivalent of a hydroxyl group of the above Intermediate Product (52) during the third step, may be provided.

According to the seventy-fifth embodiment of the present invention, the method of preparing an epoxy compound having an alkoxysilyl group of the sixty-ninth embodiment, in which, the third step is performed at a temperature from room temperature to 120° C. for 1 to 72 hours, may be provided.

According to the seventy-sixth embodiment of the present invention, there is provided a method of preparing an epoxy compound having an alkoxysilyl group including a first step of preparing one Intermediate Product (61) of following Formulae A61 to H61 by reacting one starting material of following Formulae AS to HS with epichlorohydrin in the presence of a base and an optional solvent, and a second step of preparing one target product of following Formulae AI to HI by reacting the above Intermediate Product (61) with isocyanate-based alkoxysilane of following Formula M3 in the presence of an optional base and an optional solvent.

[Starting Material]

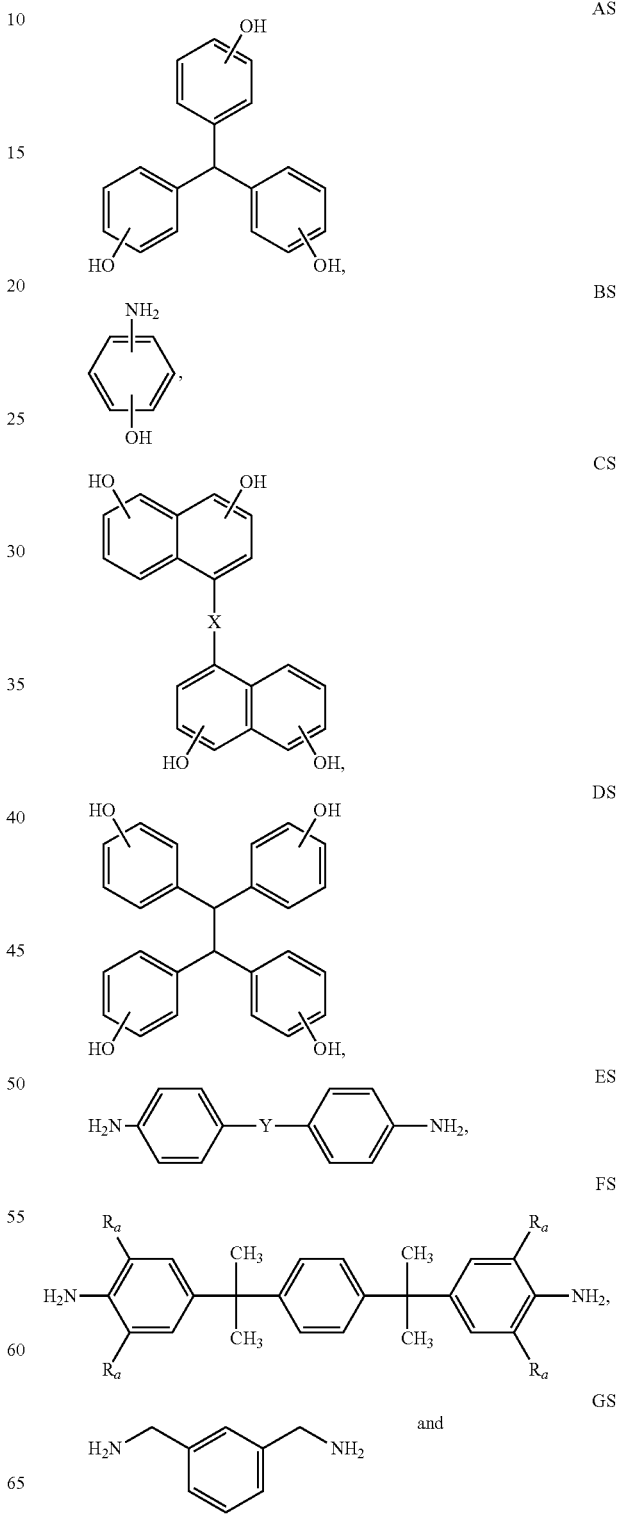

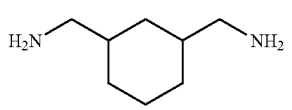

A meta position of oxygen in Formula BS above may be substituted with a linear or branched C1-C10 alkyl group.

X in Formula CS is a direct linkage, —CH₂— or

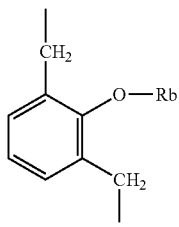

where Rb is H or a C1-C3 alkyl group.

Y in Formula ES is —CH₂—, —C(CH₃)₂—, —C(CF₃)₂—, —S— or —SO₂—.

Ra in Formula FS is H or a C1-C3 alkyl group.

X—(CH₂)$_{z-2}$—CH=CH₂  [Formula M1]

In Formula M1, X is a halide of Cl, Br or I, —O—SO₂—CH₃, —O—SO₂—CF₃, or —O—SO₂—C₆H₄—CH₃, and z is an integer from 3 to 10.

[Intermediate Product (61)]

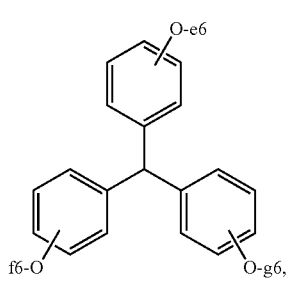

A61

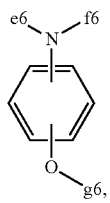

B61

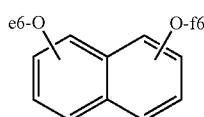

C61

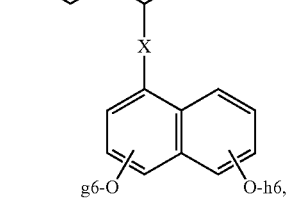

HS

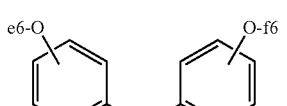

D61

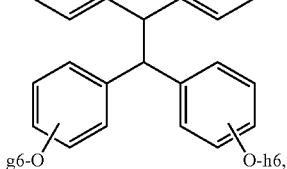

E61

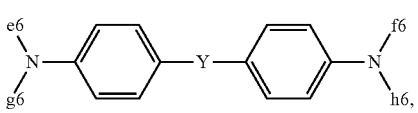

F61

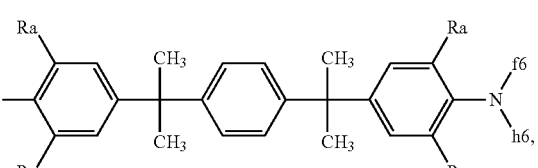

G61

 and

H61

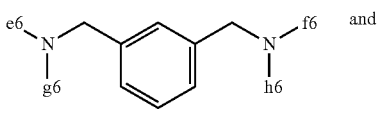

One or two of substituents e6 to g6 in Formula A61 or B61 have the form of Formula S1, and the remainder thereof are hydrogen.

One to three of substituents e6 to h6 in Formulae C61 to H61 have the form of Formula S1, and the remainder thereof are hydrogen.

A meta position of oxygen in Formula B61 above may be substituted with a linear or branched C1-C10 alkyl group.

X in Formula C61 is a direct linkage, —CH₂— or

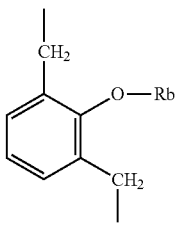

where Rb is H or a C1-C3 alkyl group.

Y in Formula E61 is —CH₂—, —C(CH₃)₂—, —C(CF₃)₂—, —S— or —SO₂—.

Ra in Formula F61 is H or a C1-C3 alkyl group.

[Formula S1]

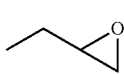

-continued

OCN—(CH$_2$)$_z$—SiR$_1$R$_2$R$_3$ [Formula M3]

In Formula M3, at least one of R$_1$ to R$_3$ is a C1-C10 alkoxy group, the remainder thereof are linear or branched C1-C10 alkyl groups, the alkoxy group and the alkyl group are a linear chain or a branched chain alkoxy group or alkyl group, and z is an integer from 3 to 10.

[Target Product]

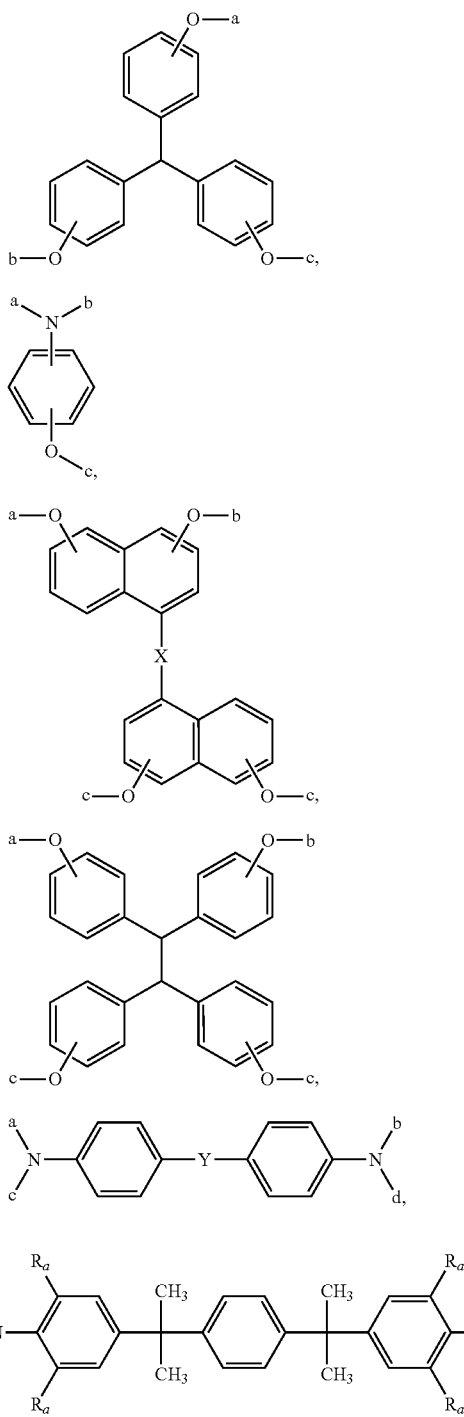

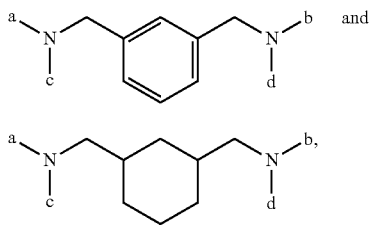

One or two of substituents a to c in Formula AI or BI are the above Formula S1, one or two thereof have the form of Formula S3, and the remainder thereof may be hydrogen or —(CH$_2$)$_{z-2}$CH=CH$_2$ where z is an integer from 3 to 10.

One to three of substituents a to d in Formulae CI to HI are the above Formula S1, one to three thereof have the form of Formula S3, and the remainder thereof may be hydrogen or —(CH$_2$)$_{z-2}$CH=CH$_2$ where z is an integer from 3 to 10.

A meta position of oxygen in Formula BI may be substituted with a linear or branched C1-C10 alkyl group.

X in Formula CI is a direct linkage, —CH$_2$— or

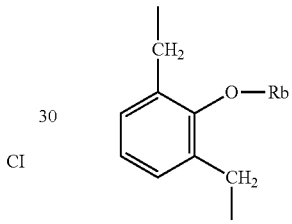

where Rb is H or a C1-C3 alkyl group.

Y in Formula EI is —CH$_2$—, —C(CH$_3$)$_2$—, —C(CF$_3$)$_2$—, —S— or —SO$_2$—.

Ra in Formula FI is H or a C1-C3 alkyl group.

—CONH(CH$_2$)$_z$—SiR$_1$R$_2$R$_3$ [Formula S3]

In Formula S3, at least one of R$_1$ to R$_3$ is an alkoxy group having 1 to 10 carbon atoms, the remainder thereof are alkyl groups having 1 to 10 carbon atoms, the alkoxy group and the alkyl group are a linear chain or a branched chain alkoxy group or alkyl group, and z is an integer from 3 to 10.

According to the seventy-seventh embodiment of the present invention, the method of preparing an epoxy compound having an alkoxysilyl group of the seventy-sixth embodiment, in which, 1 to 10 equivalents of a glycidyl group of the epichlorohydrin react with 1 equivalent of a hydroxyl group of the starting material during the first step, may be provided.

According to the seventy-eighth embodiment of the present invention, the method of preparing an epoxy compound having an alkoxysilyl group of the seventy-sixth embodiment, in which, the first step is performed at a temperature from room temperature to 100° C. for 1 to 120 hours, may be provided.

According to the seventy-ninth embodiment of the present invention, the method of preparing an epoxy compound having an alkoxysilyl group of the seventy-sixth embodiment, in which, 1 to 5 equivalents of isocyanate-based alkoxysilane of Formula M3 react with 1 equivalent of a hydroxyl group of the above Intermediate Product (61) during the second step, may be provided.

According to the eightieth embodiment of the present invention, the method of preparing an epoxy compound having an alkoxysilyl group of the seventy-sixth embodiment, in which, the second step is performed at a temperature from room temperature to 120° C. for 1 to 72 hours, may be provided.

Advantageous Effects

Chemical bonding may be formed through the chemical reaction between an alkoxysilyl group and a filler (fiber and/or particles) and the chemical reaction between alkoxysilyl groups in the composite and/or the cured product of a novel epoxy composition including an epoxy compound having an alkoxysilyl group according to the present invention. Due to the formation of the chemical bonding, heat resistance properties may be improved. That is, the CTE of an epoxy composite may be decreased, and a glass transition temperature may be increased or the glass transition temperature may not be exhibited (hereinafter, 'Tg-less'). In addition, a cured product including the epoxy compound having an alkoxysilyl group in accordance with the present invention may show good flame retardant property through the introduction of the alkoxysilyl group.

Further, when the epoxy composition is applied in a metal film of a substrate, good adhesive properties may be exhibited with respect to the metal film due to the chemical bonding between the functional group at the surface of the metal film and the alkoxysilyl group. In addition, due to the increase in chemical bonding efficiency of the composition including the alkoxysilylated isocyanurate epoxy compound, a silane coupling agent used in a common epoxy composition may be unnecessarily in the composition including the alkoxysilylated epoxy compound. The epoxy composition including the epoxy compound may have good curing efficiency, and a composite formed through the curing thereof may exhibit good thermal expansion properties such as a low CTE and a high glass transition temperature or Tg-less.

DESCRIPTION OF DRAWINGS

The above and other embodiments, features and other advantages of the present invention will be more clearly understood from the following detailed description taken in conjunction with the accompanying drawings, in which.

BEST MODE FOR INVENTION

Figure 1:
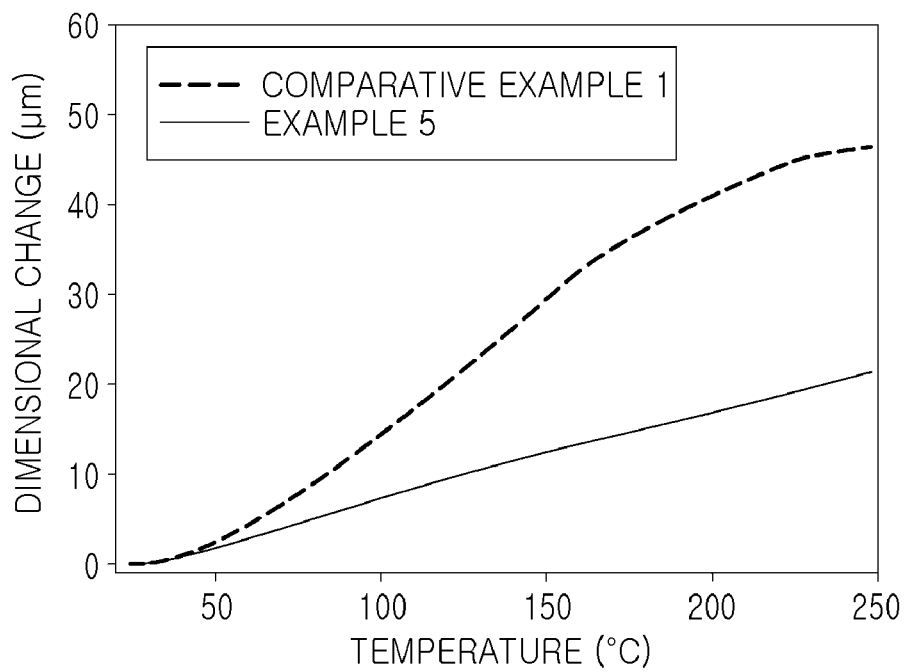
FIG. 1 is a graph illustrating dimensional changes with the change of a temperature of composites according to Example 4 and Comparative Example 1.

Exemplary embodiments of the present invention will now be described in detail with reference to the accompanying drawings.

The disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

The present invention provides a novel alkoxysilylated epoxy compound, a composite obtained by curing thereof exhibiting improved heat resistance properties, particularly a low CTE and a higher Tg or Tg-less and/or a cured product thereof exhibiting good flame retardant property, an epoxy composition including the same, a cured product formed by using the composition, a use of the composition, and a method of preparing the alkoxysilylated epoxy compound.

In the present invention, "composite" refers to a cured product formed by using a composition including an epoxy compound and a filler (fiber and/or inorganic particles). In the present invention, "cured product" refers to a cured product formed by using a composition including an epoxy compound as general meaning, for example, a cured product formed by using a composition including an epoxy compound and a curing agent, and at least one selected from the group consisting of a filler, an additional curing agent, an optional curing accelerator and other additives. In addition, the term "cured product" is also used to denote a "partially-cured product". Generally, only a cured product reinforced with inorganic particles or a fiber is referred to as a composite. Thus, the cured product has a broader meaning than the composite. The cured product reinforced with the inorganic particles or the fiber may be considered to have the same meaning as the composite.

When forming a composite through curing the alkoxysilylated epoxy compound in accordance with the present invention, an epoxy group may react with a curing agent to conduct a curing reaction, and the alkoxysilyl group may form an interface bonding with the surface of the filler (fiber and/or inorganic particles) and/or a chemical bonding between alkoxysilyl groups. Thus, very high chemical bonding efficiency in an epoxy composite system may be obtained, and thus, a low CTE and high glass transition temperature increasing effect or Tg-less may be achieved. Therefore, dimensional stability may be improved. In addition, any additional silane coupling agents are not necessary. Further, the cured product including the alkoxysilylated epoxy compound according to the present invention may exhibit good flame retardant property.

In addition, when applying the epoxy composition of the present invention on a chemically-treated metal film such as a copper film, a chemical bonding may be formed with a —OH group or the like at the surface of the metal produced through the metal surface treatment, thereby showing good adhesion with the metal film.

Hereinafter, an alkoxysilylated epoxy compound, an epoxy composition including the same, a cured product thereof, a use thereof, and a method of preparing the alkoxysilylated epoxy compound according to an embodiment of the present invention will be described in detail.

1. Alkoxysilylated Epoxy Compounds

In accordance with one embodiment of the present invention, an epoxy compound having an alkoxysilyl group having a structure selected from the group consisting of the following Formulae AI to HI is provided.

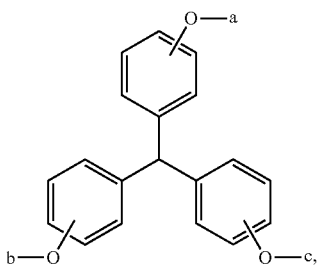

AI

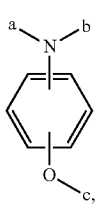

BI

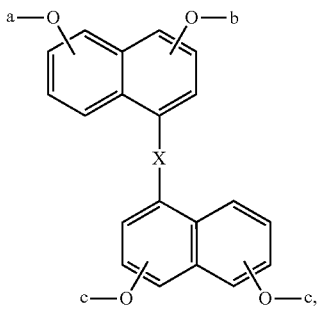

CI

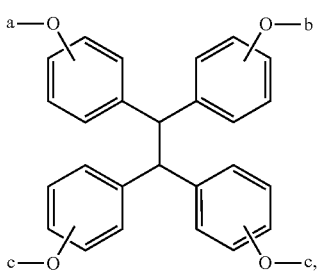

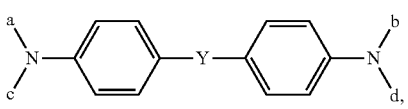

EI

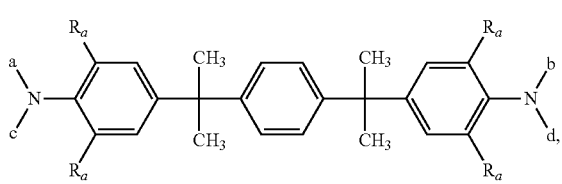

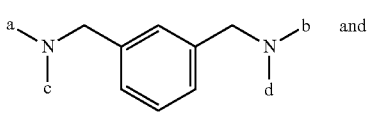 and

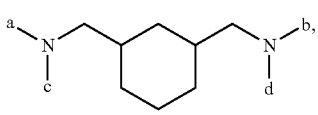

One or two of substituents a to c in Formula AI or BI are the following Formula S1, one or two thereof are the following Formula S2 or S3, and the remainder thereof may be hydrogen or —$(CH_2)_{Z-2}$ CH=$CH_2$ where z is an integer from 3 to 10. The substituent may be hydrogen or —$(CH_2)_{Z-2}$ CH=$CH_2$ where z is an integer from 3 to 10 when an unreacted site is present during synthesizing the above compounds, which will be described later. Preferably, one or two of substituents a to c are the following Formula S1, and one or two thereof are the following Formula S2 or S3.

One to three of substituents a to d in Formulae CI to HI are the following Formula S1, one to three thereof are the following Formula S2 or S3, and the remainder thereof may be hydrogen or —$(CH_2)_{z-2}CH$=$CH_2$ where z is an integer from 3 to 10. The substituent may be hydrogen or —$(CH_2)_{z-2}CH$=$CH_2$ where z is an integer from 3 to 10 when an unreacted site is present during synthesizing the above compounds, which will be described later. Preferably, one to three of substituents a to d are the following Formula S1, and one to three thereof have the form of the following Formula S2 or S3.

A meta position of oxygen in Formula BI may be substituted with a linear or branched C1-C10 alkyl group.

X in Formula CI is a direct linkage, —$CH_2$— or

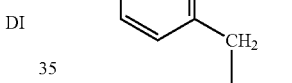

where Rb is H or a C1-C3 alkyl group.

Y in Formula EI is —$CH_2$—, —$C(CH_3)_2$—, —$C(CF_3)_2$—, —S— or —$SO_2$—.

Ra in Formula FI is H or a C1-C3 alkyl group.

 [Formula S1]

FI  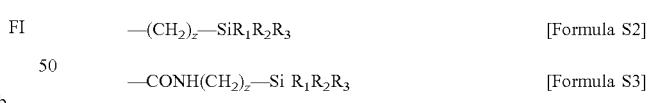 [Formula S2]

 [Formula S3]

In Formulae S2 and S3, at least one of $R_1$ to $R_3$ is an alkoxy group having 1 to 10 carbon atoms, preferably, an ethoxy group, the remainder thereof are alkyl groups having 1 to 10 carbon atoms, z is an integer from 3 to 10, and the alkyl group and the alkoxy group are a linear chain or a branched chain alkyl group or alkoxy group.

GI

The term "alkoxy" used in the present application refers to a monovalent —OR (R is an alkyl) group which may be a linear or branched group.

HI

The term "alkyl" used in the present application refers to a monovalent hydrocarbon group which may be a linear or branched group.

In an embodiment of the present invention, the epoxy compound having an alkoxysilyl group may be, for example, one selected from the group consisting of the compounds of the following Formula F.

[Formula F]
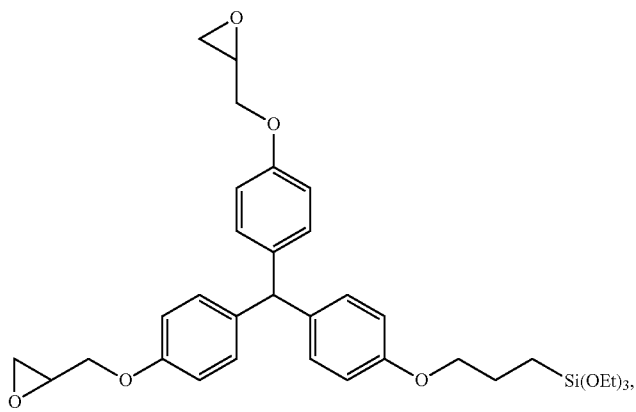
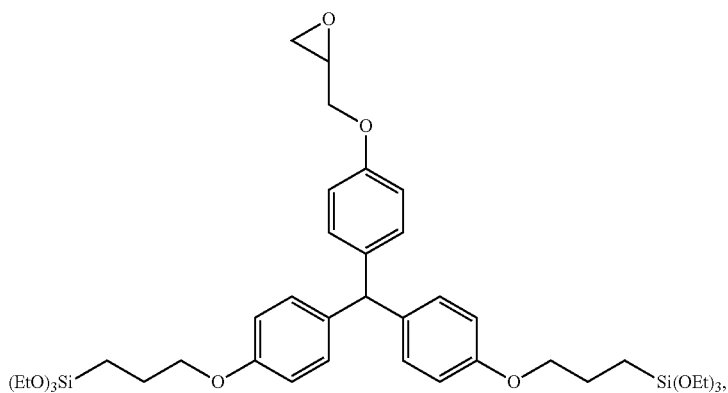
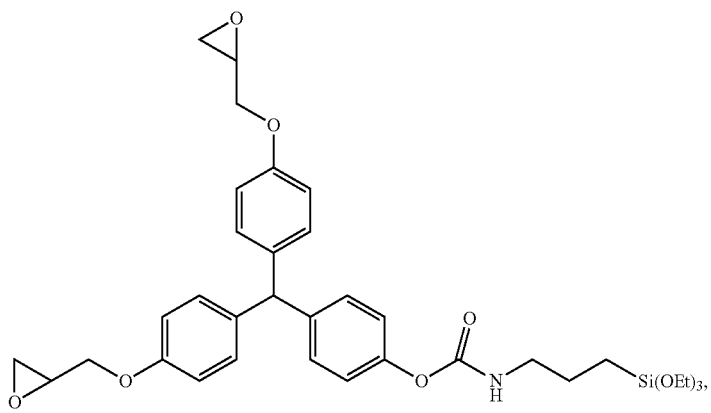
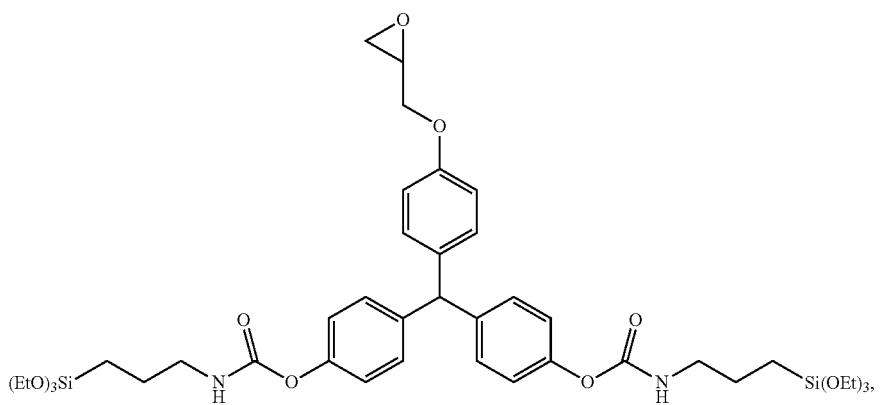

81    -continued    82
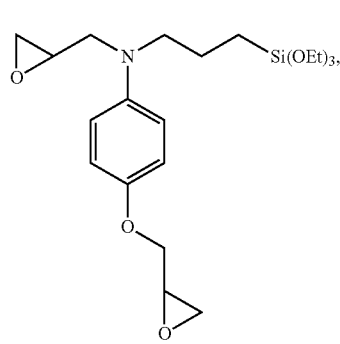 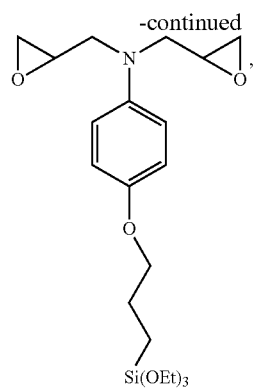 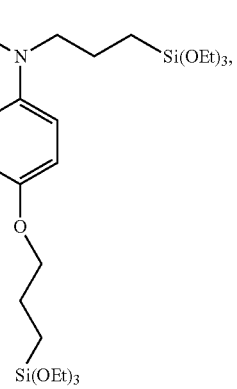
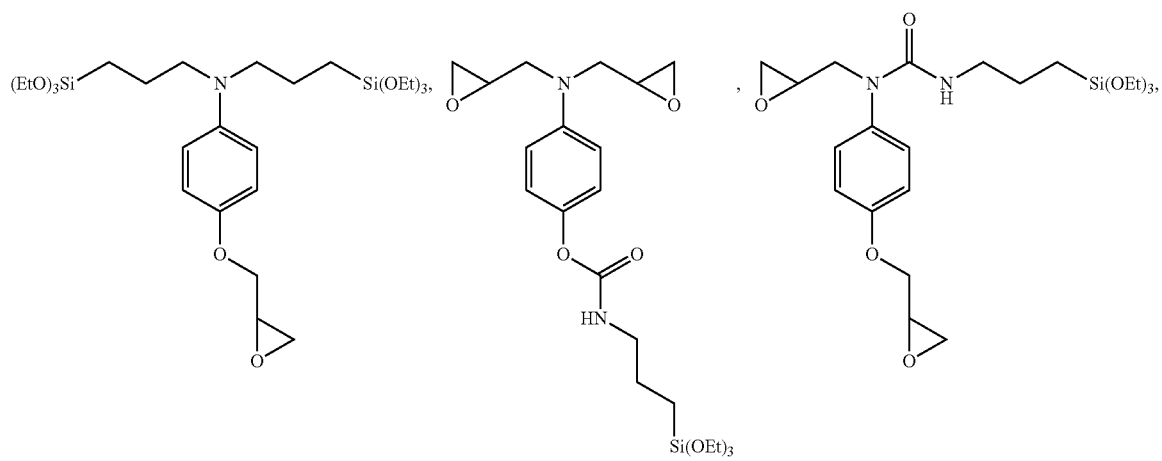
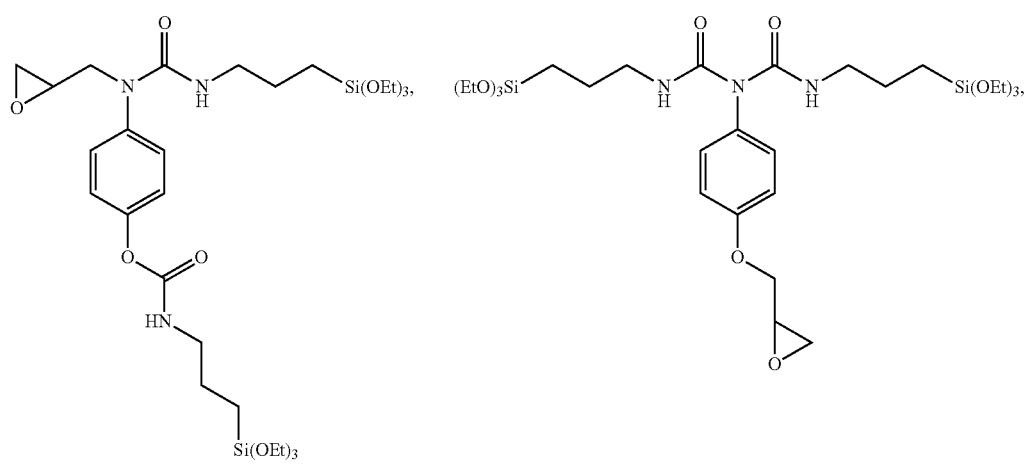
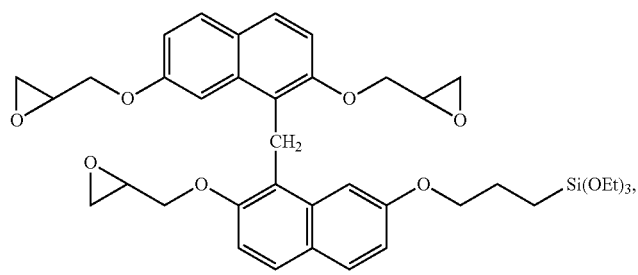

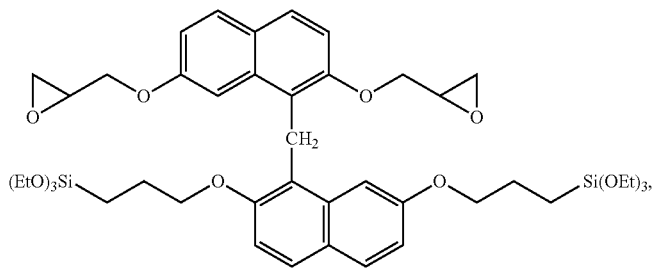
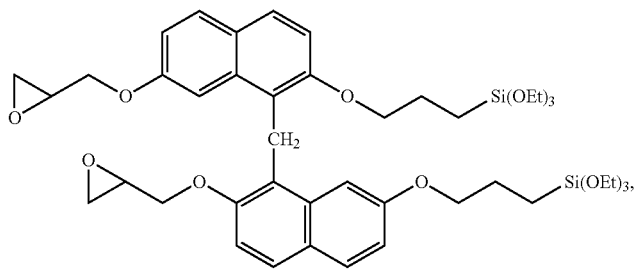
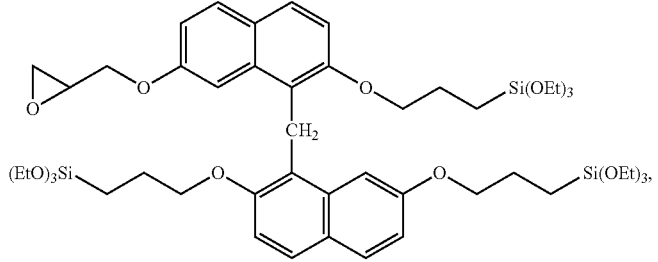
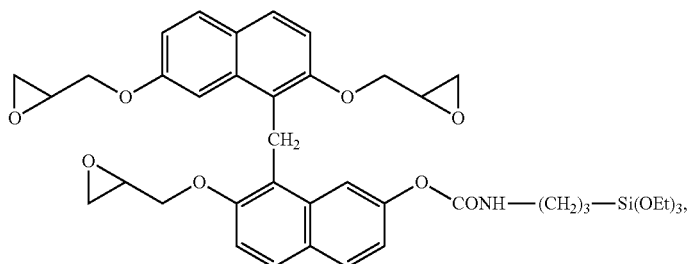
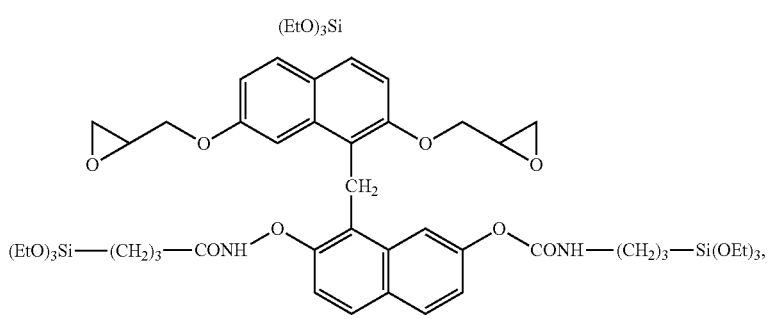
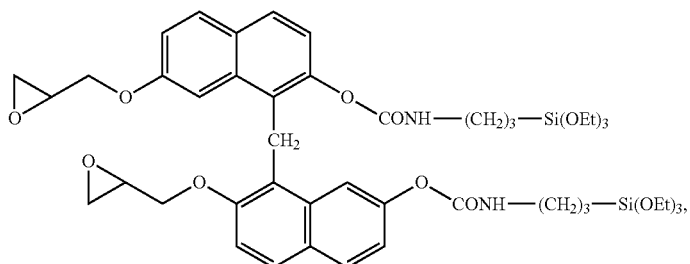

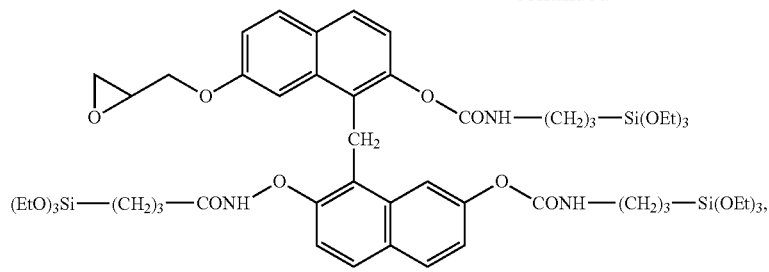
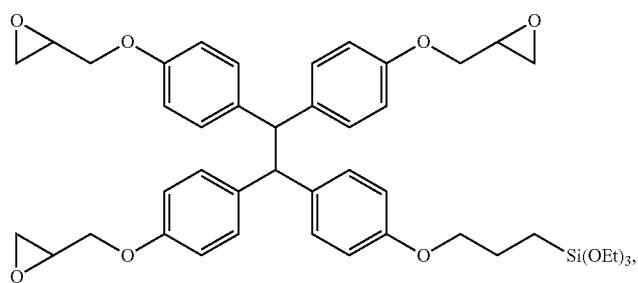
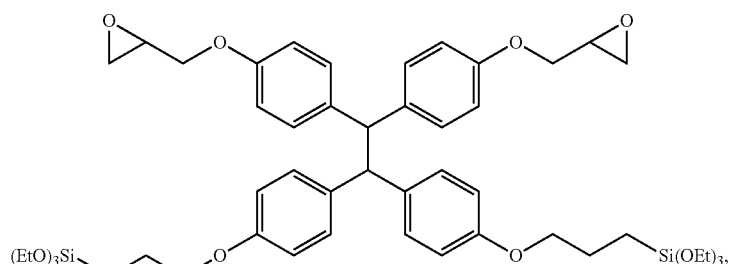
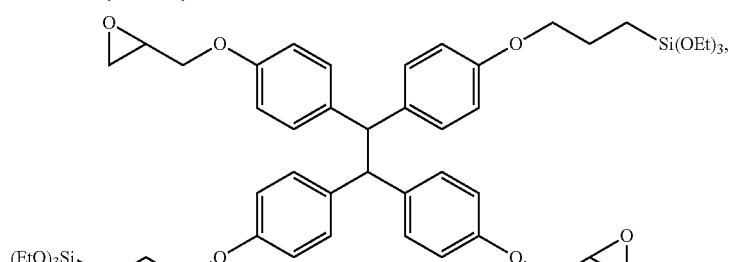
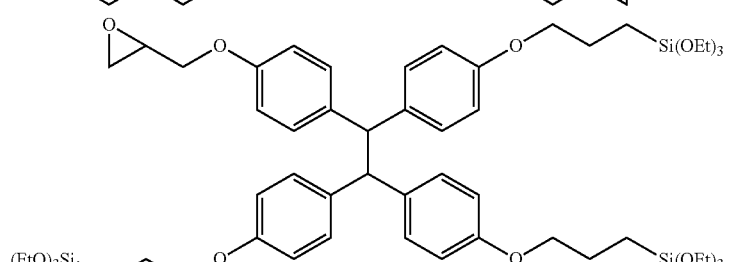
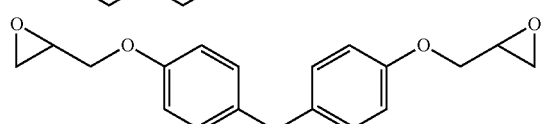
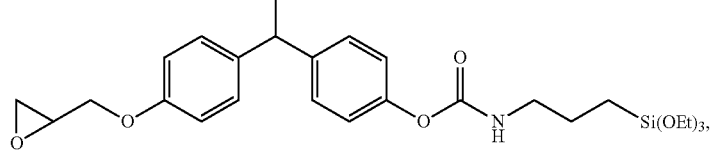

-continued
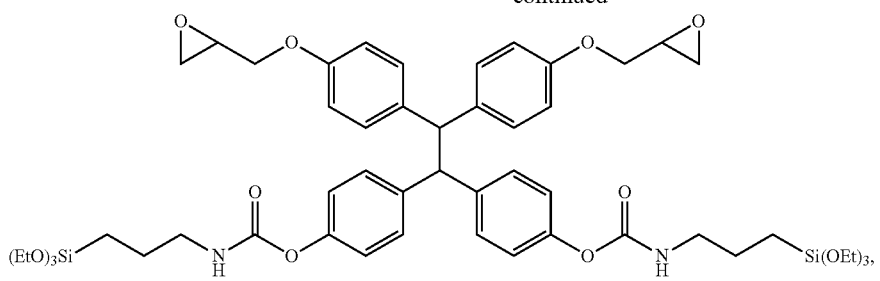
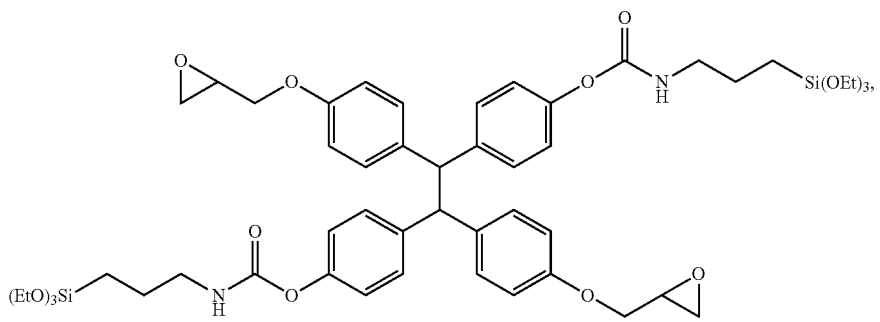
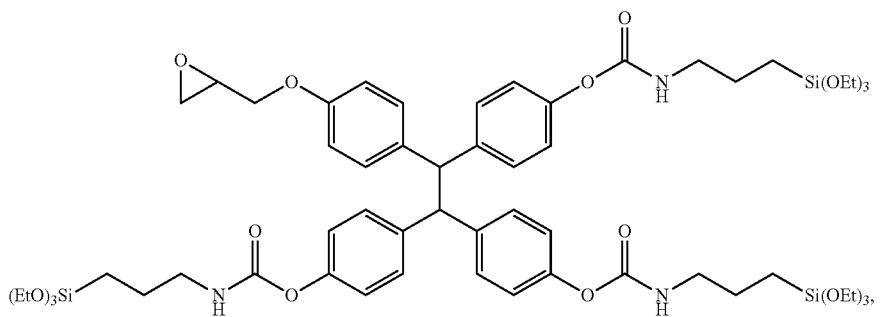
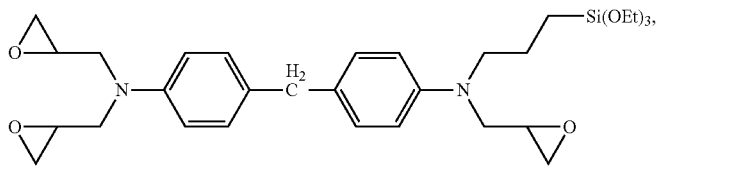
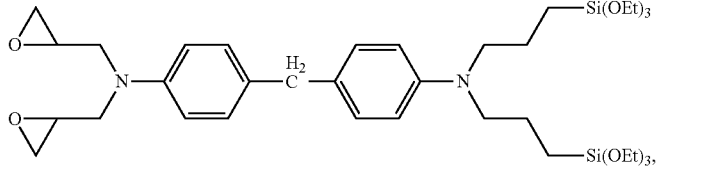
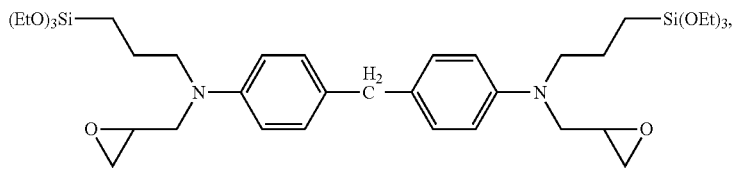
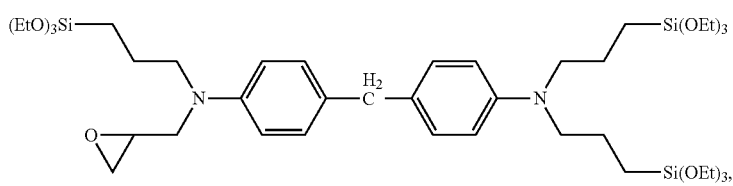

-continued
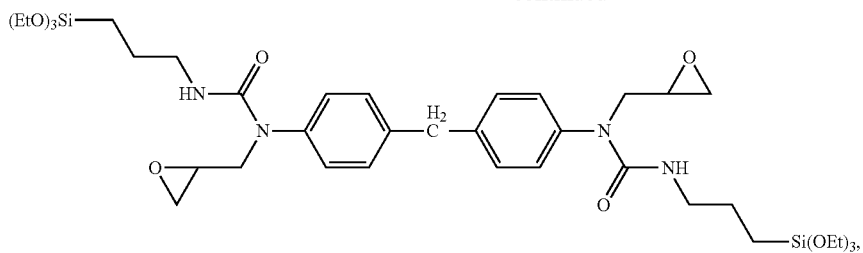
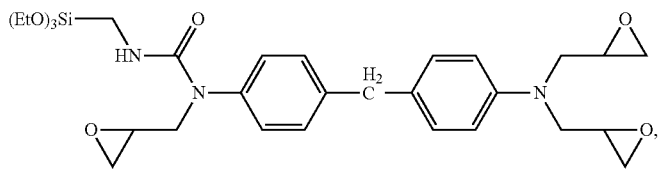
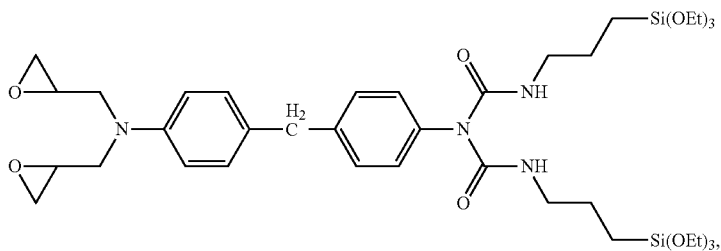
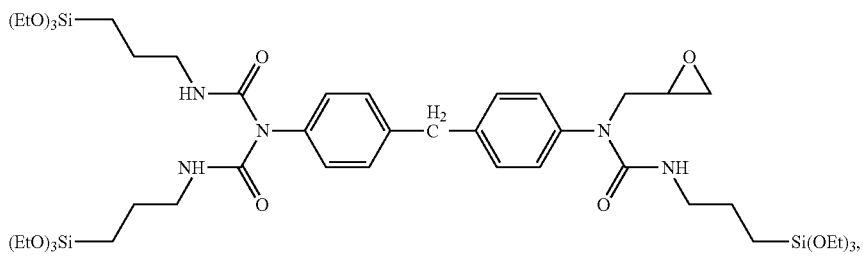
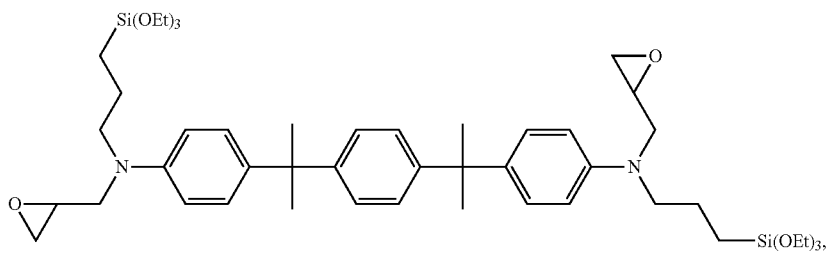
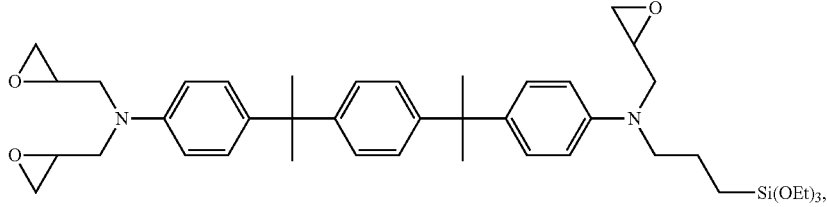
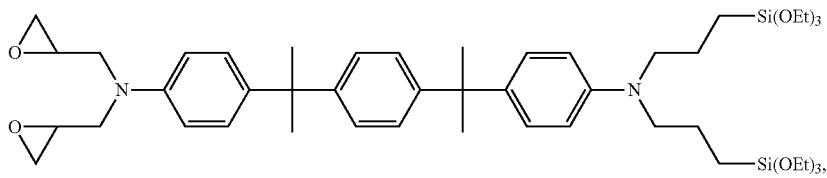

-continued
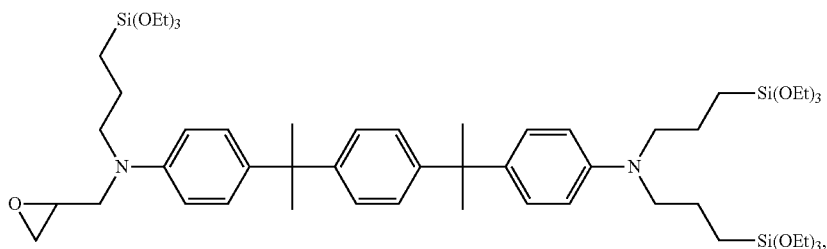
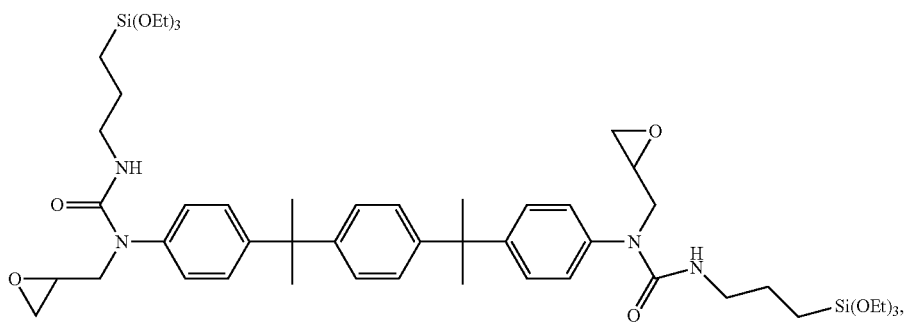
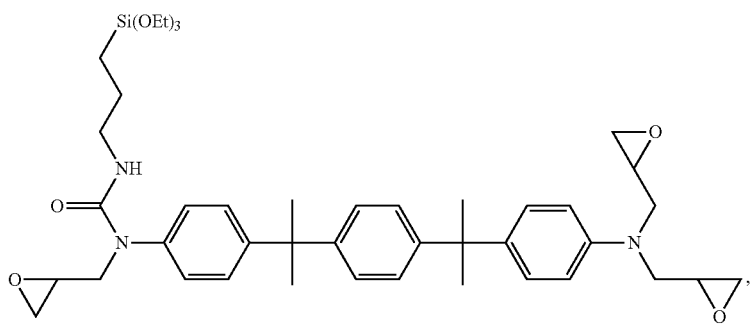
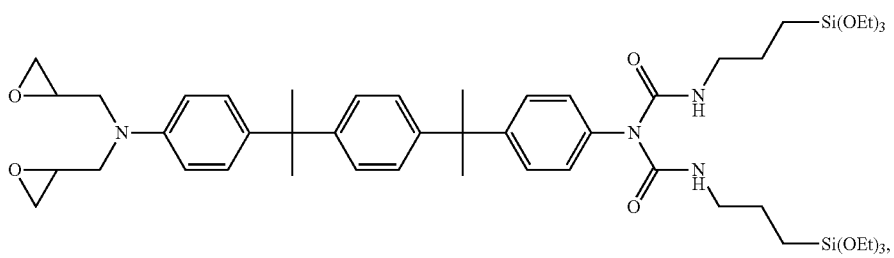
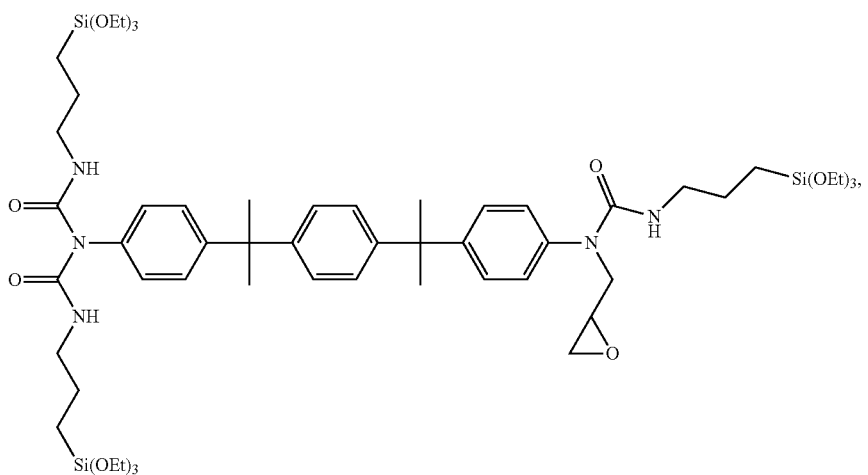

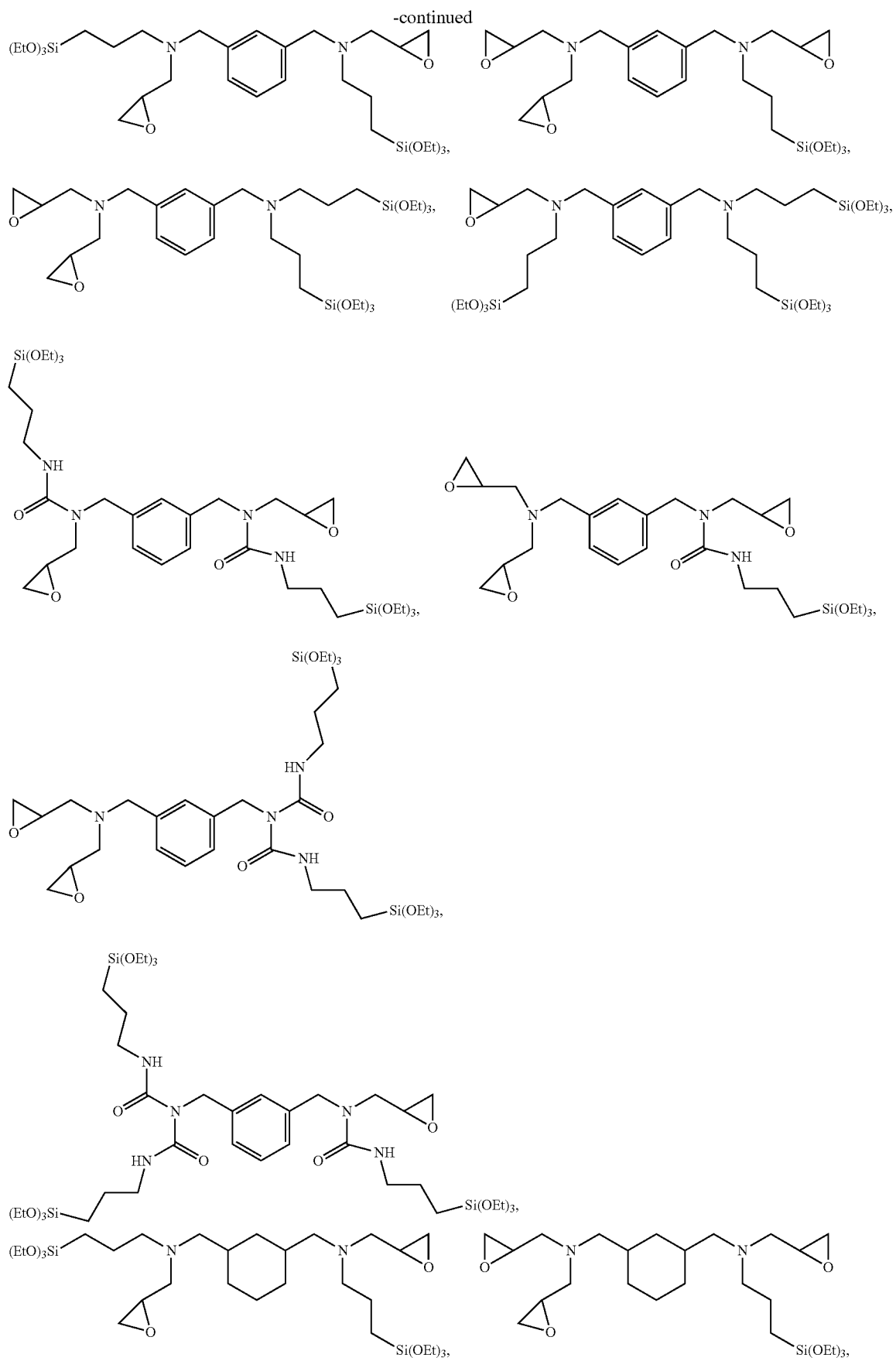

-continued
95
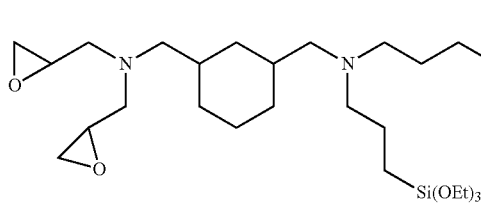
96
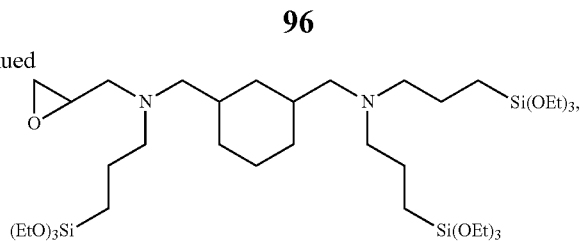
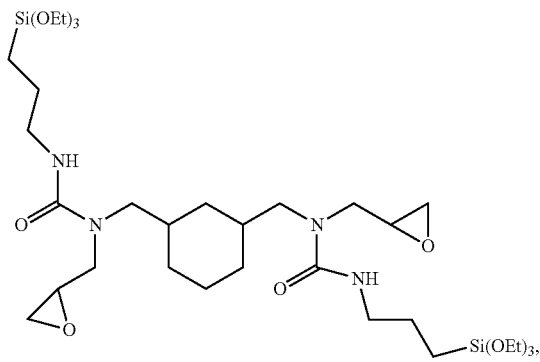
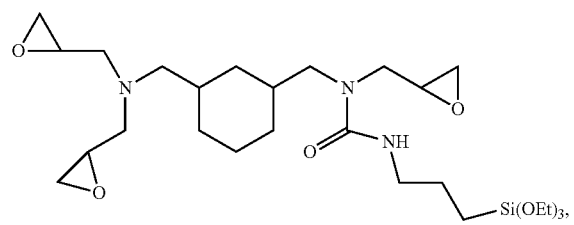
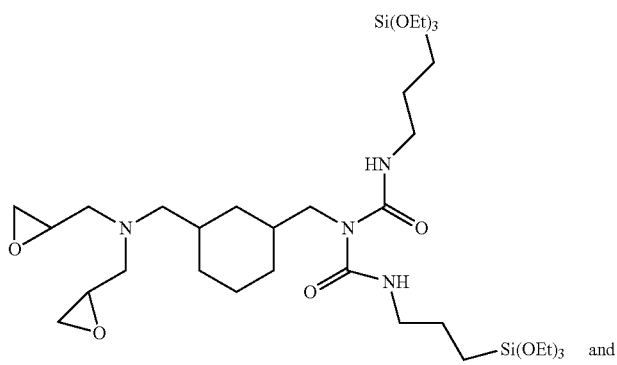 and
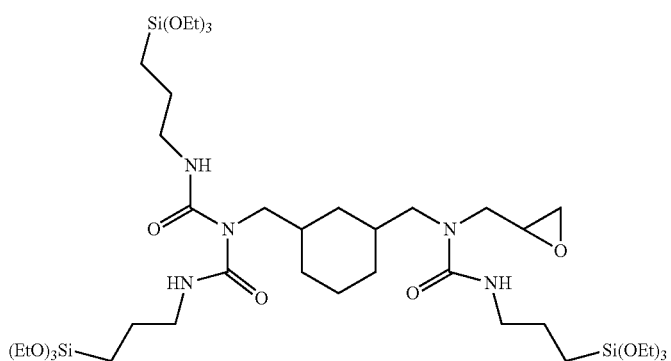

In another embodiment of the present invention, at least one polymer selected from the group consisting of the compounds of the following Formula P is provided.
[Formula P]
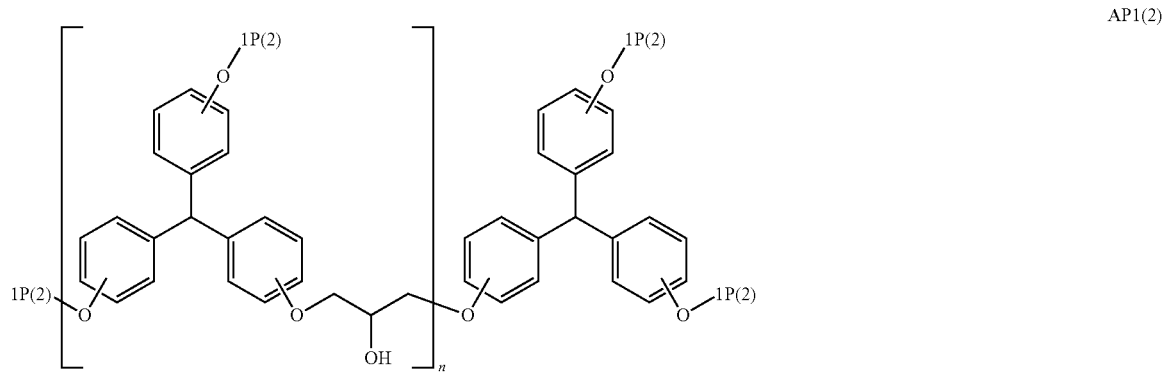
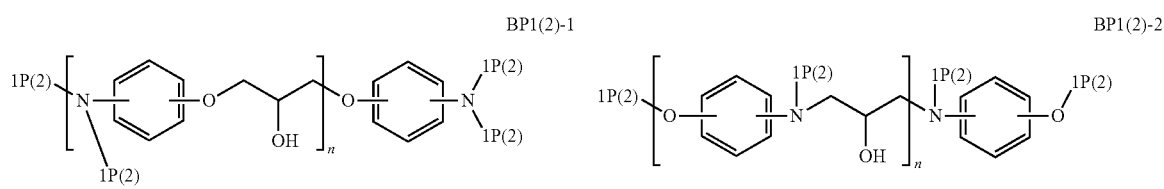
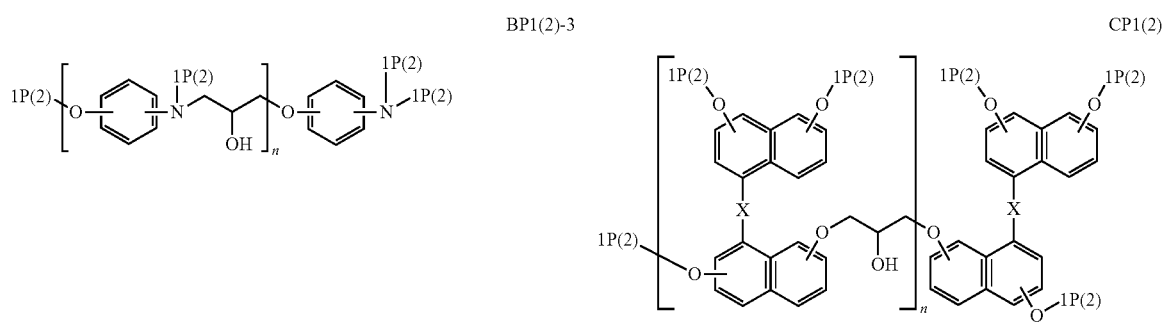
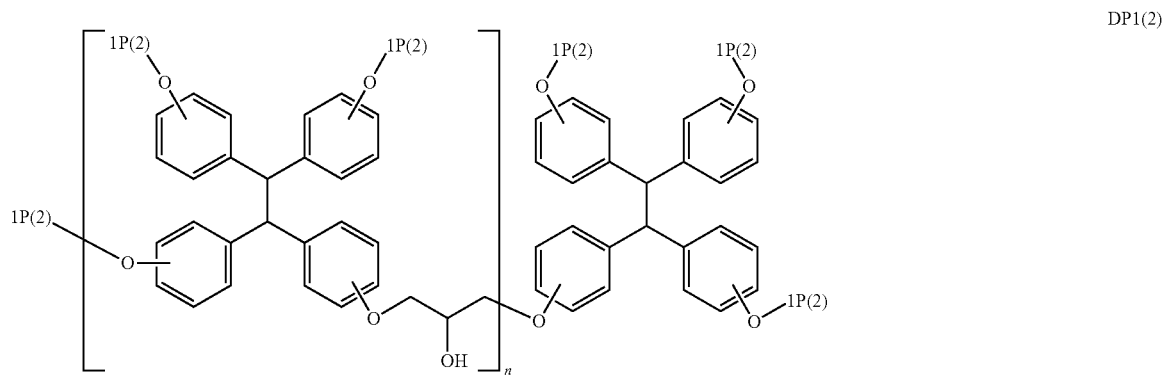
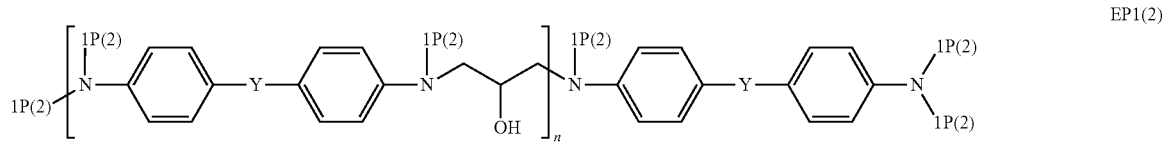

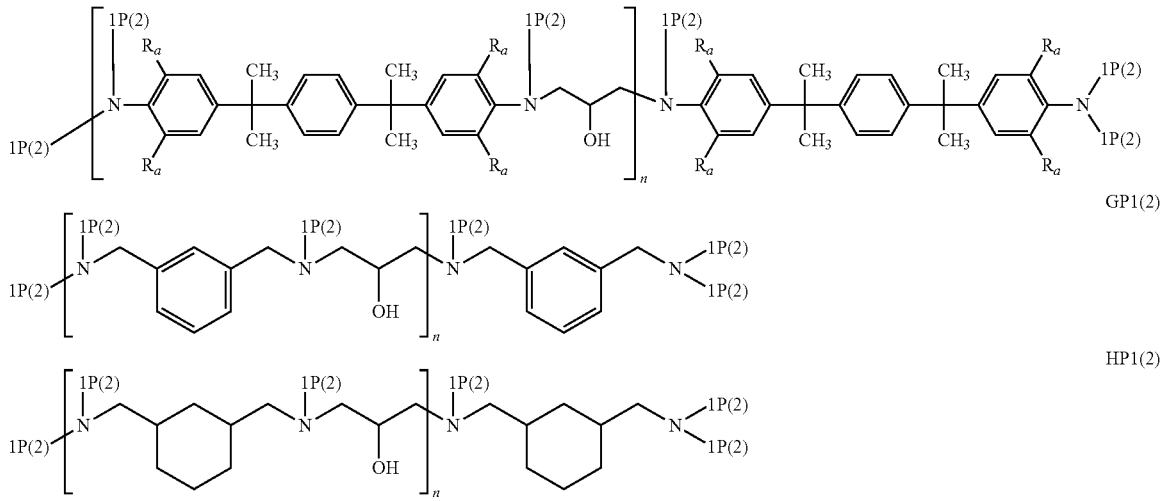

In Formula P, each of 1P(2) is independently selected from an epoxy group of the above Formula S1, the above Formula S2, —(CH$_2$)$_{z-2}$CH=CH$_2$ where z is an integer from 3 to 10, and hydrogen. Particularly, at least one of each of the epoxy group of the above Formula S1 and the above Formula S2 is included. 1P(2) may be —(CH$_2$)$_{z-2}$CH=CH$_2$ where z is an integer from 3 to 10 and/or hydrogen when an unreacted site is present during synthesizing the above compounds. Preferably, each of 1P(2) is independently at least one of the epoxy group of the above Formula S1 and at least one of the above Formula S2.

A meta position of oxygen in Formulae BP1(2)-1 to BP1(2)-3 may be substituted with a linear or branched C1-C10 alkyl group.

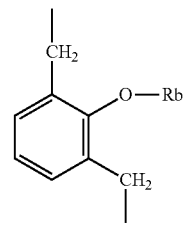

X in CP1(2) is a single bond, —CH$_2$— or where Rb is H or a C1-C3 alkyl group.

Y in Formula EP1(2) is —CH$_2$—, —C(CH$_3$)$_2$—, —C(CF$_3$)$_2$—, —S— or —SO$_2$—.

Ra in Formula FP1(2) is H or a C1-C3 alkyl group.

n is an integer from 1 to 100.

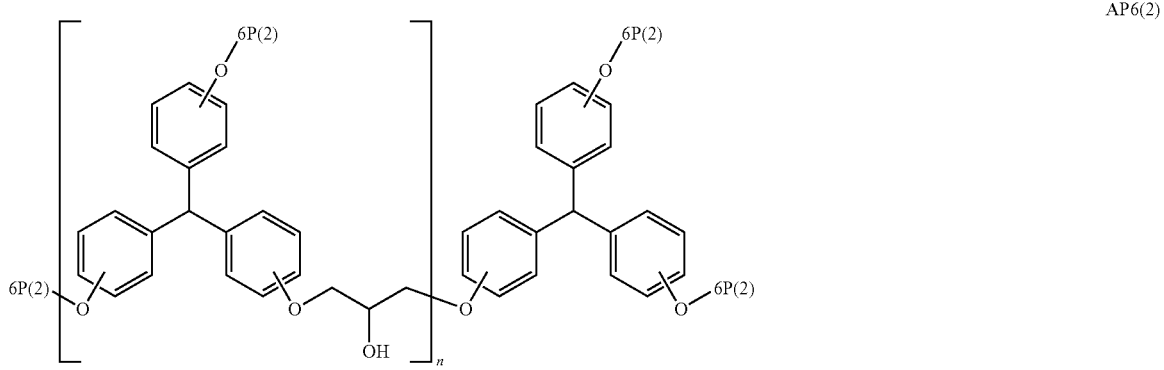

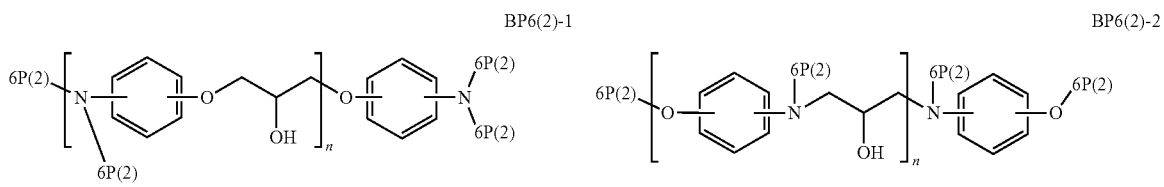

BP6(2)-3

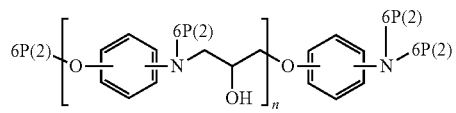

CP6(2)

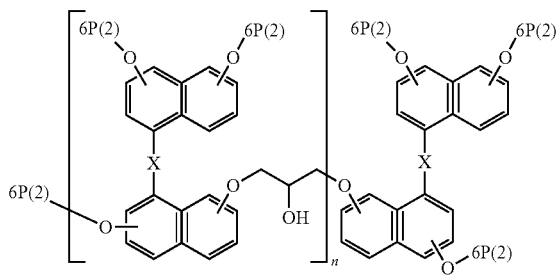

DP6(2)

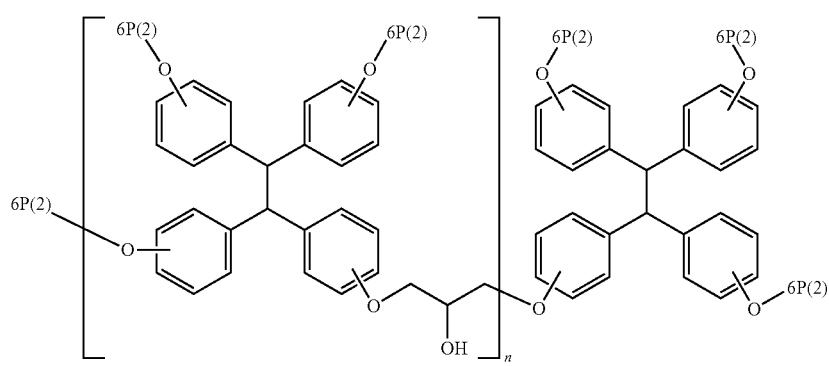

EP6(2)

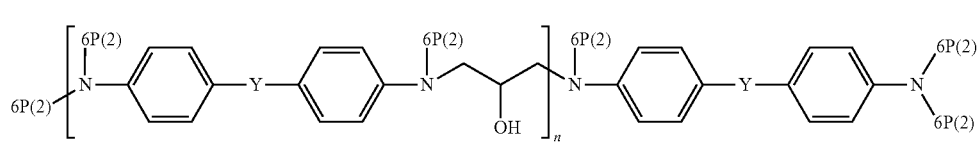

FP6(2)

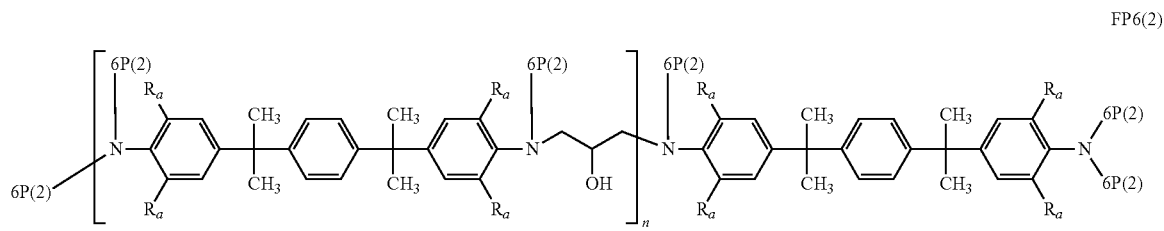

GP6(2)

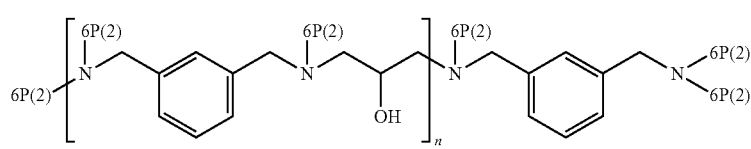

HP6(2)

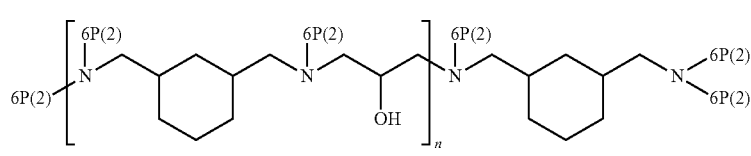

Each of 6P(2) is independently selected from the epoxy group of the above Formula S1, the above Formula S3, and hydrogen. Particularly, at least one of each of the epoxy group of the above Formula S1 and the above Formula S3 is included. 6P(2) may be hydrogen when an unreacted site is present during synthesizing the above compounds. Preferably, each of 6P(2) is independently at least one of the epoxy group of the above Formula S1 and at least one of the above Formula S3.

A meta position of oxygen in Formulae BP6(2)-1 to BP6(2)-3 may be substituted with a linear or branched C1-C10 alkyl group.

X in Formula CP6(2) is a direct linkage, —CH$_2$— or

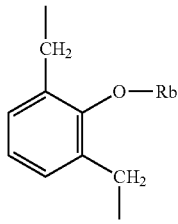

where Rb is H or a C1-C3 alkyl group.

Y in Formula EP6(2) is —CH$_2$—, —C(CH$_3$)$_2$—, —C(CF$_3$)$_2$—, —S— or —SO$_2$—.

Ra in Formula FP6(2) is H or a C1-C3 alkyl group.

n is an integer from 1 to 100.

2. Epoxy Compositions

According to another embodiment of the present invention, there is provided a composition including at least one alkoxysilylated epoxy compound selected from the group consisting of the above Formulae AI to HI according to an embodiment of the present invention.

Any compositions provided in the present invention may be used in various uses such as an electronic material, for example, a semiconductor substrate such as an IC substrate, an encapsulating material (packaging material), a build-up film, an electronic part such as a printed circuit board, an adhesive, a paint composition, a composite material, or the like, without limitation. In addition, any compositions provided in the present invention may be a curable composition and/or a curable composition including an inorganic material.

Any epoxy compositions according to any embodiments described above or later in the present invention may include any kind and/or any mixing ratio known in the art only when including at least one epoxy compound selected from the group consisting of the above Formulae AI to HI (hereinafter an 'epoxy compound of the present invention'). In this case, the kind and the mixing ratio of the curing agent, the curing accelerator (catalyst), the inorganic material (filler) (for example, inorganic particles and/or a fiber), other common epoxy compounds and other additives are not limited.

Further, the epoxy composition, the cured product and/or the composite may be used with various kinds of common epoxy compounds in consideration of the controlling feature of physical properties according to the application and/or use thereof. Thus, in the epoxy compositions according to any embodiments described above or later in the present invention, the epoxy compound may include at least one alkoxysilylated epoxy compound selected from the group consisting of the above Formulae AI to HI, and any kind of epoxy compound commonly known in this art (hereinafter a 'common epoxy compound').

The common epoxy compounds may be any epoxy compounds commonly known in this art without limitation, and may be, for example, at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound. Further, the common epoxy compound may be at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound including bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolak unit, as a core structure.

For example, the common epoxy compound may be at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound including bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolak unit, as a core structure.

Any epoxy compositions in accordance with an embodiment of the present invention may include without limitation, based on the total amount of an epoxy compound, from 1 wt % to 100 wt % of the epoxy compound according to any embodiments of the present invention and from 0 wt % to 99 wt % of the common epoxy compound; for example, from 10 wt % to 100 wt % of the epoxy compound of the present invention and from 0 wt % to 90 wt % of the common epoxy compound; for example, from 30 wt % to 100 wt % of the epoxy compound of the present invention and from 0 wt % to 70 wt % of the common epoxy compound; for example, from 50 wt % to 100 wt % of the epoxy compound of the present invention and from 0 wt % to 50 wt % of the common epoxy compound; for example, from 10 wt % to below 100 wt % of the epoxy compound of the present invention and from excess of 0 wt % to 90 wt % of the common epoxy compound; for example, from 30 wt % to below 100 wt % of the epoxy compound of the present invention and from excess of 0 wt % to 70 wt % of the common epoxy compound; for example, from 50 wt % to below 100 wt % of the epoxy compound of the present invention and from excess of 0 wt % to 50 wt % of the common epoxy compound.

Further, in accordance with an embodiment of the present invention, an epoxy composition including at least one epoxy compound selected from the group consisting of the above Formulae AI to HI and an inorganic material (filler) (for example, inorganic particles and/or a fiber) according to any embodiments of the present invention (hereinafter a 'composite composition') is provided. The composite composition is considered to include an epoxy composition having any kind and/or any mixing ratio commonly known in this art only when including at least one epoxy compound selected from the group consisting of the above Formulae AI to HI and the filler. The kinds and the mixing ratios of the curing agent, the curing accelerator (catalyst), the inorganic material (filler) (for example, inorganic particles and/or a fiber) composing the epoxy composition, and the kinds of the common epoxy compound and other additives are not limited.

The above-described composite composition and any compositions described above or later according to the present invention may additionally include inorganic particles and/or a fiber.

Any inorganic particles known to be used to reinforce the physical properties of a common organic resin may be used.

Examples of the inorganic particles may include, without limitation, at least one selected from the group consisting of at least one metal oxide selected from the group consisting of silica (including, for example, fused silica and crystalline silica), zirconia, titania, alumina, silicon nitride and aluminum nitride, T-10 type silsesquioxane, ladder type silsesquioxane, and cage type silsesquioxane. The inorganic particles may be used alone or as a mixture of two or more thereof.

In the case that particularly a large amount of the silica is mixed, the fused silica is preferably used. The fused silica may have any shape among a cataclastic shape and a spherical shape. However, the spherical shape is preferable to increase the mixing ratio of the fused silica and to restrain the increase of the fused viscosity of a forming material.

The inorganic particles having a particle size of 0.5 nm to several tens of μm (for example, from 50 μm to 100 μm) may be used in consideration of the use of a composite, particularly, the dispersibility of the inorganic particles, or the like. Since the dispersibility of the inorganic particle in the epoxy matrix may be different according to the particle size, the inorganic particles having the above-described size may preferably be used. In addition, the distribution range of the inorganic particles to be mixed is preferably increased to increase the mixing ratio of the inorganic particles.

In the epoxy composition in accordance with an embodiment of the present invention, the mixing amount of the inorganic particles with respect to the epoxy compound may be appropriately controlled in consideration of the CTE decrease of an epoxy composite and an appropriate viscosity required while applying. For example, the amount of the inorganic particles may be 5 wt % to 95 wt %, for example, 5 wt % to 90 wt %, for example, 10 wt % to 90 wt %, for example, 30 wt % to 95 wt %, for example, 30 wt % to 90 wt %, for example, 5 wt % to 60 wt %, for example, 10 wt % to 50 wt % based on the total amount of the solid content of the epoxy compound (based on the total amount of the epoxy cured product for the epoxy cured product).

More particularly, in an exemplary embodiment, when the epoxy composition is used as a semiconductor EMC (epoxy molding compound), or the like, the amount of the inorganic particles may be, for example, 30 wt % to 95 wt %, for example, 30 wt % to 90 wt %, without limitation, based on the amount of the solid content of the epoxy compound (based on the total amount of the epoxy cured product for the epoxy cured product) in consideration of the CTE value and material processability. In other exemplary embodiments, when the epoxy composition is used in a semiconductor substrate, the amount of the inorganic particles may be 5 wt % to 60 wt %, for example, 10 wt % to 50 wt % based on the total solid content of the epoxy compound (based on the total amount of the epoxy cured product for the epoxy cured product) considering the CTE value and the modulus of the substrate.

Meanwhile, when the fiber is used as the inorganic material, a composite may be obtained by mainly an immersing method of the fiber with the epoxy composition. Thus, the size of the fiber may not be specifically limited. Any kind of fiber commonly used in this field may be used and dimensions thereof are not limited.

Any commonly used fibers used for improving physical properties of a common organic resin cured product may be used without limitation. Particularly, a glass fiber, an organic fiber or a mixture thereof may be used. In addition, the term 'glass fiber' used in this application may include a glass fiber fabric, a glass fiber non woven product, or the like, as well as the glass fiber. Examples of the glass fibers may include, without limitation, the glass fiber of an E-glass fiber, a T-glass fiber, an S-glass fiber, an NE-glass fiber, a D-glass fiber, a quartz glass fiber, or the like. For example, the glass fiber of E or T may be included. An organic fiber may include at least one selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber. These fibers may be used alone or as a combination of two or more.

The amount of the fiber in the epoxy composition according to the present invention, for example, in a glass fiber composite epoxy composition, may be 10 wt % to 90 wt %, for example, 30 wt % to 70 wt %, in addition, for example, 35 wt % to 65 wt % based on the total weight of the solid content of the epoxy composition. In addition, the amount of the fiber in the cured product of the epoxy composition, for example, in a glass fiber composite, may be 10 wt % to 90 wt %, for example, 30 wt % to 70 wt %, in addition, for example, 35 wt % to 65 wt % based on the total amount of the cured product. Thus, the resin content may be 10 wt % to 90 wt %, for example, 30 wt % to 70 wt %, in addition, for example, 35 wt % to 65 wt %. The amount of the fiber within the above-described range may be preferred in consideration of the increase in heat resistance and the processability aspect. Meanwhile, in the epoxy composition, the cured product, or the like. including the fiber, solid parts excluding the fiber from the total solid content is referred to as the resin. In the epoxy composition including the fiber, the remaining amount other than the fiber is the resin content.

Further, in the epoxy composition including the fiber may additionally include inorganic particles as occasion demands. In this case, the inorganic particles may be included by 1 wt % to 70 wt % in the resin component based on the total amount of the resin in consideration of the improvement of the physical properties and processability. In this case, the kind of the inorganic particles is not specifically limited, and any inorganic particles known in this art may be used. For example, the above-described inorganic particles may be used.

According to further another embodiment of the present invention, an epoxy composition including at least one epoxy compound selected from the group consisting of the above Formulae AI to HI according to any embodiments of the present invention and a curing agent is provided (hereinafter a 'curing agent-containing composition'). Any curing agent-containing compositions may include an epoxy composition having any kind and/or any mixing ratio known in the art only when including at least one alkoxysilylated epoxy compound selected from the group consisting of the above Formulae AI to HI and a curing agent. However, the kinds and the mixing ratios of the curing agent, the curing accelerator (catalyst), the inorganic material (filler) (for example, inorganic particles and/or fiber), other common epoxy compounds and other additives composing the epoxy composition are not limited.

According to further another embodiment of the present invention, an epoxy composition including at least one epoxy compound selected from the group consisting of the above Formulae AI to HI according to any embodiments of the present invention and an alkoxysilyl reaction catalyst (hereinafter a 'reaction catalyst') is provided (hereinafter a 'reaction catalyst-containing composition'). Any reaction catalyst-containing compositions may include an epoxy composition having any kind and/or any mixing ratio known in the art only when including at least one alkoxysilylated epoxy compound selected from the group consisting of the above Formulae AI to HI and a reaction catalyst. However, the kinds and the mixing ratios of the curing agent, the curing accelerator (catalyst), the inorganic material (filler) (for example, inorganic particles and/or fiber), other common epoxy compounds and other additives composing the epoxy composition are not limited. In the case that the alkoxysilyl reaction catalyst is included, improved processability (for example, rapid curing rate and/or low curing temperature) may be expected.

The curing agent-containing composition and the reaction catalyst-containing composition may also include the common epoxy compound as the epoxy compound. In this case, the kind of the common epoxy compound and the mixing ratios of the alkoxysilylated epoxy compound and the common epoxy compound are the same as described above.

When a curing agent is included in the curing agent-containing composition and the composition according to an embodiment of the present invention, any curing agents commonly known as a curing agent of an epoxy compound may be used. For example, an amine compounds, a phenol compounds, an anhydrous oxide compound may be used, without limitation.

More particularly, an aliphatic amine, an alicyclic amine, an aromatic amine, other amines and a modified amine may be used as the amine-based curing agent without limitation. In addition, an amine compound including two or more primary amine groups may be used. Particular examples of the amine curing agents may include at least one aromatic amine selected from the group consisting of 4,4'-dimethylaniline (diamino diphenyl methane, DAM or DDM), and diamino diphenyl sulfone (DDS), and m-phenylene diamine, at least one aliphatic amine selected from the group consisting of diethylene triamine (DETA), diethylene tetramine, triethylene tetramine (TETA), m-xylene diamine (MXTA), methane diamine (MDA), N,N'-diethylenediamine (N,N'-DEDA), tetraethylenepentaamine (TEPA), and hexamethylenediamine, at least one alicyclic amine selected from the group consisting of isophorone diamine (IPDI), N-aminoethyl piperazine (AEP), bis(4-amino 3-methylcyclohexyl) methane, and larominc 260, other amines such as dicyanamide (DICY), or the like, and a modified amine such as a polyamide-based compound, an epoxide-based compound, or the like.

Examples of the phenol curing agent may include, without limitation, a phenol novolak resin, a cresol novolak resin, a bisphenol A novolak resin, a xylene novolak resin, a triphenyl novolak resin, a biphenyl novolak resin, a dicyclopentadiene novolak resin, phenol p-xylene, a naphthalene-based phenol novolak resin, a triazine-based compound, or the like.

Examples of the acid anhydride curing agent may include, without limitation, an aliphatic acid anhydride such as dodecenyl succinic anhydride (DDSA), poly azelaic poly anhydride, or the like, an alicyclic acid anhydride such as hexahydrophthalic anhydride (HHPA), methyl tetrahydrophthalic anhydride (MeTHPA), methylnadic anhydride (MNA), or the like, an aromatic acid anhydride such as trimellitic anhydride (TMA), pyromellitic acid dianhydride (PMDA), benzophenonetetracarboxylic dianhydride (BTDA), or the like, and a halogen-based anhydrous compound such as tetrabromophthalic anhydride (TBPA), chlorendic anhydride, or the like.

In general, the crosslinking density of an epoxy composite may be controlled by the extent of reaction of the curing agent with the epoxy group. According to the target crosslinking density, the stoichiometric ratio of the curing agent to epoxy compound may be controlled. For example, when an amine curing agent is used, the stoichimetric equivalent ratio of the epoxy to amine may be preferably controlled to 0.5 to 2.0, for example, 0.8 to 1.5 in an reaction of the amine curing agent with the epoxy group.

Though the mixing ratio of the curing agent has been explained with respect to the amine curing agent, a phenol curing agent, an acid anhydride curing agent and any curing agents for curing epoxy compounds not separately illustrated in this application but used for curing may be used by appropriately mixing a stoichiometric amount according to the chemical reaction of the epoxy functional group and the reactive functional group of the curing agent based on the concentration of the total epoxy group in the epoxy composition according to the desired range of the crosslinking density. The above-described parts are commonly known in this field.

An optional curing accelerator (catalyst) may be additionally included as occasion demands to promote the curing reaction in any epoxy compositions provided in the present invention. Any curing accelerators (catalysts) commonly used for curing an epoxy composition in this art may be used without limitation, for example, an imidazoles, a tertiary amines, a quaternary ammonium compounds, an organic acid salt, Lewis acids, a phosphorous compounds may be used as curing accelerators.

More particularly, for example, the imidazole-based curing accelerator such as dimethylbenzylamine, 2-methylimidazole (2MZ), 2-undecylimidazole, 2-ethyl-4-methylimidazole (2E4M), 2-phenylimidazole, 1-(2-cyanoethyl)-2-alkyl imidazole, and 2-heptadecylimidazole (2HDI); the tertiary amine-based curing accelerator such as benzyldimethylamine (BDMA), tris dimethylaminomethyl phenol (DMP-30), and triethylenediamine; the quaternary ammonium-based curing accelerator such as tetrabutylammonium bromide, or the like; diazabicycloundecene (DBU), or an organic acid of DBU; the phosphor compound-based curing accelerator such as triphenyl phosphine, phosphoric acid ester, or the like, and a Lewis acid such as $BF_3$-monoethylamine ($BF_3$-MEA), or the like, may be illustrated without limitation. Latent curing accelerators may also be used, which are provided by microcapsulating the accelerators and forming complex salts with accelerators, for example. These compounds may be used alone or a mixture of two or more thereof according to curing conditions.

The mixing amount of the curing accelerator may be a commonly applied mixing amount in this art without limitation. For example, 0.1 to 10 phr (parts per hundred parts of resin, parts by weight based on 100 parts by weight of the epoxy compound), for example, 0.2 to 5 phr of the curing accelerator based on the epoxy compound may be used. The above-described range of the curing accelerator may be preferably used in consideration of curing reaction accelerating effect and the control of curing reaction rate. Through using the above-described range of the curing accelerator, the curing may be rapidly achieved, and the improvement of working throughput may be expected.

When the reaction catalyst for alkoxysilyl group is included in the curing catalyst-containing composition and a composition according to any embodiments of the present invention, the reaction catalyst for alkoxysilyl group may be at least one selected from the group consisting of at least one inorganic acid selected from the group consisting of, for example, nitric acid, sulfuric acid, hydrochloric acid, acetic acid and phosphoric acid, ammonia, KOH, $NH_4OH$, amine, a transition metal alkoxide, and a tin compound (for example, dibutyltin dilaurate and/or tin(II) 2-ethylhexanoate, or the like), without limitation. The mixing ratio of the reaction catalyst for alkoxysilyl group is not specifically limited, however 0.01 to 0.1 equivalents of the alkoxysilyl reaction catalyst may be included with respect to 1 equivalent of the alkoxysilyl group.

In the composition including the reaction catalyst for alkoxysilyl group, water may be additionally included to increase the efficiency of the alkoxysilyl reaction catalyst. The mixing ratio of is not specifically limited, however 0.01 to 20 equivalents of water may be included with respect to 1 equivalent of the alkoxysilyl group.

In the epoxy composition, other additives such as a releasing agent, a surface treating agent, a flame retardant, a plasticizer, bactericides, a leveling agent, a defoaming agent, a colorant, a stabilizer, a coupling agent, a viscosity controlling agent, a diluent, or the like may be mixed to control the physical properties of the epoxy composition within the range of undamaging the physical properties of the epoxy composition as occasion demands.

As described above, the term "epoxy composition" used in the present application is understood to include an epoxy compound of the present invention and other constituents composing the epoxy composition, for example, an optional curing agent, a curing accelerator (catalyst), an inorganic material (filler) (for example, inorganic particles and/or a fiber), other common epoxy compounds, a solvent and other additives mixed as occasion demands in this field. In general, the solvent may be optionally used to control the amount and/or the viscosity of the solid content of the epoxy composition in consideration of the processability of the epoxy composition, and the like. In addition, in the "epoxy composition" according to any embodiments of the present invention, a polymer type epoxy compound as described above may be included.

The epoxy composition provided in accordance with an exemplary embodiment of the present invention may be used as an electronic material. The electronic material may include, for example, a substrate for semiconductor, a film, a prepreg, a laminate obtained by placing a metal layer on a base layer formed by using the composition of the present invention, a substrate, an encapsulating material (a packaging material), a build-up film (substrate), a printed circuit board, or the like. In addition, the epoxy composition may be used in various applications such as an adhesive, a paint composition and a composite material. In accordance with other exemplary embodiments of the present invention, an electronic material including or manufactured by using a composition including the alkoxysilylated epoxy compound of the present invention is provided. Further, a semiconductor apparatus including or manufactured by using the electronic material, is provided. Particularly, the semiconductor apparatus may be a semiconductor apparatus including a printed circuit board (for example, for installing a semiconductor device) including or manufactured by using the composition including the alkoxysilylated epoxy compound of the present invention and/or may be a semiconductor apparatus including a semiconductor packaging material. In addition, a curing agent, an adhesive, a paint composition or a composite material including or manufactured by using any epoxy compositions provided in any embodiments of the present invention, may be provided.

In accordance with other exemplary embodiments of the present invention, a cured product including or manufactured by using the epoxy composition provided in accordance with an exemplary embodiment of the present invention may be provided. In the case that applying the epoxy composition provided in an exemplary embodiment of the present invention is practically used, for example, when the epoxy composition is applied as the electronic material, or the like, a cured product formed of the epoxy composition may be used. In this art, the cured product formed of the composition including the epoxy compound and the filler of the inorganic component may be commonly referred to as a composite.

The alkoxysilylated epoxy compound provided in above-described exemplary embodiments of the present invention may show good heat resistance in the composite and/or good flame retardant property in the cured product.

Particularly, the composite may exhibit a low CTE, for example, 15 ppm/° C. or less, for example, 12 ppm/° C. or less, for example, 10 ppm/° C. or less, for example, 8 ppm/° C. or less, for example, 6 ppm/° C. or less, for example, 4 ppm/° C. or less. The physical properties of the composite are good when the CTE value is small, and the lower value of the CTE is not particularly delimited.

For example, a composite including any alkoxysilylated epoxy compounds in accordance with exemplary embodiments of the present invention as the epoxy compound, and a glass fiber, for example, an E-glass fiber and/or a T-glass fiber as the inorganic material, and having the resin content (the resin content may or may not include inorganic particles) of 30 wt % to 60 wt % may have a CTE of 10 ppm/° C. or less, for example, 8 ppm/° C. or less, for example, 6 ppm/° C. or less, for example, 4 ppm/° C. or less.

In addition, for example, a composite including an alkoxysilylated epoxy compound in accordance with exemplary embodiments of the present invention as the epoxy compound, and inorganic particles as the inorganic material, for example, silica particles of 60 wt % to 80 wt %, for example, 70 wt % to 80 wt %, may have a CTE of 20 ppm/° C. or less, for example, 15 ppm/° C. or less, for example, 10 ppm/° C. or less, for example, 8 ppm/° C. or less, for example, 6 ppm/° C. or less, for example, 4 ppm/° C. or less.

In addition, Tg of the composite (a cured product including an inorganic material) according to the present invention may be higher than 100° C., for example, 130° C. or over, in addition, for example, 250° C. or over. Otherwise, the composite may be Tg-less. The physical properties of the composite are good when the Tg value is large, and the upper value of the Tg is not particularly delimited.

Meanwhile, the cured product formed by using the alkoxysilylated isocyanurate epoxy compound itself (a cured product excluding an inorganic material) according to the present invention may have a CTE of 50 ppm/° C. to 150 ppm/° C.

In the present application, the values delimited by the range include the lower limit, the upper limit, any sub ranges in the range, and all numerals included in the range, unless otherwise specifically stated. For example, C1 to C10 is understood to include all of C1, C2, C3, C4, C5, C6, C7, C8, C9 and C10. In addition, in the case when the lower limit or the upper limit of the numerical range is not defined, it would be found that the smaller or the larger value may provide the better properties. In addition, in the case when the limit is not defined, any values may be included. For example, CTE of 4 ppm/° C. or less is understood to include every values in the range such as the CTE of 4, 3.5, 3, 2.7, 2, 1.4, 1, 0.5 ppm/° C., or the like.

3. Method of Preparing Alkoxysilylated Epoxy Compounds

The alkoxysilylated epoxy compounds of the above Formulae AI to HI according to the present invention may be prepared by the following six methods, and each of the methods will be explained in detail.

A. Method of Preparing an Alkoxysilylated Epoxy Compound Having a Substituent of —(CH$_2$)$_z$—SiR$_1$R$_2$R$_3$ (1) Method 1

The alkoxysilylated epoxy compound having a substituent of —(CH$_2$)$_z$—SiR$_1$R$_2$R$_3$ may be prepared by the alkenylation and epoxidation of a starting material (first step) and alkoxysilylation (second step).

In the first step, one of the starting materials of the following Formulae AS to HS reacts with an alkenyl compound of the following Formula M1 (alkenylation), and subsequently, epichlorohydrin is added and reacted in situ (epoxidation) to obtain Intermediate Product (11).

In the first step, 1 to 10 equivalents of an alkenyl group of the alkenyl compound of the following Formula M1 is added with respect to 1 equivalent of a hydroxyl group of one of the starting materials of the following Formulae AS to HS to conduct the reaction. Then, 1 to 10 equivalents of epichlorohydrin is added in situ with respect to 1 equivalent of a hydroxyl group of one of the starting materials of the following Formulae AS to HS to conduct the reaction. The reaction of the first step may be performed in the presence of a base and an optional solvent. In addition, the reaction of the first step is performed at a temperature from room temperature to 100° C. for 1 to 120 hours to obtain Intermediate Product (11).

[Starting Material]

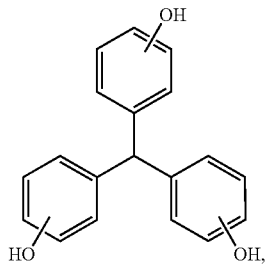
AS

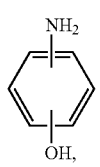
BS

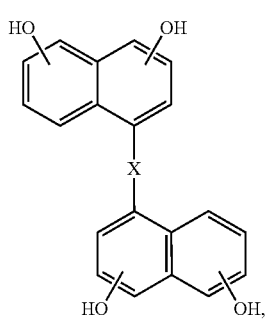
CS

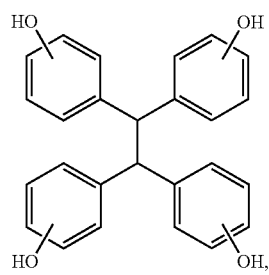
DS

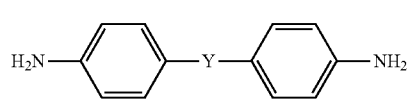
ES

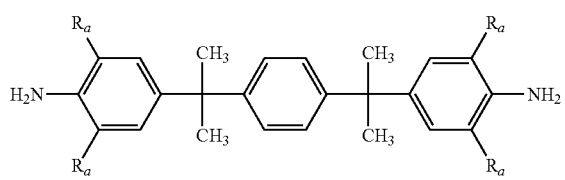
FS

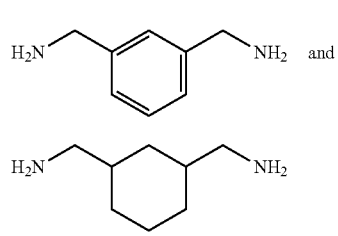
GS and

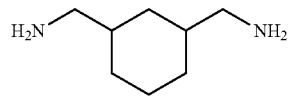
HS

A meta position of oxygen in Formula BS may be substituted with a linear or branched C1-C10 alkyl group.

X in Formula CS is a direct linkage, —CH$_2$— or

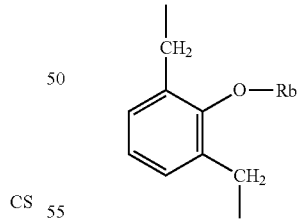

where Rb is H or a C1-C3 alkyl group.

Y in Formula ES is —CH$_2$—, —C(CH$_3$)$_2$—, —C(CF$_3$)$_2$—, —S— or —SO$_2$—.

Ra in Formula FS is H or a C1-C3 alkyl group.

X—(CH$_2$)$_{z-2}$—CH=CH$_2$ [Formula M1]

In Formula M1, X is a halide of Cl, Br or I, —O—SO$_2$—CH$_3$, —O—SO$_2$—CF$_3$, or —O—SO$_2$—C$_6$H$_4$—CH$_3$, and z is an integer from 3 to 10.

[Intermediate Product (11)]

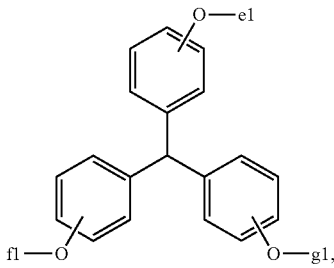
A11

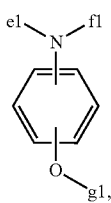
B11

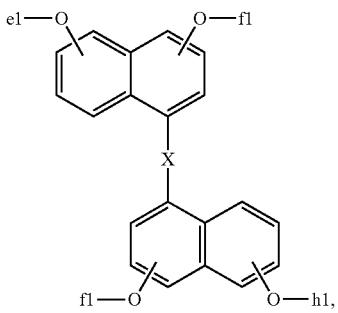
C11

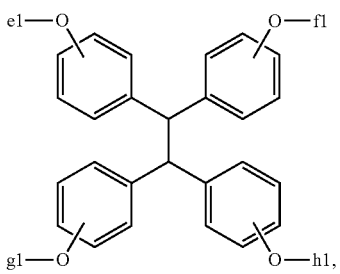
D11

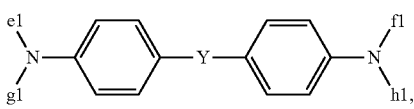
E11

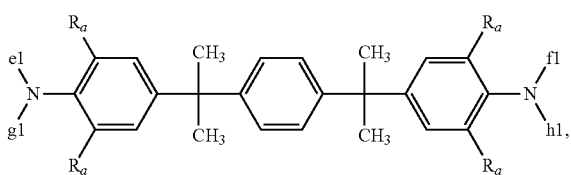
F11

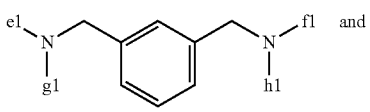
G11 and

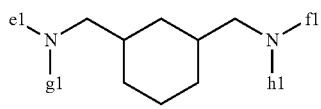
H11

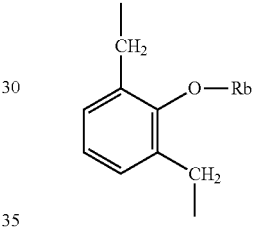

One or two of substituents e1, f1, and g1 in Formula A11 or B11 are the above Formula S1, and at least one thereof is —$(CH_2)_{z-2}$—CH=$CH_2$ where z is an integer from 3 to 10 and may be hydrogen when an unreacted site is present. Preferably, one or two of the substituents are the above Formula S1, and at least one thereof is —$(CH_2)_{z-2}$—CH=$CH_2$ where z is an integer from 3 to 10.

One to three of substituents e1, f1, g1, and h1 in Formulae C11 to H11 are the above Formula S1, at least one thereof is —$(CH_2)_{z-2}$—CH=$CH_2$ where z is an integer from 3 to 10, and may be hydrogen when an unreacted site is present. Preferably, one to three of the substituents have the form of the above Formula S1, and at least one thereof is —$(CH_2)_{z-2}$—CH=$CH_2$ where z is an integer from 3 to 10.

A meta position of oxygen in Formula B11 may be substituted with a linear or branched C1-C10 alkyl group.

X in Formula C11 is a direct linkage, —$CH_2$— or where Rb is H or a C1-C3 alkyl group.

Y in Formula E11 is —$CH_2$—, —$C(CH_3)_2$—, —$C(CF_3)_2$—, —S— or —$SO_2$—.

Ra in Formula F11 is H or a C1-C3 alkyl group.

The reaction temperature and the reaction time of the first step are dependent on the kind of reactants materials. For example, the reaction of the first step is performed at a temperature from room temperature (for example, 15° C. to 25° C.) to 100° C. for 1 to 120 hours to obtain Intermediate Product (11).

The base used may include, for example, KOH, NaOH, $K_2CO_3$, $Na_2CO_3$, $KHCO_3$, $NaHCO_3$, NaH, triethylamine, and diisopropylethylamine, without limitation. These bases may be used alone or as a combination of two or more. 1 to 5 equivalents of the base may be used based on 1 equivalent of the hydroxyl group of the starting material in consideration of reaction efficiency. The base may be separately added during the alkenylation step and the epoxidation step, or the total amount of the base required for the alkenylation and the epoxidation may be added in the alkenylation step one time.

The solvents may be optionally used as occasion demands during the first step reaction. For example, when the viscosity of the reacting materials at a reaction temperature is appropriate for conducting the reaction without a solvent in the first step reaction, the solvent may not be necessary. That is, when the viscosity of the reacting materials is sufficiently low that the mixing and the stirring of the reacting materials may be conducted smoothly without a solvent, use of the solvent may not be necessary. This state may be easily understood by a person skilled in the art. When the solvent is used, any organic solvents that may easily dissolve the reacting materials, that do not have any adverse effects, and that may be easily removed after the reaction, may be used without limitation. For example, acetonitrile, tetrahydrofuran (THF), methyl ethyl ketone (MEK), dimethylformamide (DMF), dimethyl sulfoxide (DMSO), methylene chloride (MC), $H_2O$, or the like may be used. These solvents may be used alone or as a mixture of two or more thereof. The amount of the solvent may not be limited to a specific range, and an appropriate amount of the solvent may be used within a range for sufficiently dissolving the reactants and not adversely affecting the reaction. A person skilled in the art may select an appropriate amount of the solvent in consideration of the above-mentioned points.

In the second step, the alkoxysilylated epoxy compound of Formulae AI to HI having a substituent of $-(CH_2)_z-SiR_1R_2R_3$ may be prepared by alkoxysilylation of the Intermediate Product (11) in the presence of a metal catalyst. In the second step, the alkenyl group of the above Intermediate Product (11) and the alkoxysilane react by the equivalent ratios according to stoichiometry. Thus, the reaction of the above Intermediate Product (11) and the alkoxysilane of the following Formula M2 may be performed by using 1 to 5 equivalents of the alkoxysilane of the following Formula M2 based on 1 equivalent of the alkenyl group of the above Intermediate Product (11).

$HSiR_1R_2R_3$ [Formula M2]

In the above Formula M2, at least one of $R_1$ to $R_3$ is a C1-C10 alkoxy group, preferably, ethoxy group, the remainder thereof are C1-C10 alkyl groups, and the alkoxy group and the alkyl group are a linear chain or a branched chain alkoxy group or alkyl group.

The reaction temperature and the reaction time of the second step are different according to reacting materials. For example, the alkoxysilylated epoxy compound of the above Formulae AI to HI having a substituent of $-(CH_2)_z-SiR_1R_2R_3$ may be prepared by performing at from room temperature (for example, 15° C. to 25° C.) to 120° C. for 1 to 72 hours.

In the second step reaction, the metal catalyst may include, for example, a platinum catalyst such as $PtO_2$ or $H_2PtCl_6$ (chloroplatinic acid), without limitation. $1 \times 10^{-4}$ to 0.05 equivalents of the platinum catalyst with respect to 1 equivalent of the alkenyl group of Intermediate Product (11) may be preferably used in consideration of reaction efficiency.

The solvents may be optionally used as occasion demands in the second step reaction. For example, when the viscosity of the reacting materials at a reaction temperature is appropriate for conducting the reaction without a solvent in the second step reaction, the solvent may not be necessary. That is, when the viscosity of the reacting materials is sufficiently low that the mixing and the stirring of the reacting materials may be conducted smoothly without the solvent, the use of a solvent may not be necessary. This state may be easily understood by a person skilled in the art. When the solvent is used, any aprotic solvents that may easily dissolve the reacting materials, that do not have any adverse effects, and that may be easily removed after the reaction, may be used without limitation. For example, toluene, acetonitrile, THF, MEK, DMF, DMSO, MC, or the like, may be used. These solvents may be used alone or as a mixture of two or more thereof. The amount of the solvent may not be limited to a specific range, and an appropriate amount of the solvent may be used within a range for sufficiently dissolving the reacting materials and not adversely affecting the reaction. A person skilled in the art may select an appropriate amount of a solvent considering the above-mentioned points.

The reaction scheme of the epoxy compound of Formula AI is as follows. (In the case that a structure having a ratio of the epoxy group and the alkoxysilyl group is 2:1 is synthesized)

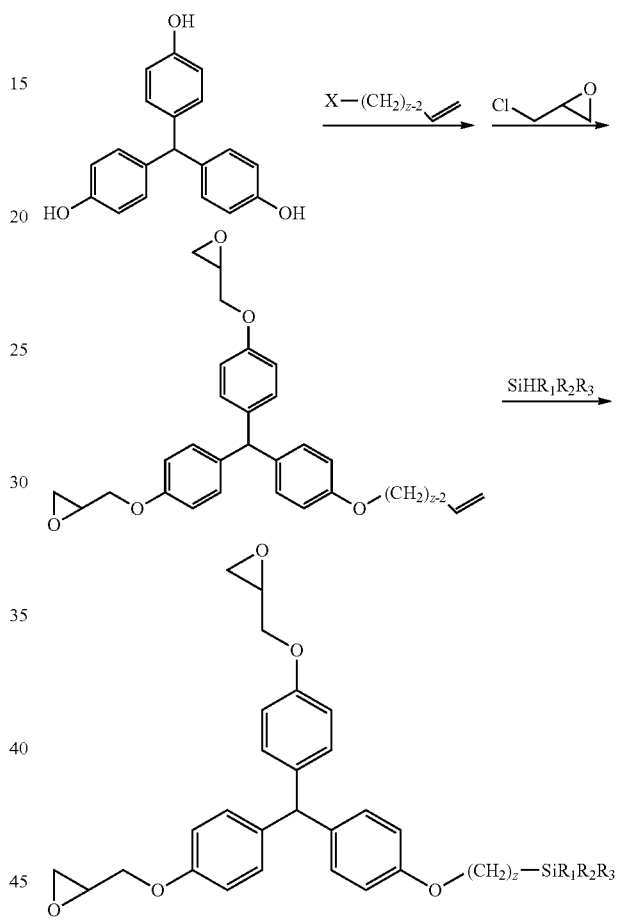

The epoxy compounds of Formulae AI to HI have an epoxy group having a structure of Formula S1 and at least one alkoxy Formula S1 as defined in the epoxy compounds of the above Formulae AI to HI. However, when an unreacted site is present in each step, hydrogen and/or an alkenyl group may be present for a to c or a to d in a target product. The substitution degree of the epoxy group and the alkoxysilyl group in Formulae AI to HI in each reaction step may be controlled by controlling the equivalents of reacting materials and the reaction temperature. A person skilled in the art may select appropriate conditions in consideration of the reactivity from the above-mentioned points. The same conditions may be applied in subsequent methods 2 to 6.

Meanwhile, in the reaction process of the first step, the epoxidized Intermediate Product (11) may react with the hydroxyl group of the starting material and form the polymers illustrated in the following Formulae AP1(1) to HP1 (1).

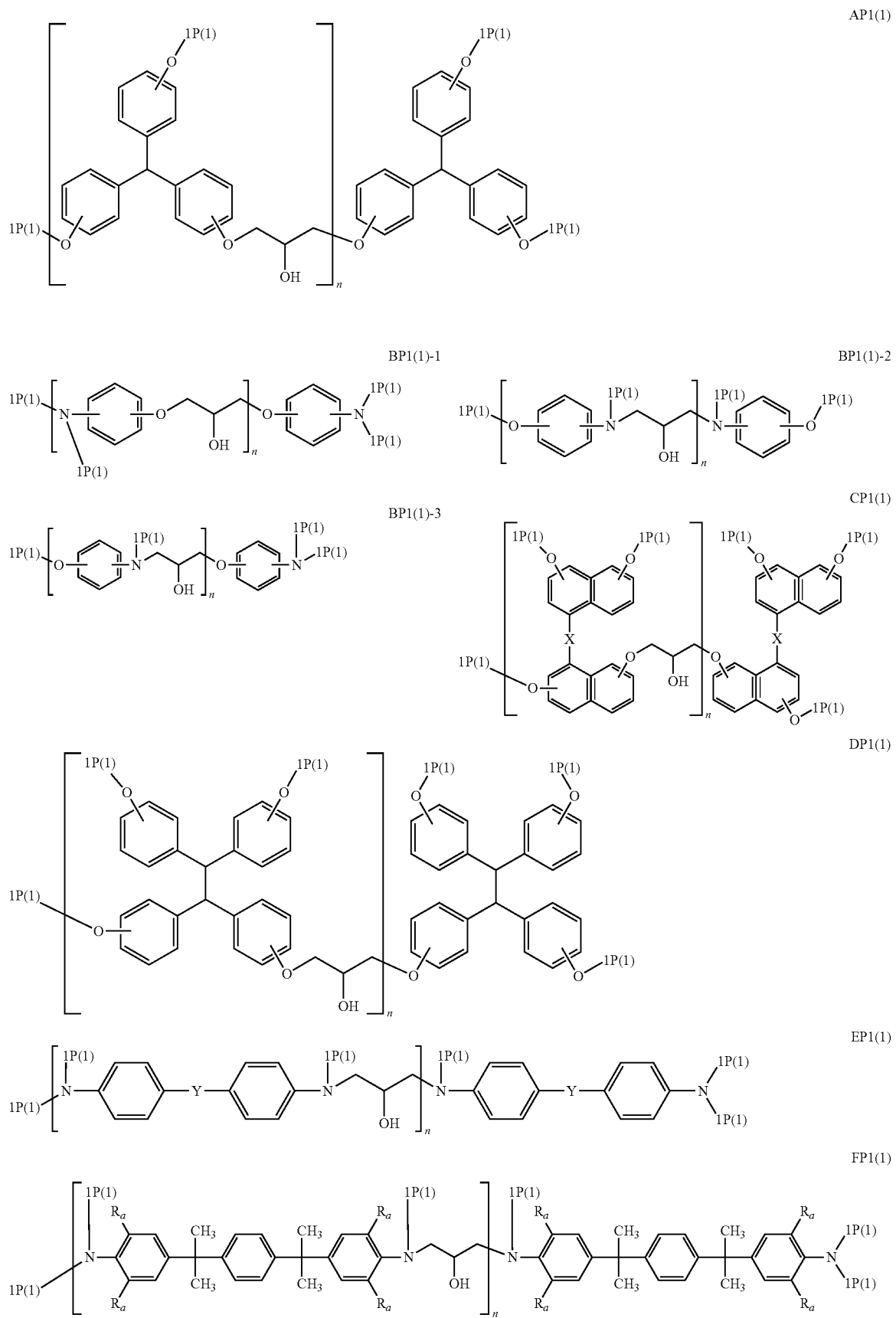

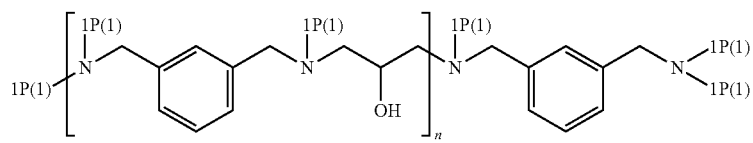

GP1(1)

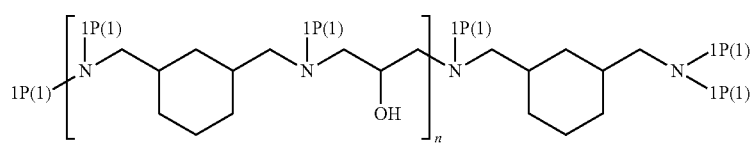

HP1(1)

In the above Formulae, each of 1P(1) is independently selected from an epoxy group of the above Formula S1, —(CH$_2$)$_{z-2}$—CH=CH$_2$ where z is an integer from 3 to 10, and hydrogen. Particularly, at least one of the epoxy group of the above Formula S1 and at least one of —(CH$_2$)$_{z-2}$—CH=CH$_2$ where z is an integer from 3 to 10 are included, and hydrogen may be included when an unreacted site is present during synthesis. Preferably, each of 1P(1) is independently at least one epoxy group of the above Formula S1 and at least one —(CH$_2$)$_{z-2}$—CH=CH$_2$ where z is an integer from 3 to 10.

A meta position of oxygen in Formulae BP1(1)-1 to BP1(1)-3 may be substituted with a linear or branched C1-C10 alkyl group.

X in Formula CP1(1) is a single bond, —CH$_2$— or

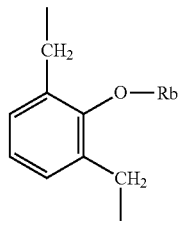

where Rb is H or a C1-C3 alkyl group.

Y in Formula EP1(1) is —CH$_2$—, —C(CH$_3$)$_2$—, —C(CF$_3$)$_2$—, —S— or —SO$_2$—.

Ra in Formula FP1(1) is H or a C1-C3 alkyl group.

n is an integer from 1 to 100.

The second step is performed with respect to the polymer prepared in the first step described above, and polymers illustrated by the following Formulae AP1(2) to HP1(2) may be formed in the second step.

AP1(2)

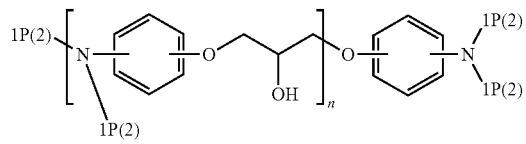

BP1(2)-1

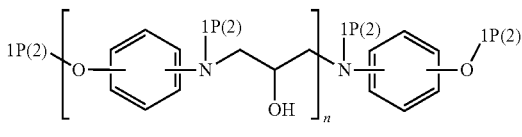

BP1(2)-2

BP1(2)-3

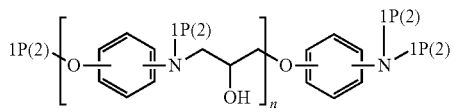

CP1(2)

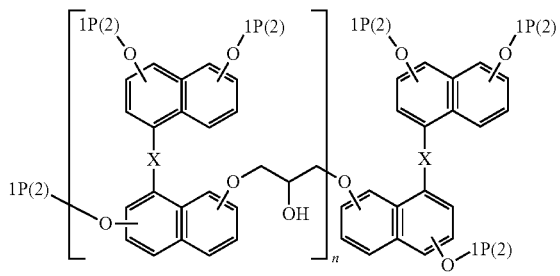

DP1(2)

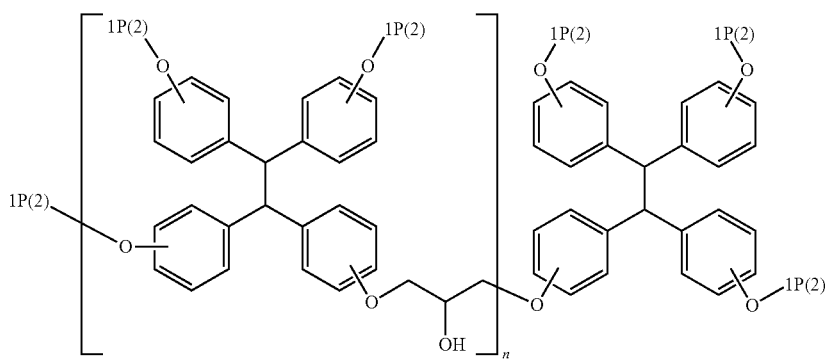

EP1(2)

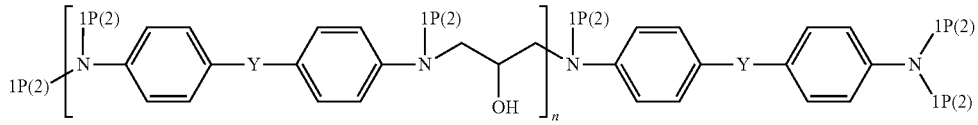

FP1(2)

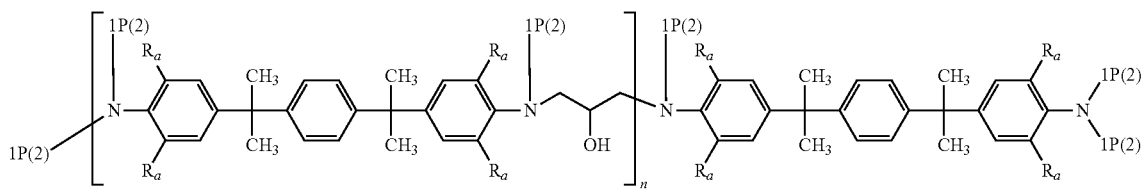

GP1(2)

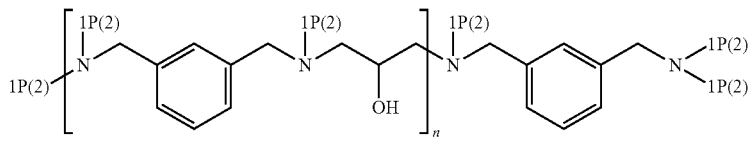

HP1(2)

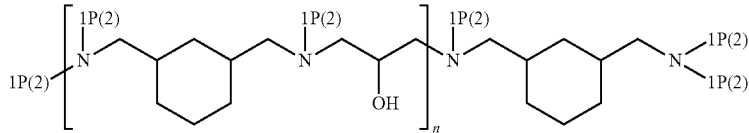

In the above Formulae, each of 1P(2) is independently selected from an epoxy group of the above Formula S1, the above Formula S2, $-(CH_2)_{z-2}-CH=CH_2$ where z is an integer from 3 to 10, and hydrogen. Particularly, at least one of the epoxy group of the above Formula S1 and at least one of the above Formula S2 are included, and $-(CH_2)_{z-2}-CH=CH_2$ where z is an integer from 3 to 10 and/or hydrogen may be used when an unreacted site is present during synthesis. Preferably, each of 1P(2) is independently at least one epoxy group of the above Formula S1 and at least one of the above Formula S2.

A meta position of oxygen in Formulae BP1(2)-1 to BP1(2)-3 may be substituted with a linear or branched C1-C10 alkyl group.

X in Formula CP1(2) is a direct linkage, —CH₂— or

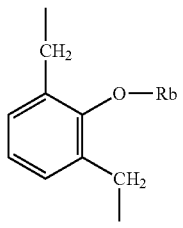

where Rb is H or a C1-C3 alkyl group.

Y in Formula EP1(2) is —CH₂—, —C(CH₃)₂—, —C(CF₃)₂—, —S— or —SO₂—.

Ra in Formula FP1(2) is H or a C1-C3 alkyl group.

n is an integer from 1 to 100.

(2) Method 2

The alkoxysilylated epoxy compound having a substituent of —(CH₂)$_z$—SiR₁R₂R₃ may be prepared by the alkenylation (first step) of a starting material, epoxidation (second step), alkenylation (third step), and alkoxysilylation (fourth step).

In the first step, one of the starting materials of the above Formulae AS to HS reacts with an alkenyl compound of the above Formula M1 for the alkenylation of a hydroxyl group of the starting material and the preparation of Intermediate Product (21) of the following Formulae A21 to H21. In this case, 1 to 10 equivalents of an alkenyl group is added with respect to 1 equivalent of the hydroxyl group of the starting material for the reaction. In addition, the first step is performed in the presence of a base and an optional solvent at from room temperature to 100° C. for 1 to 120 hours.

[Intermediate Product (21)]

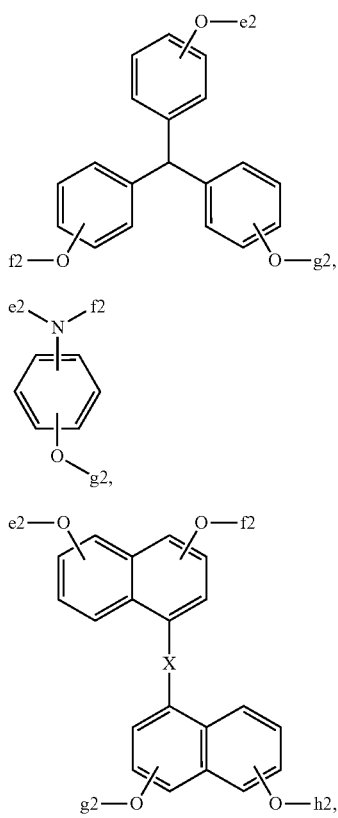

A21

B21

C21

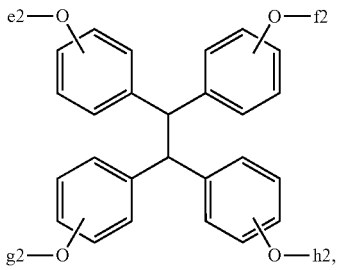

D21

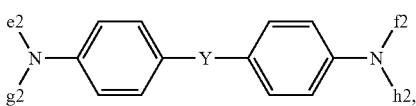

E21

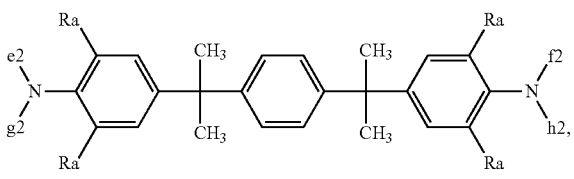

F21

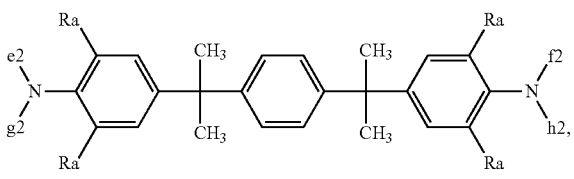

G21 and

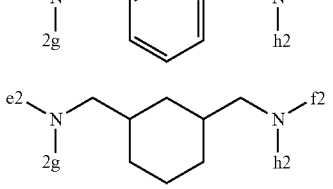

H21

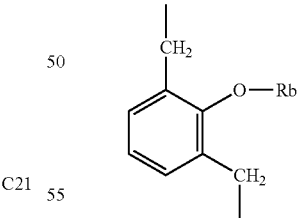

One or two of substituents e2 to g2 of the above Formulae A21 to B21 are —(CH₂)$_{z-2}$—CH═CH₂ where z is an integer from 3 to 10, and the remainder thereof are hydrogen.

One to three of substituents e2 to h2 of the above Formulae C21 to H21 are —(CH₂)$_{z-2}$—CH═CH₂ where z is an integer from 3 to 10, and the remainder thereof are hydrogen.

A meta position of oxygen in Formulae B21 to H21 may be substituted with a linear or branched C1-C10 alkyl group.

X in Formula C21 is a direct linkage, —CH₂— or where Rb is H or a C1-C3 alkyl group.

Y in Formula E21 is —CH₂—, —C(CH₃)₂—, —C(CF₃)₂—, —S— or —SO₂—.

Ra in Formula F21 is H or a C1-C3 alkyl group.

The reaction temperature and the reaction time of the first step are dependent on the kind of reacting materials. For example, the reaction of the first step is performed at a temperature from room temperature (for example, 15° C. to 25° C.) to 100° C. for 1 to 120 hours to obtain the above Intermediate Product (21).

The base used may include, for example, KOH, NaOH, $K_2CO_3$, $Na_2CO_3$, $KHCO_3$, $NaHCO_3$, NaH, triethylamine, and diisopropylethylamine, without limitation. These bases may be used alone or as a combination thereof. 1 to 5 equivalents of the base may be used based on 1 equivalent of the hydroxyl group of the starting material when considering reaction efficiency.

The solvents may be optionally used as occasion demands in the first step reaction. For example, when the viscosity of the reacting materials at a reaction temperature is appropriate for conducting the reaction without a solvent in the first step reaction, the solvent may not be necessary. That is, when the viscosity of the reacting materials is sufficiently low that the mixing and the stirring of the reacting materials may be conducted smoothly without a solvent, use of the solvent may not be necessary. This state may be easily understood by a person skilled in the art. When the solvent is used, any organic solvents that may easily dissolve the reacting materials, that do not have any adverse effects, and that may be easily removed after the reaction, may be used without limitation. For example, acetonitrile, THF, MEK, DMF, DMSO, MC, $H_2O$, or the like may be used. These solvents may be used alone or as a mixture of two or more thereof. The amount of the solvent may not be limited to a specific range, and an appropriate amount of the solvent may be used within a range for sufficiently dissolving the reacting materials and not adversely affecting the reaction. A person skilled in the art may select an appropriate amount of the solvent in consideration of the above-mentioned points.

In the second step, the alkenyl group of the above Intermediate Product (21) is oxidized and epoxidized to prepare one Intermediate Product (22) of the following Formulae A22 to H22. In the second step, the reaction is performed using 1 to 10 equivalents of a peroxide group of a peroxide with respect to 1 equivalent of the alkenyl group of the above Intermediate Product (21) in the presence of an optional base and an optional solvent.

The reaction temperature and the reaction time of the second step are dependent on the kind of reacting materials. For example, the reaction of the second step is performed at a temperature from room temperature (for example, 15° C. to 25° C.) to 100° C. for 1 to 120 hours to obtain the following Intermediate Product (22).

[Intermediate Product (22)]

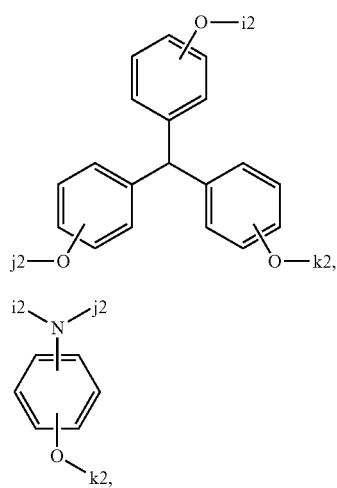

A22

B22

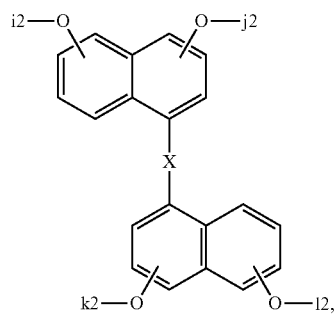

C22

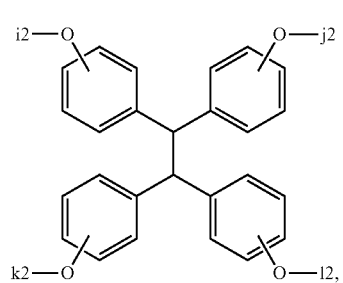

D22

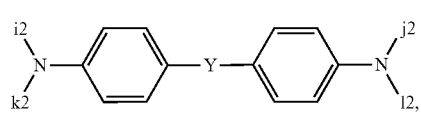

E22

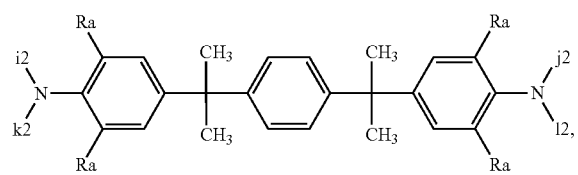

F22

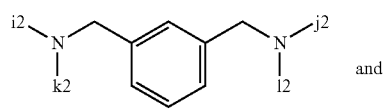

G22 and

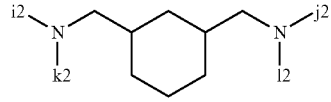

H22

One or two of substituents i2 to k2 of the above Formulae A22 to B22 are Formula S1, and at least one thereof is hydrogen and may be $-(CH_2)_{z-2}-CH=CH_2$ where z is an integer from 3 to 10 when an unreacted site is present. Preferably, one or two of substituents i2 to k2 are Formula S1, and at least one thereof is hydrogen.

One to three of substituents i2 to l2 of the above Formulae C22 to H22 are Formula S1, and at least one thereof is hydrogen and may be $-(CH_2)_{z-2}-CH=CH_2$ where z is an integer from 3 to 10 when an unreacted site is present. Preferably, one to three of substituents i2 to k2 are Formula S1, and at least one thereof is hydrogen.

A meta position of oxygen in Formula B22 may be substituted with a linear or branched C1-C10 alkyl group.

X in Formula C22 is a direct linkage, —CH$_2$— or

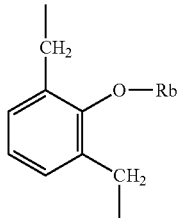

where Rb is H or a C1-C3 alkyl group.

Y in Formula E22 is —CH$_2$—, —C(CH$_3$)$_2$—, —C(CF$_3$)$_2$—, —S— or —SO$_2$—.

Ra in Formula F22 is H or a C1-C3 alkyl group.

The peroxide may include, for example, meta-chloroperoxybenzoic acid (CPBA), H$_2$O$_2$, and dimethyldioxirane (DMSO), without limitation. These peroxide compounds may be used alone or as a combination thereof.

In the second step, the base may be optionally used as occasion demands. The base is used to neutralize an acid component that may remain after reaction according to the kind of the peroxide. The base used may include, for example, KOH, NaOH, K$_2$CO$_3$, KHCO$_3$, NaHCO$_3$, triethylamine, and diisopropylethylamine, without limitation. These bases may be used alone or as a combination thereof. If used, 0.1 to 5 equivalents of the base may be used based on the alkenyl group of Intermediate Product A21 in consideration of reaction efficiency.

The solvents may be optionally used as occasion demands in the second step reaction. For example, when the viscosity of the reacting materials at a reaction temperature is appropriate for conducting the reaction without a solvent in the first step reaction, the solvent may not be necessary. That is, when the viscosity of the reacting materials is sufficiently low that the mixing and the stirring of the reacting materials may be conducted smoothly without a solvent, use of the solvent may not be necessary. This state may be easily understood by a person skilled in the art. When the solvent is used, any organic solvents that may easily dissolve the reacting materials, that do not have any adverse effects, and that may be easily removed after the reaction, may be used without limitation. For example, acetonitrile, THF, MEK, DMF, DMSO, MC, H$_2$O, or the like may be used. These solvents may be used alone or as a mixture of two or more thereof. The amount of the solvent may not be limited to a specific range, and an appropriate amount of the solvent may be used within a range for sufficiently dissolving the reacting materials and not adversely affecting the reaction. A person skilled in the art may select an appropriate amount of the solvent in consideration of the above-mentioned points.

In the third step, through the reaction of the above Intermediate Product (22) and the alkenyl compound of the above Formula M1, the hydroxyl group of Intermediate Product (22) is alkenylated, and one Intermediate Product (23) of the following Formulae A23 to H23 is prepared. In this case, the reaction of the above Intermediate Product (22) and the alkenyl compound of the above Formula M1 is performed so that 1 to 10 equivalents of an alkenyl group based on 1 equivalent of the hydroxyl group of Intermediate Product (22) is used in the presence of a base and an optional solvent to obtain the following Intermediate Product (23).

[Intermediate Product (23)]

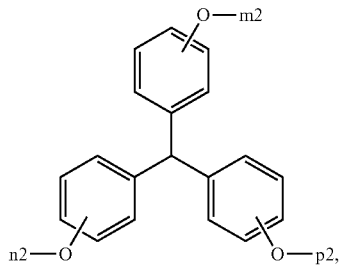
A23

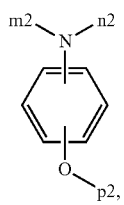
B23

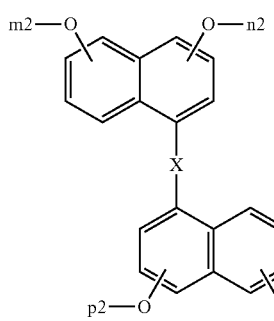
C23

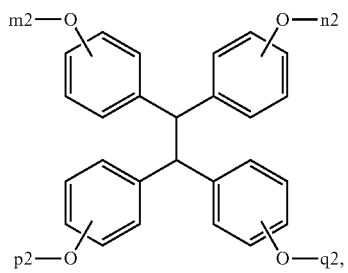
D23

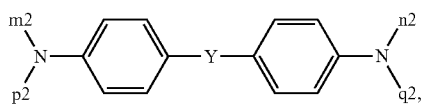
E23

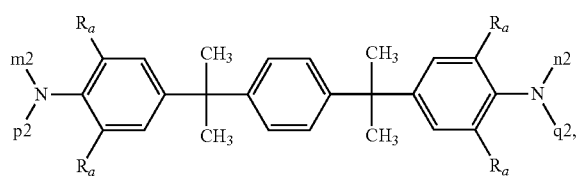
F23

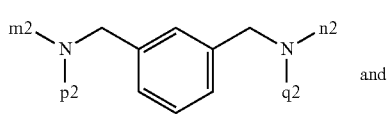
G23 and

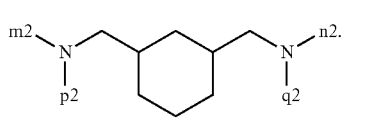
H23

One or two of substituents m2, n2 and p2 in the above Formula A23 or B23 are the above Formula S1, and at least one thereof is —$(CH_2)_{z-2}$—CH=$CH_2$ where z is an integer from 3 to 10 and may be hydrogen when an unreacted site is present. Preferably, one or two of the substituents are the above Formula S1, and at least one thereof is —$(CH_2)_{z-2}$—CH=$CH_2$ where z is an integer from 3 to 10.

One to three of substituents m2, n2, p2, and q2 in the above Formulae C23 or H23 are the above Formula S1, and at least one thereof is —$(CH_2)_{z-2}$—CH=$CH_2$ where z is an integer from 3 to 10 and may be hydrogen when an unreacted site is present. Preferably, one to three of the substituents are the above Formula S1, and at least one thereof is —$(CH_2)_{z-2}$—CH=$CH_2$ where z is an integer from 3 to 10.

A meta position of oxygen in Formula B23 may be substituted with linear or branched C1-C10 alkyl group.

X in Formula C23 is a direct linkage, —$CH_2$— or

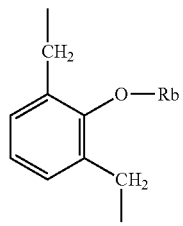

where Rb is H or a C1-C3 alkyl group.

Y in Formula E23 is —$CH_2$—, —$C(CH_3)_2$—, —$C(CF_3)_2$—, —S— or —$SO_2$—.

Ra in Formula F23 is H or a C1-C3 alkyl group.

The reaction temperature and the reaction time of the third step are dependent on the kind of reacting materials. For example, the reaction of the third step is performed at a temperature from room temperature (for example, 15° C. to 25° C.) to 100° C. for 1 to 120 hours to obtain the above Intermediate Product (23).

The base used may include, for example, KOH, NaOH, $K_2CO_3$, $Na_2CO_3$, $KHCO_3$, $NaHCO_3$, NaH, triethylamine, and diisopropylethylamine, without limitation. These bases may be used alone or as a combination thereof. 1 to 5 equivalents of the base may be used based on 1 equivalent of the hydroxyl group of Intermediate Product (22) in consideration of reaction efficiency.

The solvents may be optionally used as occasion demands in the third step reaction. For example, when the viscosity of the reacting materials at a reaction temperature is appropriate for conducting the reaction without a solvent in the first step reaction, the solvent may not be necessary. That is, when the viscosity of the reacting materials is sufficiently low that the mixing and the stirring of the reacting materials may be conducted smoothly without a solvent, use of the solvent may not be necessary. This state may be easily understood by a person skilled in the art. When the solvent is used, any organic solvents that may easily dissolve the reacting materials, that do not have any adverse effects, and that may be easily removed after the reaction, may be used without limitation. For example, acetonitrile, THF, MEK, DMF, DMSO, MC, $H_2O$, or the like may be used. These solvents may be used alone or as a mixture of two or more thereof. The amount of the solvent may not be limited to a specific range, and an appropriate amount of the solvent may be used within a range for sufficiently dissolving the reacting materials and not adversely affecting the reaction. A person skilled in the art may select an appropriate amount of the solvent in consideration of the above-mentioned points.

In the fourth step, the alkoxysilylated epoxy compound of Formulae AI to HI having a substituent of —$(CH_2)_z$—$SiR_1R_2R_3$ may be prepared by alkoxysilylation of the above Intermediate Product (23) in the presence of a metal catalyst. In the fourth step, the alkenyl group of the above Intermediate Product (23) and the alkoxysilane react by the equivalent ratio according to stoichiometry. Thus, the reaction of the above Intermediate Product (23) and the alkoxysilane of the following Formula M2 may be performed by using 1 to 5 equivalents of the alkoxysilane of the following Formula M2 based on 1 equivalent of the alkenyl group of the above Intermediate Product (23).

$HSiR_1R_2R_3$ [Formula M2]

In the above Formula M2, at least one of $R_1$ to $R_3$ is a C1-C10 alkoxy group, preferably ethoxy group, and the remainder thereof are linear or branched C1-C10 alkyl groups.

The reaction temperature and the reaction time of the fourth step are different according to reacting materials. For example, the alkoxysilylated epoxy compound of the above Formulae AI to HI having a substituent of —$(CH_2)_z$—$SiR_1R_2R_3$ may be prepared by performing at a temperature from room temperature (for example, 15° C. to 25° C.) to 120° C. for 1 to 72 hours.

In the fourth step reaction, the metal catalyst may include, for example, a platinum catalyst such as $PtO_2$ or $H_2PtCl_6$ (chloroplatinic acid), without limitation. $1 \times 10^{-4}$ to 0.05 equivalents of the platinum catalyst with respect to 1 equivalent of the alkenyl group of Intermediate Product (14) may be preferably used in consideration of reaction efficiency.

The solvents may be optionally used as occasion demands in the fourth step reaction. For example, when the viscosity of the reacting materials at a reaction temperature is appropriate for conducting the reaction without a solvent in the second step reaction, the solvent may not be necessary. That is, when the viscosity of the reacting materials is sufficiently low that the mixing and the stirring of the reacting materials may be conducted smoothly without the solvent, the use of a solvent may not be necessary. This state may be easily understood by a person skilled in the art. When the solvent is used, any aprotic solvents that may easily dissolve the reactants, that do not have any adverse effects, and that may be easily removed after the reaction, may be used without limitation. For example, toluene, acetonitrile, THF, MEK, DMF, DMSO, MC, or the like, may be used. These solvents may be used alone or as a mixture of two or more thereof. The amount of the solvent may not be limited to a specific range, and an appropriate amount of the solvent may be used within a range for sufficiently dissolving the reacting materials and not adversely affecting the reaction. A person skilled in the art may select an appropriate amount of a solvent in consideration of the above-mentioned points.

For example, the reaction scheme of the epoxy compound of Formula AI is as follows. (In the case that a structure having a ratio of the epoxy group and the alkoxysilyl group is 2:1 is synthesized)

(3) Method 3

The alkoxysilylated epoxy compound having a substituent of —(CH$_2$)$_z$—SiR$_1$R$_2$R$_3$ may be prepared by the alkenylation (first step) of a starting material, epoxidation (second step), and alkoxysilylation (third step).

In the first step, one of the starting materials of the above Formulae AS to HS reacts with an alkenyl compound of the above Formula M1 for the alkenylation of a hydroxyl group of the starting material and for the preparation of Intermediate Product (31). In this case, 1 to 10 equivalents of an alkenyl group is added with respect to 1 equivalent of the hydroxyl group of the starting material for the reaction. The first step is performed in the presence of a base and an optional solvent to obtain Intermediate Product (31).

[Intermediate Product (31)]

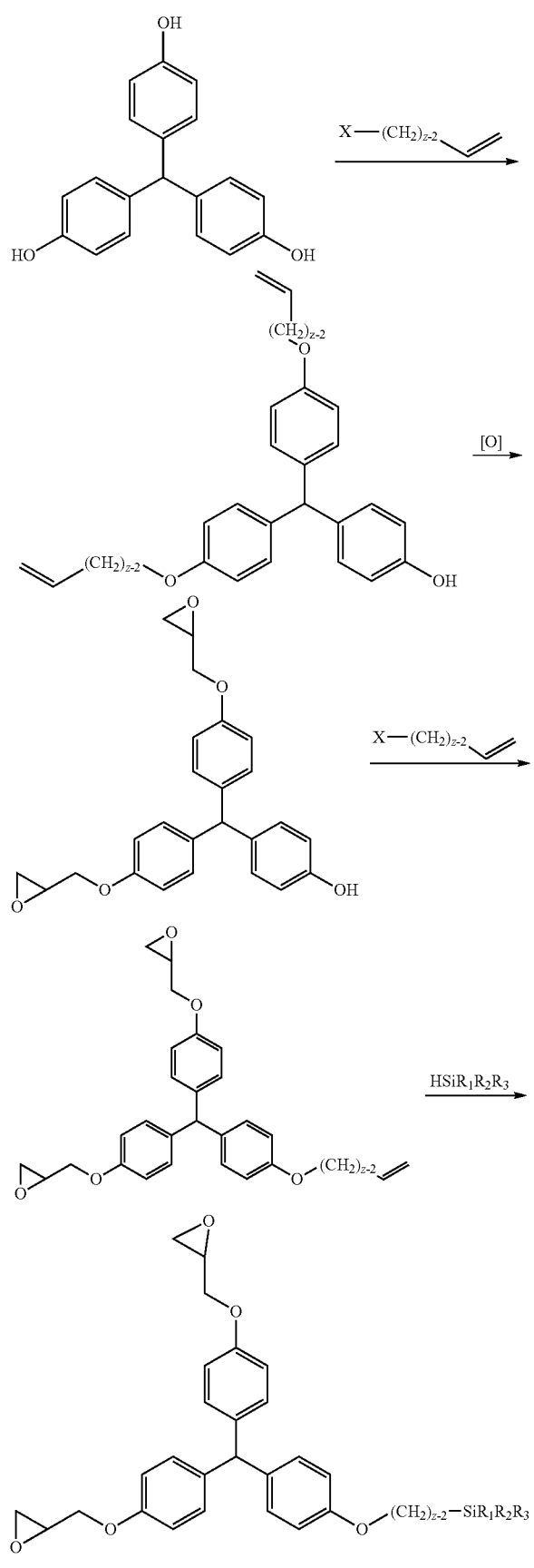

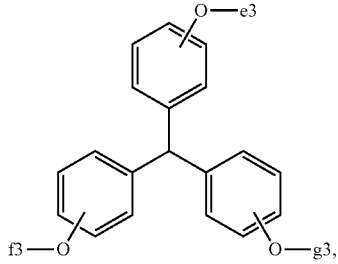
A31

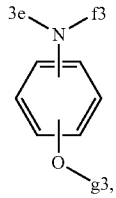
B31

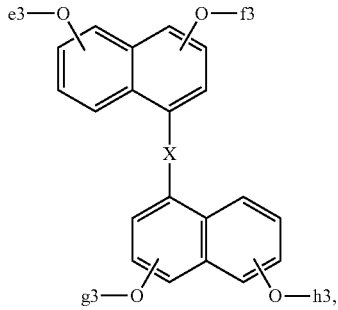
C31

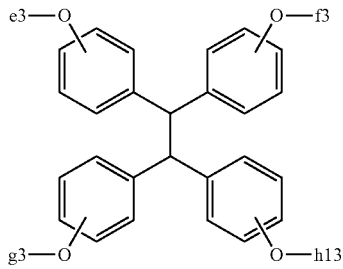
D31

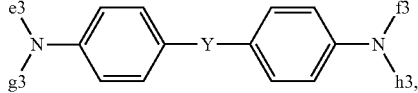
E31

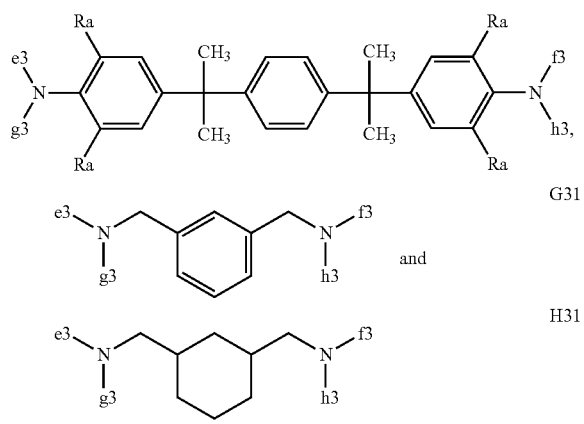

At least two, preferably three of substituents e3 to g3 of the above Formulae A31 to B31 are —(CH$_2$)$_{z-2}$—CH=CH$_2$ where z is an integer from 3 to 10, and the remainder thereof are hydrogen (when an unreacted site is present).

At least two, preferably three, more preferably four of substituents e3 to h3 of the above Formulae C31 to H31 are —(CH$_2$)$_{z-2}$—CH=CH$_2$ where z is an integer from 3 to 10, and the remainder thereof are hydrogen when an unreacted site is present.

A meta position of oxygen in Formula B31 may be substituted with a linear or branched C1-C10 alkyl group.

X in Formula C31 is a direct linkage, —CH$_2$— or

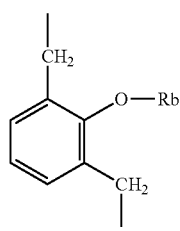

where Rb is H or a C1-C3 alkyl group.

Y in Formula E31 is —CH$_2$—, —C(CH$_3$)$_2$—, —C(CF$_3$)$_2$—, —S— or —SO$_2$—.

Ra in Formula F31 is H or a C1-C3 alkyl group.

The reaction temperature and the reaction time of the first step are dependent on the kind of reacting materials. For example, the reaction of the first step is performed at a temperature from room temperature (for example, 15° C. to 25° C.) to 100° C. for 1 to 120 hours to obtain the above Intermediate Product (31).

The base used may include, for example, KOH, NaOH, K$_2$CO$_3$, Na$_2$CO$_3$, KHCO$_3$, NaHCO$_3$, NaH, triethylamine, and diisopropylethylamine, without limitation. These bases may be used alone or as a mixture of two or more thereof. 1 to 5 equivalents of the base may be used based on 1 equivalent of the hydroxyl group of the starting material in consideration of reaction efficiency.

The solvents may be optionally used as occasion demands in the first step reaction. For example, when the viscosity of the reacting materials at a reaction temperature is appropriate for conducting the reaction without a solvent in the first step reaction, the solvent may not be necessary. That is, when the viscosity of the reacting materials is sufficiently low that the mixing and the stirring of the reacting materials may be conducted smoothly without a solvent, use of the solvent may not be necessary. This state may be easily understood by a person skilled in the art. When the solvent is used, any organic solvents that may easily dissolve the reacting materials, that do not have any adverse effects, and that may be easily removed after the reaction, may be used without limitation. For example, acetonitrile, THF, MEK, DMF, DMSO, MC, H$_2$O, or the like may be used. These solvents may be used alone or as a mixture of two or more thereof. The amount of the solvent may not be limited to a specific range, and an appropriate amount of the solvent may be used within a range for sufficiently dissolving the reacting materials and not adversely affecting the reaction. A person skilled in the art may select an appropriate amount of the solvent in consideration of the above-mentioned points.

In the second step, the alkenyl group of the above Intermediate Product (31) is oxidized and epoxidized to prepare one Intermediate Product (32) of the following Formulae A32 to H32. In the second step, the reaction is performed using 1 to 10 equivalents of a peroxide group of the peroxide with respect to 1 equivalent of the alkenyl group of the above Intermediate Product (31) in the presence of an optional base and an optional solvent.

[Intermediate Product (32)]

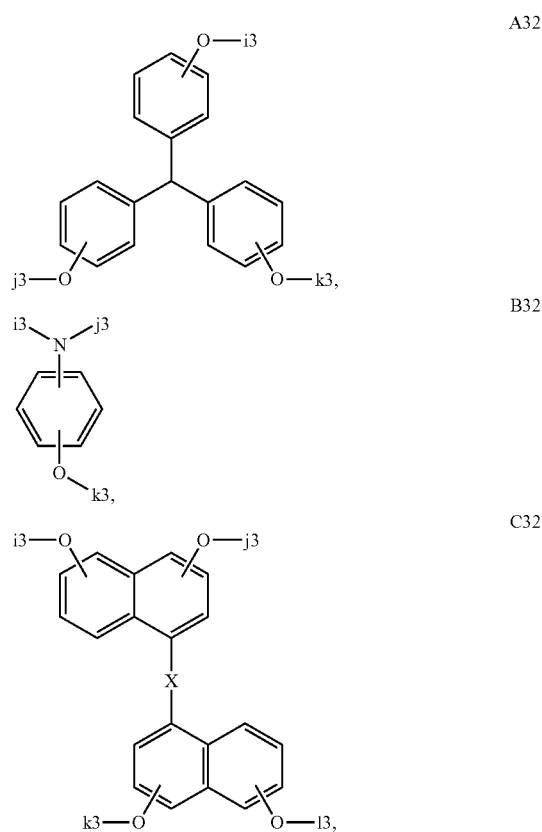

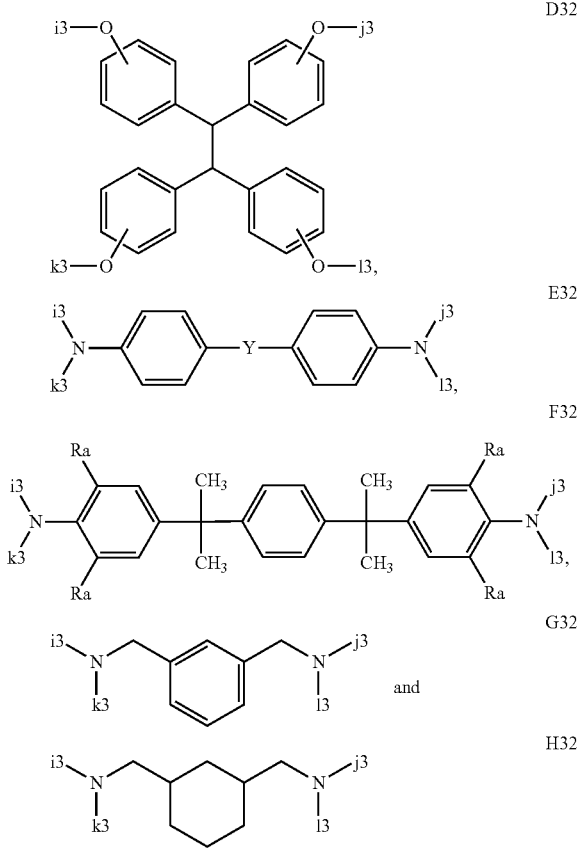

One or two of substituents i3 to k3 of the above Formulae A32 to B32 are the above Formula S1, and at least one thereof is —(CH$_2$)$_{z-2}$—CH=CH$_2$ where z is an integer from 3 to 10 and may be hydrogen when an unreacted site is present. Preferably, one or two of the substituents are the above Formula S1, and at least one thereof is —(CH$_2$)$_{z-2}$—CH=CH$_2$ where z is an integer from 3 to 10.

One to three of substituents i3 to l3 of the above Formulae C32 to H32 are the above Formula S1, and at least one thereof is —(CH$_2$)$_{z-2}$—CH=CH$_2$ where z is an integer from 3 to 10 and may be hydrogen when an unreacted site is present. Preferably, one to three of the substituents are the above Formula S1, and at least one thereof is —(CH$_2$)$_{z-2}$—CH=CH$_2$ where z is an integer from 3 to 10.

A meta position of oxygen in Formula B32 may be substituted with a linear or branched C1-C10 alkyl group.

X in Formula C32 is a direct linkage, —CH$_2$— or CH$_2$

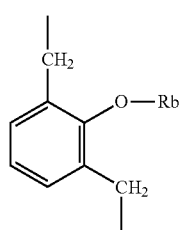

where Rb is H or a C1-C3 alkyl group.

Y in Formula E32 is —CH$_2$—, —C(CH$_3$)$_2$—, —C(CF$_3$)$_2$—, —S— or —SO$_2$—.

Ra in Formula F32 is H or a C1-C3 alkyl group.

The reaction temperature and the reaction time of the second step are dependent on the kind of reacting materials. For example, the reaction of the first step is performed at a temperature from room temperature (for example, 15° C. to 25° C.) to 100° C. for 1 to 120 hours to obtain the above Intermediate Product (32).

The peroxide may include, for example, meta-chloroperoxybenzoic acid (CPBA), H$_2$O$_2$, and dimethyldioxirane (DMDO), without limitation. These peroxide compounds may be used alone or as a mixture of two or more thereof.

In the second step, the base may be optionally used as occasion demands. The base is used to neutralize an acid component that may remain after reaction according to the kind of the peroxide. The base used may include, for example, KOH, NaOH, K$_2$CO$_3$, KHCO$_3$, NaHCO$_3$, triethylamine, and diisopropylethylamine, without limitation. These bases may be used alone or as a mixture of two or more thereof. If used, 0.1 to 5 equivalents of the base may be used based on 1 equivalent of the alkenyl group of Intermediate Product (31) in consideration of reaction efficiency.

The solvents may be optionally used as occasion demands in the second step reaction. For example, when the viscosity of the reacting materials at a reaction temperature is appropriate for conducting the reaction without a solvent in the first step reaction, the solvent may not be necessary. That is, when the viscosity of the reacting materials is sufficiently low that the mixing and the stirring of the reacting materials may be conducted smoothly without a solvent, use of the solvent may not be necessary. This state may be easily understood by a person skilled in the art. When the solvent is used, any organic solvents that may easily dissolve the reacting materials, that do not have any adverse effects, and that may be easily removed after the reaction, may be used without limitation. For example, acetonitrile, THF, MEK, DMF, DMSO, MC, methanol, or the like may be used. These solvents may be used alone or as a mixture of two or more thereof. The amount of the solvent may not be limited to a specific range, and an appropriate amount of the solvent may be used within a range for sufficiently dissolving the reacting materials and not adversely affecting the reaction. A person skilled in the art may select an appropriate amount of the solvent in consideration of the above-mentioned points.

The reaction conditions, or the line, of the alkoxysilylation during the third step are the same as those of the second step of method 1 and the fourth step of method 2 except for using Intermediate Product (32) instead of Intermediate Product (11) or (23).

The reaction scheme of the alkoxysilylated epoxy compound of Formula AI is as follows. (In the case that a structure having a ratio of the epoxy group and the alkoxysilyl group is 2:1 is synthesized)

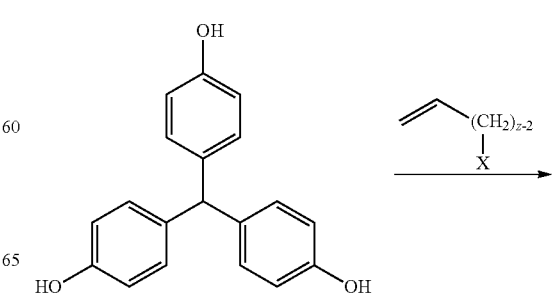

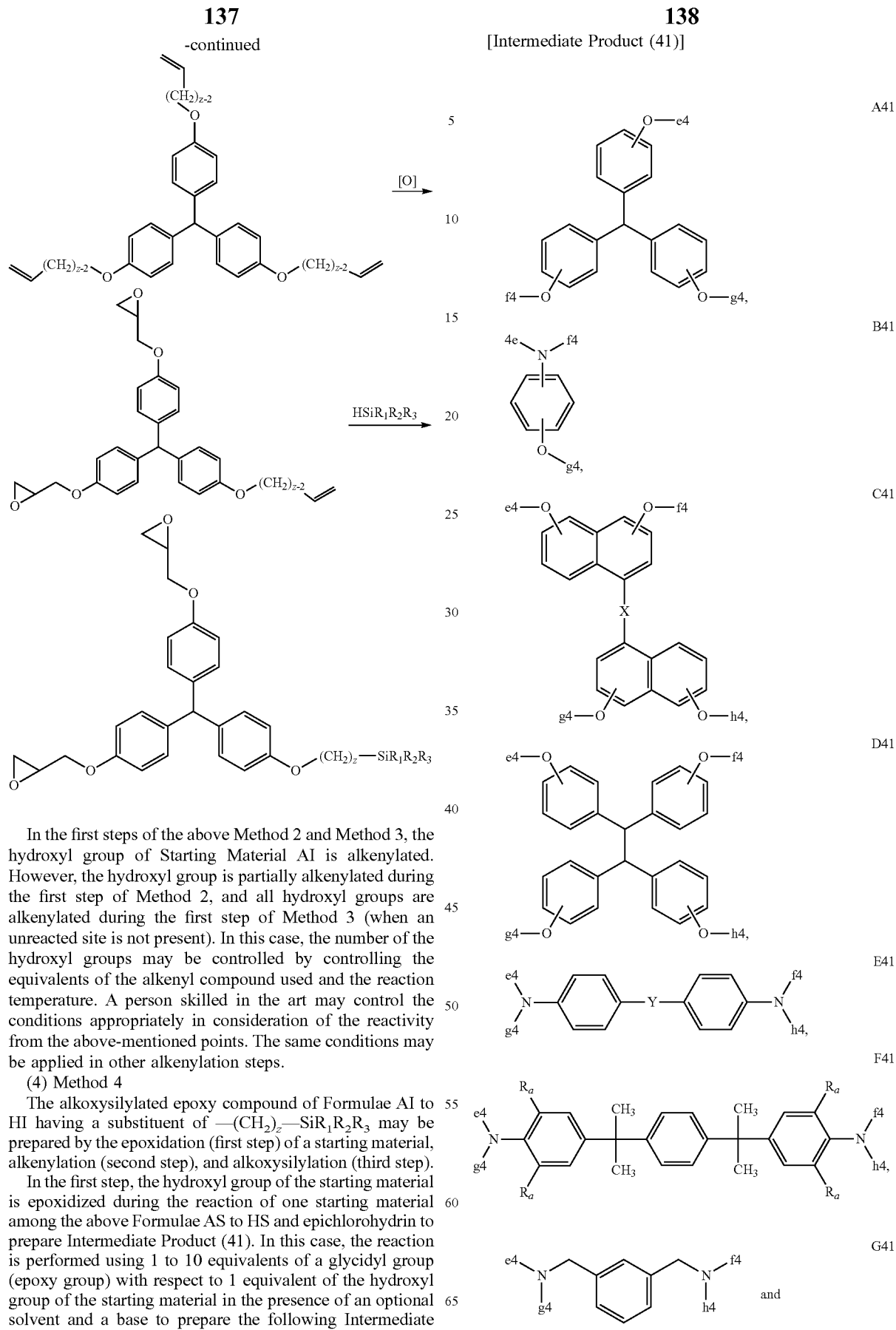

In the first steps of the above Method 2 and Method 3, the hydroxyl group of Starting Material AI is alkenylated. However, the hydroxyl group is partially alkenylated during the first step of Method 2, and all hydroxyl groups are alkenylated during the first step of Method 3 (when an unreacted site is not present). In this case, the number of the hydroxyl groups may be controlled by controlling the equivalents of the alkenyl compound used and the reaction temperature. A person skilled in the art may control the conditions appropriately in consideration of the reactivity from the above-mentioned points. The same conditions may be applied in other alkenylation steps.

(4) Method 4

The alkoxysilylated epoxy compound of Formulae AI to HI having a substituent of —$(CH_2)_z$—$SiR_1R_2R_3$ may be prepared by the epoxidation (first step) of a starting material, alkenylation (second step), and alkoxysilylation (third step).

In the first step, the hydroxyl group of the starting material is epoxidized during the reaction of one starting material among the above Formulae AS to HS and epichlorohydrin to prepare Intermediate Product (41). In this case, the reaction is performed using 1 to 10 equivalents of a glycidyl group (epoxy group) with respect to 1 equivalent of the hydroxyl group of the starting material in the presence of an optional solvent and a base to prepare the following Intermediate Product (41).

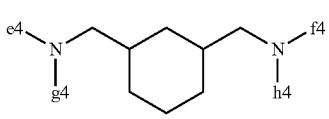 H41

One or two of substituents e4 to g4 of the above Formulae A41 to B41 have the form of the above Formula S1, and the remainder thereof are hydrogen.

One to three of substituents e4 to h4 of the above Formulae C41 to H41 have the form of the above Formula S1, and the remainder thereof are hydrogen.

A meta position of oxygen in Formula B41 may be substituted with a linear or branched C1-C10 alkyl group.

X in Formula C41 is a direct linkage, —$CH_2$— or

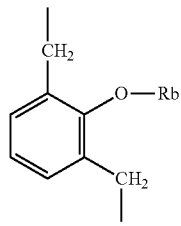

where Rb is H or a C1-C3 alkyl group.

Y in Formula E41 is —$CH_2$—, —$C(CH_3)_2$—, —$C(CF_3)_2$—, —S— or —$SO_2$—.

Ra in Formula F41 is H or a C1-C3 alkyl group.

The reaction temperature and the reaction time of the first step are dependent on the kind of reacting materials. For example, the reaction of the first step is performed at a temperature from room temperature (for example, 15° C. to 25° C.) to 100° C. for 1 to 120 hours to obtain the above Intermediate Product (41).

The base used may include, for example, KOH, NaOH, $K_2CO_3$, $Na_2CO_3$, $KHCO_3$, $NaHCO_3$, NaH, triethylamine, and diisopropylethylamine, without limitation. These bases may be used alone or as a combination thereof. 1 to 5 equivalents of the base may be used based on the hydroxyl group of Starting Material AI in consideration of reaction efficiency.

The solvents may be optionally used as occasion demands in the first step reaction. For example, when the viscosity of the reacting materials at a reaction temperature is appropriate for conducting the reaction without a solvent in the first step reaction, the solvent may not be necessary. That is, when the viscosity of the reacting materials is sufficiently low that the mixing and the stirring of the reacting materials may be conducted smoothly without a solvent, use of the solvent may not be necessary. This state may be easily understood by a person skilled in the art. When the solvent is used, any organic solvents that may easily dissolve the reactants, that do not have any adverse effects, and that may be easily removed after the reaction, may be used without limitation. For example, acetonitrile, THF, MEK, DMF, DMSO, MC, or the like may be used. These solvents may be used alone or as a mixture of two or more thereof. The amount of the solvent may not be limited to a specific range, and an appropriate amount of the solvent may be used within a range for sufficiently dissolving the reacting materials and not adversely affecting the reaction. A person skilled in the art may select an appropriate amount of the solvent in consideration of the above-mentioned points.

Subsequently, the above Intermediate Product (41) of Formulae A41 to H41 thus prepared is alkenylated (second step) to obtain Intermediate Product (42), and alkoxysilylated (third step) to obtain an epoxy compound of Formulae AI to HI having the epoxy group of Formula S3 and the alkoxysilyl group of —$(CH_2)_z$—$SiR_1R_2R_3$. The alkenylation during the second step may be performed by the same conditions and methods as those during the third step of Method 2, and the alkoxysilylation during the third step may be performed by the same conditions and methods as those during the fourth step of Method 2.

[Intermediate Product (42)]

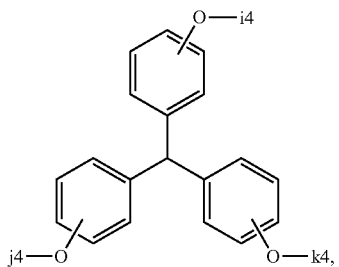 A42

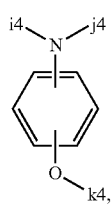 B42

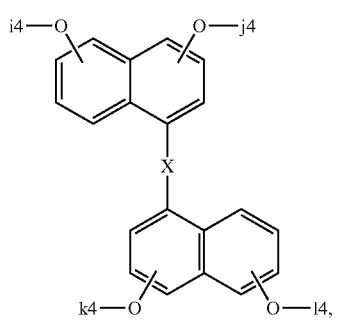 C42

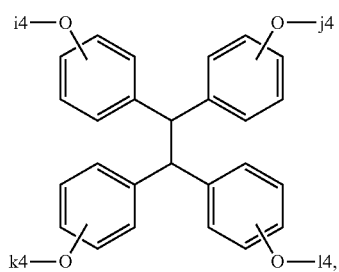 D42

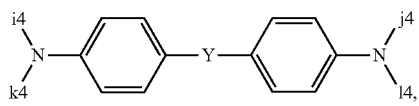 E42

-continued

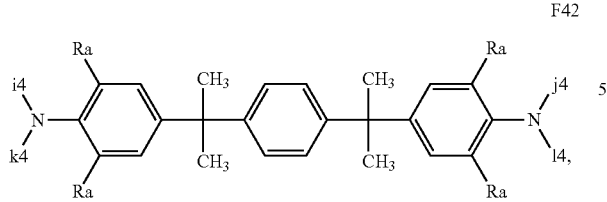
F42

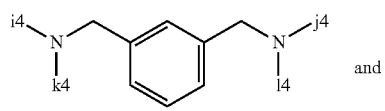
G42
and

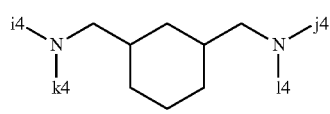
H42

At least two of substituents i4 to k4 of the above Formula A42 or B42 are the above Formula S1, and at least one thereof is —$(CH_2)_{z-2}$—CH═$CH_2$ where z is an integer from 3 to 10 and may be hydrogen when an unreacted site is present. Preferably, one or two of the substituents are the above Formula S1, and at least one thereof is —$(CH_2)_{z-2}$—CH═$CH_2$ where z is an integer from 3 to 10.

One to three of substituents i4 to 14 of the above Formulae C42 to H42 are the above Formula S1, and at least one thereof is —$(CH_2)_{z2}$—CH═$CH_2$ where z is an integer from 3 to 10 and may be hydrogen when an unreacted site is present. Preferably, one to three of the substituents are the above Formula S1, and at least one thereof is —$(CH_2)_{z-2}$—CH═$CH_2$ where z is an integer from 3 to 10.

A meta position of oxygen in Formula B42 may be substituted with a linear or branched C1-C10 alkyl group, and X in Formula C42 is a direct linkage, —$CH_2$— or

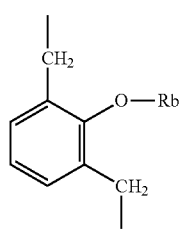

where Rb is H or a C1-C3 alkyl group.

Y in Formula E42 is —$CH_2$—, —$C(CH_3)_2$—, —$C(CF_3)_2$—, —S— or —$SO_2$—.

Ra in Formula F42 is H or a C1-C3 alkyl group.

An exemplary reaction scheme of the alkoxysilylated epoxy compound of Formula AI is as follows. (In the case that a structure having a ratio of the epoxy group and the alkoxysilyl group is 2:1 is synthesized)

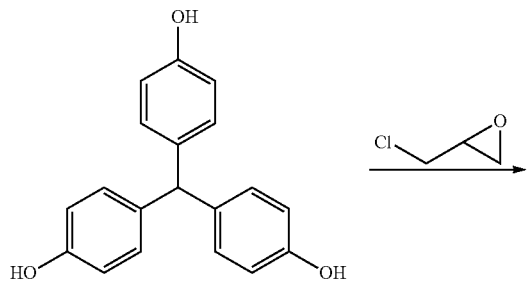

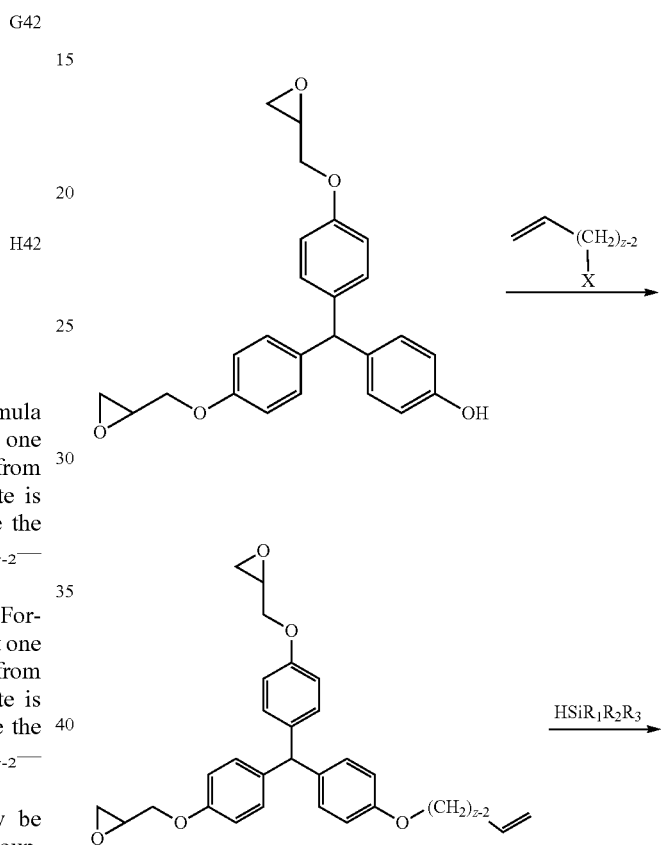

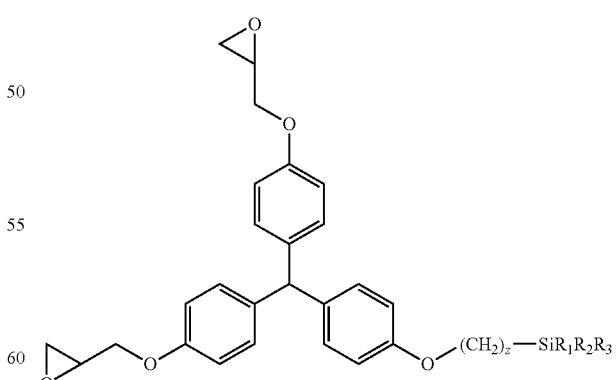

In the first step of the above Method 4, the epoxidized Intermediate Product (41) reacts with the hydroxyl group of the starting material to form polymers illustrated as the following Formulae AP4(1) to HP4(1).

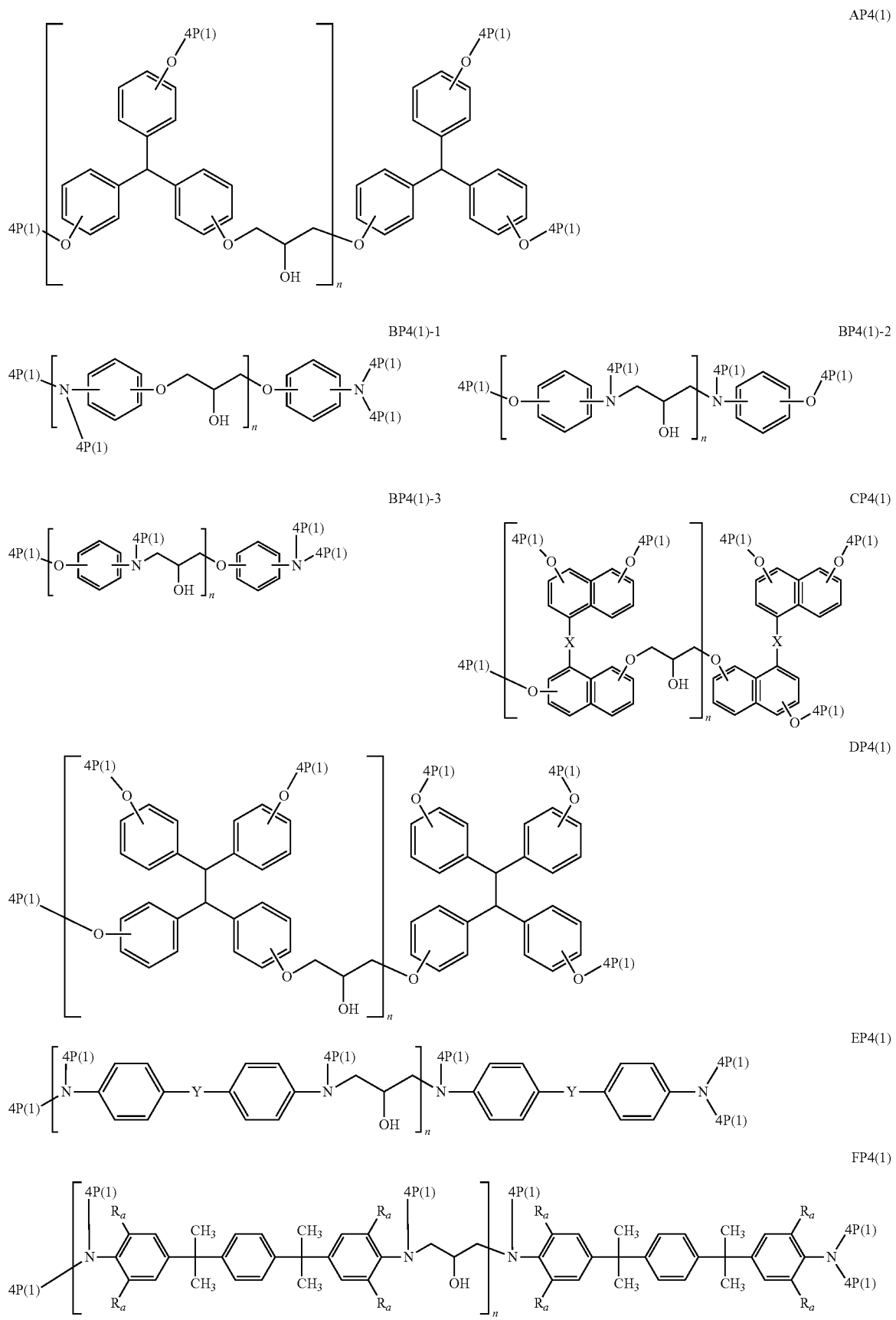

-continued

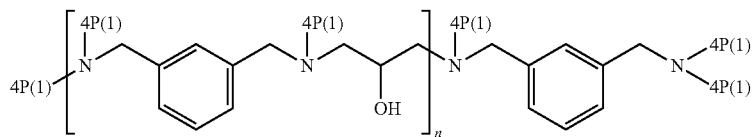
GP4(1)

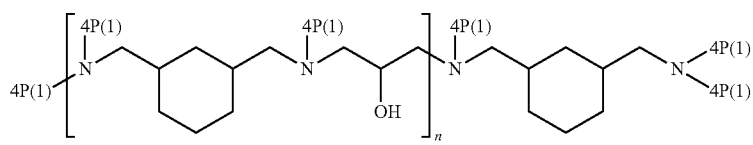
HP4(1)

In the above Formulae, each of 4P(1) is independently selected from an epoxy group of the above Formula S1 and hydrogen. Particularly, 4P(1) has at least one of the epoxy group of the above Formula S1 and at least one hydrogen.

A meta position of oxygen in Formulae BP4(1)-1 to BP4(1)-3 may be substituted with a linear or branched C1-C10 alkyl group.

X in Formula CP4(1) is a direct linkage, —CH$_2$— or

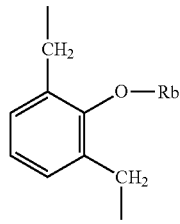

where Rb is H or a C1-C3 alkyl group.

Y in Formula EP4(1) is —CH$_2$—, —C(CH$_3$)—, —C(CF$_3$)$_2$—, —S— or —SO$_2$—.

Ra in Formula FP4(1) is H or a C1-C3 alkyl group.

N is an integer from 1 to 100.

Meanwhile, with respect to the polymers of Formulae AP4(1) to HP4(1), that may be formed in the first step, the second step and the third step may be performed. Through the second step, polymers of the following Formulae AP4(2) to HP4(2) may be obtained, and through the third step, polymers of the following Formulae AP1(2) to HP1(2) may be obtained.

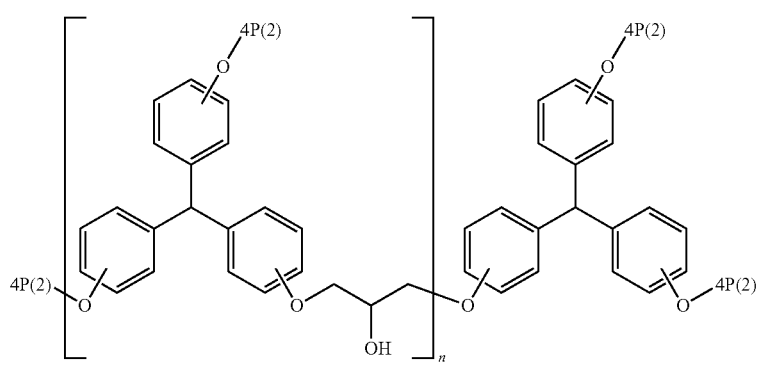
AP4(2)

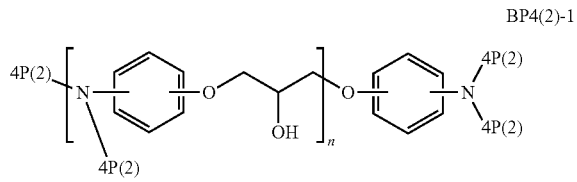
BP4(2)-1

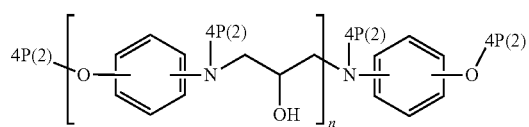
BP4(2)-2

-continued

BP4(2)-3
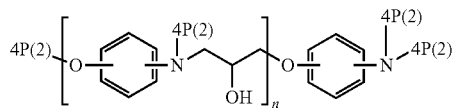

CP4(2)
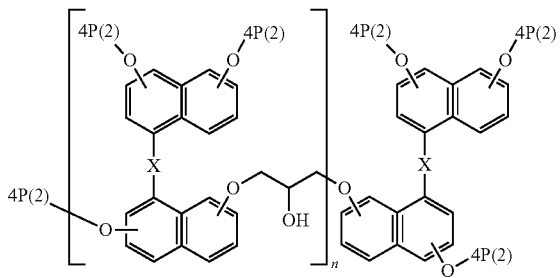

DP4(2)
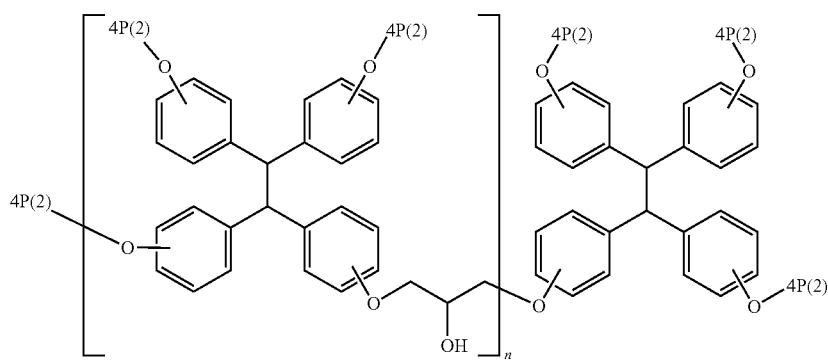

EP4(2)
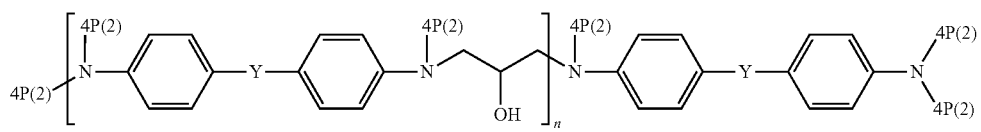

FP4(2)
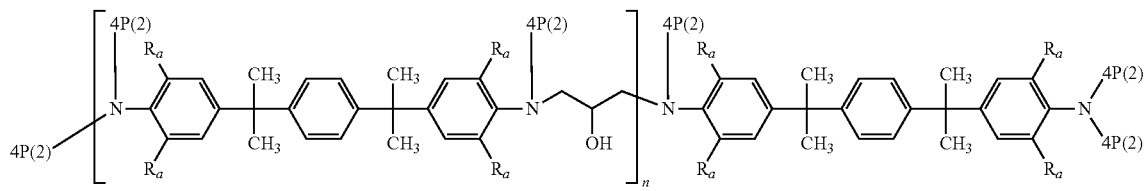

GP4(2)
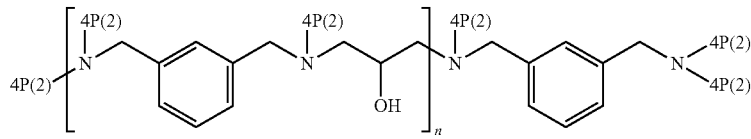

HP4(2)
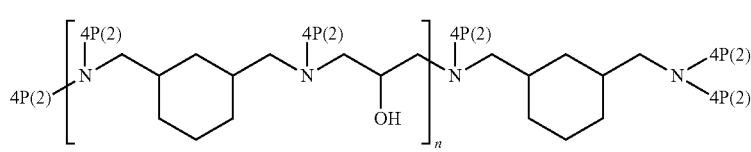

In the above Formulae, each of 4P(2) is independently selected from an epoxy group of the above Formula S1, —(CH$_2$)$_{z-2}$CH=CH$_2$ where z is an integer from 3 to 10, and hydrogen. Particularly, 4P(2) has at least one of the epoxy group of the above Formula S1 and at least one —(CH$_2$)$_{z-2}$CH=CH$_2$ where z is an integer from 3 to 10. 4P(2) may be hydrogen when an unreacted site is present, however hydrogen is undesirable.

A meta position of oxygen in Formulae BP4(2)-1 to BP4(2)-3 may be substituted with a linear or branched C1-C10 alkyl group.

X in Formula CP4(2) is a direct linkage, —CH$_2$— or

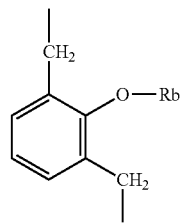

where Rb is H or a C1-C3 alkyl group.

Y in Formula EP4(2) is —CH$_2$—, —C(CH$_3$)$_2$—, —C(CF$_3$)$_2$—, —S— or —SO$_2$—.

Ra in Formula FP4(2) is H or a C1-C3 alkyl group.

n is an integer from 1 to 100.

B. Method of Preparing an Alkoxysilylated Epoxy Compound of Formulae AI to HI Having a Substituent of —CONH(CH$_2$)$_z$—SiR$_1$R$_2$R$_3$ (5) Method 5

The alkoxysilylated epoxy compound of Formulae AI to HI having a substituent of —CONH(CH$_2$)$_z$—SiR$_1$R$_2$R$_3$ may be prepared by the alkenylation (first step) of a starting material, epoxidation (second step), and alkoxysilylation (third step).

In the first step, one of the starting materials of the above Formulae AS to HS reacts with an alkenyl compound of the above Formula M1 for the preparation of Intermediate Product (51). The first step is the same as the first step of Method 2.

[Intermediate Product (51)]

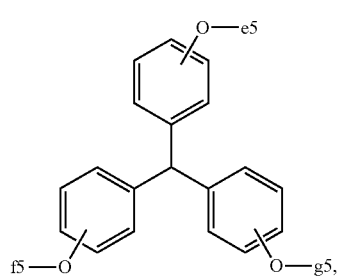

A51

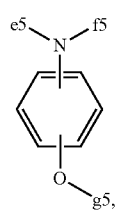

B51

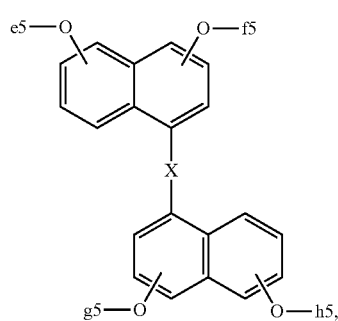

C51

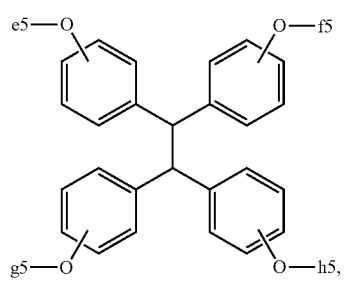

D51

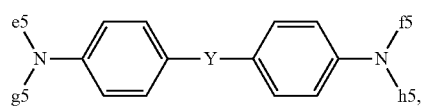

E51

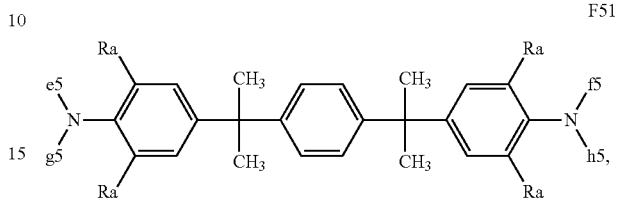

F51

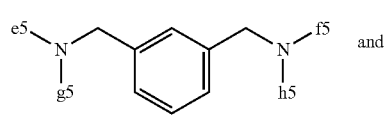

G51 and

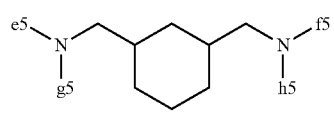

H51

One or two of substituents e5 to g5 of the above Formula A51 or B51 are —(CH$_2$)$_{z-2}$—CH=CH$_2$ where z is an integer from 3 to 10, and the remainder thereof are hydrogen.

One to three of substituents e5 to h5 of the above Formulae C51 to H51 are —(CH$_2$)$_{z-2}$—CH=CH$_2$ where z is an integer from 3 to 10, and the remainder thereof are hydrogen.

A meta position of oxygen in Formula B51 may be substituted with a linear or branched C1-C10 alkyl group.

X in Formula C51 is a direct linkage, —CH$_2$— or

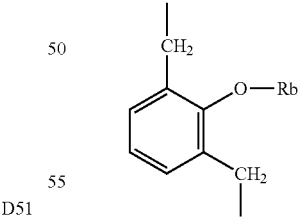

where Rb is H or a C1-C3 alkyl group.

Y in Formula E51 is —CH$_2$—, —C(CH$_3$)$_2$—, —C(CF$_3$)$_2$—, —S— or —SO$_2$—.

Ra in Formula F51 is H or a C1-C3 alkyl group.

In the second step, the alkenyl group of the above Intermediate Product (51) is oxidized and epoxidized to prepare the following Intermediate Product (52). The second step is the same as that of the second step in Method 2.

[Intermediate Product (52)]

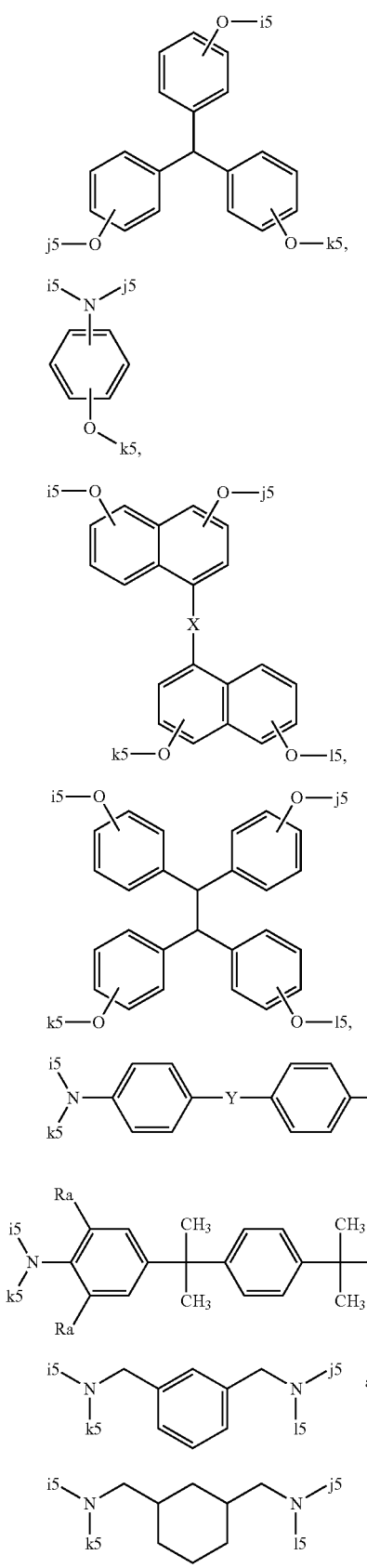

One or two of substituents i5 to k5 of the above Formulae A52 to D52 are the above Formula S1, and at least one thereof is hydrogen and may be —(CH$_2$)$_{z-2}$—CH=CH$_2$ where z is an integer from 3 to 10 when an unreacted site is present. Preferably, one or two of the substituents have the form of the above Formula S1, and at least one thereof is hydrogen.

One to three of substituents i5 to l5 of the above Formulae C52 to H52 are the above Formula S1, and at least one thereof is hydrogen and may be —(CH$_2$)$_{z-2}$—CH=CH$_2$ where z is an integer from 3 to 10 when an unreacted site is present. Preferably, one to three of the substituents have the form of the above Formula S1, and at least one thereof is hydrogen.

A meta position of oxygen in Formula B52 may be substituted with a linear or branched C1-C10 alkyl group.

X in Formula C52 is a direct linkage, —CH$_2$— or

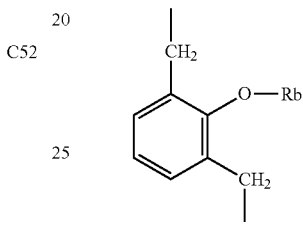

where Rb is H or a C1-C3 alkyl group.

Y in Formula E52 is —CH$_2$—, —C(CH$_3$)$_2$—, —C(CF$_3$)$_2$—, —S— or —SO$_2$—.

Ra in Formula F52 is H or a C1-C3 alkyl group.

Subsequently, in the third step, the above Intermediate Product (52) is alkoxysilylated to prepare an alkoxysilylated epoxy compound of Formulae AI to HI having a substituent of —(CH$_2$)$_z$—SiR$_1$R$_2$R$_3$. In the third step, reaction of the above Intermediate Product (52) and isocyanate-based alkoxysilane of the following Formula M3 is performed so that 1 to 5 equivalents of the isocyanate-based alkoxysilane of Formula M3 is used based on 1 equivalent of the hydroxyl group of the above Intermediate Product (52) in the presence of an optional solvent.

OCN—(CH$_2$)$_z$—SiR$_1$R$_2$R$_3$ [Formula M3]

In the above Formula M3, at least one of R$_1$ to R$_3$ is an alkoxy group having 1 to 10 carbon atoms, preferably an ethoxy group, the remainder thereof are alkyl groups having 1 to 10 carbon atoms, and z is an integer from 3 to 10, preferably an integer from 3 to 6.

In the third step, the above Intermediate Product (52) and the isocyanate-based alkoxysilane react by the equivalent ratio according to stoichiometry of the hydroxyl group of Intermediate Product (52) and the alkoxysilane. Thus, the reaction of Intermediate Product (52) and the isocyanate-based alkoxysilane may be performed by using 1 to 5 equivalents of the alkoxysilane based on 1 equivalent of the hydroxyl group of Intermediate Product (52).

The reaction temperature and the reaction time of the third step are dependent on the kind of reacting materials. For example, the reaction of the third step is performed at a temperature from room temperature (for example, 15° C. to 25° C.) to 120° C. for 1 to 72 hours to obtain the alkoxysilylated epoxy compound of Formulae AI to HI having the substituent of CONH—(CH$_2$)$_z$—SiR$_1$R$_2$R$_3$.

In the third step, the base may be optionally used as occasion demands. The reaction may be performed without using the base separately; however the reaction rate may be slow. The reaction rate may be increased by using the base. The base used may include, for example, $K_2CO_3$, $Na_2CO_3$, $KHCO_3$, $NaHCO_3$, triethylamine, and diisopropylethylamine, without limitation. These bases may be used alone or as a combination thereof. 1 to 5 equivalents of the base may be used based on 1 equivalent of the hydroxyl group of Intermediate Product 52 in consideration of reaction efficiency.

The solvents may be optionally used as occasion demands in the third step reaction. For example, when the viscosity of the reacting materials at a reaction temperature is appropriate for conducting the reaction without a solvent in the first step reaction, the solvent may not be necessary. That is, when the viscosity of the reacting materials is sufficiently low that the mixing and the stirring of the reacting materials may be conducted smoothly without a solvent, use of the solvent may not be necessary. This state may be easily understood by a person skilled in the art. When the solvent is used, any aprotic solvents that may easily dissolve the reacting materials, that do not have any adverse effects, and that may be easily removed after the reaction, may be used without limitation. For example, toluene, acetonitrile, THF, MEK, DMF, DMSO, MC, or the like may be used. These solvents may be used alone or as a mixture of two or more thereof. The amount of the solvent may not be limited to a specific range, and an appropriate amount of the solvent may be used within a range for sufficiently dissolving the reacting materials and not adversely affecting the reaction. A person skilled in the art may select an appropriate amount of the solvent in consideration of the above-mentioned points.

The reaction scheme of the alkoxysilylated epoxy compound of Formula AI is as follows. (In the case that a structure having a ratio of the epoxy group and the alkoxysilyl group is 2:1 is synthesized)

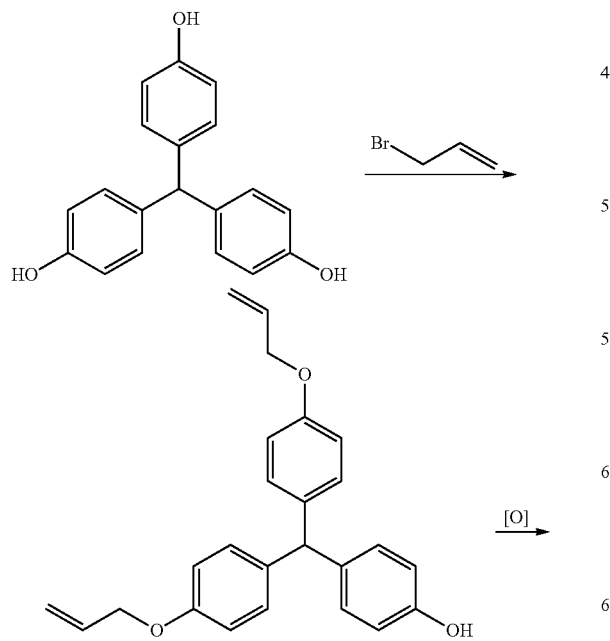

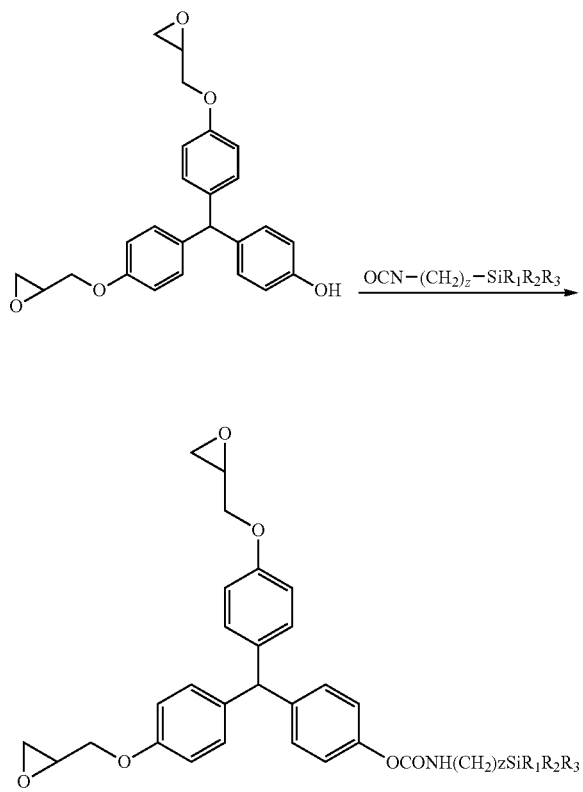

(6) Method 6

The alkoxysilylated epoxy compound of Formulae AI to HI having a substituent of —CONH $(CH_2)_z$—$SiR_1R_2R_3$ may be prepared by the epoxidation (first step) of a starting material and alkoxysilylation (second step).

In the first step, the following Intermediate Product (61) of Formulae A61 to H61 is formed by reacting a starting material with epichlorohydrin to epoxidize the starting material. Other process conditions in the first step are the same as that of the first step in Method 4.

Subsequently, in the second step, through the reaction of the above Intermediate Product (61) and an isocyanate-based alkoxysilane of the above Formula M3, the hydroxyl group of the above Intermediate Product (61) is alkoxysilylated to prepare the alkoxysilylated epoxy compound of Formulae AI to HI having the substituent of —CONH $(CH_2)_z$—$SiR_1R_2R_3$. The second step is the same as the third step of Method 5.

[Intermediate Product (61)]

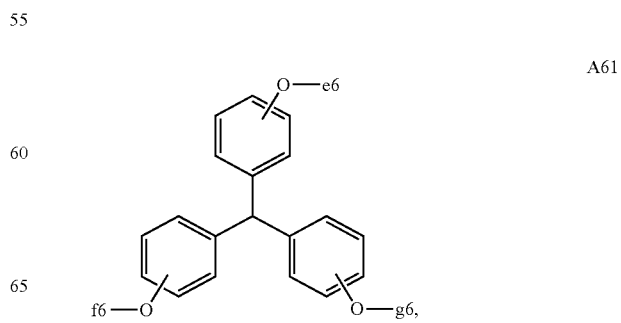

A61

B61

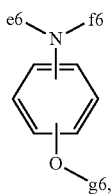

C61

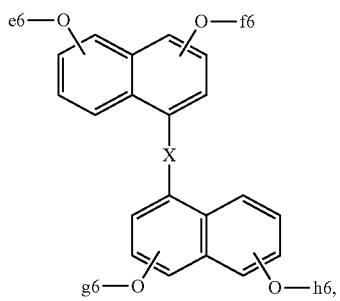

D61

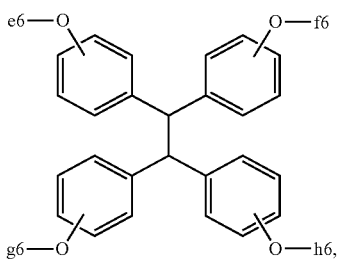

E61

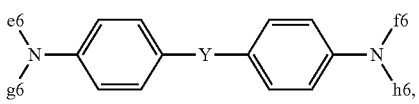

F61

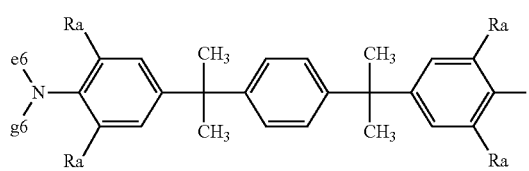

G61

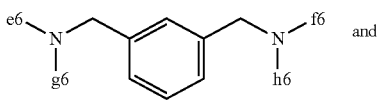

and

H61

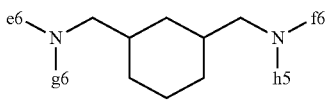

One or two of substituents e6 to g6 of the above Formula A61 or B61 are the above Formula S1, and the remainder thereof are hydrogen.

One to three of substituents e6 to h6 of the above Formulae C61 to H61 are the above Formula S1, and the remainder thereof are hydrogen.

A meta position of oxygen in Formula B61 may be substituted with a linear or branched C1-C10 alkyl group.

X in Formula C61 is a direct linkage, —CH$_2$— or

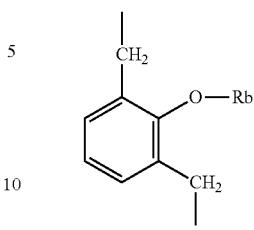

where Rb is H or a C1-C3 alkyl group.

Y in Formula E61 is —CH$_2$—, —C(CH$_3$)$_2$—, —C(CF$_3$)$_2$—, —S— or —SO$_2$—.

Ra in Formula F61 is H or a C1-C3 alkyl group.

The reaction scheme of the alkoxysilylated epoxy compound of Formula AI is as follows. (In the case that a structure having a ratio of the epoxy group and the alkoxysilyl group is 2:1 is synthesized)

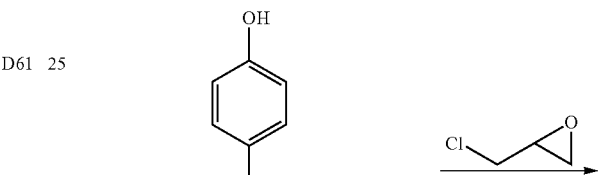

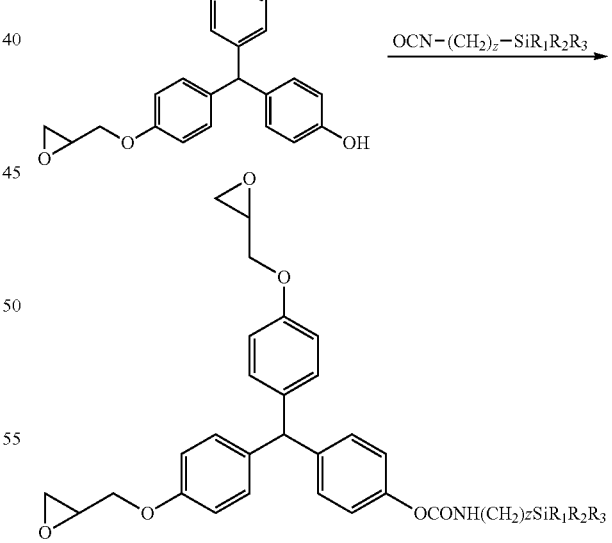

In addition, in the first step of Method 6, epoxidized Intermediate Product (61) reacts with the hydroxyl group of the starting material to form polymers as illustrated in the above Formulae AP4(1) to HP4(1), as in the first step of Method 4. Through the second step using Formulae AP4(1) to HP4(1), polymers illustrated as AP6(2) to HP6(2) may be obtained.

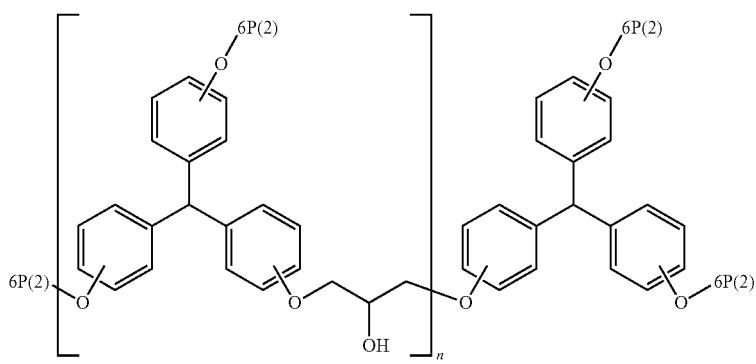
AP6(2)
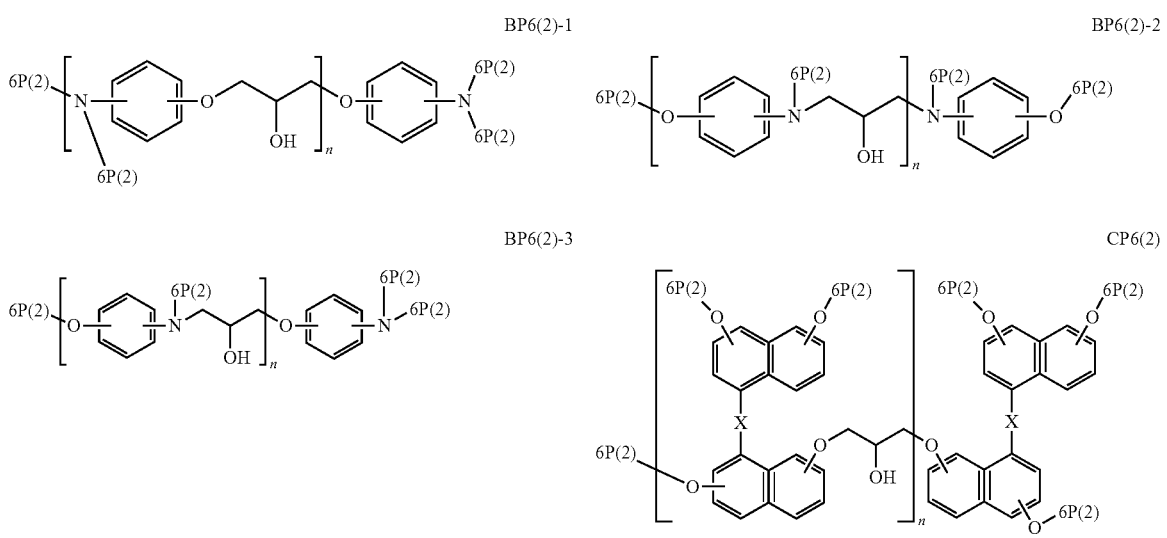
BP6(2)-1
BP6(2)-2
BP6(2)-3
CP6(2)
DP6(2)
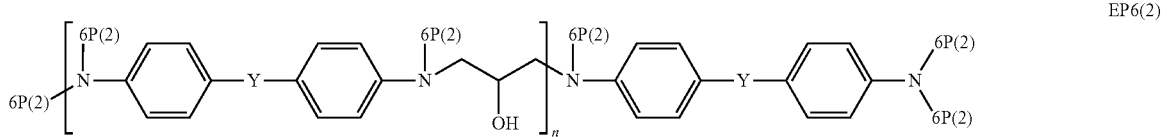
EP6(2)
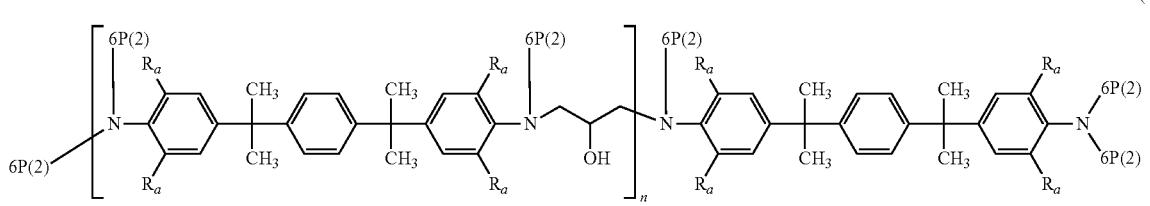
FP6(2)

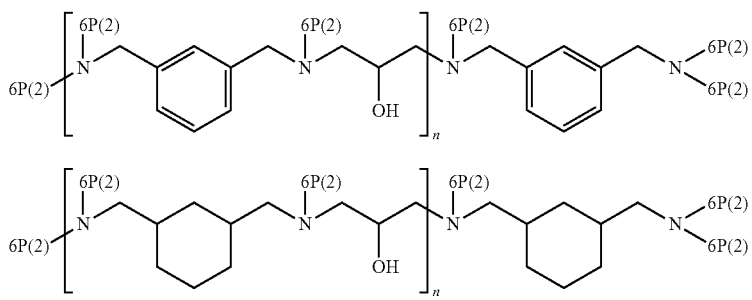

GP6(2)

HP6(2)

In the above Formulae, each of 6P(2) is independently selected from an epoxy group of the above Formula S1, the above Formula S3, and hydrogen. Particularly, at least one of the epoxy group of the above Formula S1 and at least one of the above Formula S3 are included, and hydrogen may be included when an unreacted site is present during synthesis. Preferably, each of 6P(2) is independently at least one epoxy group of the above Formula S1 and at least one of the above Formula S3.

A meta position of oxygen in Formulae BP6(2)-1 to BP6(2)-3 may be substituted with a linear or branched C1-C10 alkyl group.

X in Formula CP6(3) is a direct linkage, —CH$_2$— or

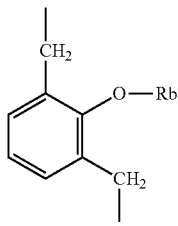

where Rb is H or a C1-C3 alkyl group.

Y in Formula EP6(3) is —CH$_2$—, —C(CH$_3$)$_2$—, —C(CF$_3$)$_2$—, —S— or —SO$_2$—.

Ra in Formula FP6(3) is H or a C1-C3 alkyl group.

n is an integer from 1 to 100.

Hereinafter, the present invention will be described in more detail referring to exemplary embodiments. The following exemplary embodiments are only illustration for assisting the understanding of the present invention, and the present invention is not limited thereto.

Synthetic Example A1(1) Synthesis of Triphenylmethane-Based Epoxy Having Alkoxysilyl Group (Formula AI) (Method 1)

According to the following methods, Formula AI having a ratio of [epoxy group]:[alkoxysilyl group]=1:1 was synthesized.

(1) First Step 25 g of tri(4-hydroxyphenyl)methane (TCI, The same may apply hereinafter), 16.6 g of allyl bromide (Sigma Aldrich, The same may apply hereinafter), and 300 ml of THF were inserted in a two-necked flask at room temperature, followed by stirring. Then, a solution with 5.8 g of sodium hydroxide dissolved in 150 ml of H$_2$O was slowly added thereto for 1 hour at room temperature, followed by stirring for 4 hours. Subsequently, 39.6 g of epichlorohydrin (Sigma Aldrich, The same may apply hereinafter) was added in the flask, and a solution with 6.8 g of sodium hydroxide dissolved in 150 mol of H$_2$O was added thereto for 10 minutes at room temperature, followed by stirring for 19 hours. After stirring, THF was removed by using an evaporator, and 400 ml of ethyl acetate was added and worked-up with H$_2$O to remove inorganic materials. In an organic layer, MgSO$_4$ was added to remove remaining H$_2$O. The organic layer thus obtained was filtered using a celite filter, evaporated and dried to obtain an Intermediate Product A11 having a ratio of [epoxy group]:[alkenyl group (allyl group)] =1:1.

$^1$H NMR (400 MHz, CDCl$_3$). δ=7.01-6.97 (m, 6H), 6.84-6.81 (m, 6H), 6.09-5.99 (m, 1.6H), 5.42-5.25 (m, 4.2H), 4.51-4.49 (m, 3.2H), 4.20-4.16 (m, 1.4H), 3.94-3.90 (m, 1.4H), 3.35-3.31 (m, 1.4H), 2.90-2.87 (m, 1.4H), 2.74-2.73 (m, 1.4H)

(2) Second Step 20 g of the above Intermediate Product A11, 0.20 g of PtO$_2$, 12.79 g of triethoxysilane (TCI, The same may apply hereinafter), and 250 ml of toluene were added in a flask, followed by stirring for 5 minutes at room temperature. Then, the temperature was increased to 80° C., and heating and stirring were performed for 12 hours. Then, the reactant was cooled to room temperature and filtered using a celite filter to remove inorganic materials. Through the drying by evaporation of toluene and complete drying using a vacuum pump, the target product of the epoxy having an alkoxysilyl group (Formula AI) having a ratio of [epoxy group]:[alkoxysilyl group]=1:1 was obtained.

$^1$H NMR (400 MHz, CDCl$_3$). δ=7.00-6.95 (m, 6H), 6.93-6.73 (m, 6H), 5.38 (s, 1H), 4.17-4.15 (m, 1.5H), 3.92-3.80 (m, 13.5H), 3.33-3.29 (m, 1.5H), 2.87-2.85 (m, 1.5H), 2.72-2.70 (m, 1.5H), 2.03-1.86 (m, 3.0H), 1.22 (t, 13.5H, 6.8 Hz), 0.78-0.74 (m, 3.0H)

The synthetic reaction of the above Synthetic Example A1(1) is as follows. In the following synthetic example, reaction for obtaining an epoxy compound having the ratio of [epoxy group]:[alkoxysilyl group]=2:1 by the Synthetic Example A1(1) is explained in particular. However, an epoxy compound having the ratio of [epoxy group]:[alkoxysilyl group]=1:2 may also be produced by the following synthetic example, and this product is illustrated in parentheses. A person skilled in the art may easily understand the synthetic reaction for obtaining the epoxy compound in the parentheses as well as the epoxy compound obtained from the explanation of the synthetic reaction. These features are similarly applied in other synthetic examples described hereinafter.

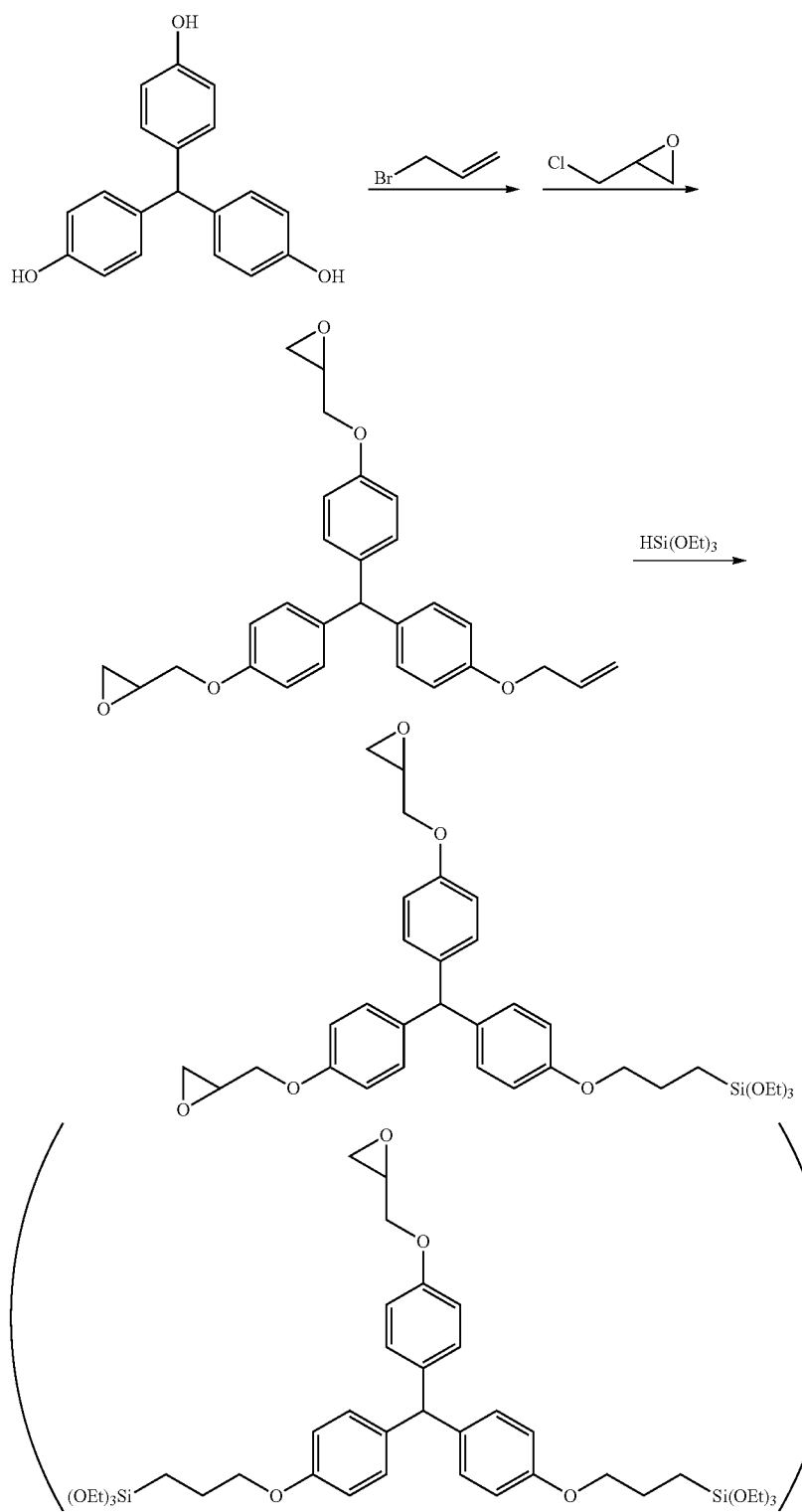

Synthetic Examples A1(2) to A1(4) Synthesis of Triphenylmethane-Based Epoxy Having Alkoxysilyl Group (Formula AI) (Method 1)

By performing the same reactions of the first step and the second step of Synthetic Example A1(1) except for using different amounts of the reacting materials, compounds of Formula AI were synthesized. The ratio of epoxy group: alkoxysilyl group of Formula AI synthesized in Synthetic Example A1(2), Synthetic Example A1(3), and Synthetic Example A1(4) were 2:1, 2.5:1, and 3:1, respectively, and the amounts of the reacting materials used in each synthetic step are illustrated in the following Tables.

TABLE A1

Amounts of reacting materials used in the
first step for synthesizing Formula AI

| Synthetic Example (1/2 step) | Tri(4-hydroxyphenyl)methane | Allyl bromide | Epichlorohydrin | THF | NaOH in 150 ml H$_2$O First insertion | NaOH in 150 ml H$_2$O Second insertion | [Epoxy group]:[alkenyl group] of Formula A11 |
|---|---|---|---|---|---|---|---|
| A1(2) | 25 g | 11.4 g | 47.5 g | 300 ml | 4.1 g | 10.3 g | 2:1 |
| A1(3) | 25 g | 9.3 g | 47.5 g | 300 ml | 3.8 g | 10.3 g | 2.5:1 |
| A1(4) | 25 g | 8.3 g | 47.5 g | 300 ml | 3.4 g | 10.3 g | 3:1 |

TABLE A2

Amounts of reacting materials used in the second step for synthesizing Formula AI

| Synthetic Example (2/2 step) | Formula A11 | PtO$_2$ | HSi(OEt)$_3$ | Toluene | [Epoxy group]:[alkoxysilyl group] of Formula AI |
|---|---|---|---|---|---|
| A1(2) | 20 g | 0.20 g | 8.87 g | 250 ml | 2:1 |
| A1(3) | 20 g | 0.20 g | 8.06 g | 250 ml | 2.5:1 |
| A1(4) | 20 g | 0.20 g | 7.32 g | 250 ml | 3:1 |

In the above Synthetic Examples A1(1) to A1(4), a mixture of the epoxy compounds having the ratio of epoxy group:alkoxysilyl group of 1:2 to 2:1 is obtained. The ratio of epoxy group:alkoxysilyl group illustrated in Table A2 means the ratio of epoxy group:alkoxysilyl group of the total epoxy compounds present as the mixture of the compounds having the above-described different ratios of epoxy group:alkoxysilyl group.

Synthetic Example A2 Synthesis of Triphenylmethane-Based Epoxy Having Alkoxysilyl Group (Formula AI) (Method 2)

(1) First Step 25 g of tri(4-hydroxyphenyl)methane, 100 g of allyl bromide, and 400 ml of THF were inserted in a two-necked flask, followed by stirring at room temperature. Then, a solution with 7.5 g of sodium hydroxide dissolved in 400 ml of H$_2$O was slowly added thereto for 1 hour at room temperature, followed by stirring for 1 hour. After stirring, THF was removed by using an evaporator, and 400 ml of ethyl acetate was added and worked-up with H$_2$O to remove inorganic materials. In an organic layer, MgSO$_4$ was added to remove remaining H$_2$O. The organic layer thus obtained was filtered using a celite filter, evaporated and dried to obtain 20 g of Intermediate Product A21.

$^1$H NMR (400 MHz, CDCl$_3$). δ=6.99 (d, 4H, J=8.8 Hz), 6.94 (d, 2H, J=8.8 Hz), 6.82 (d, 4H, J=8.8 Hz) 6.73 (d, 2H, J=8.8 Hz), 6.09-5.99 (m, 2H), 5.42-5.02 (m, 6H), 4.50 (dt, 4H, J=5.2 Hz, 1.2 Hz)

(2) Second Step 10 g of the above Intermediate Product A21, 1.0 g of KHCO$_3$, 20 g of CH$_3$CN, and 150 ml of methanol were added in a two-necked flask, followed by stirring at room temperature. Subsequently, 15 g of a 30 wt % H$_2$O$_2$ solution was slowly added thereto for 10 minutes and stirred at room temperature for 12 hours. After stirring, CH$_3$CN and methanol were removed by using an evaporator, and ethyl acetate was added and worked-up with H$_2$O to remove remaining H$_2$O$_2$. An organic layer was separated, and MgSO$_4$ was added in the organic layer to remove remaining H$_2$O. The organic layer thus obtained was filtered using a celite filter, evaporated and dried to obtain 9 g of Intermediate Product A22.

$^1$H NMR (400 MHz, CDCl$_3$). δ=6.99 (d, 4H, J=8.8 Hz), 6.95 (d, 2H, J=8.8 Hz), 6.82 (d, 4H, J=8.8 Hz) 6.73 (d, 2H, J=8.8 Hz), 5.41 (s, 1H), 4.17 (dd, 2H, J=12.0 Hz, 3.6 Hz), 3.94 (dd, 2H, J=11.9 Hz, 5.6 Hz), 3.36-3.31 (m, 2H), 2.90-2.88 (m, 2H), 2.75-2.72 (m, 2H)

(3) Third Step

In a two-necked flask, 10 g of the above Intermediate Product A22, 5.12 g of K$_2$CO$_3$, and 250 ml of a CH$_3$CN solvent were added and stirred at room temperature. 5.98 g of allyl bromide was added thereto at room temperature, and the temperature was increased to 80° C., followed by heating and stirring for 5 hours. Then, the reactant was cooled to room temperature and filtered using a celite filter to remove inorganic materials, and the CH$_3$CN solvent was removed by using an evaporator. The crude product thus obtained was worked-up using ethyl acetate and H$_2$O three times. An organic layer was separated, and MgSO$_4$ was added in the organic layer to remove remaining H$_2$O. The organic layer thus obtained was filtered, evaporated and dried to obtain Intermediate Product A23.

$^1$H NMR (400 MHz, CDCl$_3$). δ=7.01-6.97 (m, 6H), 6.84-6.81 (m, 6H), 6.09-5.99 (m, 1H), 5.42-5.25 (m, 3H), 4.51-4.49 (m, 2H), 4.20-4.16 (m, 2H), 3.94-3.90 (m, 2H), 3.35-3.31 (m, 2H), 2.90-2.87 (m, 2H), 2.74-2.73 (m, 2H)

(4) Fourth Step 10 g of the above Intermediate Product A23, 0.10 g of PtO$_2$, 4.43 g of triethoxysilane, and 150 ml of toluene were added in a flask, followed by stirring for 5 minutes at room temperature. Then, the temperature was increased to 80° C., and heating and stirring were performed for 12 hours. Then, the reactant was cooled to room temperature and filtered using a celite filter to remove inorganic materials. By removing toluene through drying by evaporation and complete drying using a vacuum pump, Target Product AI was obtained.

$^1$H NMR (400 MHz, CDCl$_3$). δ=7.00-6.95 (m, 6H), 6.93-6.73 (m, 6H), 5.38 (s, 1H), 4.17-4.15 (m, 2H), 3.92-3.80 (m, 10H), 3.33-3.29 (m, 2H), 2.87-2.85 (m, 2H), 2.72-2.70 (m, 2H), 2.03-1.86 (m, 2H), 1.22 (t, 9H, 6.8 Hz), 0.78-0.74 (m, 2H)
The synthetic reaction of the above Synthetic Example A2 is as follows.
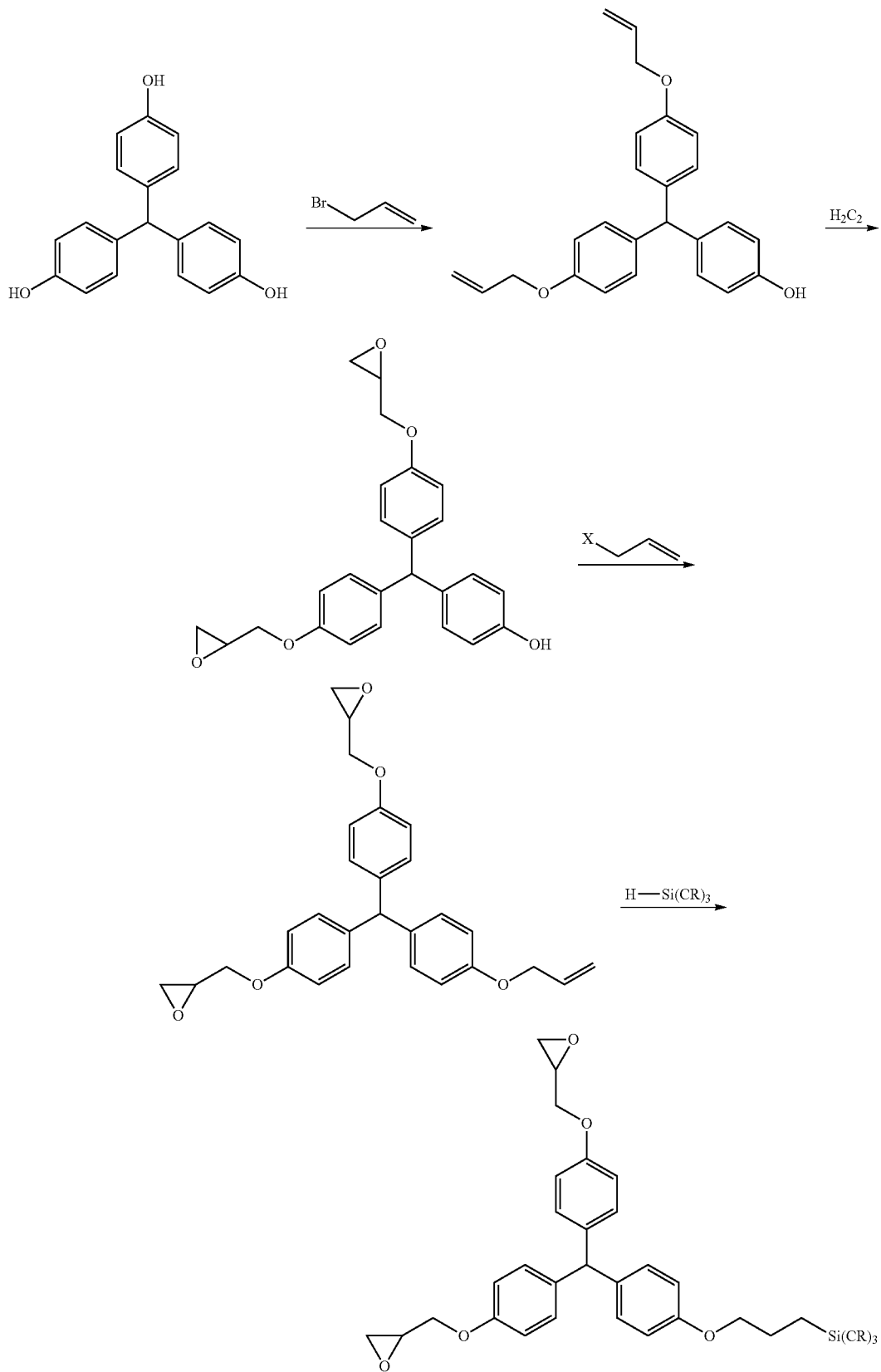

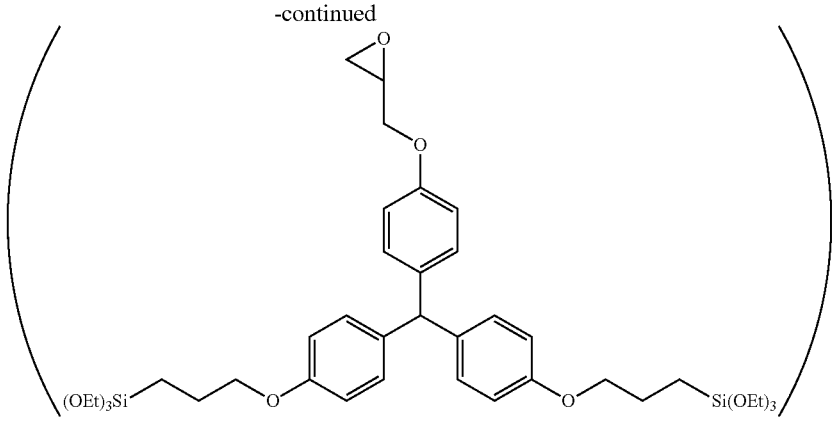

Synthetic Example A3 Synthesis of Triphenylmethane-Based Epoxy Having Alkoxysilyl Group (Formula AI) (Method 3)

(1) First Step 25 g of tri(4-hydroxyphenyl)methane, 103.5 g of allyl bromide, and 400 ml of THF were inserted in a two-necked flask, followed by stirring at room temperature. Then, a solution of 20 g with sodium hydroxide dissolved in 400 ml of $H_2O$ was slowly added thereto for 1 hour at room temperature, followed by further stirring for 4 hours. After stirring, THF was removed by using an evaporator, and 400 ml of ethyl acetate was added and worked-up with $H_2O$ to remove inorganic materials. In an organic layer, $MgSO_4$ was added to remove remaining $H_2O$. The organic layer thus obtained was filtered using a celite filter, evaporated and dried to obtain Intermediate Product A31.

$^1$H NMR (400 MHz, $CDCl_3$). δ=7.00-6.98 (m, 6H), 6.5-6.81 (m, 6H), 6.09-5.98 (m, 3H), 5.43-5.25 (m, 6H), 4.52-4.49 (m, 6H)

(2) Second Step 10 g of the above Intermediate Product A31, 0.54 g of $KHCO_3$, 6.0 g of $CH_3CN$, and 150 ml of a methanol solvent were added in a two-necked flask, followed by stirring at room temperature. Subsequently, 11.0 g of a 30 wt % $H_2O_2$ solution was slowly added thereto for 10 minutes and stirred at room temperature for 6 hours. After stirring, $CH_3CN$ and methanol were removed by using an evaporator, and ethyl acetate was added and worked-up with $H_2O$ to remove remaining $H_2O_2$. An organic layer was separated, and $MgSO_4$ was added in the organic layer to remove remaining $H_2O$. The organic layer thus obtained was filtered using a celite filter, evaporated and dried to obtain Intermediate Product A32.

$^1$H NMR (400 MHz, $CDCl_3$). δ=7.01-6.97 (m, 6H), 6.84-6.81 (m, 6H), 6.09-5.99 (m, 1H), 5.42-5.25 (m, 3H), 4.51-4.49 (m, 2H), 4.20-4.16 (m, 2H), 3.94-3.90 (m, 2H), 3.35-3.31 (m, 2H), 2.90-2.87 (m, 2H), 2.74-2.73 (m, 2H)

(3) Third step 10 g of the above Intermediate Product A32, 0.10 g of $PtO_2$, 4.43 g of triethoxysilane, and 150 ml of toluene were added in a flask, followed by stirring for 5 minutes at room temperature. Then, the temperature was increased to 80° C., and heating and stirring were performed for 12 hours. Then, the reactant was cooled to room temperature and filtered using a celite filter to remove inorganic materials. By removing toluene through drying by evaporation and complete drying using a vacuum pump, Target Product AI was obtained.

$^1$H NMR (400 MHz, $CDCl_3$). δ=7.00-6.95 (m, 6H), 6.93-6.73 (m, 6H), 5.38 (s, 1H), 4.17-4.15 (m, 2H), 3.92-3.80 (m, 10H), 3.33-3.29 (m, 2H), 2.87-2.85 (m, 2H), 2.72-2.70 (m, 2H), 2.03-1.86 (m, 2H), 1.22 (t, 9H, 6.8 Hz), 0.78-0.74 (m, 2H)

The synthetic reaction of the above Synthetic Example A3 is as follows.

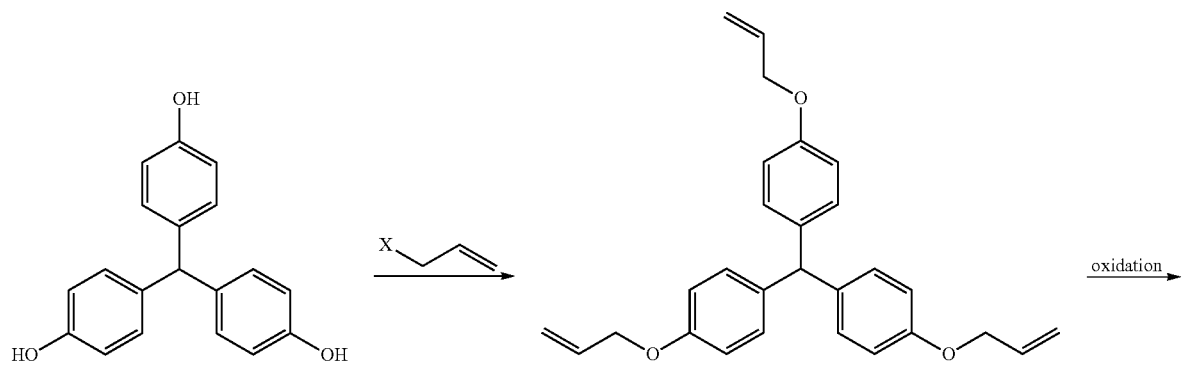

-continued

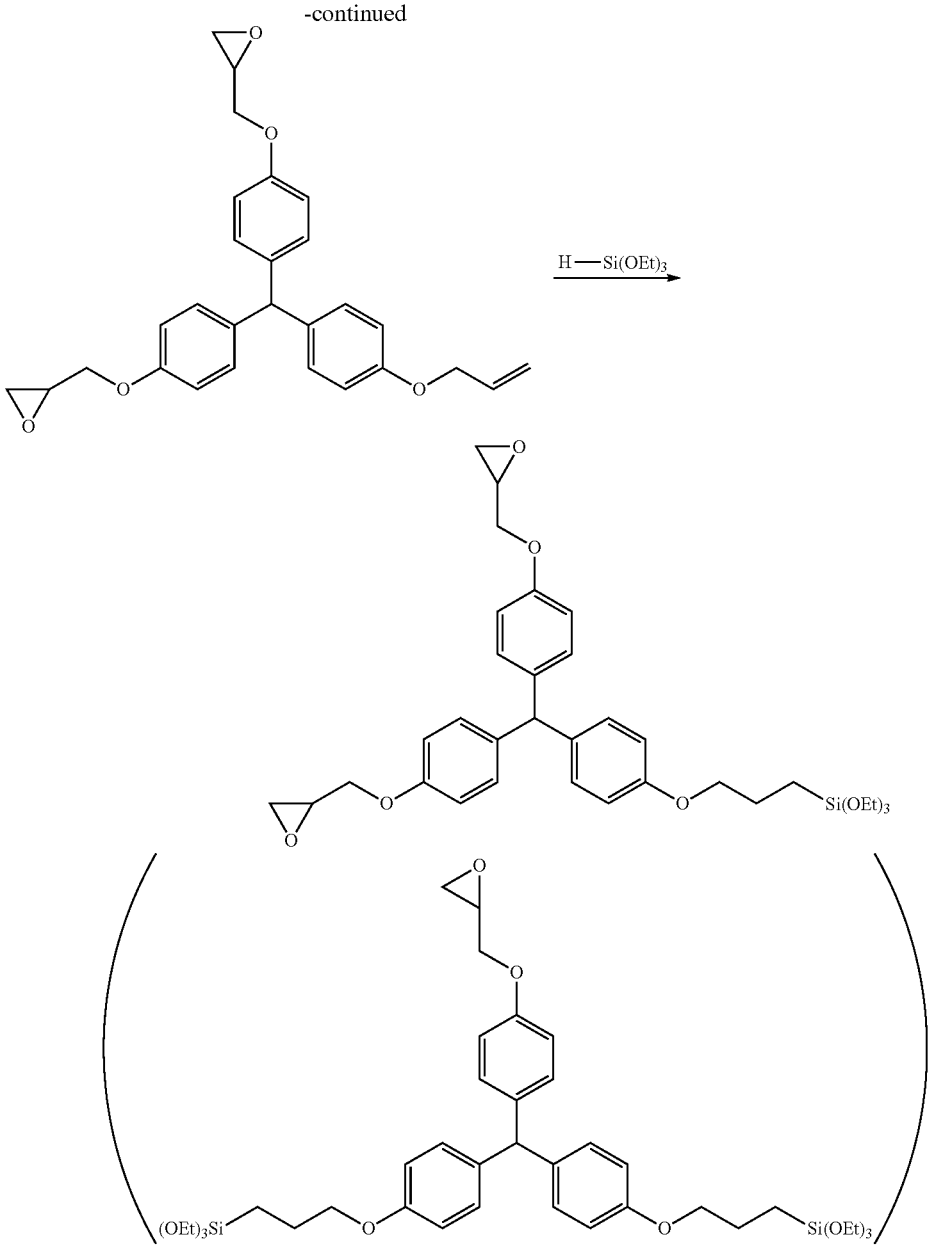

Synthetic Example A4 Synthesis of Triphenylmethane-Based Epoxy Having Alkoxysilyl Group (Formula AI) (Method 4)

(1) First Step 10 g of tri(4-hydroxyphenyl)methane, 31.6 g of epichlorohydrin (Sigma Aldrich, The same may apply hereinafter), and 200 ml of THF were inserted in a two-necked flask, followed by stirring at room temperature. Then, a solution with 3.0 g of sodium hydroxide dissolved in 180 ml of $H_2O$ was slowly added thereto for 1 hour at room temperature, followed by stirring for 2 hours. After stirring, THF was removed by using an evaporator, and 200 ml of ethyl acetate was added and worked-up with $H_2O$ to remove inorganic materials. In an organic layer, $MgSO_4$ was added to remove remaining $H_2O$. The organic layer thus obtained was filtered using a celite filter, evaporated and dried to obtain 7.6 g of Intermediate Product A41.

$^1$H NMR (400 MHz, $CDCl_3$). δ=6.99 (d, 4H, J=8.8 Hz), 6.95 (d, 2H, J=8.8 Hz), 6.82 (d, 4H, J=8.8 Hz) 6.73 (d, 2H, J=8.8 Hz), 5.41 (s, 1H), 4.17 (dd, 2H, J=12.0 Hz, 3.6 Hz), 3.94 (dd, 2H, J=11.9 Hz, 5.6 Hz), 3.36-3.31 (m, 2H), 2.90-2.88 (m, 2H), 2.75-2.72 (m, 2H)

(2) Second step 10 g of the above Intermediate Product A41, 5.12 g of $K_2CO_3$, 6.0 g and 250 ml of a $CH_3CN$ solvent were added in a two-necked flask, followed by stirring at room temperature. Subsequently, 5.98 g of allyl bromide was added thereto at room temperature, the temperature was increased to 80° C., and heating and stirring were performed for 5 hours. Then, the reactant was cooled to room temperature and filtered using a celite filter to remove inorganic materials, and the $CH_3CN$ solvent was removed by using an evaporator. The crude product thus obtained was worked-up using ethyl acetate and $H_2O$ three times. An organic layer was separated, and MgSO$_4$ was added in the organic layer to remove remaining H$_2$O. The organic layer thus obtained was filtered, evaporated and dried to obtain Intermediate Product A42.

$^1$H NMR (400 MHz, CDCl$_3$). δ=7.01-6.97 (m, 6H), 6.84-6.81 (m, 6H), 6.09-5.99 (m, 1H), 5.42-5.25 (m, 3H), 4.51-4.49 (m, 2H), 4.20-4.16 (m, 2H), 3.94-3.90 (m, 2H), 3.35-3.31 (m, 2H), 2.90-2.87 (m, 2H), 2.74-2.73 (m, 2H)

(3) Third step 10 g of the above Intermediate Product A42, 0.10 g of PtO$_2$, 4.43 g of triethoxysilane, and 150 ml of toluene were added in a flask, followed by stirring for 5 minutes at room temperature. Then, the temperature was increased to 80° C., and heating and stirring were performed for 12 hours. Then, the reactant was cooled to room temperature and filtered using a celite filter to remove inorganic materials. By removing toluene through drying by evaporation and complete drying using a vacuum pump, Target Product AI was obtained.

$^1$H NMR (400 MHz, CDCl$_3$). δ=7.00-6.95 (m, 6H), 6.93-6.73 (m, 6H), 5.38 (s, 1H), 4.17-4.15 (m, 2H), 3.92-3.80 (m, 10H), 3.33-3.29 (m, 2H), 2.87-2.85 (m, 2H), 2.72-2.70 (m, 2H), 2.03-1.86 (m, 2H), 1.22 (t, 9H, 6.8 Hz), 0.78-0.74 (m, 2H)

The synthetic reaction of the above Synthetic Example A4 is as follows.

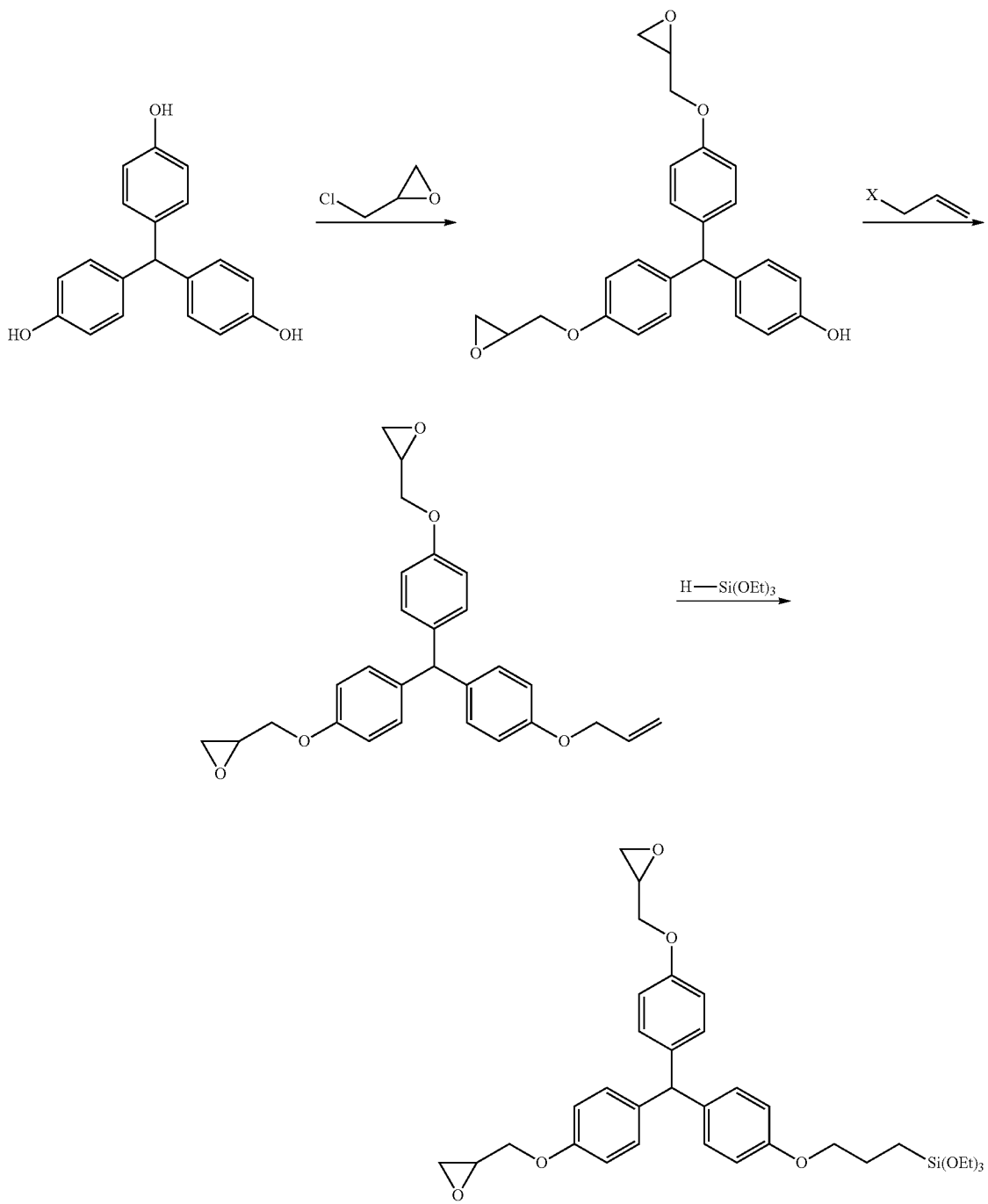

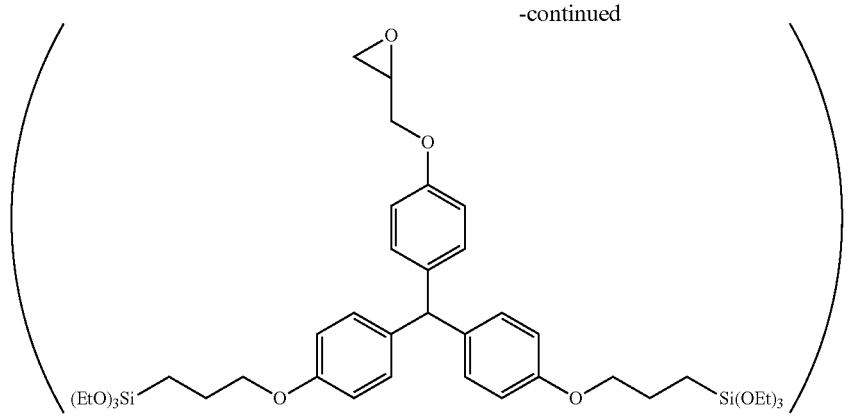

Synthetic Example A5 Synthesis of Triphenylmethane-Based Epoxy Having Alkoxysilyl Group (Formula AI) (Method 5)

(1) First Step 25 g of tri(4-hydroxyphenyl)methane, 100 g of allyl bromide, and 400 ml of THF were inserted in a two-necked flask, followed by stirring at room temperature. Then, a solution with 7.5 g of sodium hydroxide dissolved in 400 ml of $H_2O$ was slowly added thereto for 1 hour at room temperature, followed by further stirring for 1 hour. After stirring, THF was removed by using an evaporator, and 400 ml of ethyl acetate was added and worked-up with $H_2O$ to remove inorganic materials. In an organic layer, $MgSO_4$ was added to remove remaining $H_2O$. The organic layer thus obtained was filtered using a celite filter and dried by evaporation to obtain 20 g of Intermediate Product A51.

$^1$H NMR (400 MHz, $CDCl_3$). δ=6.99 (d, 4H, J=8.8 Hz), 6.94 (d, 2H, J=8.8 Hz), 6.82 (d, 4H, J=8.8 Hz) 6.73 (d, 2H, J=8.8 Hz), 6.09-5.99 (m, 2H), 5.42-5.02 (m, 6H), 4.50 (dt, 4H, J=5.2 Hz, 1.2 Hz)

(2) Second Step 10 g of the above Intermediate Product A51, 1.0 g of $KHCO_3$, 20 g of $CH_3CN$, and 150 ml of a methanol solvent were added in a two-necked flask, followed by stirring at room temperature. Subsequently, 15 g of a 30 wt % $H_2O_2$ solution was slowly added thereto for 10 minutes and stirred at room temperature for 12 hours. After completing the stirring, $CH_3CN$ and methanol were removed by using an evaporator, and ethyl acetate was added and worked-up with $H_2O$ to remove remaining $H_2O_2$. An organic layer was separated, and $MgSO_4$ was added in the organic layer to remove remaining $H_2O$. The organic layer thus obtained was filtered using a celite filter and dried by evaporation to obtain 9 g of Intermediate Product A52.

$^1$H NMR (400 MHz, $CDCl_3$). δ=6.99 (d, 4H, J=8.8 Hz), 6.95 (d, 2H, J=8.8 Hz), 6.82 (d, 4H, J=8.8 Hz) 6.73 (d, 2H, J=8.8 Hz), 5.41 (s, 1H), 4.17 (dd, 2H, J=12.0 Hz, 3.6 Hz), 3.94 (dd, 2H, J=11.9 Hz, 5.6 Hz), 3.36-3.31 (m, 2H), 2.90-2.88 (m, 2H), 2.75-2.72 (m, 2H)

(3) Third Step 10 g of the above Intermediate Product A52, 7.0 g of diisopropylethylamine (DIPEA) (Sigma Aldrich, The same may apply hereinafter), and 200 ml of methylene chloride were added in a flask, followed by stirring for 5 minutes at room temperature. Then, 9.2 g of triethoxysilylpropyl isocyanate (Sigma Aldrich, The same may apply hereinafter) was added thereto at room temperature, the temperature was increased to 60° C., and the reaction was performed for 12 hours. After completing the reaction, the reactant was cooled to room temperature and worked-up using $H_2O$. An organic layer was separated and $MgSO_4$ was added in the organic layer to remove remaining $H_2O$. The organic layer thus obtained was filtered using a celite filter and dried by evaporation to obtain 13.7 g of Target Product AI.

$^1$H NMR (400 MHz, $CDCl_3$). δ=7.05-6.97 (m, 8H), 6.84-6.80 (m, 4H), 5.42 (s, 1H), 5.32 (t, 1H, 6.0 Hz), 4.17 (dd, 2H, J=12.0 Hz, 3.6 Hz), 3.94 (dd, 2H, J=11.9 Hz, 5.6 Hz), 3.83 (q, 6H, J=6.8 Hz), 3.36-3.32 (m, 2H), 3.26 (q, 2H, J=6.8 Hz), 2.90-2.88 (m, 2H), 2.75-2.73 (m, 2H), 1.74-1.66 (m, 2H), 1.24 (t, 9H, J=7.2 Hz), 0.70-0.66 (m, 2H)

The synthetic reaction of the above Synthetic Example A5 is as follows.

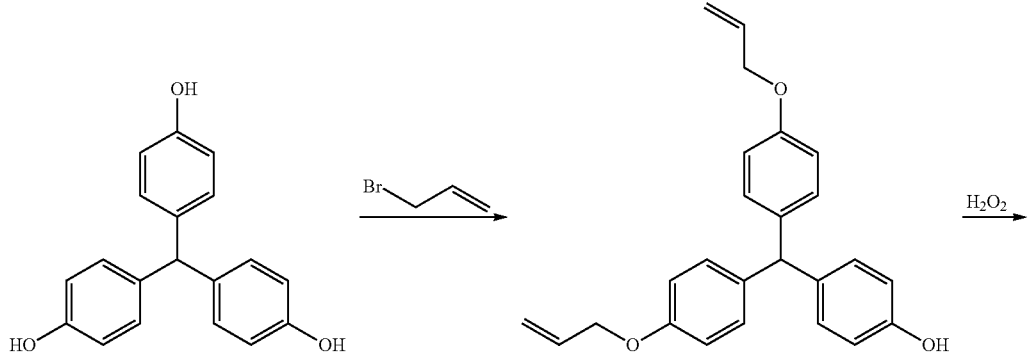

-continued

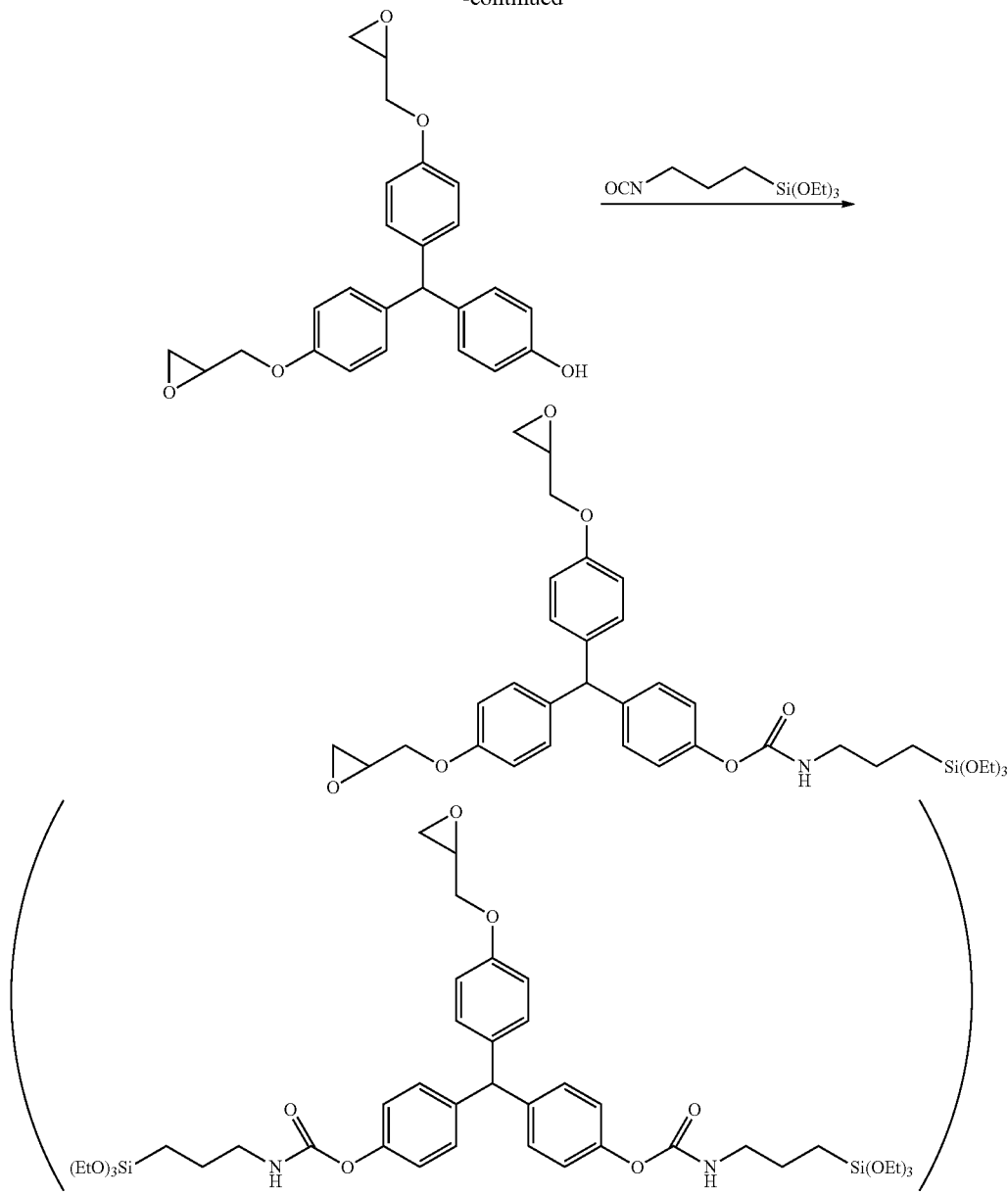

Synthetic Example A6 Synthesis of Triphenylmethane-Based Epoxy Having Alkoxysilyl Group (Formula AI) (Method 6)

(1) First Step 10 g of 4,4',4"-tri(4-hydroxyphenyl)methane (Sigma Aldrich, The same may apply hereinafter), 31.6 g of epichlorohydrin, and 200 ml of THF were inserted in a two-necked flask, followed by stirring at room temperature. Then, a solution with 3.0 g of sodium hydroxide dissolved in 180 ml of $H_2O$ was slowly added thereto for 1 hour at room temperature, followed by stirring for 2 hours. After stirring, THF was removed by using an evaporator, and 200 ml of ethyl acetate was added and worked-up with $H_2O$ to remove inorganic materials. In an organic layer, $MgSO_4$ was added to remove remaining $H_2O$. The organic layer thus obtained was filtered using a celite filter and dried by evaporation to obtain 7.6 g of Intermediate Product A61.

$^1$H NMR (400 MHz, $CDCl_3$). δ=6.99 (d, 4H, J=8.8 Hz), 6.95 (d, 2H, J=8.8 Hz), 6.82 (d, 4H, J=8.8 Hz) 6.73 (d, 2H, J=8.8 Hz), 5.41 (s, 1H), 4.17 (dd, 2H, J=12.0 Hz, 3.6 Hz), 3.94 (dd, 2H, J=11.9 Hz, 5.6 Hz), 3.36-3.31 (m, 2H), 2.90-2.88 (m, 2H), 2.75-2.72 (m, 2H)

(2) Second Step 10 g of the above Intermediate Product A61, 7.0 g diisopropylethylamine (DIPEA), and 200 ml of methylene chloride were added in a two-necked flask, followed by stirring at room temperature for 5 minutes. Then, 9.2 g of triethoxysilylpropyl isocyanate was added thereto at room temperature, the temperature was increased to 60° C., and the reaction was performed for 12 hours. After completing the reaction, the reactant was cooled to room temperature and worked-up using $H_2O$. An organic layer was separated and $MgSO_4$ was added in the organic layer to remove remaining H₂O. The organic layer thus obtained was filtered using a celite filter and dried by evaporation to obtain 13.7 g of Target Product AI.
¹H NMR (400 MHz, CDCl₃). δ=7.05-6.97 (m, 8H), 6.84-6.80 (m, 4H), 5.42 (s, 1H), 5.32 (t, 1H, 6.0 Hz), 4.17 (dd, 2H, J=12.0 Hz, 3.6 Hz), 3.94 (dd, 2H, J=11.9 Hz, 5.6 Hz), 3.83 (q, 6H, J=6.8 Hz), 3.36-3.32 (m, 2H), 3.26 (q, 2H, J=6.8 Hz), 2.90-2.88 (m, 2H), 2.75-2.73 (m, 2H), 1.74-1.66 (m, 2H), 1.24 (t, 9H, J=7.2 Hz), 0.70-0.66 (m, 2H)
The synthetic reaction of the above Synthetic Example A6 is as follows.
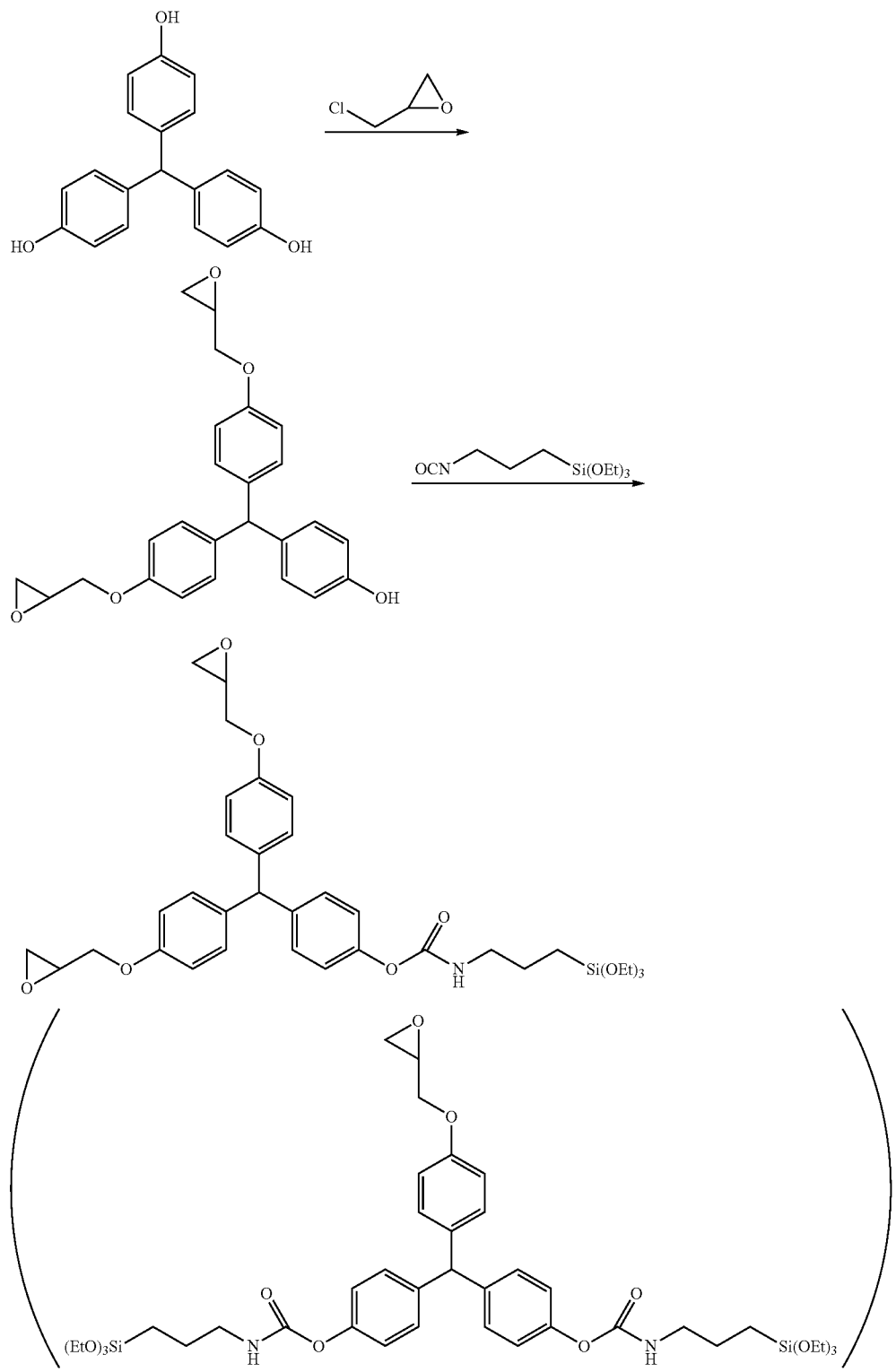

Synthetic Example B1(1) Synthesis of Aminophenol-Based Epoxy Having Alkoxysilyl Group (Formula BI) (Method 1)

According to the following methods, Formula BI having a ratio of [epoxy group]:[alkoxysilyl group]=1:1 was synthesized.

(1) First Step 25 g of aminophenol (Sigma Aldrich, The same may apply hereinafter), 44.3 g of allyl bromide, and 300 ml of THF were inserted in a two-necked flask at room temperature, followed by stirring. Then, a solution with 16.5 g of sodium hydroxide dissolved in 150 ml of H₂O was slowly added thereto for 1 hour, followed by stirring for 4 hours. Subsequently, 106.0 g of epichlorohydrin was added in the flask, and a solution with 18.3 g of sodium hydroxide dissolved in 150 mol of H₂O was added thereto for 10 minutes at room temperature, followed by stirring for 19 hours. After stirring, THF was removed by using an evaporator, and 400 ml of ethyl acetate was added and worked-up with H₂O to remove inorganic materials. In an organic layer, MgSO₄ was added to remove remaining H₂O. The organic layer thus obtained was filtered using a celite filter, evaporated and dried to obtain Intermediate Product B11 having a ratio of [epoxy group]:[alkenyl group (allyl group)]=1:1.

¹H NMR (400 MHz, CDCl₃). δ=6.83-6.80 (m, 2H), 6.69-6.62 (m, 2H), 6.08-5.82 (m, 1.6H), 5.42-5.26 (m, 3.2H), 4.20-4.16 (m, 1H), 3.94-3.90 (m, 0.4H), 3.76-3.63 (m, 4.2H), 3.49-3.40 (m, 0.4H), 3.35-3.31 (m, 1H), 3.20-3.16 (m, 0.4H), 2.90-2.73 (m, 2.4H), 2.60-2.58 (m, 0.4H)

(2) Second Step 20 g of the above Intermediate Product B11, 0.36 g of PtO₂, 22.0 g of triethoxysilane, and 250 ml of toluene were added in a flask, followed by stirring for 5 minutes at room temperature. Then, the temperature was increased to 80° C., and heating and stirring were performed for 12 hours. Then, the reactant was cooled to room temperature and filtered using a celite filter to remove inorganic materials. By removing toluene through drying by evaporation and complete drying using a vacuum pump, Target Product (Formula BI) was obtained.

¹H NMR (400 MHz, CDCl₃). δ=7.00-6.84 (m, 2H), 6.75-6.64 (m, 2H), 4.18-4.14 (m, 1H), 3.92-3.88 (m, 0.4H), 3.83 (q, 9.6H, J=6.8 Hz), 3.71-3.62 (m, 1H), 3.52-3.13 (m, 5H), 2.91-2.73 (m, 2H), 2.58-2.56 (m, 0.8H), 1.80-1.70 (m, 3.2H), 1.22 (t, 14.4H, J=7.2 Hz), 0.67-0.60 (m, 3.2H)

The synthetic reaction of the above Synthetic Example B1(1) is as follows.

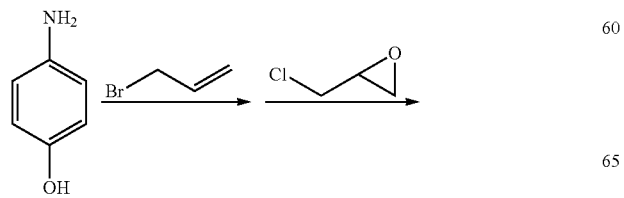

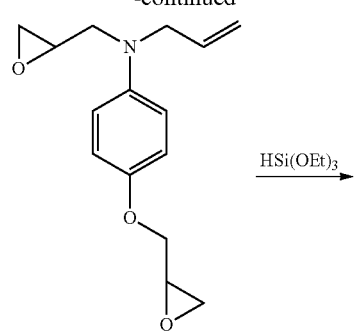

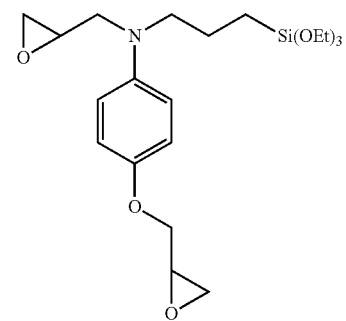

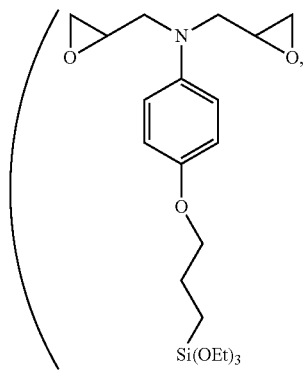

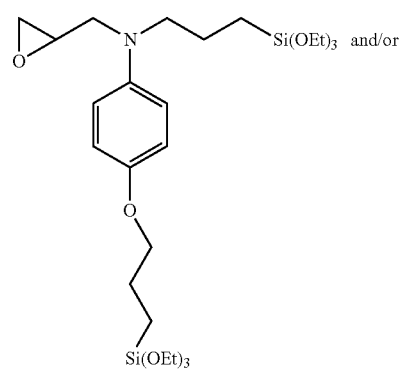

-continued

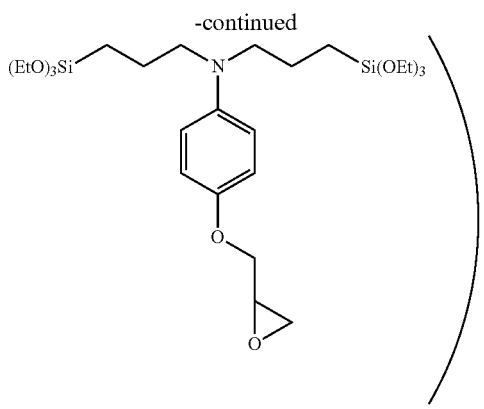

Synthetic Examples B1(2) and B1(3) Synthesis of Aminophenol-Based Epoxy Having Alkoxysilyl Group (Formula BI) (Method 1)

By performing the same methods of the first step and the second step of Synthetic Example B1(1) except for using different amounts of the reacting materials, compounds of Formula BI were synthesized. The ratio of epoxy group:alkoxysilyl group of Formula BI synthesized in Synthetic Example B1(2), and Synthetic Example B1(3) were 2:1, and 1:2, respectively, and the amounts of the reacting materials used in each synthetic step are illustrated in the following Tables.

Synthetic Example B2 Synthesis of Aminophenol-Based Epoxy Having Alkoxysilyl Group (Formula BI) (Method 2)

(1) First Step 20 g of aminophenol and 400 ml of $CH_3CN$ were inserted in a two-necked flask at room temperature, followed by stirring, and allyl bromide (6 eq., 130.6 g, 1.08 mol) was added thereto, and pyridine (2.5 eq., 35.5 g, 0.45 mol) was slowly added thereto for 1 hours, followed by reacting while stirring at 80° C. for 2 hours. After completing the reaction, the solvent was removed by using an evaporator, and the crude product was worked-up using 400 ml of ethyl acetate with a 1M NaOH solution. An organic layer was separated, and $MgSO_4$ was added in the organic layer to remove remaining $H_2O$. The organic layer thus obtained was filtered using a celite filter, and evaporated to obtain Intermediate Product B21 (33.3 g, 96 wt %).

$^1$H NMR (400 MHz, $CDCl_3$). δ=8.3 (br. s, 1H), 6.82 (d, 2H, J=9.2 Hz), 6.60 (d, 2H, J=8.8 Hz), 5.89-5.80 (m, 2H), 5.20-5.13 (m, 4H), 3.86 (d, 4H, J=4.8 Hz)

(2) Second Step 10 g of the above Intermediate Product B21 obtained in the first step, 1 g of $KHCO_3$, 24.6 g of $CH_3CN$, and 500 ml of methanol were added in a two-necked flask, followed by stirring at room temperature. Subsequently, 34.0 g of a 30 wt % $H_2O_2$ solution was slowly added thereto for 10 minutes and stirred at room temperature for 12 hours. After completing the reaction, $CH_3CN$ and methanol were removed by using an evaporator, and ethyl acetate was added and worked-up with $H_2O$ to remove remaining $H_2O_2$. An organic layer was separated, and $MgSO_4$ was added in the organic layer to remove remaining $H_2O$. The organic layer thus

TABLE B1

Amounts of reacting materials used in the first step for synthesizing Formula BI

| Synthetic Example (1/2 step) | Aminophenol | Allyl bromide | Epichlorohydrin | THF | NaOH in 150 ml $H_2O$ | | [Epoxy group]:[alkenyl group] of Formula B11 |
|---|---|---|---|---|---|---|---|
| | | | | | First insertion | Second insertion | |
| B1(2) | 25 g | 30.5 g | 127.2 g | 300 ml | 11.0 g | 27.5 g | 2:1 |
| B1(3) | 25 g | 61.0 g | 63.6 g | 300 ml | 20.2 g | 18.3 g | 1:2 |

TABLE B2

Amounts of reacting materials used in the second step for synthesizing Formula BI

| Synthetic Example (2/2 step) | Formula B11 | $PtO_2$ | $HSi(OEt)_3$ | Toluene | [Epoxy group]:[alkoxysilyl group] of Formula BI |
|---|---|---|---|---|---|
| B1(2) | 20 g | 0.35 g | 15.1 g | 250 ml | 2:1 |
| B1(3) | 20 g | 0.37 g | 29.5 g | 250 ml | 1:2 |

In the above Synthetic Examples B1(1) to B1(3), a mixture of the epoxy compounds having the ratio of epoxy group:alkoxysilyl group of 1:2 to 2:1 was obtained. The ratio of epoxy group:alkoxysilyl group illustrated in Table B2 means the ratio of epoxy group:alkoxysilyl group of the total epoxy compounds present as the mixture of the compounds having the above-described different ratios of epoxy group:alkoxysilyl group.

obtained was filtered using a celite filter and evaporated to obtain Intermediate Product B22 (86 wt %, 10.1 g).

$^1$H NMR (400 MHz, $CDCl_3$). δ=8.3 (br. s, 1H), 6.81 (d, 2H, J=9.2 Hz), 6.60 (d, 2H, J=8.8 Hz), 4.13-4.01 (m, 2H), 3.94-3.90 (m, 2H), 3.34-3.30 (m, 2H), 2.89-2.86 (m, 2H), 2.73-2.71 (m, 2H)

(3) Third Step

In a two-necked flask, 20 g of 4-(bis(oxirane-2-ylmethyl) amino)phenol, that is, the above Intermediate Product B22 obtained in the second step, 50 g of allyl bromide, and 400 ml of a THF were added and stirred at room temperature. 10 g of a solution with 10 g of sodium hydroxide dissolved in 400 ml of $H_2O$ was slowly added thereto for 1 hour at room temperature, followed by further stirring for 2 hours. After completing the reaction, THF was removed by using an evaporator, and the crude product thus obtained was worked-up using 500 ml of ethyl acetate and $H_2O$ to remove inorganic materials. $MgSO_4$ was added in an organic layer to remove remaining $H_2O$. The organic layer thus obtained was filtered and evaporated to obtain Intermediate Product B23 (98 wt %, 20.6 g).

$^1$H NMR (400 MHz, $CDCl_3$). δ=6.83 (d, 2H, J=9.2 Hz), 6.67 (d, 2H, J=8.8 Hz), 6.09-5.99 (m, 1H), 5.42-5.25 (m, 2H), 4.52-4.49 (m, 2H), 4.13-4.01 (m, 2H), 3.94-3.90 (m, 2H), 3.34-3.30 (m, 2H), 2.89-2.86 (m, 2H), 2.73-2.71 (m, 2H)

(4) Fourth Step 10 g of the above Intermediate Product B23 obtained in the third step, 0.17 g of $PtO_2$, 7.5 g of triethoxysilane, and 400 ml of toluene were added in a flask, followed by stirring for 5 minutes at room temperature. Then, the temperature was increased to 80° C., and heating and stirring were performed for 12 hours. After completing the reaction, the reactant was cooled to room temperature and filtered using a celite filter to remove inorganic materials. Then, organic materials were evaporated to remove toluene, and dried by using a vacuum pump to obtain Target Product BI (15.4 g, 95 wt %).

1H NMR (400 MHz, $CDCl_3$). δ=7.00-6.84 (m, 2H), 6.75-6.64 (m, 2H), 4.18-3.83 (m 8H), 3.94-3.90 (m, 2H), 3.34-3.30 (m, 2H), 3.52-3.13 (m, 2H), 2.89-2.86 (m, 2H), 2.73-2.71 (m, 2H), 1.80-1.70 (m, 2H), 1.22 (t, 9H, J=7.2 Hz), 0.67-0.60 (m, 2H)

The synthetic reaction of the above Synthetic Example B2 is as follows.

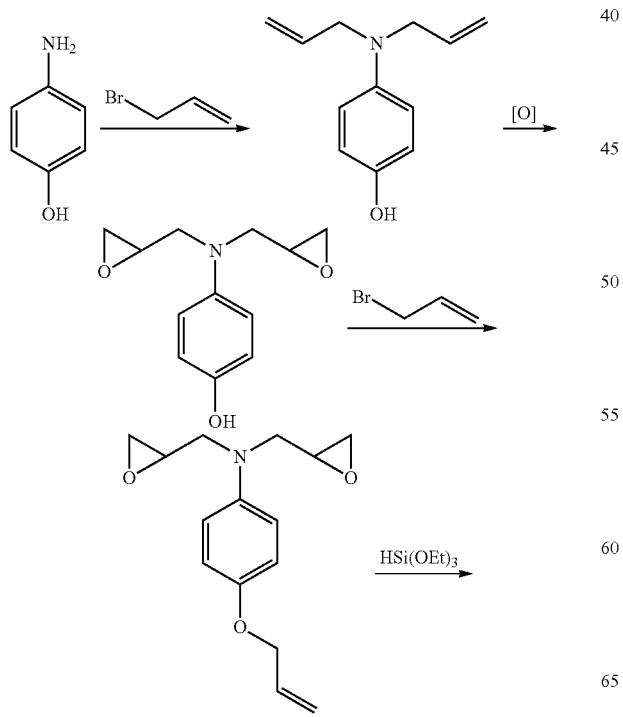

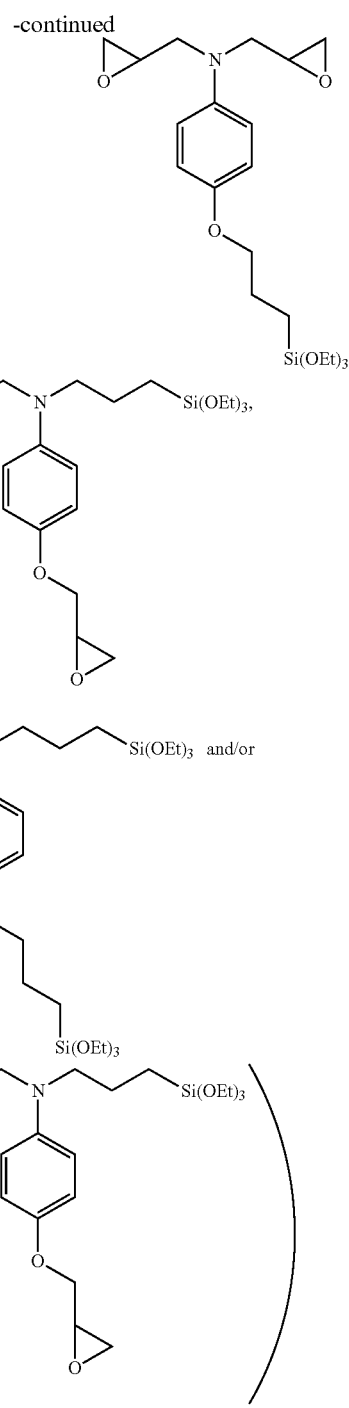

Synthetic Example B3 Synthesis of Aminophenol-Based Epoxy Having Alkoxysilyl Group (Formula BI) (Method 3)

(1) First Step 10 g of aminophenol, 108.9 g of allyl bromide, and 400 ml of THF were inserted in a two-necked flask, followed by stirring at room temperature. Then, a solution with 21.6 g of sodium hydroxide dissolved in 400 ml of $H_2O$ was slowly added thereto for 1 hour at room temperature, followed by stirring for 2 hours for performing the reaction. After completing the reaction, THF was removed by using an evaporator, and 500 ml of ethyl acetate was added and worked-up with H₂O to remove inorganic materials. In an organic layer, MgSO₄ was added to remove remaining H₂O. The organic layer thus obtained was filtered using a celite filter and evaporated to obtain Intermediate Product B31 (98 wt %, 20.6 g).

¹H NMR (400 MHz, CDCl₃). δ=6.83 (d, 2H, J=9.2 Hz), 6.67 (d, 2H, J=8.8 Hz), 5.98-5.80 (m, 3H), 5.40-5.13 (m, 6H), 4.69-4.60 (m, 2H), 3.75-3.63 (m, 4H)

(2) Second step 10 g of the above Intermediate Product B31 of the second step, 0.88 g of KHCO₃, 10.8 g of CH₃CN, and 300 ml of methanol were added in a two-necked flask, followed by stirring at room temperature. Subsequently, 19.9 g of a 30 wt % H₂O₂ solution was slowly added thereto for 10 minutes and stirred at room temperature for 6 hours. After completing the reaction, CH₃CN and methanol were removed by using an evaporator, and 300 ml of ethyl acetate was added and worked-up with 400 ml of H₂O to remove remaining H₂O₂. An organic layer was separated, and MgSO₄ was added in the organic layer to remove remaining H₂O. The organic layer thus obtained was filtered using a celite filter to obtain Intermediate Product B32 (45 wt %, 5.1 g).

¹H NMR (400 MHz, CDCl₃). δ=6.83-6.80 (m, 2H), 6.69-6.62 (m, 2H), 6.08-5.82 (m, 1H), 5.42-5.26 (m, 2H), 4.20-4.16 (m, 2H), 3.94-3.90 (m, 2H), 3.76-3.63 (m, 2H), 3.49-3.40 (m, 0.8H), 3.35-3.31 (m, 1.2H), 3.20-3.16 (m, 0.8H), 2.90-2.73 (m, 2.4H), 2.60-2.58 (m, 0.8H)

(3) Third Step 10 g of the above Intermediate Product B32 of the second step, 0.17 g of PtO₂, 7.5 g of triethoxysilane, and 400 ml of toluene were added in a flask, followed by stirring for 5 minutes at room temperature. Then, the temperature was increased to 80° C., and heating and stirring were performed for 12 hours for performing the reaction. After completing the reaction, the reactant was cooled to room temperature and filtered using a celite filter to remove inorganic materials. By removing toluene through the evaporation of organic materials and drying using a vacuum pump, Target Product BI was obtained (15.4 g, 95 wt %).

¹H NMR (400 MHz, CDCl₃). δ=7.00-6.84 (m, 2H), 6.75-6.64 (m, 2H), 4.18-4.14 (m, 0.8H), 3.92-3.88 (m, 1.2H), 3.83 (q, 6H, J=6.8 Hz), 3.71-3.62 (m, 0.8H), 3.52-3.13 (m, 5.2 H), 2.91-2.73 (m, 3.2H), 2.58-2.56 (m, 0.8H), 1.80-1.70 (m, 2H), 1.22 (t, 9H, J=7.2 Hz), 0.67-0.60 (m, 2H)

The synthetic reaction of the above Synthetic Example B3 is as follows.

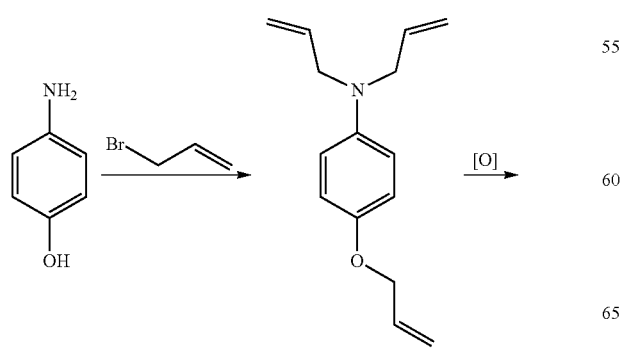

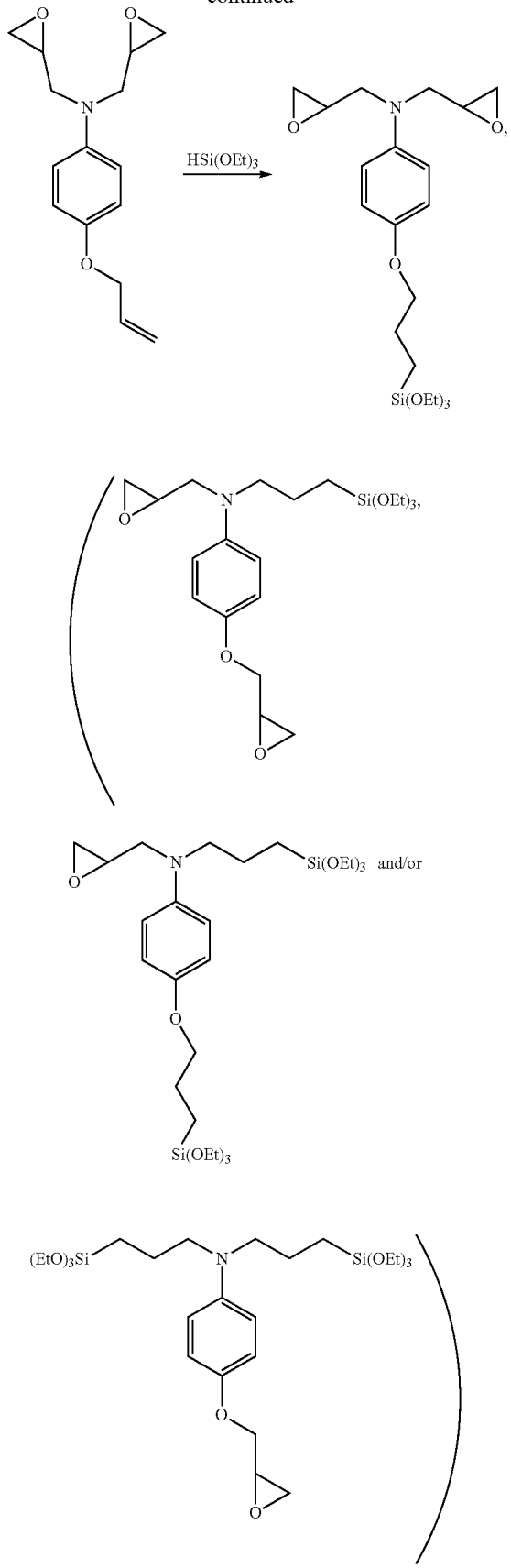

Synthetic Example B4 Synthesis of Aminophenol-Based Epoxy Having Alkoxysilyl Group (Formula BI) (Method 4)

(1) First Step 20 g of aminophenol, and 400 ml of $CH_3CN$ were inserted in a two-necked flask, followed by stirring at room temperature. Then, 101.7 g of epichlorohydrin was added thereto at room temperature, and 35.5 g of pyridine was slowly added for 1 hour, followed by stirring at room temperature for removed by using an evaporator. An organic layer was separated by working-up using 400 ml of ethyl acetate and a 1M NaOH solution. In an organic layer, $MgSO_4$ was added to remove remaining $H_2O$. The organic layer thus obtained was filtered and evaporated to obtain Intermediate Product B41 (16.2 g, 40 wt %).

$^1$H NMR (400 MHz, $CDCl_3$). δ=8.3 (br. s, 1H), 6.81 (d, 2H, J=9.2 Hz), 6.60 (d, 2H, J=8.8 Hz), 4.13-4.01 (m, 2H), 3.94-3.90 (m, 2H), 3.34-3.30 (m, 2H), 2.89-2.86 (m, 2H), 2.73-2.71 (m, 2H)

(2) Second Step and Third Step

The second step was conducted by using Intermediate Product B41 of the first step and by performing the same method as the third step of the above Synthetic Example B2, and the third step was conducted by using the intermediate product of the second step and by performing the same method as the fourth step of the above Synthetic Example B2, to obtain Target Product BI, that is the same as Synthetic Example B2.

The synthetic reaction of the above Synthetic Example B4 is as follows.

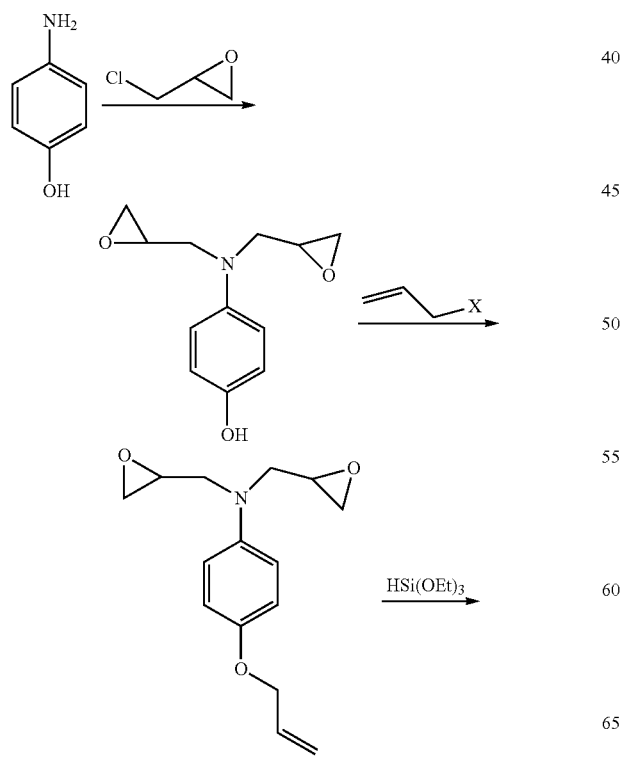

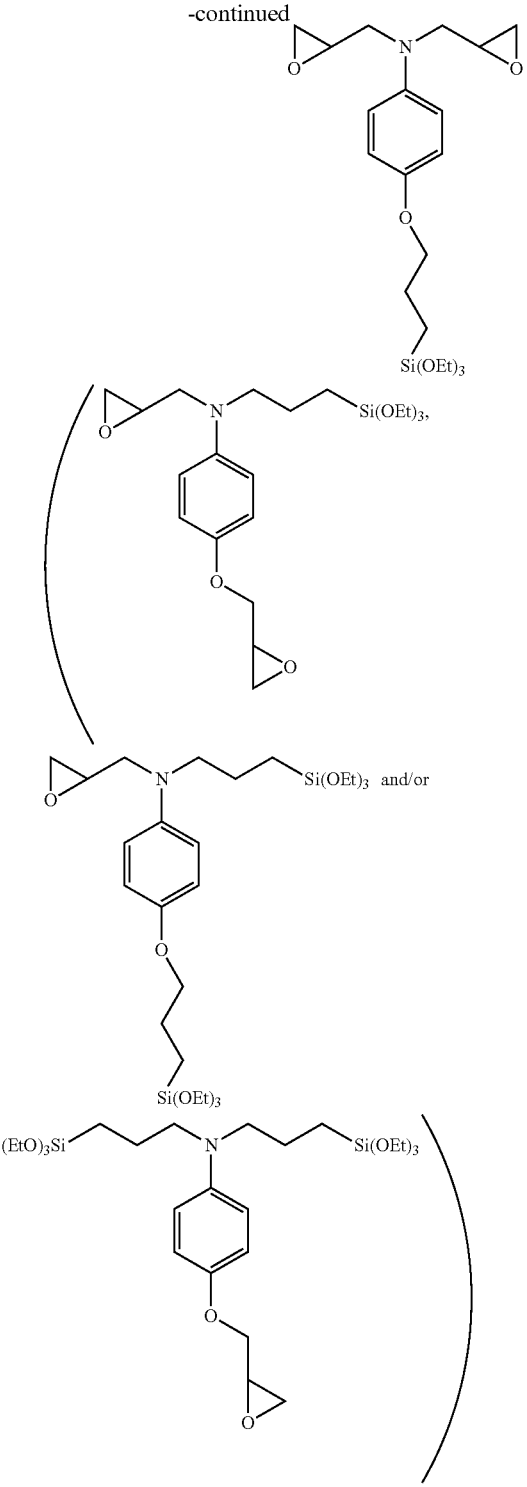

Synthetic Example B5 Synthesis of Aminophenol-Based Epoxy Having Alkoxysilyl Group (Formula BI) (Method 5)

The same intermediate product as that of the second step of Synthetic Example B2 was obtained by performing the first step and the second step of Synthetic Example B2. Then, as the third step, 10 g of the intermediate product of the second step, 11.7 g of diisopropylethylamine (DIPEA), and 500 ml of methylene chloride were added in a two-necked flask, followed by stirring at room temperature. Then, 16.7 g of triethoxysilylpropyl isocyanate was added thereto at room temperature, the temperature was increased to 60° C., and the reaction was performed for 12 hours. After completing the reaction, the reactant was cooled to room temperature and worked-up using H$_2$O. An organic layer was separated and MgSO$_4$ was added in the organic layer to remove remaining H$_2$O. The organic layer thus obtained was filtered using a celite filter and evaporated to obtain Target Product BI (18.6 g, 88 wt %).

$^1$H NMR (400 MHz, CDCl$_3$). δ=7.20 (d, 2H, J=9.2 Hz), 6.85 (d, 2H, J=8.8 Hz), 5.35 (t, 1H, J=6.0 Hz), 4.13-4.00 (m, 2H), 3.93-3.90 (m, 2H), 3.84 (q, 6H, J=6.8 Hz), 3.37-3.29 (m, 4H), 2.90-2.85 (m, 2H), 2.72-2.68 (m, 2H), 1.73-1.64 (m, 2H), 1.23 (t, 9H, J=7.2 Hz), 0.72-0.66 (m, 2H)

The synthetic reaction of the above Synthetic Example B5 is as follows.

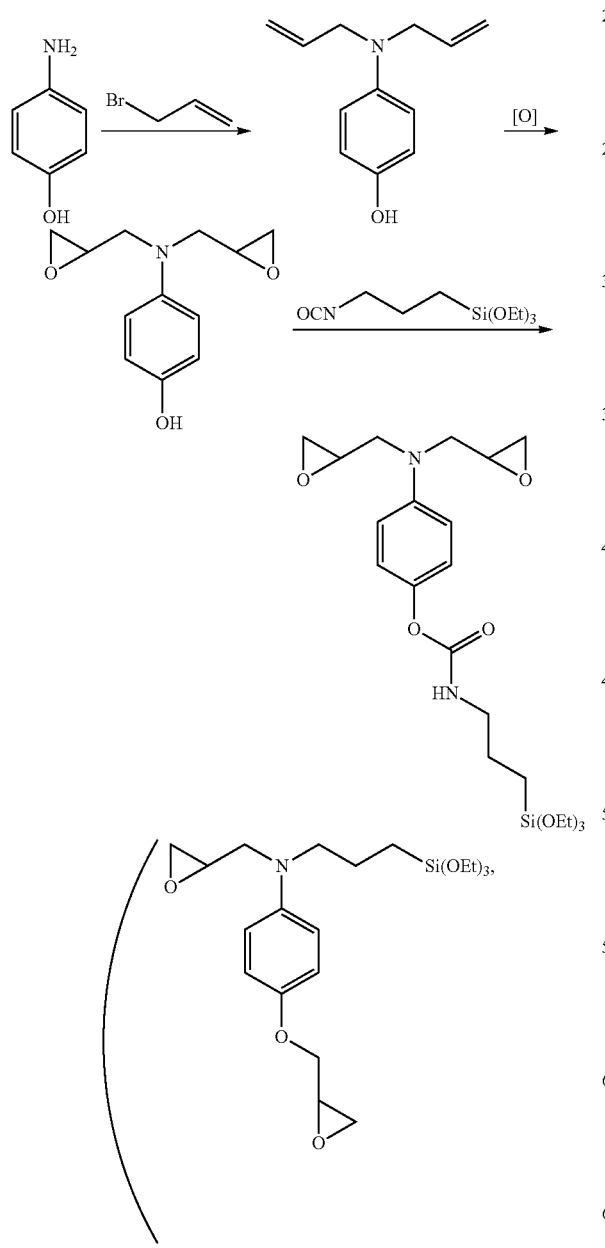

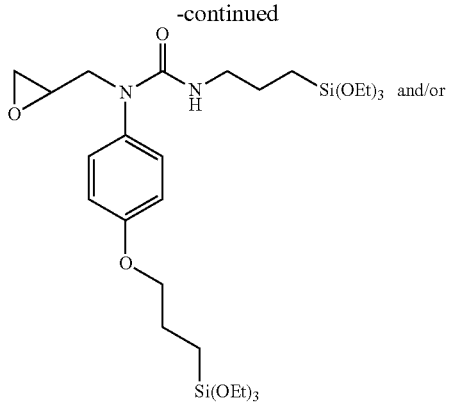

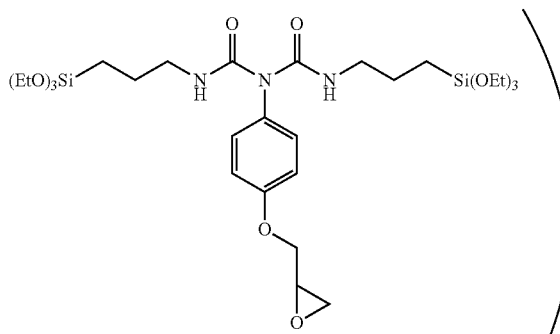

Synthetic Example B6 Synthesis of Aminophenol-Based Epoxy Having Alkoxysilyl Group (Formula BI) (Method 6)

The same intermediate product as that of the first step of Synthetic Example B4 was obtained by performing the same reaction as the first step of Synthetic Example B4. Then, the same reaction as that of the third step of Synthetic Example B5 was performed using the above intermediate product to obtain the same Target Product BI as that of Synthetic Example B6.

The synthetic reaction of the above Synthetic Example B6 is as follows.

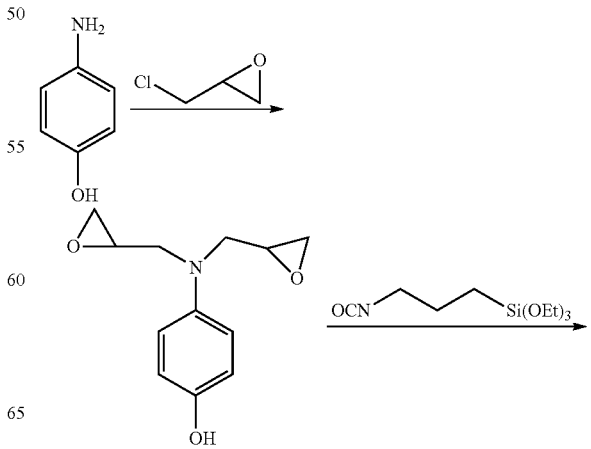

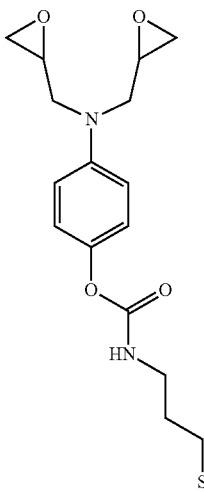

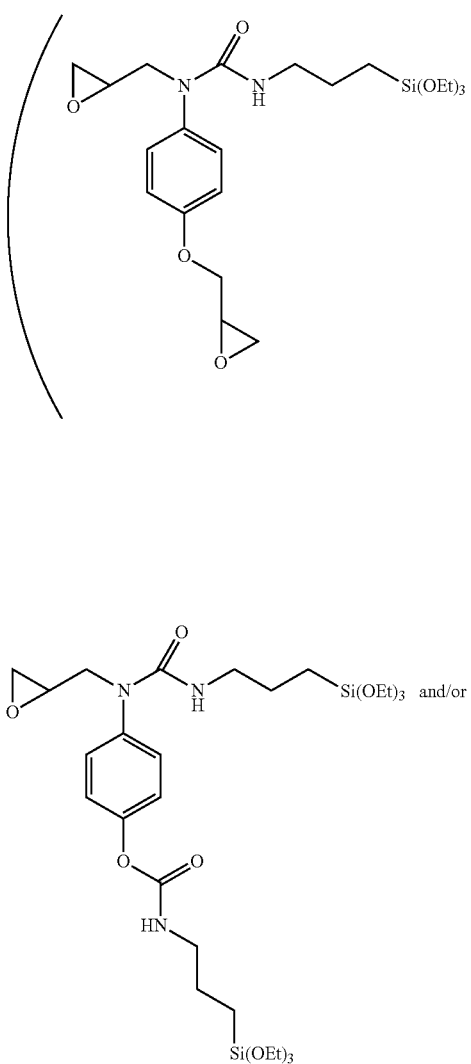

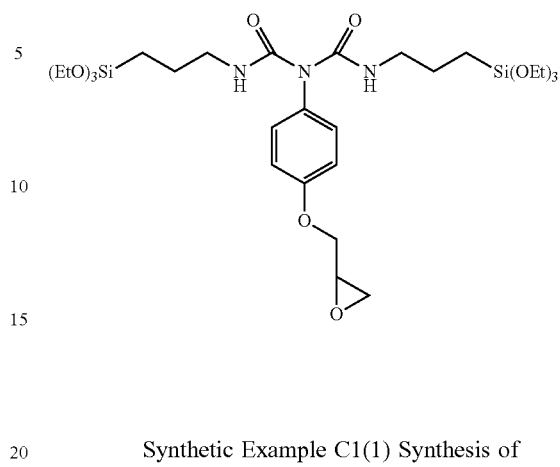

Synthetic Example C1(1) Synthesis of Binaphthalene-Based Epoxy Having Alkoxysilyl Group (Formula CI) (Method 1)

According to the following methods, Formula CI having a ratio of [epoxy group]:[alkoxysilyl group]=1:1 was synthesized.

(1) First Step 25 g of 1,1'-methylenedinaphthalene-2,7-diol (Sigma Aldrich, The same may apply hereinafter), 20.0 g of allyl bromide, and 300 ml of THF were inserted in a two-necked flask at room temperature, followed by stirring. Then, a solution with 7.5 g of sodium hydroxide dissolved in 150 ml of $H_2O$ was slowly added thereto for 1 hour at room temperature, followed by stirring for 4 hours. 34.8 g of epichlorohydrin was added in the flask, and a solution with 7.5 g of sodium hydroxide dissolved in 150 mol of $H_2O$ was added thereto for 10 minutes at room temperature, followed by stirring for 19 hours. After stirring, THF was removed by using an evaporator, and 400 ml of ethyl acetate was added and worked-up with $H_2O$ to remove inorganic materials. In an organic layer, $MgSO_4$ was added to remove remaining $H_2O$. The organic layer thus obtained was filtered using a celite filter, evaporated and dried to obtain Intermediate Product C11 having a ratio of [epoxy group]:[alkenyl group]=1:1.

$^1$H NMR (400 MHz, $CDCl_3$). δ=7.50 (d, 1H, J=8.5 Hz), 7.48 (d, 1H, J=8.5 Hz), 7.44 (d, 1H, J=8.5 Hz), 7.43 (d, 1H, J=8.5 Hz), 7.34 (s, 1H), 7.32 (s, 1H), 6.95 (d, 1H, J=8.5 Hz), 6.91 (d, 1H, J=8.5 Hz), 6.92 (d, 1H, J=7.5 Hz), 6.83 (d, 1H, J=7.5 Hz), 5.96-5.80 (m, 2H), 5.30-5.10 (m, 4H), 4.49 (s, 2H), 4.49 (dt, 4H, J=5.2 Hz, 1.2 Hz), 4.12-4.06 (m, 2H), 3.84-3.78 (m, 2H), 3.31-3.25 (m, 2H), 2.89-2.83 (m, 2H), 2.69-2.64 (m, 2H)

(2) Second Step 20 g of the above intermediate product, 0.17 g of $PtO_2$, 14.4 g of triethoxysilane, and 250 ml of toluene were added in a flask, followed by stirring for 5 minutes at room temperature. Then, the temperature was increased to 80° C., and heating and stirring were performed for 12 hours. Then, the reactant was cooled to room temperature and filtered using a celite filter to remove inorganic materials. By removing toluene through drying by evaporation and complete drying using a vacuum pump, Target Product CI was obtained.

$^1$H NMR (400 MHz, $CDCl_3$). δ=7.49 (d, 1H, J=8.5 Hz), 7.47 (d, 1H, J=8.5 Hz), 7.45 (d, 1H, J=8.5 Hz), 7.42 (d, 1H, J=8.5 Hz), 7.34 (s, 1H), 7.33 (s, 1H), 6.97 (d, 1H, J=8.5 Hz), 6.53 (d, 1H, J=8.5 Hz), 6.94 (d, 1H, J=7.5 Hz), 6.81 (d, 1H, J=7.5 Hz), 4.50 (s, 2H), 4.09-4.05 (m, 2H), 3.83 (q, 12H, J=6.8 Hz), 3.83-3.78 (m, 2H), 3.29-3.25 (m, 2H), 2.86-2.83 (m, 6H), 2.69-2.67 (m, 2H), 1.80-1.70 (m, 4H), 1.22 (t, 18H, J=7.2 Hz), 0.67-0.60 (m, 4H)

The synthetic reaction of the above Synthetic Example C1(1) is as follows.

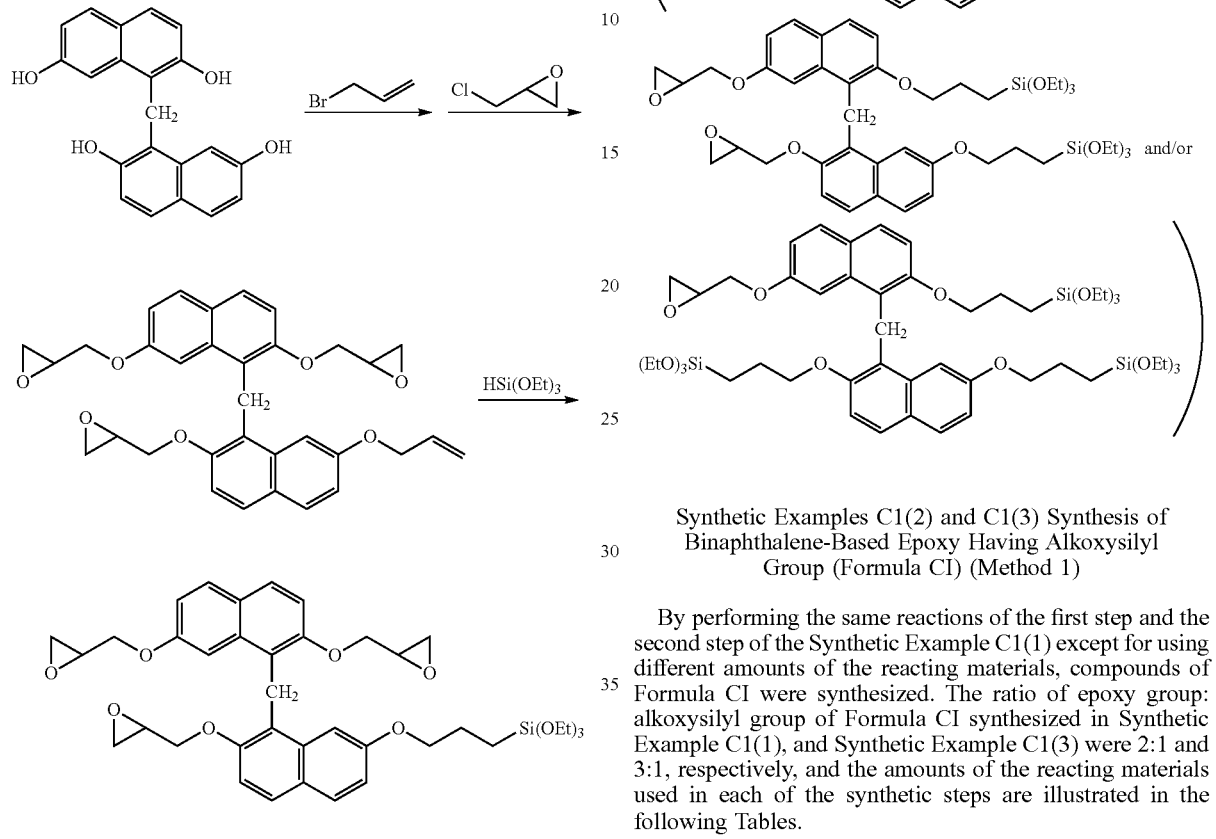

Synthetic Examples C1(2) and C1(3) Synthesis of Binaphthalene-Based Epoxy Having Alkoxysilyl Group (Formula CI) (Method 1)

By performing the same reactions of the first step and the second step of the Synthetic Example C1(1) except for using different amounts of the reacting materials, compounds of Formula CI were synthesized. The ratio of epoxy group: alkoxysilyl group of Formula CI synthesized in Synthetic Example C1(1), and Synthetic Example C1(3) were 2:1 and 3:1, respectively, and the amounts of the reacting materials used in each of the synthetic steps are illustrated in the following Tables.

TABLE C1

| | Amounts of reacting materials used in the first step for synthesizing Formula CI | | | | | | |
|---|---|---|---|---|---|---|---|
| | | | | | NaOH in 150 ml $H_2O$ | | [Epoxy group]:[alkenyl |
| Synthetic Example (1/2 step) | 1,1'-methylenedinaphthalene-2,7-diol | Allyl bromide | Epichlorohydrin | THF | First insertion | Second insertion | group] of Formula C11 |
| C1(2) | 25 g | 12.7 g | 41.7 g | 300 ml | 6.0 g | 9.0 g | 2:1 |
| C1(3) | 25 g | 10.9 g | 41.7 g | 300 ml | 4.5 g | 10.5 g | 3:1 |

TABLE C2

| | Amounts of reacting materials used in the second step for synthesizing Formula CI | | | | |
|---|---|---|---|---|---|
| Synthetic Example (2/2 step) | Formula C11 | $PtO_2$ | $HSi(OEt)_3$ | Toluene | [Epoxy group]:[alkoxysilyl group] of Formula CI |
| C1(2) | 20 g | 0.17 g | 9.1 g | 250 ml | 2:1 |
| C1(3) | 20 g | 0.17 g | 7.9 g | 250 ml | 3:1 |

In the above Synthetic Examples C1(2) and C1(3), a mixture of the epoxy compounds having the ratio of epoxy group:alkoxysilyl group of 1:3 to 3:1 is obtained as illustrated in the above Synthetic Example C1(1). The ratio of epoxy group:alkoxysilyl group illustrated in Table C2 means the ratio of epoxy group:alkoxysilyl group of the total epoxy compounds present as the mixture of the compounds having the above-described different ratios of epoxy group:alkoxysilyl group.

Synthetic Example C2 Synthesis of Binaphthalene-Based Epoxy Having Alkoxysilyl Group (Formula CI) (Method 2)

(1) First Step 20 g of 1,1'-methylenedinaphthalene-2,7-diol, 50.5 g of allyl bromide, and 300 ml of THF were inserted in a two-necked flask, followed by stirring at room temperature. A solution with 5.5 g of sodium hydroxide dissolved in 300 ml of H$_2$O was slowly added thereto at room temperature for 1 hour, followed by further stirring for 2 hours. After completing the reaction, THF was removed by using an evaporator, and the crude product was worked-up using 400 ml of ethyl acetate and H2O. MgSO$_4$ was added in an organic layer to remove remaining H$_2$O. The organic layer thus obtained was filtered using a celite filter and evaporated to obtain Intermediate Product C21 (66 wt %, 17.1 g).

$^1$H NMR (400 MHz, CDCl$_3$). δ=7.48 (d, 2H, J=8.5 Hz), 7.43 (d, 2H, J=8.5 Hz), 7.27 (s, 1H), 7.25 (s, 1H), 6.93 (d, 1H, J=8.5 Hz), 6.87 (d, 1H, J=8.5 Hz), 6.83 (d, 1H, J=7.5 Hz), 6.79 (d, 1H, J=7.5 Hz), 5.95-5.78 (m, 3H), 5.26-5.08 (m, 6H), 4.50 (s, 2H), 4.49 (dt, 6H, J=5.2 Hz, 1.2 Hz)

(2) Second Step 10 g of the above Intermediate Product C21 obtained in the first step, 0.6 g of KHCO$_3$, 12.45 g of CH$_3$CN, and 300 ml of methanol were added in a two-necked flask, followed by stirring at room temperature. Subsequently, 17.3 g of a 30 wt % H$_2$O$_2$ solution was slowly added thereto for 10 minutes and stirred at room temperature for 12 hours. After completing the reaction, CH$_3$CN and methanol were removed by using an evaporator, and 300 ml of ethyl acetate was added and worked-up with H$_2$O to remove remaining H$_2$O$_2$. An organic layer was separated, and MgSO$_4$ was added in the organic layer to remove remaining H$_2$O. The organic layer thus obtained was filtered using a celite filter and evaporated to obtain Intermediate Product C22 (80 wt %, 8.7 g).

$^1$H NMR (400 MHz, CDCl$_3$). δ=7.49 (d, 2H, J=8.5 Hz), 7.43 (d, 2H, J=8.5 Hz), 7.35 (s, 1H), 7.33 (s, 1H), 6.95 (d, 1H, J=8.5 Hz), 6.92 (d, 1H, J=8.5 Hz), 6.89 (d, 1H, J=7.5 Hz), 6.84 (d, 1H, 7.5 Hz), 4.09-4.05 (m, 3H), 3.84-3.80 (m, 3H), 3.29-3.25 (m, 3H), 2.86-2.83 (m, 3H), 2.69-2.67 (m, 3H)

(3) Third Step

In a two-necked flask, 10 g of 8-(2,7-bis(oxirane-2-ylmethoxy)naphthalene-1-yl)methyl)-7-(oxirane-2-ylmethoxy)naphthalene-2-ol, that is, the above Intermediate Product C22 obtained in the second step, 3.3 g of K$_2$CO$_3$, and 250 ml of a CH$_3$CN solvent were added and stirred at room temperature. 3.84 g of allyl bromide was added thereto at room temperature, and the temperature was increased to 80° C., followed by stirring for 5 hours. After completing the reaction, the reactant was cooled to room temperature and filtered using a celite filter to remove inorganic materials. The CH$_3$CN solvent was removed by using an evaporator, and the crude product thus obtained was worked-up using ethyl acetate and H$_2$O three times. An organic layer was separated, and MgSO$_4$ was added in the organic layer to remove remaining H$_2$O. The organic layer thus obtained was filtered and evaporated to obtain Intermediate Product C23.

$^1$H NMR (400 MHz, CDCl$_3$). δ=7.50 (d, 1H, J=8.5 Hz), 7.48 (d, 1H, J=8.5 Hz), 7.44 (d, 1H, J=8.5 Hz), 7.43 (d, 1H, J=8.5 Hz), 7.34 (s, 1H), 7.32 (s, 1H), 6.95 (d, 1H, J=8.5 Hz), 6.91 (d, 1H, J=8.5 Hz), 6.92 (d, 1H, J=7.5 Hz), 6.83 (d, 1H, J=7.5 Hz), 5.96-5.80 (m, 1H), 5.30-5.10 (m, 2H), 4.49 (s, 2H), 4.49 (dt, 2H, J=5.2 Hz, 1.2 Hz), 4.12-4.06 (m, 3H), 3.84-3.78 (m, 3H), 3.31-3.25 (m, 3H), 2.89-2.83 (m, 3H), 2.69-2.64 (m, 3H)

(4) Fourth Step 8.8 g of the above Intermediate Product C23 of the third step, 70 mg of PtO$_2$, 3.0 g of triethoxysilane, and 150 ml of toluene were added in a flask, followed by stirring for 5 minutes at room temperature. Then, the reaction temperature was increased to 80° C., and the reaction was performed for 12 hours while stirring. After completing the reaction, the reactant was cooled to room temperature and filtered using a celite filter to remove inorganic materials. Then, toluene was removed through evaporation and dried using a vacuum pump to obtain Target Product CI.

1H NMR (400 MHz, CDCl$_3$). δ=7.49 (d, 1H, J=8.5 Hz), 7.47 (d, 1H, J=8.5 Hz), 7.45 (d, 1H, J=8.5 Hz), 7.42 (d, 1H, J=8.5 Hz), 7.34 (s, 1H), 7.33 (s, 1H), 6.97 (d, 1H, J=8.5 Hz), 6.53 (d, 1H, J=8.5 Hz), 6.94 (d, 1H, J=7.5 Hz), 6.81 (d, 1H, J=7.5 Hz), 4.50 (s, 2H), 4.09-4.05 (m, 3H), 3.83 (q, 6H, J=6.8 Hz), 3.83-3.78 (m, 3H), 3.29-3.25 (m, 3H), 2.86-2.83 (m, 5H), 2.69-2.67 (m, 3H), 1.80-1.70 (m, 2H), 1.22 (t, 9H, J=7.2 Hz), 0.67-0.60 (m, 2H)

The synthetic reaction of the above Synthetic Example C2 is as follows.

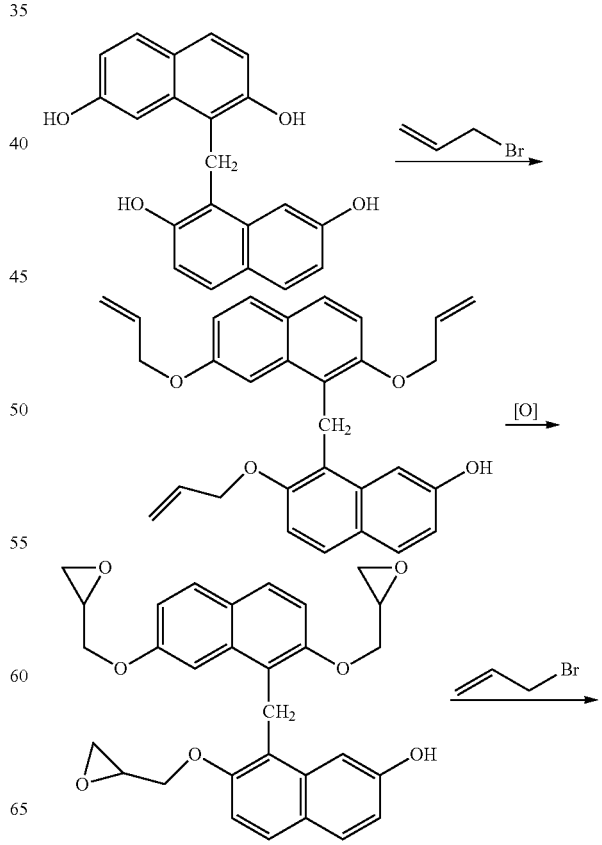

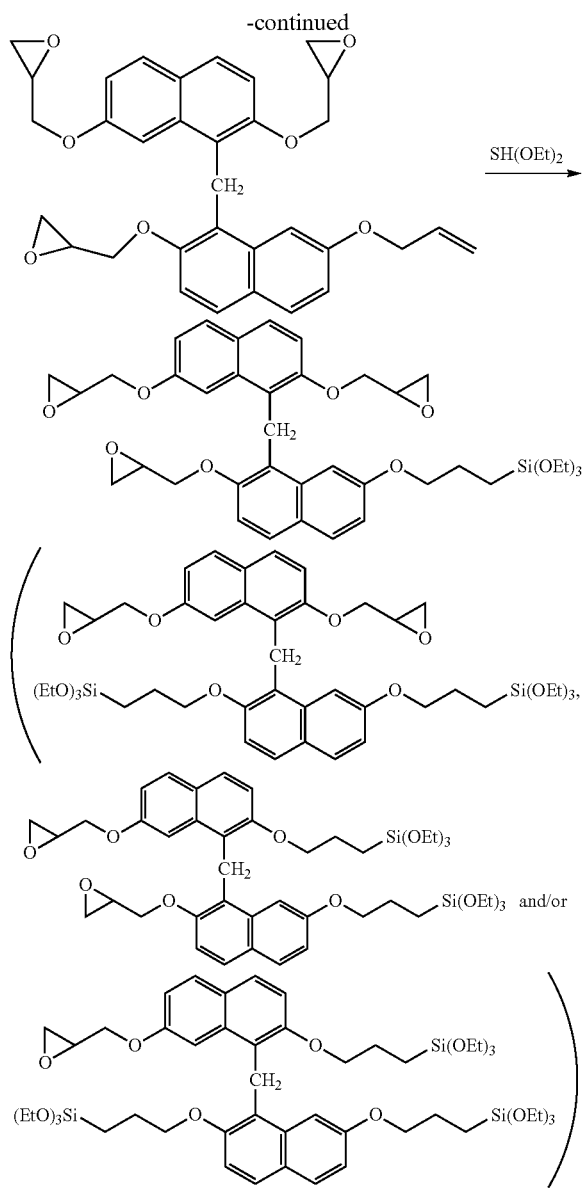

Synthetic Example C3 Synthesis of Binaphthalene-Based Epoxy Having Alkoxysilyl Group (Formula CI) (Method 3)

(1) First Step 20 g of 1,1'-methylenedinaphthalene-2,7-diol, 72.8 g of allyl bromide, and 400 ml of THF were inserted in a two-necked flask, followed by stirring at room temperature. Then, a solution with 19.2 g of sodium hydroxide dissolved in 300 ml of $H_2O$ was slowly added thereto for 1 hour at room temperature, followed by further stirring for 4 hours. After completing the reaction, THF was removed by using an evaporator, and 300 ml of ethyl acetate and 400 ml of $H_2O$ were added to work-up to remove inorganic materials. In an organic layer, $MgSO_4$ was added to remove remaining $H_2O$. The organic layer thus obtained was filtered using a celite filter to obtain Intermediate Product C31 (94%, 27.9 g).

$^1$H NMR (400 MHz, $CDCl_3$). δ=7.46 (d, 2H, J=8.5 Hz), 7.42 (d, 2H, J=8.5 Hz), 7.25 (s, 2H), 6.88 (d, 2H, J=8.5 Hz), 6.79 (d, 2H, 7.5 Hz), 5.94-5.81 (m, 4H), 5.28-5.11 (m, 8H), 4.50 (s, 2H), 4.47 (dt, 8H, J=5.2 Hz, 1.2 Hz)

(2) Second step 10 g of the above Intermediate Product C31 obtained in the first step, 0.77 g of $KHCO_3$, 7.1 g of $CH_3CN$, and 300 ml of methanol were added in a two-necked flask, followed by stirring at room temperature. Subsequently, 13.6 g of a 30 wt % $H_2O_2$ solution was slowly added thereto for 10 minutes and stirred at room temperature for 6 hours to perform the reaction. After completing the reaction, $CH_3CN$ and methanol were removed by using an evaporator, and 250 ml of ethyl acetate with 400 ml of $H_2O$ were added to work-up to remove remaining $H_2O_2$. An organic layer was separated, and $MgSO_4$ was added in the organic layer to remove remaining $H_2O$. The organic layer thus obtained was filtered using a celite filter to obtain Intermediate Product C32 (46%, 5.0 g).

$^1$H NMR (400 MHz, $CDCl_3$). δ=7.50 (d, 1H, J=8.5 Hz), 7.48 (d, 1H, J=8.5 Hz), 7.44 (d, 1H, J=8.5 Hz), 7.43 (d, 1H, J=8.5 Hz), 7.34 (s, 1H), 7.32 (s, 1H), 6.95 (d, 1H, J=8.5 Hz), 6.91 (d, 1H, J=8.5 Hz), 6.92 (d, 1H, J=7.5 Hz), 6.83 (d, 1H, J=7.5 Hz), 5.96-5.80 (m, 1H), 5.30-5.10 (m, 2H), 4.49 (s, 2H), 4.49 (dt, 2H, J=5.2 Hz, 1.2 Hz), 4.12-4.06 (m, 3H), 3.84-3.78 (m, 3H), 3.31-3.25 (m, 3H), 2.89-2.83 (m, 3H), 2.69-2.64 (m, 3H)

(3) Third Step 10 g of the above Intermediate Product C32 of the second step, 84 mg of $PtO_2$, 3.65 g of triethoxysilane, and 150 ml of toluene were added in a flask, followed by stirring for 5 minutes at room temperature. Then, the temperature was increased to 80° C., and heating and stirring were performed for 12 hours to perform the reaction. After completing the reaction, the reactant was cooled to room temperature and filtered using a celite filter to remove inorganic materials. By removing toluene through evaporation and complete drying using a vacuum pump, Target Product CI was obtained (12.8 g, 98 wt %).

$^1$H NMR (400 MHz, $CDCl_3$). δ=7.49 (d, 1H, J=8.5 Hz), 7.47 (d, 1H, J=8.5 Hz), 7.45 (d, 1H, J=8.5 Hz), 7.42 (d, 1H, J=8.5 Hz), 7.34 (s, 1H), 7.33 (s, 1H), 6.97 (d, 1H, J=8.5 Hz), 6.53 (d, 1H, J=8.5 Hz), 6.94 (d, 1H, J=7.5 Hz), 6.81 (d, 1H, J=7.5 Hz), 4.50 (s, 2H), 4.09-4.05 (m, 3H), 3.83 (q, 6H, J=6.8 Hz), 3.83-3.78 (m, 3H), 3.29-3.25 (m, 3H), 2.86-2.83 (m, 5H), 2.69-2.67 (m, 3H), 1.80-1.70 (m, 2H), 1.22 (t, 9H, J=7.2 Hz), 0.67-0.60 (m, 2H)

The synthetic reaction of the above Synthetic Example C3 is as follows.

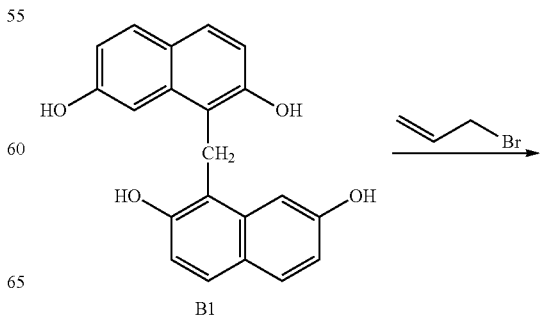

B1

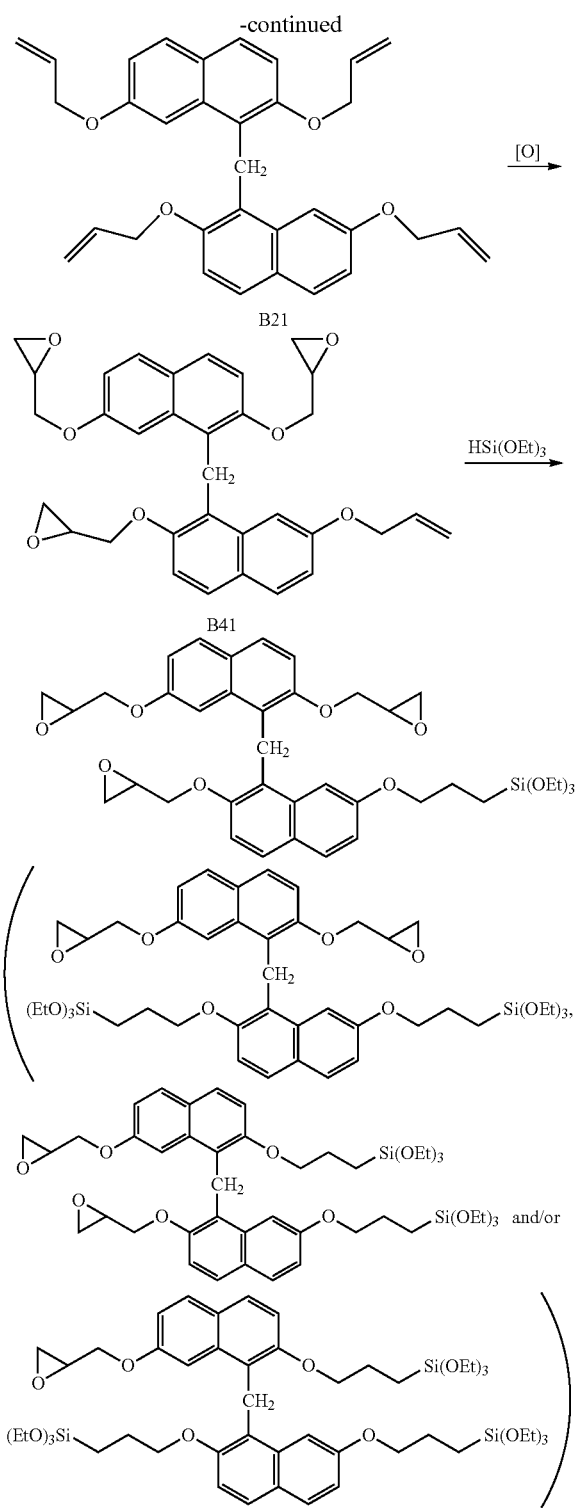

Then, 19.3 g of epichlorohydrin was added thereto at room temperature, followed by stirring at 80° C. for 5 hours. After completing the reaction, the reactant was cooled to room temperature, and filtered by using a celite filter to remove inorganic materials. Subsequently, the $CH_3CN$ solvent was removed by using an evaporator. The crude product was worked-up using ethyl acetate and $H_2O$ three times, and an organic layer was separated. In the organic layer, $MgSO_4$ was added to remove remaining $H_2O$. The organic layer thus obtained was filtered and evaporated to obtain Intermediate Product C41 (6.8 g, 48 wt %).

$^1$H NMR (400 MHz, $CDCl_3$). δ=7.49 (d, 2H, J=8.5 Hz), 7.43 (d, 2H, J=8.5 Hz), 7.35 (s, 1H), 7.33 (s, 1H), 6.95 (d, 1H, J=8.5 Hz), 6.92 (d, 1H, J=8.5 Hz), 6.89 (d, 1H, J=7.5 Hz), 6.84 (d, 1H, 7.5 Hz), 4.09-4.05 (m, 3H), 3.84-3.80 (m, 3H), 3.29-3.25 (m, 3H), 2.86-2.83 (m, 3H), 2.69-2.67 (m, 3H)

(2) Second Step and Third Step

The alkenylation (allylation) of the second step was conducted by using the above Intermediate Product C41 of the first step and by performing the same procedure as the third step of the above Synthetic Example C2, and the alkoxysilylation of the third step was conducted by using the intermediate product of the second step and by performing the same procedure as the fourth step of the above Synthetic Example C2, to obtain Target Product CI, that is the same target product as that in Synthetic Example C2.

The synthetic reaction of the above Synthetic Example C4 is as follows.

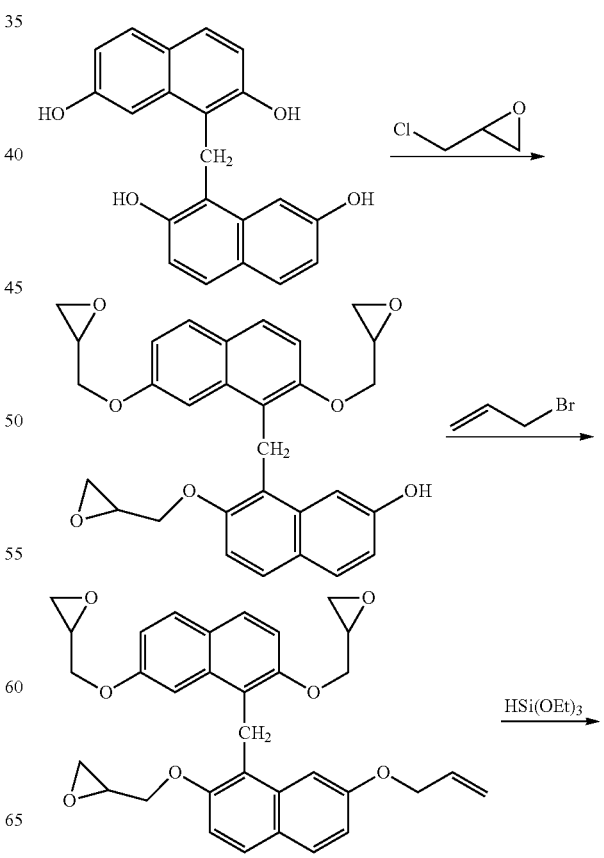

Synthetic Example C4 Synthesis of Binaphthalene-Based Epoxy Having Alkoxysilyl Group (Formula CI) (Method 4)

(1) First Step 10 g of 1,1'-methylenedinaphthalene-2,7-diol, 9.5 g of $K_2CO_3$, and 200 ml of $CH_3CN$ were inserted in a two-necked flask, followed by stirring at room temperature.

-continued

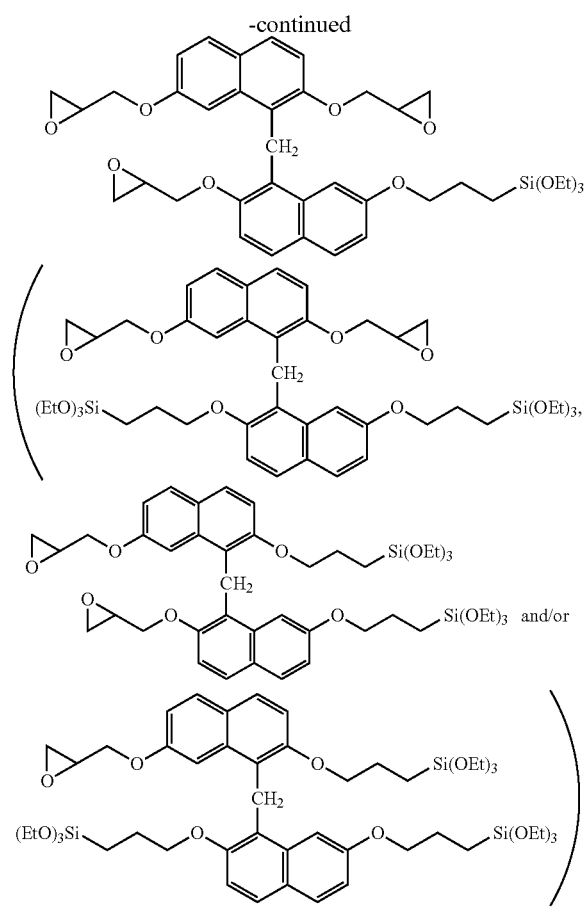

Synthetic Example C5 Synthesis of Binaphthalene-Based Epoxy Having Alkoxysilyl Group (Formula CI) (Method 5)

The same intermediate product as that of the second step of Synthetic Example C2 was obtained by performing the first step and the second step of Synthetic Example C2. Then, as the third step, 10 g of the intermediate product of the second step, that is, 8-((2,7-bis(oxirane-2-ylmethoxy)naphthalene-1-yl)methyl)-7-(oxirane-2-ylmethoxy)naphthalene-2-ol, 4.1 g of diisopropylethylamine, and 200 ml of methylene chloride were added in a two-necked flask, followed by stirring at room temperature. Then, 5.79 g of triethoxysilylpropyl isocyanate was added thereto at room temperature, the temperature was increased to 60° C., and the reaction was performed for 12 hours. After completing the reaction, the reactant was cooled to room temperature and worked-up using $H_2O$. An organic layer was separated and $MgSO_4$ was added in the organic layer to remove remaining $H_2O$. The organic layer thus obtained was filtered using a celite filter and evaporated to obtain Target Product CI (12.5 g, 87 wt %).

$^1$H NMR (400 MHz, $CDCl_3$). δ=7.48 (d, 2H, J=8.5 Hz), 7.42 (d, 2H, J=8.5 Hz), 7.34 (s, 1H), 7.33 (s, 1H), 6.96 (d, 1H, J=8.5 Hz), 6.92 (d, 1H, J=8.5 Hz), 6.89 (d, 1H, J=7.5 Hz), 6.84 (d, 1H, J=7.5 Hz), 5.37 (t, 1H, 6.0 Hz), 4.49 (s, 2H), 4.09-4.05 (m, 3H), 3.84 (q, 6H, J=6.8 Hz), 3.84-3.77 (m, 3H), 3.36-3.30 (m, 2H), 3.26-3.22 (m, 3H), 2.89-2.81 (m, 3H), 2.66-2.63 (m, 3H), 1.75-1.67 (m, 2H), 1.23 (t, 9H, J=7.2 Hz), 0.71-0.66 (m, 2H)

The synthetic reaction of the above Synthetic Example C5 is as follows.

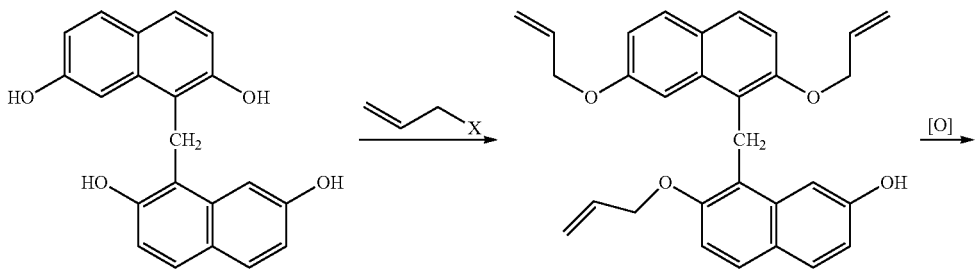

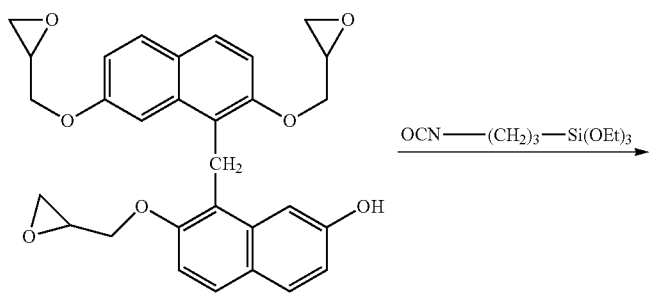

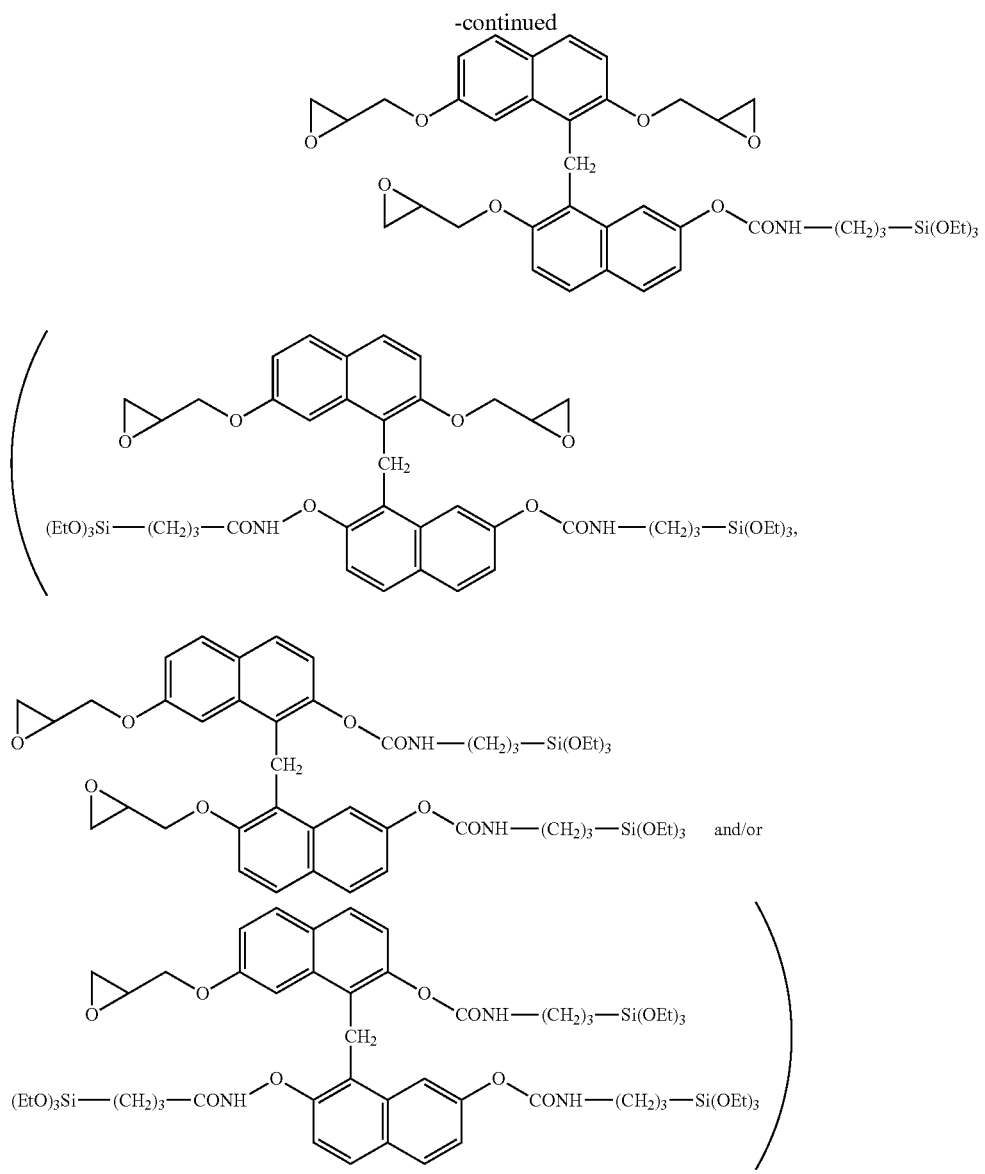

Synthetic Example C6 Synthesis of Binaphthalene-Based Epoxy Having Alkoxysilyl Group (Formula CI) (Method 6)

The same intermediate product as that of the first step of Synthetic Example C4 was obtained by performing the same reaction as the first step of Synthetic Example C4. Then, the same reaction as that of the third step of Synthetic Example C5 was performed using the intermediate product thus obtained to produce the same Target Product CI as that of Synthetic Example C5.

The synthetic reaction of the above Synthetic Example C6 is as follows.

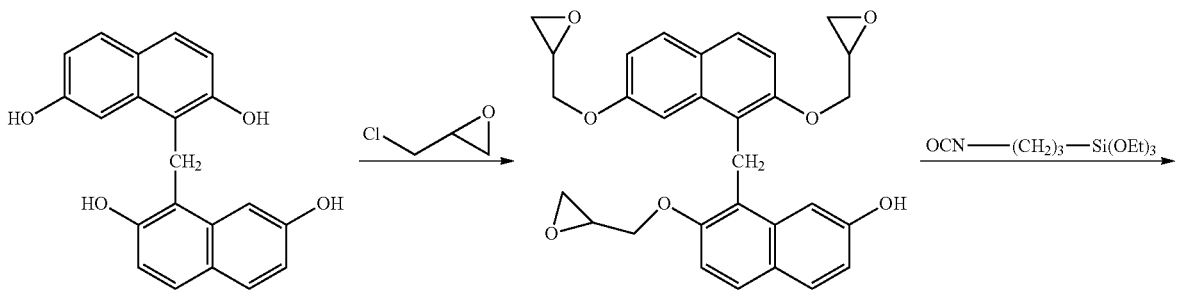

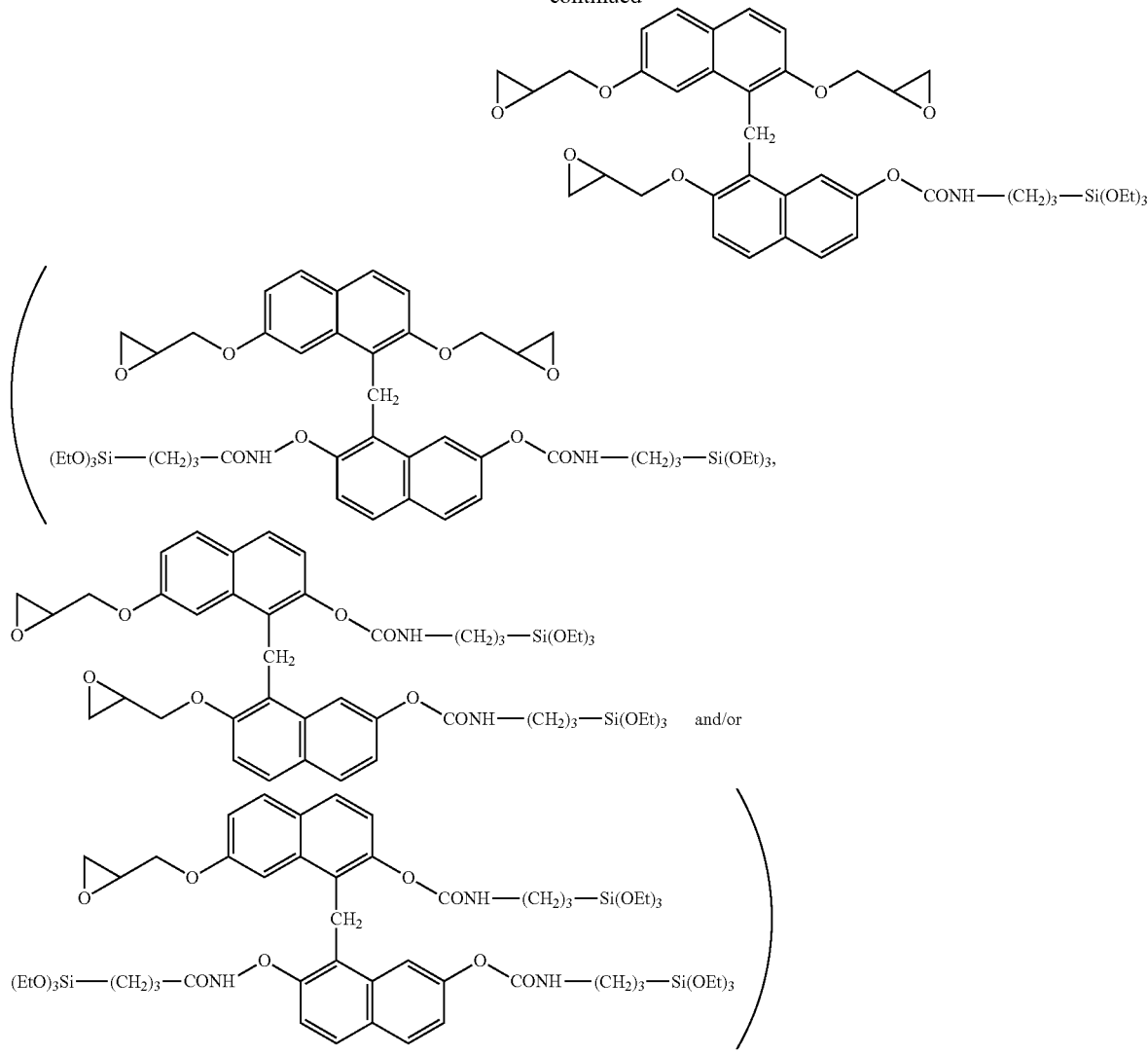

Synthetic Example D1(1) Synthesis of Tetraphenylethane-Based Epoxy Having Alkoxysilyl Group (Formula DI) (Method 1)

According to the following methods, Formula DI having a ratio of [epoxy group]:[alkoxysilyl group]=1:1 was synthesized.

(1) First Step 25 g of 1,1,2,2-tetrakis(p-hydroxyphenyl)ethane (Sigma Aldrich, The same may apply hereinafter), 16.7 g of allyl bromide, and 300 ml of THF were inserted in a two-necked flask at room temperature, followed by stirring. Then, a solution with 6.27 g of sodium hydroxide dissolved in 150 ml of $H_2O$ was slowly added thereto for 1 hour at room temperature, followed by stirring for 4 hours. 29.0 g of epichlorohydrin was added in the flask, and a solution with 6.27 g of sodium hydroxide dissolved in 150 mol of $H_2O$ was added thereto for 10 minutes at room temperature, followed by stirring for 19 hours. After stirring, THF was removed by using an evaporator, and 400 ml of ethyl acetate was added and worked-up with $H_2O$ to remove inorganic materials. In an organic layer, $MgSO_4$ was added to remove remaining $H_2O$. The organic layer thus obtained was filtered using a celite filter, evaporated and dried to obtain Intermediate Product D11 having a ratio of [epoxy group]:[alkenyl group]=1:1.

$^1$H NMR (400 MHz, $CDCl_3$). δ=6.98 (d, 6H, J=8.8 Hz), 6.88 (d, 2H, J=8.8 Hz), 6.65 (d, 6H, J=8.8 Hz), 6.55 (d, 2H, J=8.8 Hz), 5.94-5.82 (m, 2H), 5.28-5.11 (m, 4H), 4.54 (br. s, 2H), 4.47 (dt, 4H, J=5.2 Hz, 1.2 Hz), 4.11-4.05 (m, 2H), 3.84-3.80 (m, 2H), 3.29-3.25 (m, 2H), 2.86-2.83 (m, 2H), 2.69-2.67 (m, 2H)

(2) Second Step 20 g of the above Intermediate Product D11, 0.15 g of $PtO_2$, 12.8 g of triethoxysilane, and 250 ml of toluene were added in a flask, followed by stirring for 5 minutes at room temperature. Then, the temperature was increased to 80° C., and heating and stirring were performed for 12 hours. Then, the reactant was cooled to room temperature and filtered using a celite filter to remove inorganic materials. By removing toluene through drying by evaporation and complete drying using a vacuum pump, the target product was obtained.

$^1$H NMR (400 MHz, CDCl$_3$). δ=6.98 (d, 6H, J=8.8 Hz), 6.87 (d, 2H, J=8.8 Hz), 6.66 (d, 6H, J=8.8 Hz), 6.55 (d, 2H, J=8.8 Hz), 4.54 (br. s, 2H), 4.12-4.05 (m, 2H), 3.83 (q, 12H, J=6.8 Hz), 3.81-3.79 (m, 2H), 3.29-3.25 (m, 6H), 2.86-2.83 (m, 2H), 2.69-2.67 (m, 2H), 1.80-1.70 (m, 4H), 1.22 (t, 18H, J=7.2 Hz), 0.67-0.60 (m, 4H)

The synthetic reaction of the above Synthetic Example D1(1) is as follows.

Synthetic Examples D1(2) and D1(3) Synthesis of Tetraphenylethane-Based Epoxy Having Alkoxysilyl Group (Formula DI) (Method 1)

By performing the same reactions as the first step and the second of the Synthetic Example D1(1) except for using different amounts of the reacting materials, compounds of Formula DI were synthesized. The ratio of epoxy group: alkoxysilyl group of Formula DI synthesized in Synthetic Example D1(2) and Synthetic Example D1(3) were 2:1 and

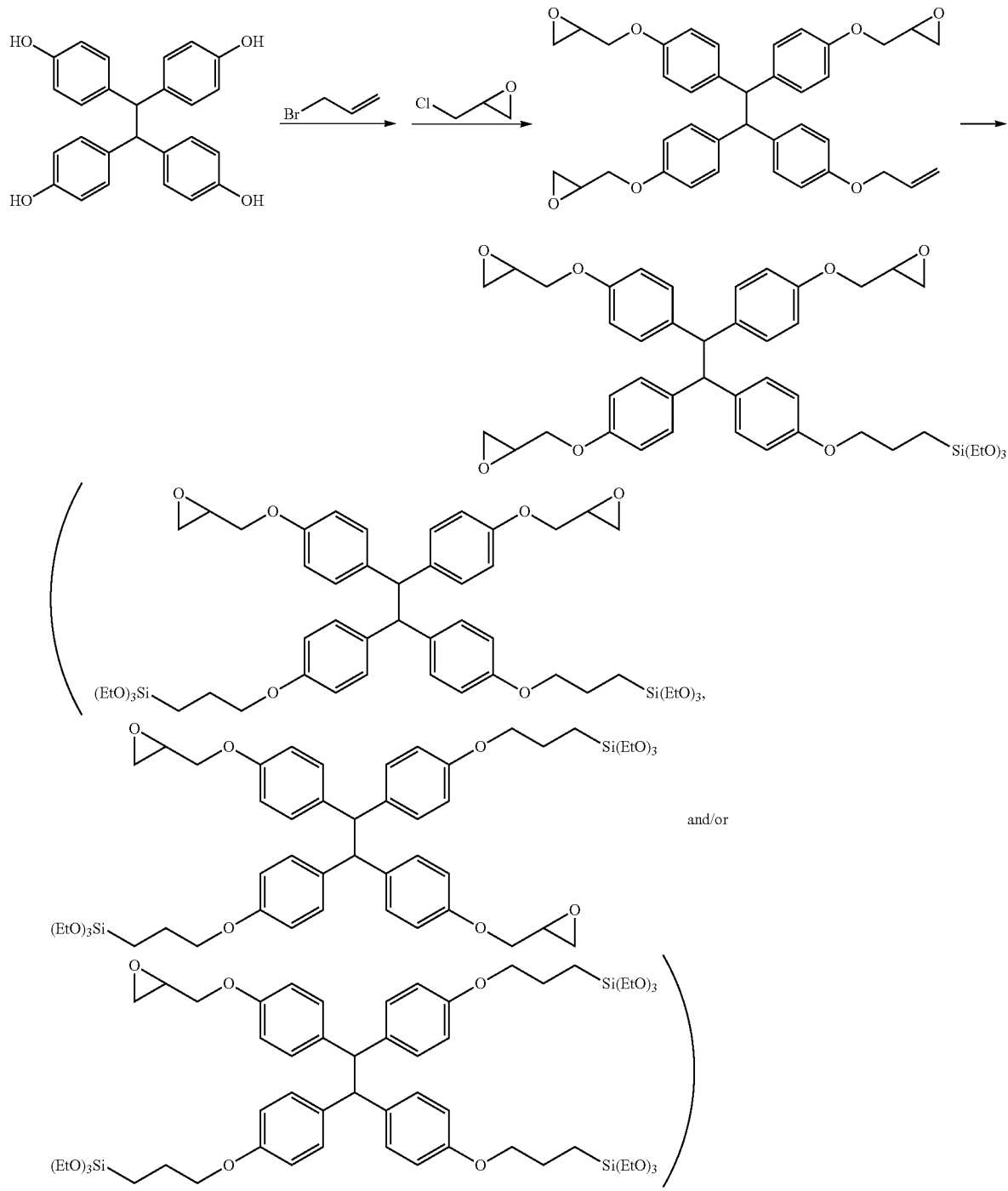

3:1, respectively, and the amounts of the reacting materials used in each of the synthetic steps are illustrated in the following Tables.

TABLE D1

Amounts of reacting materials used in the first step for synthesizing Formula DI

| Synthetic Example (1/2 step) | 1,1,2,2-tetrakis(p-hydroxyphenyl)ethane | Allyl bromide | Epichlorohydrin | THF | NaOH in 150 ml $H_2O$ First insertion | Second insertion | [Epoxy group]:[alkenyl group] of Formula D11 |
|---|---|---|---|---|---|---|---|
| D1(2) | 25 g | 10.6 g | 34.8 g | 300 ml | 5.0 g | 7.5 g | 2:1 |
| D1(3) | 25 g | 9.1 g | 34.8 g | 300 ml | 3.8 g | 8.8 g | 3:1 |

TABLE D2

Amounts of reacting materials used in the second step for synthesizing Formula DI

| Synthetic Example (2/2 step) | Formula D11 | $PtO_2$ | $HSi(OEt)_3$ | Toluene | [Epoxy group]:[alkoxysilyl group] of Formula DI |
|---|---|---|---|---|---|
| D1(2) | 20 g | 0.15 g | 8.1 g (1.5 eq.) | 250 ml | 2:1 |
| D1(3) | 20 g | 0.15 g | 7.0 g (1.3 eq.) | 250 ml | 3:1 |

In the above Synthetic Examples D1(1) to D1(3), a mixture of the epoxy compounds having the ratio of epoxy group:alkoxysilyl group of 1:3 to 3:1 is obtained as illustrated in the above Synthetic Example D1(1). The ratio of epoxy group:alkoxysilyl group illustrated in Table D2 means the ratio of epoxy group:alkoxysilyl group of the total epoxy compounds present as the mixture of the compounds having the above-described different ratios of epoxy group:alkoxysilyl group.

Synthetic Example D2 Synthesis of Tetraphenylethane-Based Epoxy Having Alkoxysilyl Group (Formula DI) (Method 2)

(1) First Step 20 g of 1,1,2,2-tetrakis(p-hydroxyphenyl)ethane, 60.7 g of allyl bromide, and 300 ml of THF were inserted in a two-necked flask at room temperature, followed by stirring. A solution of 6.6 g of sodium hydroxide dissolved in 300 ml of $H_2O$ was slowly added thereto at room temperature for 1 hour, followed by further stirring for 2 hours. After completing the reaction, THF was removed by using an evaporator, and the crude product was worked-up using 400 ml of ethyl acetate and $H_2O$. $MgSO_4$ was added in an organic layer to remove remaining $H_2O$. The organic layer thus obtained was filtered using a celite filter and evaporated to obtain Intermediate Product D21 having three allyl functional groups (66 wt %, 17.1 g).

$^1$H NMR (400 MHz, $CDCl_3$). δ=6.88 (d, 6H, J=8.8 Hz), 6.83 (d, 2H, J=8.8 Hz), 6.61 (d, 6H, J=8.8 Hz), 6.56 (d, 2H, J=8.8 Hz), 5.94-5.81 (m, 3H), 5.28-5.11 (m, 7H), 4.55 (br. s, 2H), 4.47 (dt, 6H, J=5.2 Hz, 1.2 Hz)

(2) Second Step 10 g of the above Intermediate Product D21 obtained in the first step, 0.7 g of $KHCO_3$, 14.2 g of $CH_3CN$, and 300 ml of methanol were added in a two-necked flask, followed by stirring at room temperature. Subsequently, 19.7 g of a 30 wt % $H_2O_2$ solution was slowly added thereto for 10 minutes and stirred at room temperature for 12 hours. After completing the reaction, $CH_3CN$ and methanol were removed by using an evaporator, and 300 ml of ethyl acetate was added and worked-up with $H_2O$ to remove remaining $H_2O_2$. An organic layer was separated, and $MgSO_4$ was added in the organic layer to remove remaining $H_2O$. The organic layer thus obtained was filtered using a celite filter and evaporated to obtain Intermediate Product D22 (80%, 8.7 g).

$^1$H NMR (400 MHz, $CDCl_3$). δ=6.98 (d, 6H, J=8.8 Hz), 6.88 (d, 2H, J=8.8 Hz), 6.65 (d, 6H, J=8.8 Hz), 6.55 (d, 2H, J=8.8 Hz), 5.43 (s, 1H), 4.54 (br. s, 2H), 4.09-4.05 (m, 3H), 3.84-3.80 (m, 3H), 3.29-3.25 (m, 3H), 2.86-2.83 (m, 3H), 2.69-2.67 (m, 3H)

(3) Third Step

In a two-necked flask, 10 g of the above Intermediate Product D22 obtained in the second step, 3.7 g of $K_2CO_3$, and 250 ml of a $CH_3CN$ solvent were added and stirred at room temperature. 4.35 g of allyl bromide was added thereto at room temperature, and the temperature was increased to 80° C., followed by stirring for 5 hours. After completing the reaction, the reactant was cooled to room temperature and filtered using a celite filter to remove inorganic materials. The $CH_3CN$ solvent was removed by using an evaporator, and the crude product thus obtained was worked-up using ethyl acetate and $H_2O$ three times. An organic layer was separated, and $MgSO_4$ was added in the organic layer to remove remaining $H_2O$. The organic layer thus obtained was filtered and evaporated to obtain Intermediate Product D23 having an alkenyl group and three functional groups.

$^1$H NMR (400 MHz, $CDCl_3$). δ=6.98 (d, 6H, J=8.8 Hz), 6.88 (d, 2H, J=8.8 Hz), 6.65 (d, 6H, J=8.8 Hz), 6.55 (d, 2H, J=8.8 Hz), 5.94-5.82 (m, 1H), 5.28-5.11 (m, 2H), 4.54 (br. s, 2H), 4.47 (dt, 2H, J=5.2 Hz, 1.2 Hz), 4.09-4.05 (m, 3H), 3.84-3.80 (m, 3H), 3.29-3.25 (m, 3H), 2.86-2.83 (m, 3H), 2.69-2.67 (m, 3H)

(4) Fourth Step 10 g of the above Intermediate Product D23 of the third step, 75 mg of $PtO_2$, 3.15 g of triethoxysilane, and 150 ml of toluene were added in a flask, followed by stirring for 5 minutes at room temperature. Then, the reaction temperature was increased to 80° C., and the reaction was performed for 12 hours while stirring. After completing the reaction, the reactant was cooled to room temperature and filtered using a celite filter to remove inorganic materials. Then, toluene was removed through the evaporation of the reactant excluding the inorganic materials and completely dried using a vacuum pump to obtain Target Product DI (12.4 g, 98 wt %).

$^1$H NMR (400 MHz, CDCl$_3$). δ=6.98 (d, 6H, J=8.8 Hz), 6.87 (d, 2H, J=8.8 Hz), 6.66 (d, 6H, J=8.8 Hz), 6.55 (d, 2H, J=8.8 Hz), 4.54 (br. s, 2H), 4.09-4.05 (m, 3H), 3.83 (q, 6H, J=6.8 Hz), 3.81-3.79 (m, 3H), 3.29-3.25 (m, 5H), 2.86-2.83 (m, 3H), 2.69-2.67 (m, 3H), 1.80-1.70 (m, 2H), 1.22 (t, 9H, J=7.2 Hz), 0.67-0.60 (m, 2H)

The synthetic reaction of the above Synthetic Example D2 is as follows.

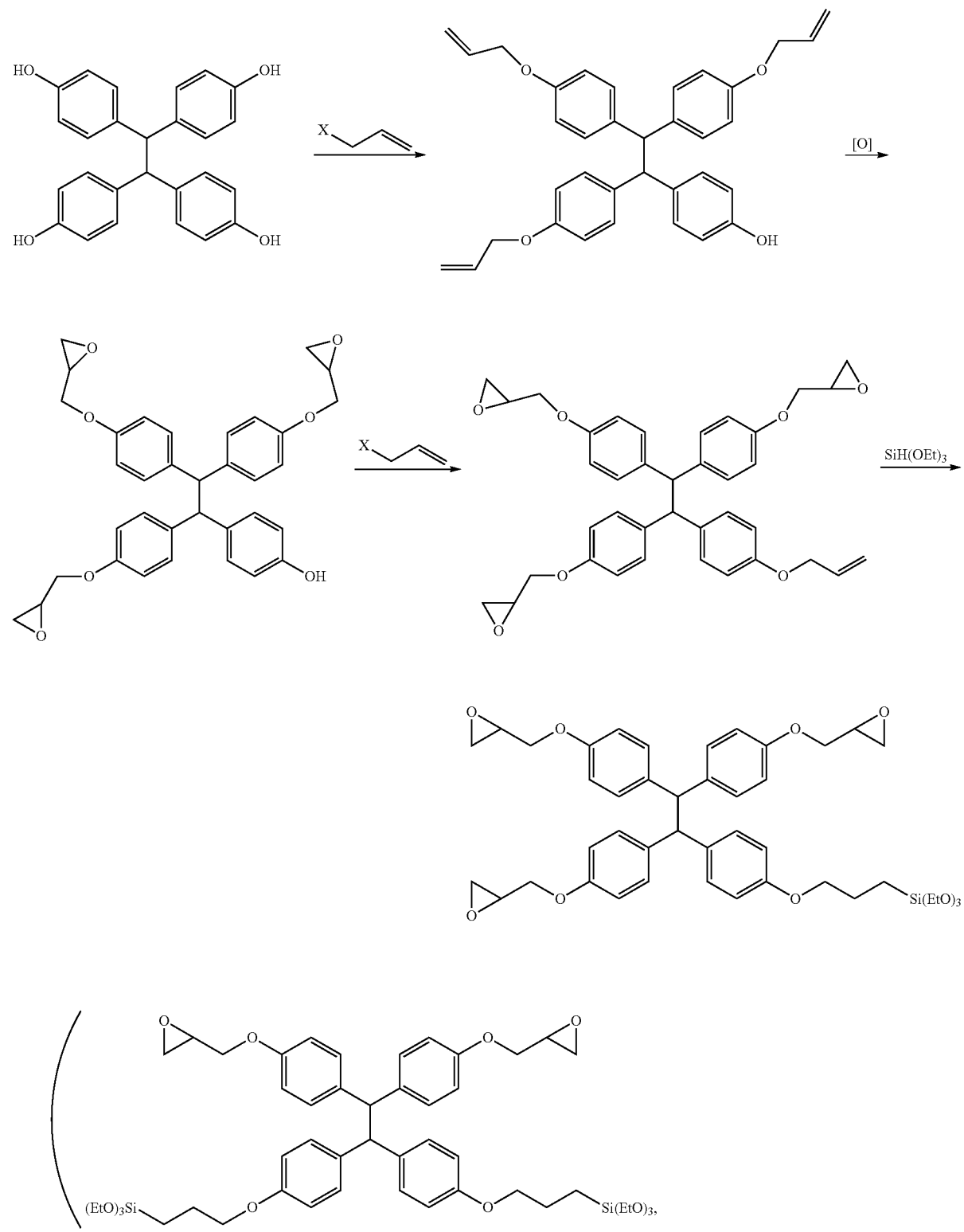

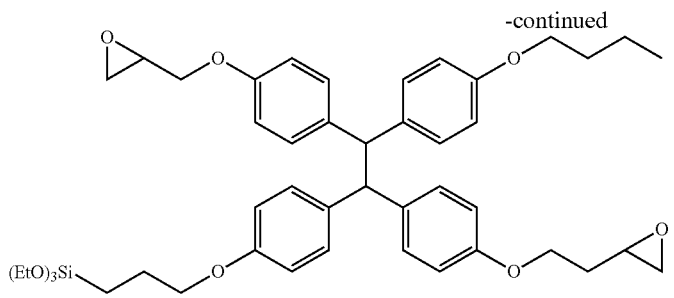

and/or 

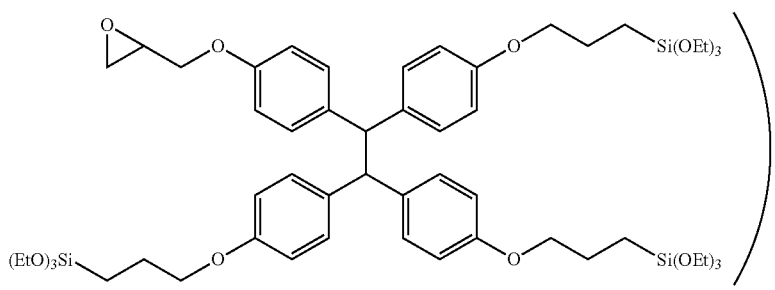

Synthetic Example D3 Synthesis of Tetraphenylethane-Based Epoxy Having Alkoxysilyl Group (Formula DI) (Method 3)

(1) First Step 20 g of 1,1,2,2-tetrakis(p-hydroxyphenyl)ethane, 60.5 g of allyl bromide, and 300 ml of THF were inserted in a two-necked flask, followed by stirring at room temperature. Then, a solution with 16 g of sodium hydroxide dissolved in 300 ml of $H_2O$ was slowly added thereto for 1 hour at room temperature, followed by further stirring for 4 hours. After completing the reaction, THF was removed by using an evaporator, and 300 ml of ethyl acetate and 400 ml of $H_2O$ were added to work-up three times to remove inorganic materials. In an organic layer, $MgSO_4$ was added to remove remaining $H_2O$. The organic layer thus obtained was filtered using a celite filter to obtain Intermediate Product D31 (95 wt %, 26.6 g).

$^1$H NMR (400 MHz, $CDCl_3$). δ=7.01 (d, 8H, J=8.8 Hz), 6.66 (d, 8H, J=8.8 Hz), 5.94-5.81 (m, 4H), 5.28-5.11 (m, 8H), 4.54 (s, 2H), 4.47 (dt, 8H, J=5.2 Hz, 1.2 Hz)

(2) Second Step 10 g of the above Intermediate Product D31 obtained in the first step, 0.77 g of $KHCO_3$, 7.1 g of $CH_3CN$, and 300 ml of methanol were added in a two-necked flask, followed by stirring at room temperature. Subsequently, 13.6 g of a 30 wt % $H_2O_2$ solution was slowly added thereto for 10 minutes and stirred at room temperature for 6 hours. After completing the reaction, $CH_3CN$ and MeOH were removed by using an evaporator, and 250 ml of ethyl acetate with 400 ml of $H_2O$ were added to work-up and to remove remaining $H_2O_2$. An organic layer was separated, and $MgSO_4$ was added in the organic layer to remove remaining $H_2O$. The organic layer thus obtained was filtered using a celite filter to obtain Intermediate Product D32 (49 wt %, 5.3 g).

$^1$H NMR (400 MHz, $CDCl_3$). δ=6.98 (d, 6H, J=8.8 Hz), 6.88 (d, 2H, J=8.8 Hz), 6.65 (d, 6H, J=8.8 Hz), 6.55 (d, 2H, J=8.8 Hz), 5.94-5.82 (m, 1H), 5.28-5.11 (m, 2H), 4.54 (br. s, 2H), 4.47 (dt, 2H, J=5.2 Hz, 1.2 Hz), 4.09-4.05 (m, 3H), 3.84-3.80 (m, 3H), 3.29-3.25 (m, 3H), 2.86-2.83 (m, 3H), 2.69-2.67 (m, 3H)

(3) Third Step 10 g of the above Intermediate Product D32 of the second step, 75 mg of $PtO_2$, 3.15 g of triethoxysilane, and 150 ml of toluene were added in a flask, followed by stirring for 5 minutes at room temperature. Then, the temperature was increased to 80° C., and heating and stirring were performed for 12 hours. After completing the reaction, the reactant was cooled to room temperature and filtered using a celite filter to remove inorganic materials. By removing toluene through evaporation and complete drying using a vacuum pump, Target Product DI was obtained (12.4 g, 98 wt %).

$^1$H NMR (400 MHz, $CDCl_3$). δ=6.98 (d, 6H, J=8.8 Hz), 6.87 (d, 2H, J=8.8 Hz), 6.66 (d, 6H, J=8.8 Hz), 6.55 (d, 2H, J=8.8 Hz), 4.54 (br. s, 2H), 4.09-4.05 (m, 3H), 3.83 (q, 6H, J=6.8 Hz), 3.81-3.79 (m, 3H), 3.29-3.25 (m, 5H), 2.86-2.83 (m, 3H), 2.69-2.67 (m, 3H), 1.80-1.70 (m, 2H), 1.22 (t, 9H, J=7.2 Hz), 0.67-0.60 (m, 2H)

The synthetic reaction of the above Synthetic Example D3 is as follows.

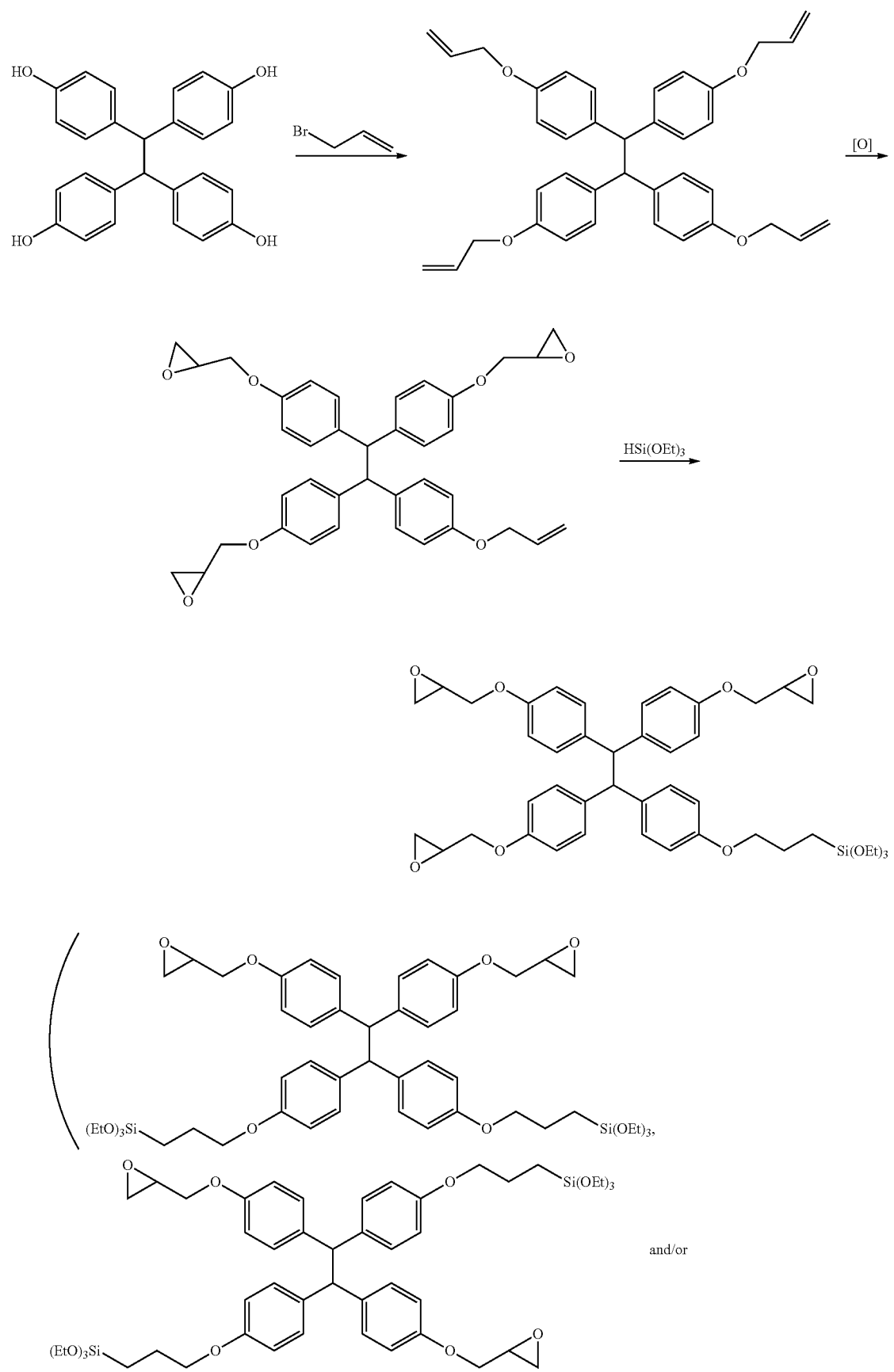

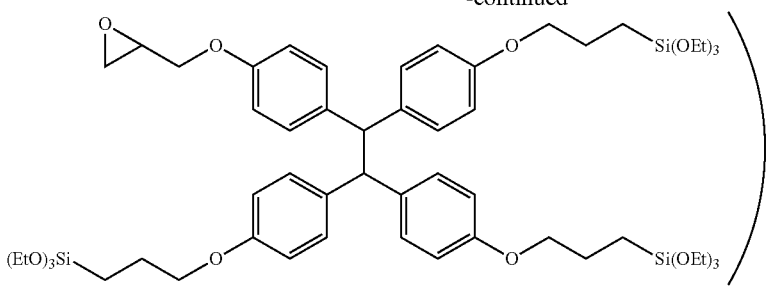

Synthetic Example D4 Synthesis of Tetraphenylethane-Based Epoxy Having Alkoxysilyl Group (Formula DI) (Method 4)

(1) First Step 10 g of 1,1,2,2-tetrakis(p-hydroxyphenyl)ethane, 11.4 g of $K_2CO_3$, and 200 ml of $CH_3CN$ were inserted in a two-necked flask, followed by stirring at room temperature. Then, 23.1 g of epichlorohydrin was added thereto at room temperature, followed by stirring at 80° C. for 5 hours. After completing the reaction, the reactant was cooled to room temperature, and filtered by using a celite filter to remove inorganic materials. The $CH_3CN$ solvent was removed by using an evaporator. The crude product was worked-up using ethyl acetate and $H_2O$ three times, and an organic layer was separated. In the organic layer, $MgSO_4$ was added to remove remaining $H_2O$. The organic layer thus obtained was filtered and evaporated to obtain Intermediate Product D41 (6.8 g, 48 wt %).

$^1$H NMR (400 MHz, $CDCl_3$). δ=6.98 (d, 6H, J=8.8 Hz), 6.88 (d, 2H, J=8.8 Hz), 6.65 (d, 6H, J=8.8 Hz), 6.55 (d, 2H, J=8.8 Hz), 5.43 (s, 1H), 4.54 (br. s, 2H), 4.09-4.05 (m, 3H), 3.84-3.80 (m, 3H), 3.29-3.25 (m, 3H), 2.86-2.83 (m, 3H), 2.69-2.67 (m, 3H)

(2) Second Step and Third Step

By using the above Intermediate Product D41 of the first step and performing the same method as described in the third step and the fourth step of the above Synthetic Example D2, Target Product DI, which is the same target product as that of Synthetic Example 1 was obtained.

The synthetic reaction of the above Synthetic Example D4 is as follows.

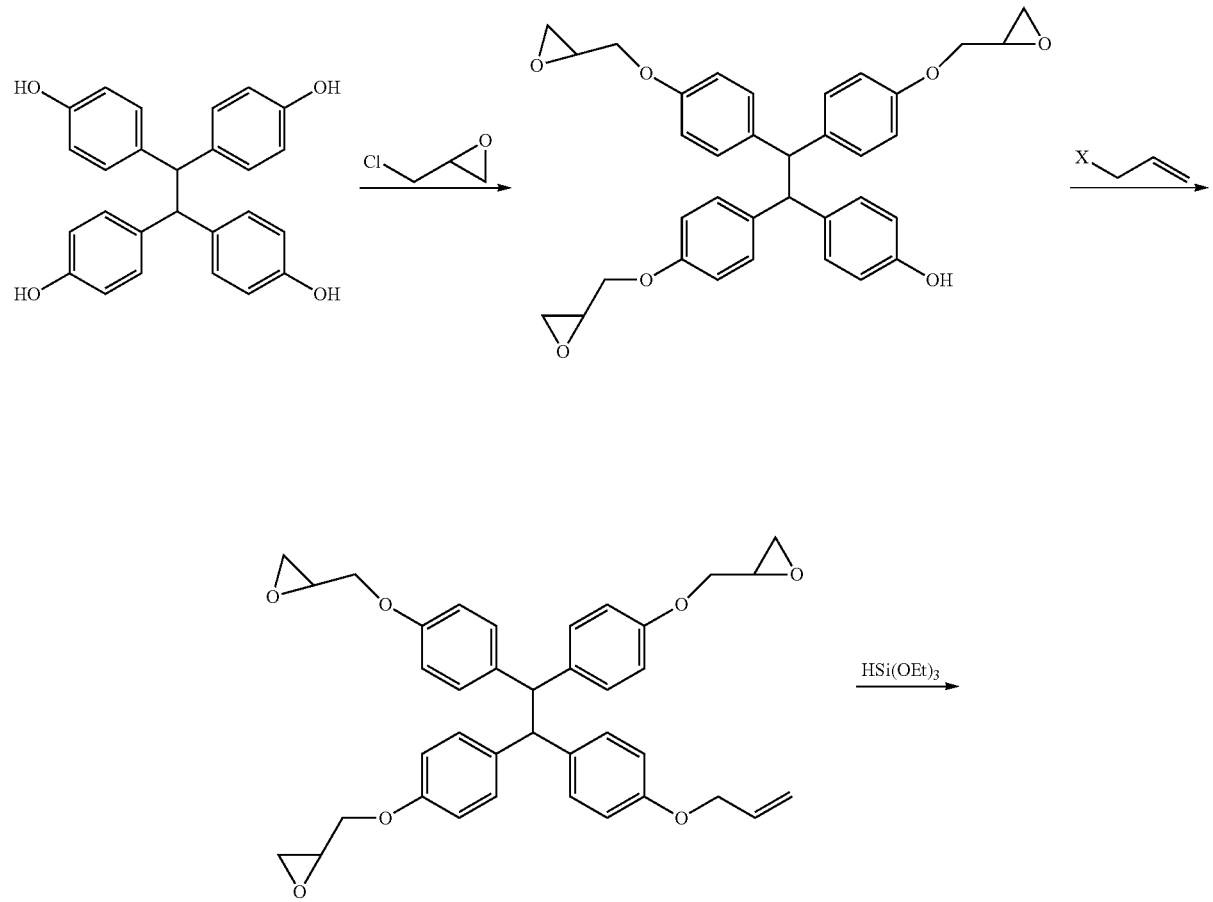

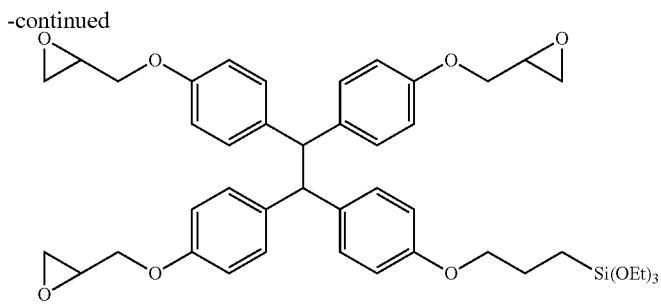

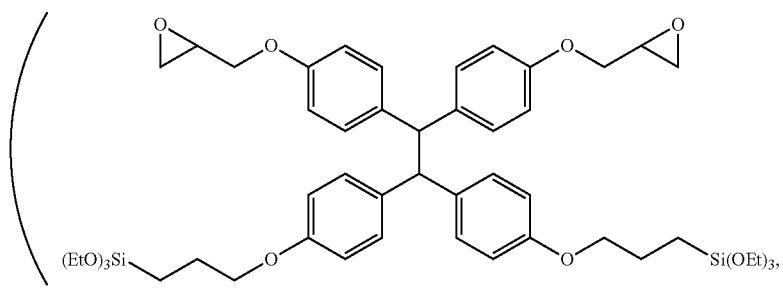

and/or

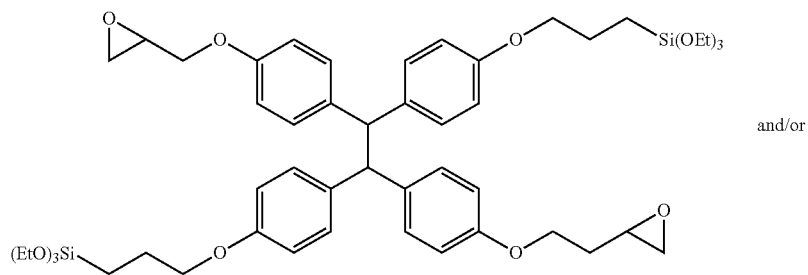

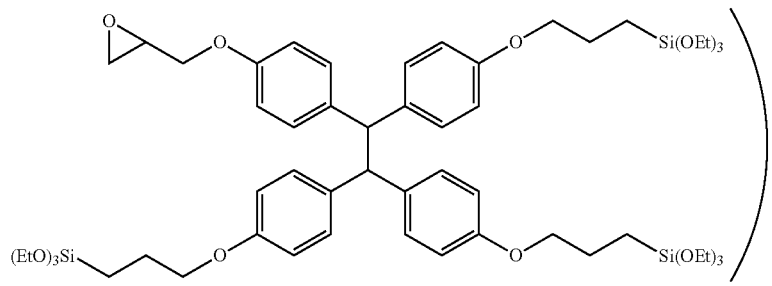

Synthetic Example D5 Synthesis of Tetraphenylethane-Based Epoxy Having Alkoxysilyl Group (Formula DI) (Method 5)

The same intermediate product as that of the second step of Synthetic Example D2 was obtained by performing the first step and the second step of Synthetic Example D2. Then, as the third step, 10 g of the intermediate product of the second step, that is, 4-(1,2,2-tris(4-(oxirane-2-yl-methoxy)phenyl)ethyl)phenol, 4.6 g of diisopropylethylamine, and 200 ml of methylene chloride were added in a two-necked flask, followed by stirring at room temperature. Then, 6.55 g of triethoxysilylpropyl isocyanate was added thereto at room temperature, the temperature was increased to 60° C., and the reaction was performed for 12 hours. After completing the reaction, the reactant was cooled to room temperature and worked-up using $H_2O$. An organic layer was separated, and $MgSO_4$ was added in the organic layer to remove remaining $H_2O$. The organic layer thus obtained was filtered using a celite filter and evaporated to obtain Target Product DI (12.5 g, 87 wt %).

$^1$H NMR (400 MHz, $CDCl_3$). δ=7.3-7.1 (m, 10H), 6.68 (d, 6H, J=8.8 Hz), 5.32 (t, 1H, 6.0 Hz), 4.54 (s, 2H), 4.08-4.04 (m, 3H), 3.83 (q, 6H, J=6.8 Hz), 3.81-3.77 (m, 3H), 3.36-3.32 (m, 2H), 3.25-3.23 (m, 3H), 2.88-2.81 (m, 3H), 2.67-2.65 (m, 3H), 1.74-1.66 (m, 2H), 1.24 (t, 9H, J=7.2 Hz), 0.70-0.66 (m, 2H)

The synthetic reaction of the above Synthetic Example D5 is as follows.

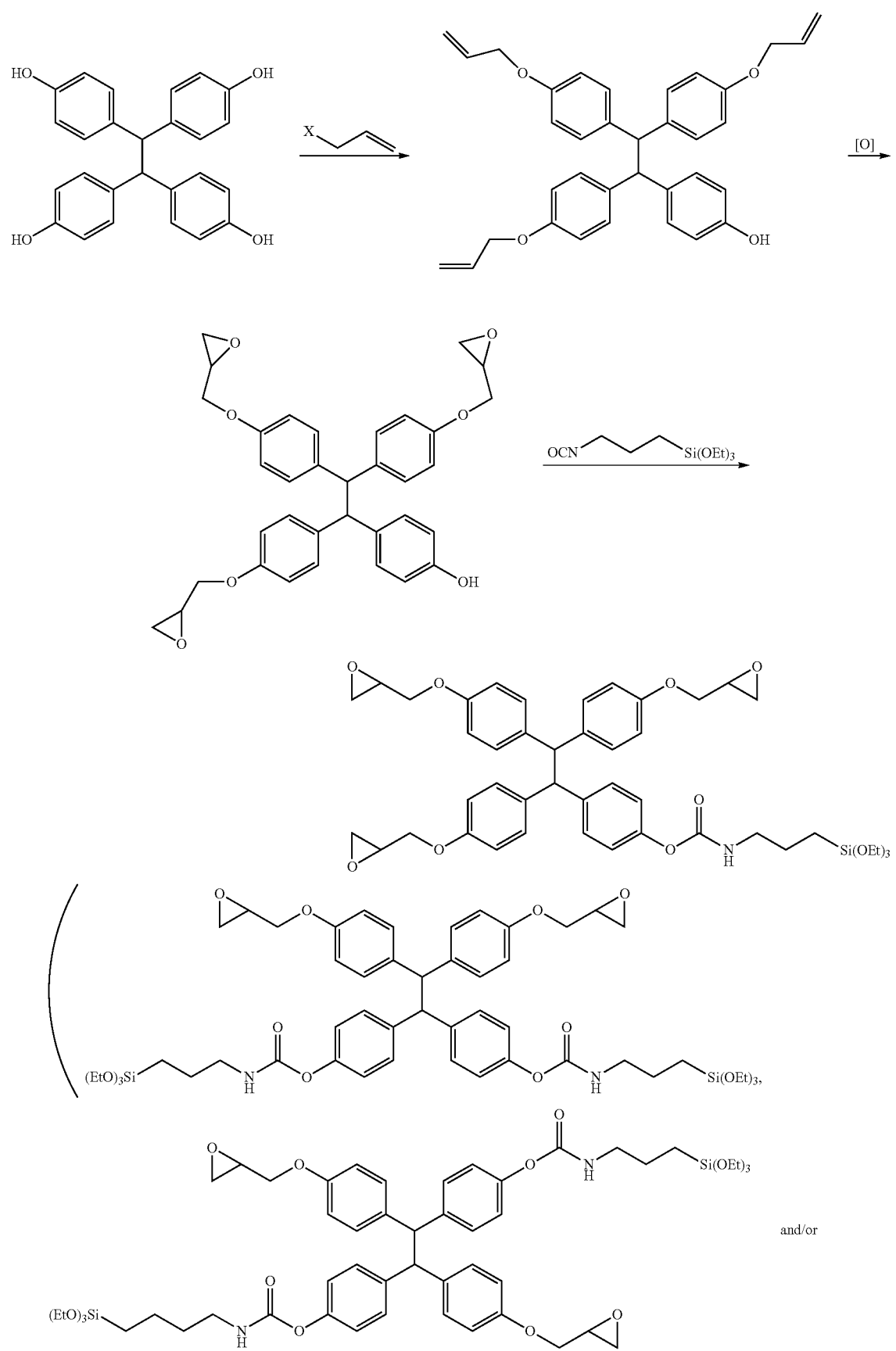

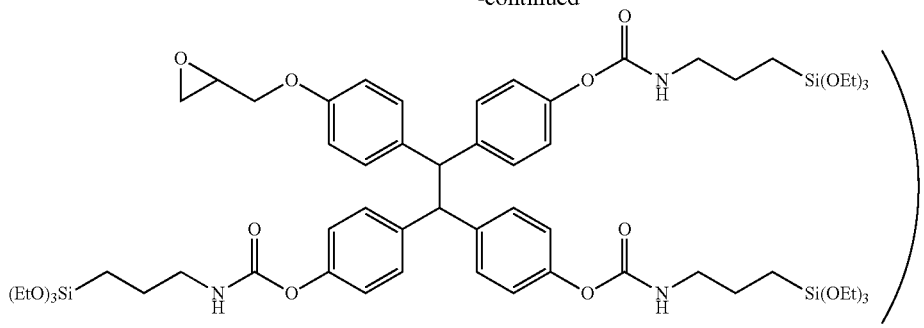

Synthetic Example D6 Synthesis of Tetraphenylethane-Based Epoxy Having Alkoxysilyl Group (Formula DI) (Method 6)

The same intermediate product as that of the first step of Synthetic Example D4 was obtained by performing the same reaction as that of the first step of Synthetic Example D4.

Then, the same reaction as that of the third step of Synthetic Example D5 was performed using the intermediate product to obtain the same Target Product DI as that of Synthetic Example D5.

The synthetic reaction of the above Synthetic Example D6 is as follows.

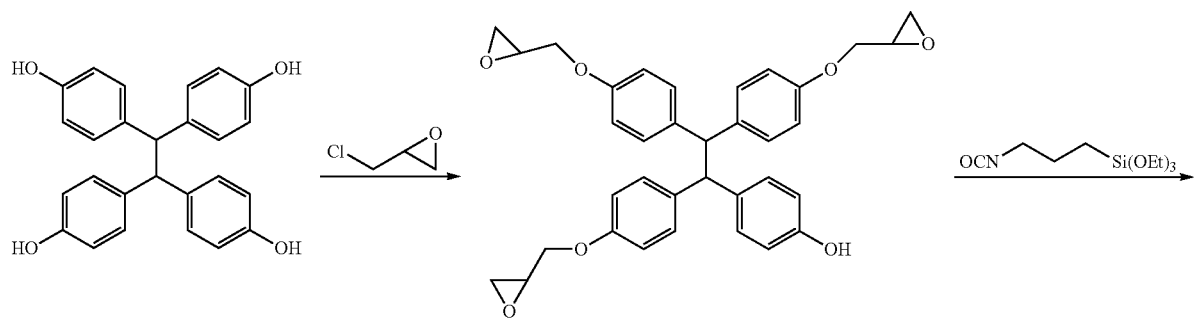

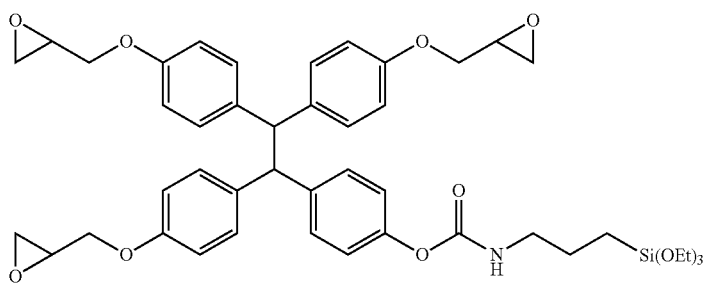

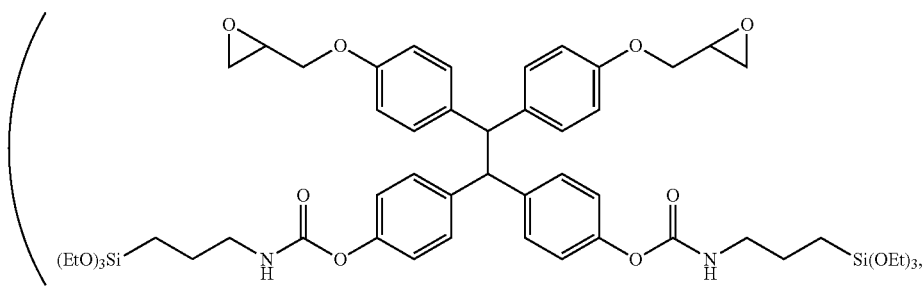

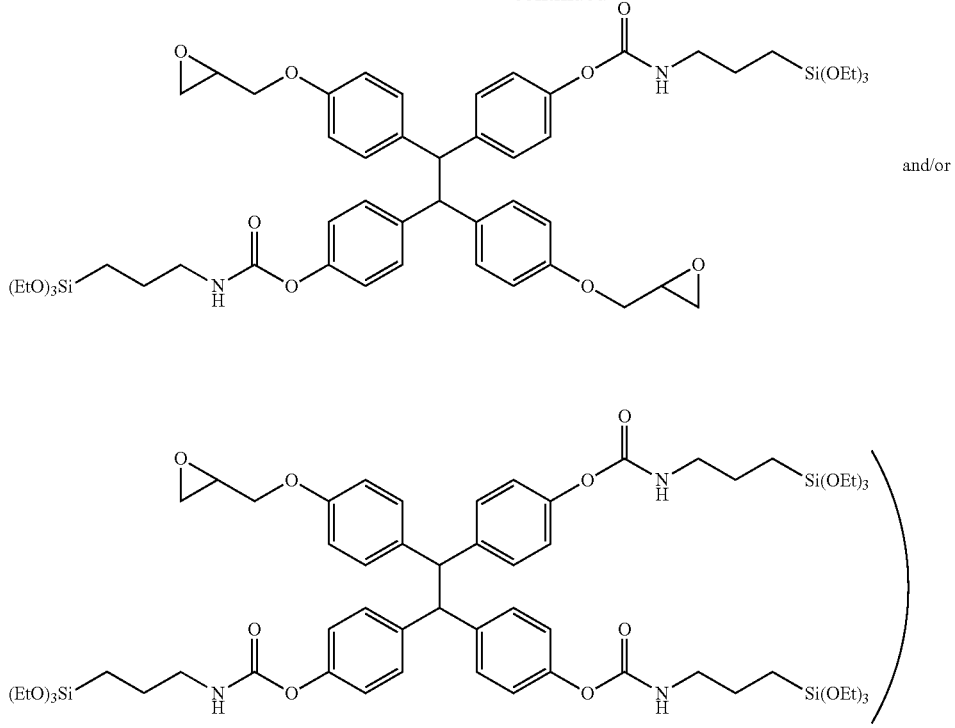

and/or

Synthetic Example E1(1) Synthesis of Methylenedianiline-Based Epoxy Having Alkoxysilyl Group (Formula EI) (Method 1)

According to the following methods, Formula E1 having a ratio of [epoxy group]:[alkoxysilyl group]=1:1 was synthesized.

(1) First Step 25 g of 4,4'-methylenedianiline (Sigma Aldrich, The same may apply hereinafter), 33.6 g of allyl bromide, and 300 ml of THF were inserted in a two-necked flask at room temperature, followed by stirring. Then, a solution with 12.6 g of sodium hydroxide dissolved in 150 ml of H$_2$O was slowly added thereto for 1 hour at room temperature, followed by stirring for 4 hours. 58.3 g of epichlorohydrin was added in the flask, and a solution with 12.6 g of sodium hydroxide dissolved in 150 ml of H$_2$O was added thereto for 10 minutes at room temperature, followed by stirring for 19 hours. After stirring, THF was removed by using an evaporator, and 400 ml of ethyl acetate was added and worked-up with H$_2$O to remove inorganic materials. In an organic layer, MgSO$_4$ was added to remove remaining H$_2$O. The organic layer thus obtained was filtered using a celite filter, evaporated and dried to obtain Intermediate Product E11 having a ratio of [epoxy group]:[alkenyl group]=1:1.

$^1$H NMR (400 MHz, CDCl$_3$). δ=7.12-7.08 (m, 4H), 6.77-6.74 (m, 4H), 5.93-5.80 (m, 2.2H), 5.48-5.30 (m, 4.4H), 3.82 (s, 2H), 3.76-3.62 (m, 6.2H), 3.49-3.40 (m, 1.8H), 3.20-3.16 (m, 1.8H), 2.81-2.78 (m, 1.8H), 2.60-2.58 (m, 1.8H)

(2) Second Step 20 g of the above Intermediate Product E11, 0.23 g of PtO$_2$, 19.3 g of triethoxysilane, and 250 ml of toluene were added in a flask, followed by stirring for 5 minutes at room temperature. Then, the temperature was increased to 80° C., and heating and stirring were performed for 12 hours. Then, the reactant was cooled to room temperature and filtered using a celite filter to remove inorganic materials. By removing toluene through drying by evaporation and complete drying using a vacuum pump, Target Product EI was obtained.

$^1$H NMR (400 MHz, CDCl$_3$). δ=7.12-7.08 (m, 4H), 6.77-6.74 (m, 4H), 3.84 (q, 10.8H, J=6.8 Hz), 3.82 (s, 2H), 3.76-3.62 (m, 1.8H), 3.49-3.40 (m, 1.8H), 3.22-3.16 (m, 5.4H), 2.81-2.78 (m, 1.8H), 2.60-2.58 (m, 1.8H), 1.80-1.70 (m, 3.6H), 1.22 (t, 16.2H, J=7.2 Hz), 0.67-0.60 (m, 3.6H)

The synthetic reaction of the above Synthetic Example E1(1) is as follows.

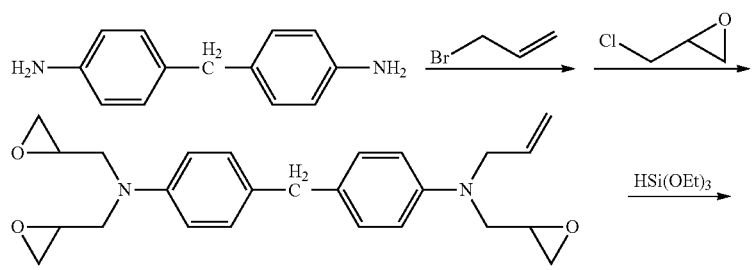

-continued

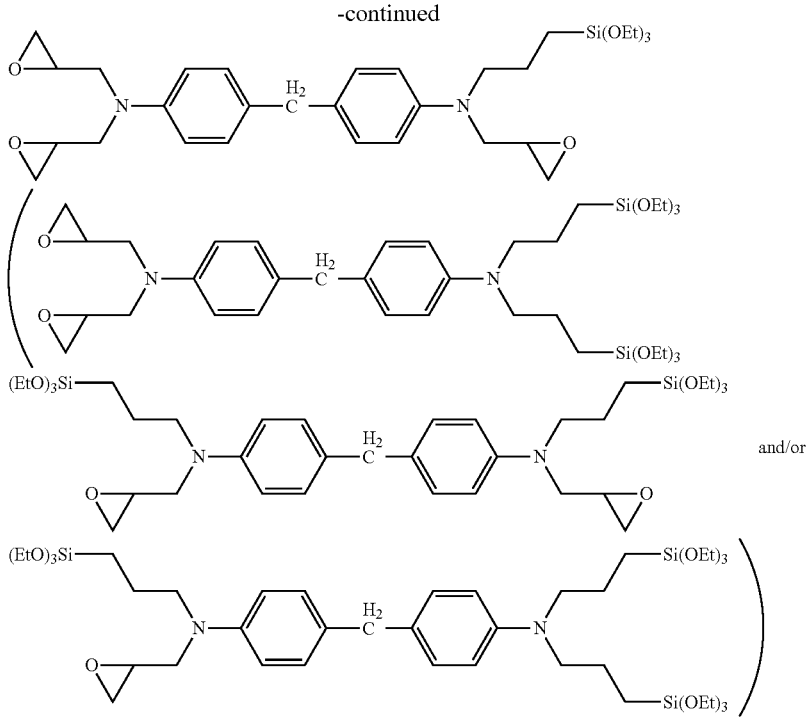
and/or

Synthetic Examples E1(2) and E1(3) Synthesis of Methylenedianiline-Based Epoxy Having Alkoxysilyl Group (Formula EI) (Method 1)

By performing the same method as that of the first step and the second of the Synthetic Example E1(1) except for using different amounts of the reacting materials, compounds of Formula EI were synthesized. The ratio of epoxy group:alkoxysilyl group of Formula EI synthesized in Synthetic Example E1(2) and Synthetic Example E1(3) were 2:1 and 3:1, respectively, and the amounts of the reacting materials used in each of the synthetic steps are illustrated in the following Tables.

In the above Synthetic Examples E1(1) to E1(3), a mixture of the epoxy compounds having the ratio of epoxy group:alkoxysilyl group of 1:3 to 3:1 is obtained. The ratio of epoxy group:alkoxysilyl group illustrated in Table E2 means the ratio of epoxy group:alkoxysilyl group of the total epoxy compounds present as the mixture of the compounds having the above-described different ratios of epoxy group:alkoxysilyl group.

Expected Synthetic Example E2 Synthesis of Methylenedianiline-Based Epoxy Having Alkoxysilyl Group (Formula EI) (Method 2)

(1) First Step
20 g of 4,4'-methylenediamiline, 24.4 g of allyl bromide, and 300 ml of THF are inserted in a two-necked flask at

TABLE E1

Amounts of reacting materials used in the first step for synthesizing Formula EI

| Synthetic Example (1/2 step) | 4,4'-diaminodiphenylmethane | Allyl bromide | Epichlorohydrin | THF | NaOH in 150 ml H$_2$O First insertion | NaOH in 150 ml H$_2$O Second insertion | [Epoxy group]:[alkenyl group] of Formula E11 |
|---|---|---|---|---|---|---|---|
| E1(2) | 25 g | 21.4 g | 70.0 g | 300 ml | 10.1 g | 15.1 g | 2:1 |
| E1(3) | 25 g | 18.3 g | 70.0 g | 300 ml | 7.6 g | 17.7 g | 3:1 |

TABLE E2

Amounts of reacting materials used in the second step for synthesizing Formula EI

| Synthetic Example (2/2 step) | Formula E11 | PtO$_2$ | HSi(OEt)$_3$ | Toluene | [Epoxy group]:[alkoxysilyl group] of Formula EI |
|---|---|---|---|---|---|
| E1(2) | 20 g | 0.22 g | 12.1 g | 250 ml | 2:1 |
| E1(3) | 20 g | 0.22 g | 10.5 g | 250 ml | 3:1 | room temperature, followed by stirring. A solution with 10.1 g of sodium hydroxide dissolved in 300 ml of $H_2O$ is slowly added thereto at room temperature for 1 hour, followed by further stirring for 2 hours. After completing the reaction, THF is removed by using an evaporator, and the crude product is worked-up using 400 ml of ethyl acetate and $H_2O$ to remove inorganic materials. $MgSO_4$ is added in an organic layer to remove remaining $H_2O$. The organic layer thus obtained is filtered using a celite filter and evaporated to obtain Intermediate Product E21 having two allyl functional groups.

(2) Second Step 10 g of the above Intermediate Product E21 obtained in the first step, 1.44 g of $KHCO_3$, 29.5 g of $CH_3CN$, and 300 ml of methanol are added in a two-necked flask, followed by stirring at room temperature. Subsequently, 20.4 g of a 30 wt % $H_2O_2$ solution is slowly added thereto for 10 minutes and stirred at room temperature for 12 hours. After completing the reaction, $CH_3CN$ and methanol are removed by using an evaporator, and 300 ml of ethyl acetate is added and worked-up with $H_2O$ to remove remaining $H_2O_2$. An organic layer is separated, and $MgSO_4$ is added in the organic layer to remove remaining $H_2O$. The organic layer thus obtained is filtered using a celite filter and evaporated to obtain Intermediate Product E22.

(3) Third Step

In a two-necked flask, 10 g of the above Intermediate Product E22 obtained in the second step, 17.8 g of $K_2CO_3$, and 250 ml of a $CH_3CN$ solvent are added and stirred at room temperature. Then, 19.5 g of allyl bromide is added thereto at room temperature, and the temperature is increased to 80° C., followed by stirring for 5 hours for performing the reaction. After completing the reaction, the reactant is cooled to room temperature and filtered using a celite filter to remove inorganic materials. The $CH_3CN$ solvent is removed by using an evaporator, and the crude product thus obtained is worked-up using ethyl acetate and $H_2O$ three times. An organic layer is separated, and $MgSO_4$ is added in the organic layer to remove remaining $H_2O$. The organic layer thus obtained is filtered and evaporated to obtain Intermediate Product E23 having an allyl group.

(4) Fourth Step 20 g of the above Intermediate Product E23, 0.23 g of $PtO_2$, 18.5 g of triethoxysilane, and 250 ml of toluene are added in a flask, followed by stirring for 5 minutes at room temperature. The reaction temperature is increased to 80° C., and the reaction is performed for 12 hours while heating and stirring. After completing the reaction, the reactant is cooled to room temperature and filtered using a celite filter to remove inorganic materials. Then, toluene is removed through evaporation, and complete drying is performed using a vacuum pump to obtain Target Product EI.

The synthetic reaction of the above Expected Synthetic Example E2 is as follows.

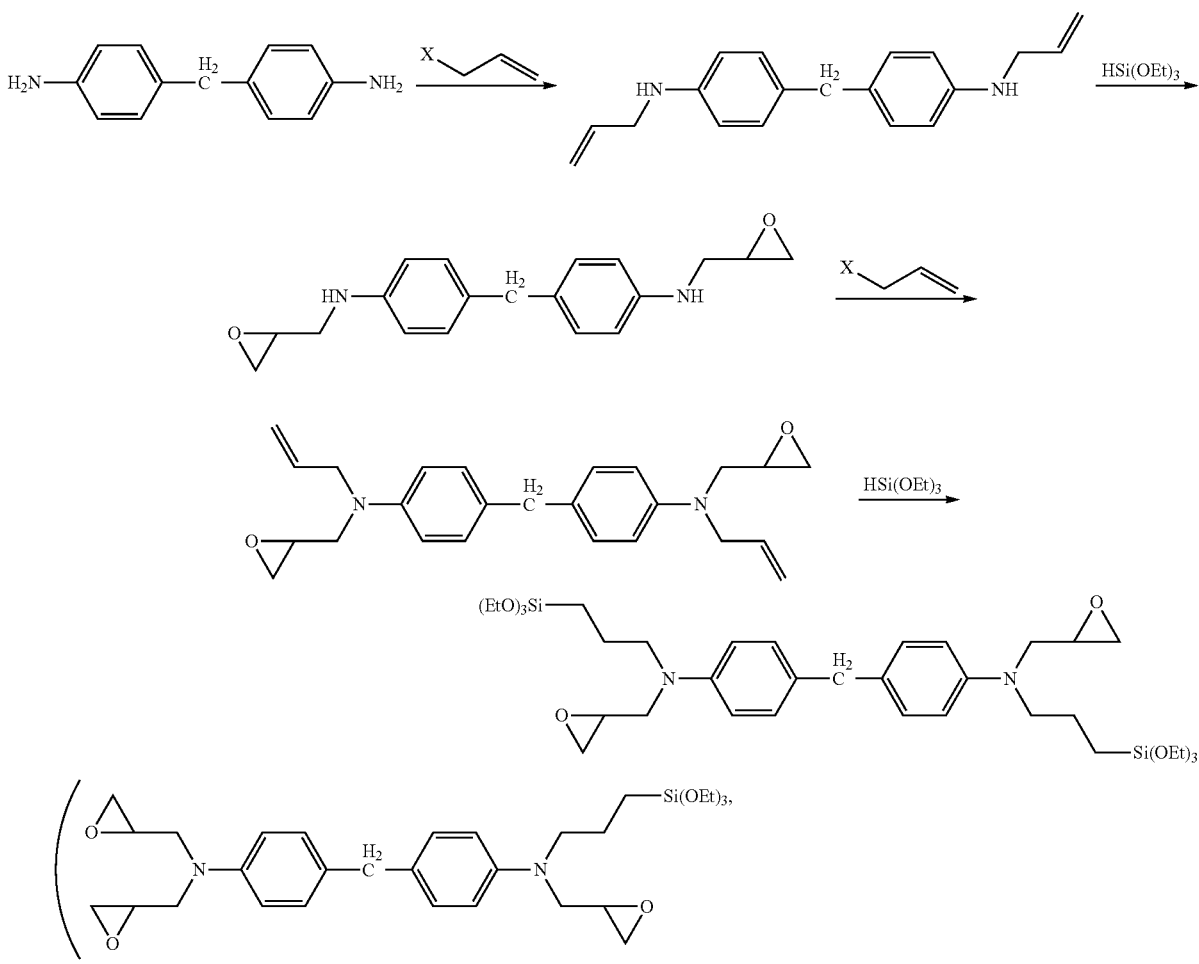

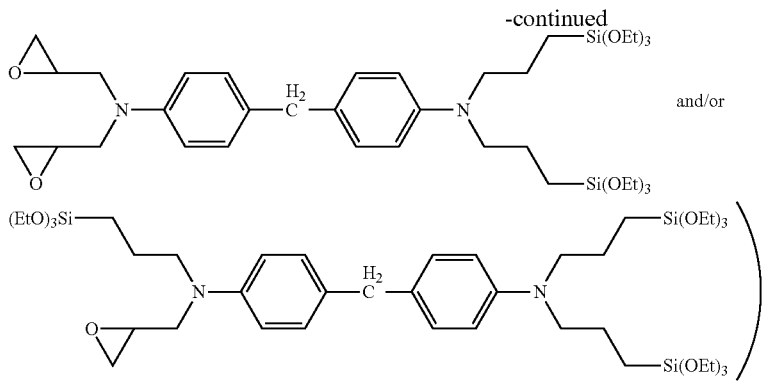

Expected Synthetic Example E3 Synthesis of Methylenedianiline-Based Epoxy Having Alkoxysilyl Group (Formula EI) (Method 3)

(1) First Step 20 g of 4,4'-methylenedianile, 51.3 g of allyl bromide, and 300 ml of THF are inserted in a two-necked flask, followed by stirring at room temperature. Then, a solution with 20.2 g of sodium hydroxide dissolved in 300 ml of $H_2O$ is slowly added thereto for 1 hour at room temperature, followed by further stirring for 4 hours. After completing the reaction, THF is removed by using an evaporator, and 300 ml of ethyl acetate and 400 ml of $H_2O$ are added to work-up three times to remove inorganic materials. In an organic layer, $MgSO_4$ is added to remove remaining $H_2O$. The organic layer thus obtained is filtered using a celite filter to obtain Intermediate Product E31.

(2) Second Step 10 g of the above Intermediate Product E31 obtained in the first step, 0.6 g of $KHCO_3$, 6.9 g of $CH_3CN$, and 300 ml of methanol are added in a two-necked flask, followed by stirring at room temperature. Subsequently, 12.6 g of a 30 wt % $H_2O_2$ solution is slowly added thereto for 10 minutes and stirred at room temperature for 6 hours to perform the reaction. After completing the reaction, $CH_3CN$ and MeOH are removed by using an evaporator, and 250 ml of ethyl acetate and 400 ml of $H_2O$ are added to work-up to remove remaining $H_2O_2$. An organic layer is separated, and $MgSO_4$ is added in the organic layer to remove remaining $H_2O$. The organic layer thus obtained is filtered using a celite filter to obtain Intermediate Product E32.

(3) Third Step 20 g of the above Intermediate Product E32, 0.23 g of $PtO_2$, 18.5 g of triethoxysilane, and 250 ml of toluene are added in a flask, followed by stirring for 5 minutes at room temperature. Then, the temperature is increased to 80° C., and heating and stirring are performed for 12 hours. After completing the reaction, the reactant is cooled to room temperature and filtered using a celite filter to remove inorganic materials. By removing toluene through evaporation and complete drying using a vacuum pump, Target Product EI is obtained.

The synthetic reaction of the above Expected Synthetic Example E3 is as follows.

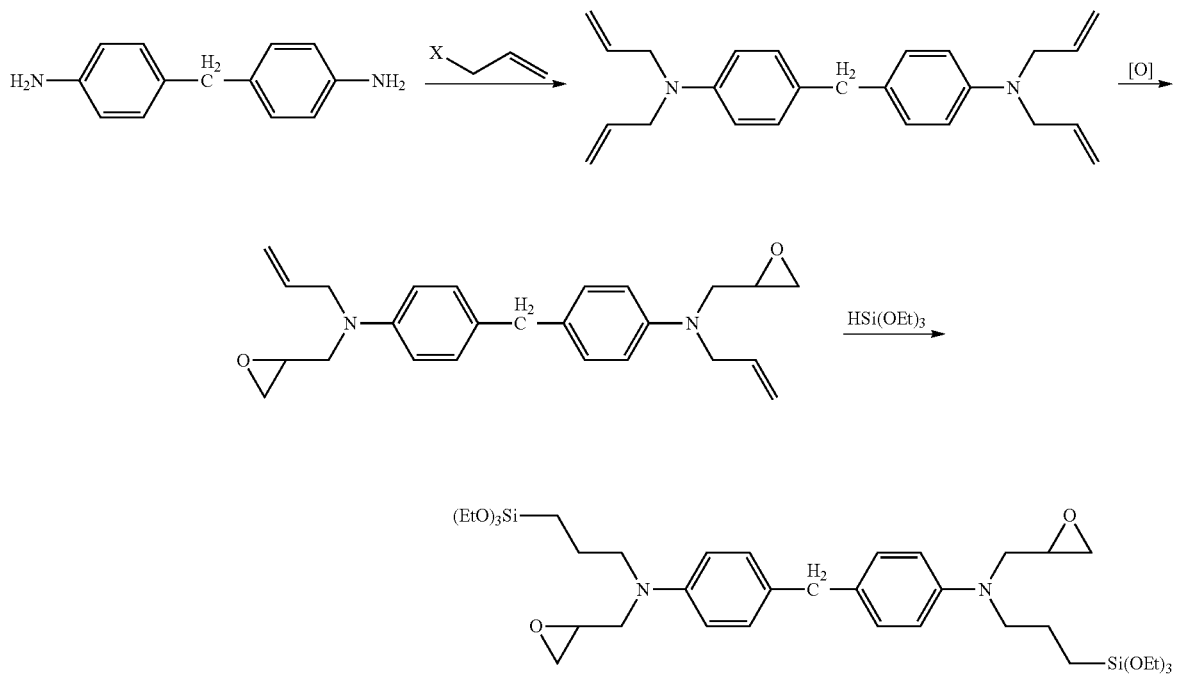

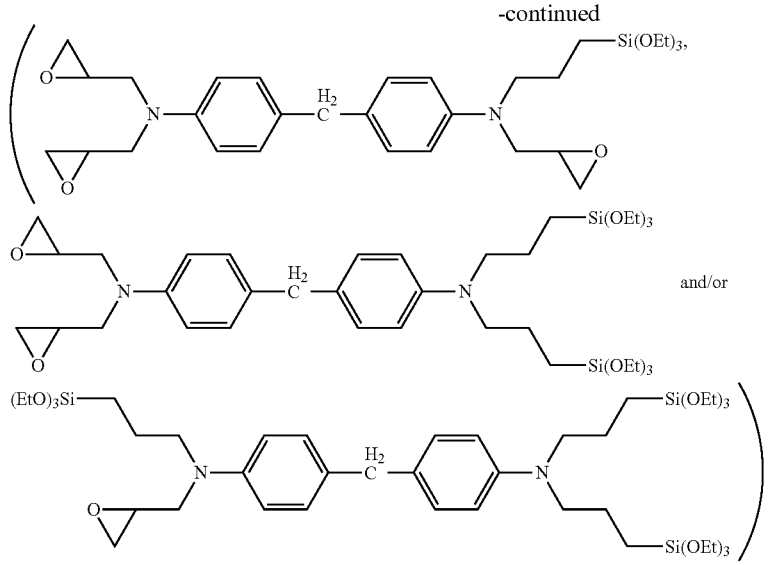

and/or

Expected Synthetic Example E4 Synthesis of Methylenedianiline-Based Epoxy Having Alkoxysilyl Group (Formula EI) (Method 4)

(1) First Step 10 g of 4,4'-methylenedianiline, 15.3 g of $K_2CO_3$, and 300 ml of $CH_3CN$ are inserted in a two-necked flask, followed by stirring at room temperature. Then, 9.3 g of epichlorohydrin is added thereto at room temperature, followed by stirring at 80° C. for 5 hours to perform the reaction. After completing the reaction, the reactant is cooled to room temperature, and filtered by using a celite filter to remove inorganic materials. The $CH_3CN$ solvent is removed by using an evaporator. The crude product is worked-up using ethyl acetate and $H_2O$ three times, and an organic layer is separated. In the organic layer, $MgSO_4$ is added to remove remaining $H_2O$. The organic layer thus obtained is filtered and evaporated to obtain Intermediate Product E41.

(2) Second Step and Third Step

By using the above Intermediate Product E41 of the first step and performing the same method as described in the third step and the fourth step of the above Expected Synthetic Example E2, Target Product EI is obtained.

The synthetic reaction of the above Expected Synthetic Example E4 is as follows.

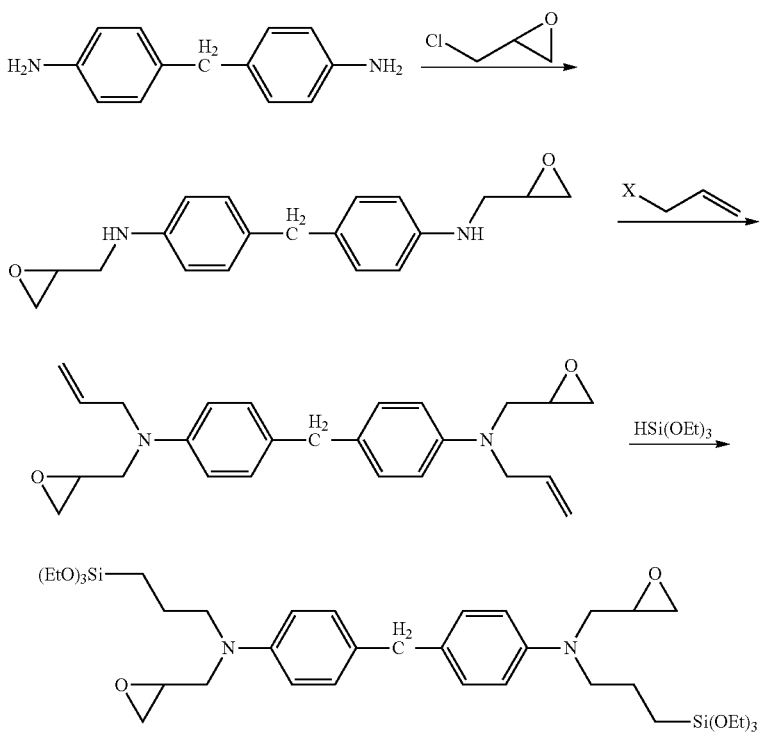

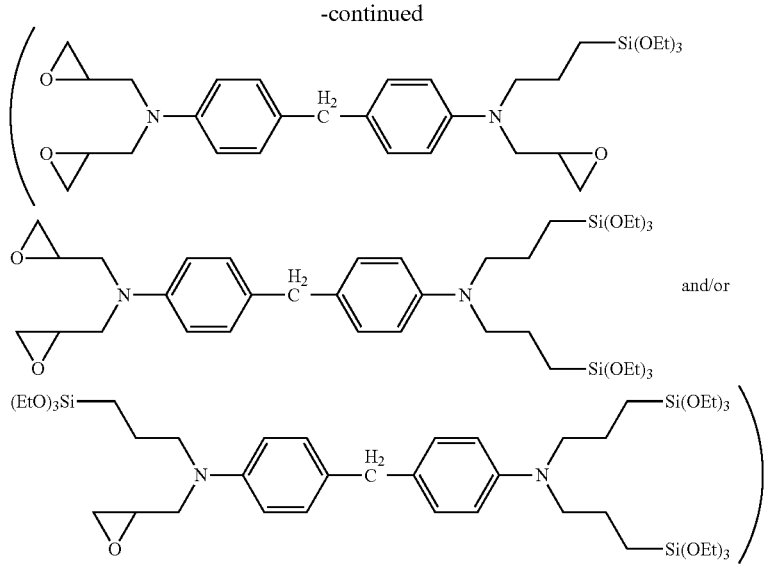

Expected Synthetic Example E5 Synthesis of Methylenedianiline-Based Epoxy Having Alkoxysilyl Group (Formula EI) (Method 5)

The same Intermediate Product E22 as that of the second step of Expected Synthetic Example E2 is obtained by performing the first step and the second step of Expected Synthetic Example E2. Then, as the third step, 10 g of Intermediate Product E22 of the second step, 12.5 g of diisopropylethylamine, and 200 ml of methylene chloride are added in a two-necked flask, followed by stirring at room temperature. Then, 16.0 g of triethoxysilylpropyl isocyanate is added thereto at room temperature, the temperature is increased to 60° C., and the reaction is performed for 12 hours. After completing the reaction, the reactant is cooled to room temperature and worked-up using $H_2O$. An organic layer is separated, and $MgSO_4$ is added in the organic layer to remove remaining $H_2O$. The organic layer thus obtained is filtered using a celite filter and evaporated to obtain Target Product EI.

The synthetic reaction of the above Expected Synthetic Example E5 is as follows.

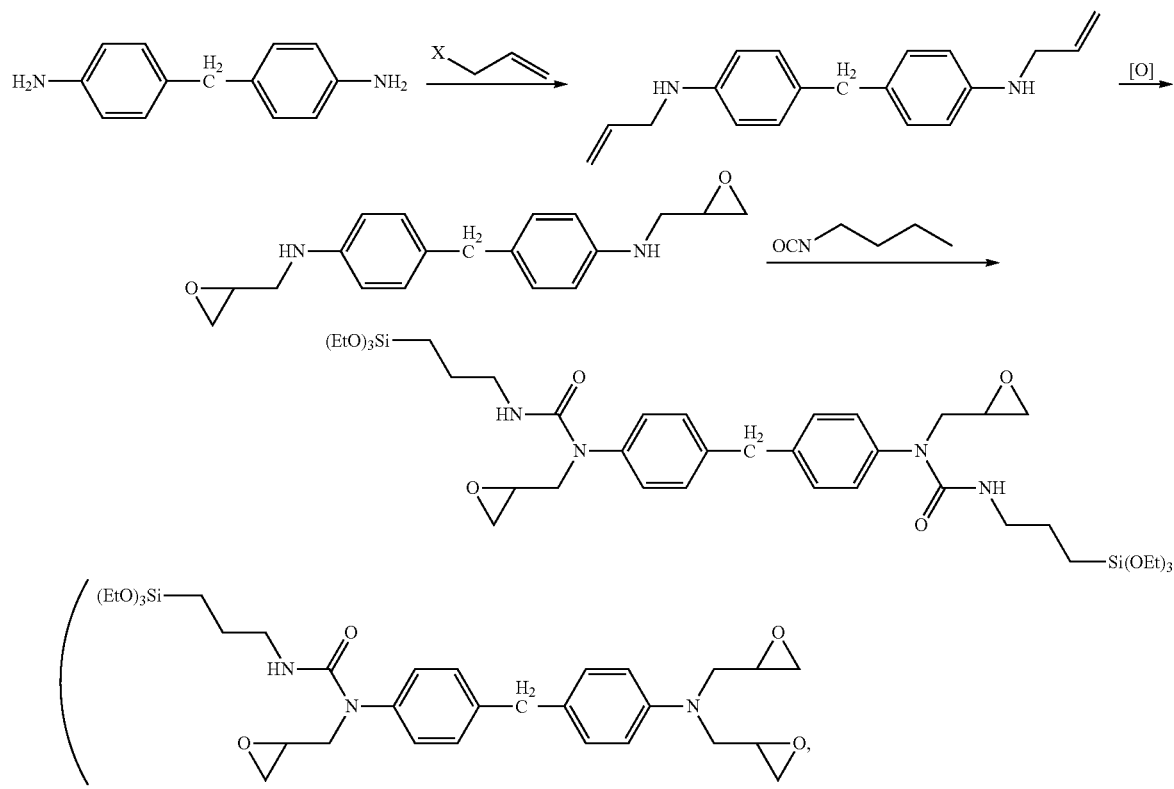

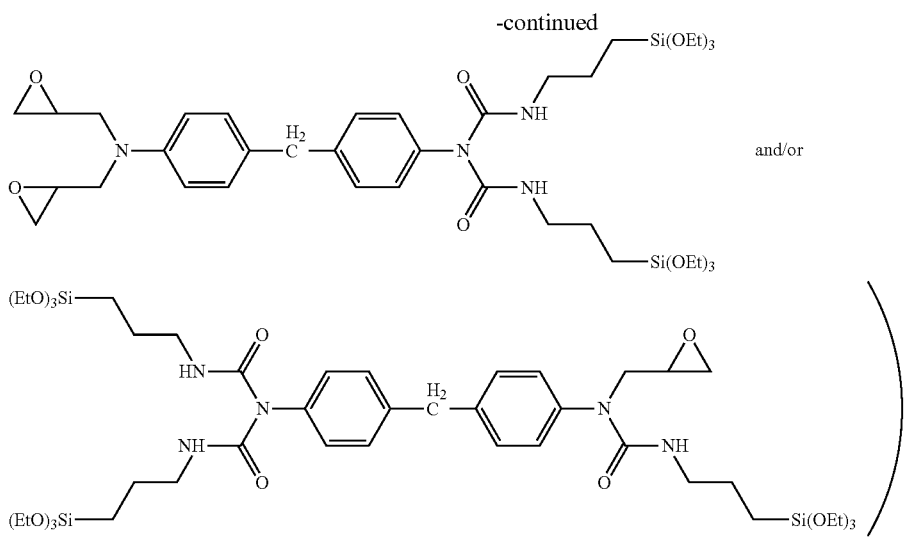

Expected Synthetic Example E6 Synthesis of Methylenedianiline-Based Epoxy Having Alkoxysilyl Group (Formula EI) (Method 6)

The same Intermediate Product E41 as that of the first step of Expected Synthetic Example E4 is obtained by performing the same reaction as the first step of Expected Synthetic Example E4. Then, the same reaction as that of the third step of Expected Synthetic Example E5 is performed using Intermediate Product E41 to obtain the same Target Product EI as that of Expected Synthetic Example E5.

The synthetic reaction of the above Expected Synthetic Example E6 is as follows.

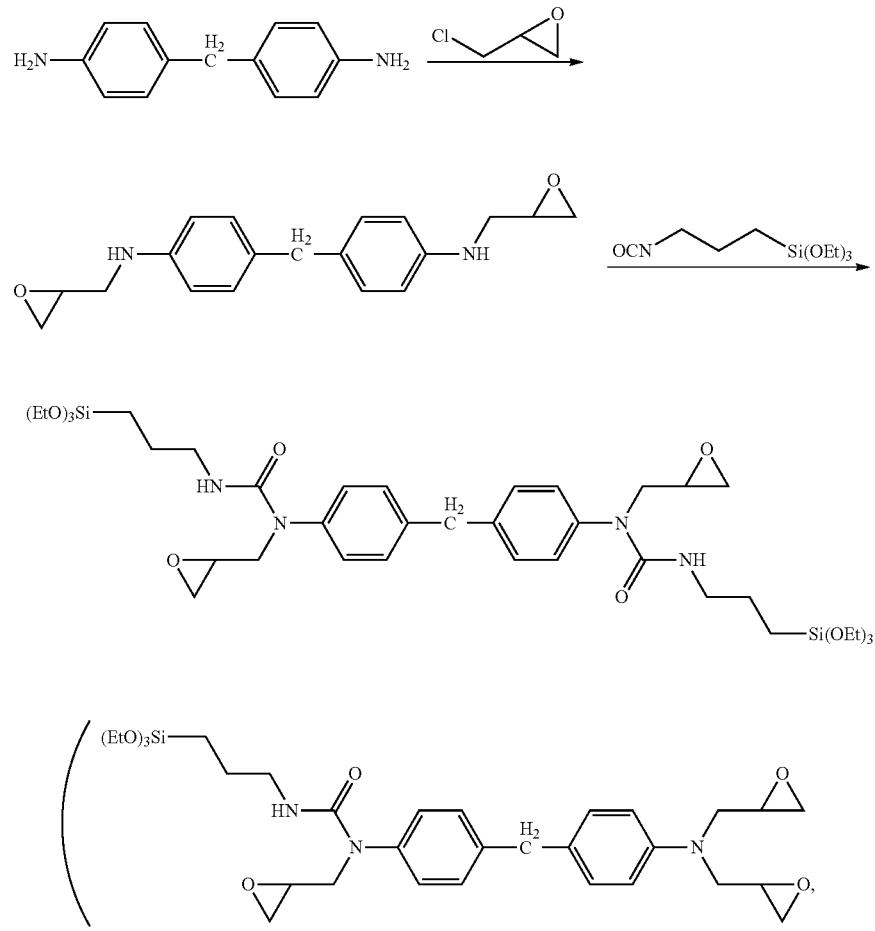

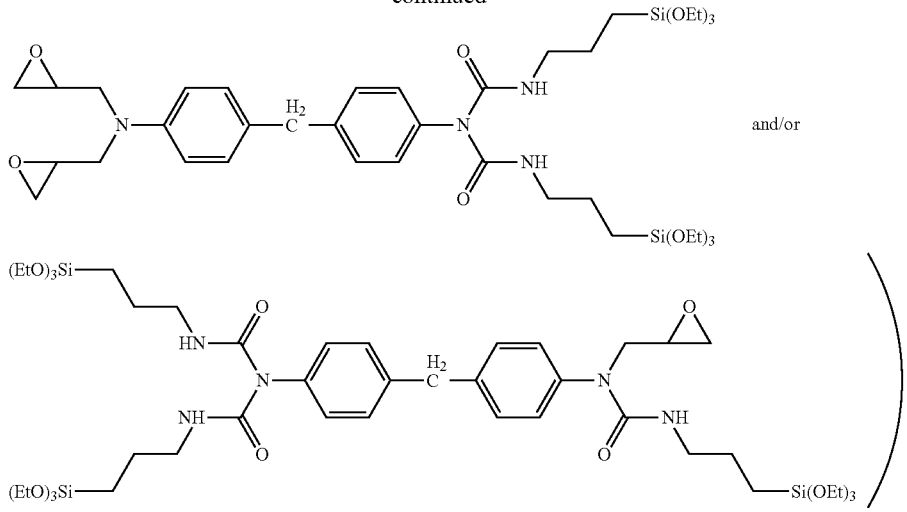

and/or

Expected Synthetic Example F1 Synthesis of Phenylenedibenzeneamine-Based Epoxy Having Alkoxysilyl Group (Formula FI) (Method 1)

(1) First Step 25 g of 4,4'-(2,2'-(1,4-phenylene)bis(propane-2,2-diyl))dibenzeneamine, 17.6 g of allyl bromide, and 300 ml of THF are inserted in a two-necked flask at room temperature, followed by stirring. Then, a solution with 6.4 g of sodium hydroxide dissolved in 150 ml of $H_2O$ is slowly added thereto for 1 hour at room temperature, followed by stirring for 4 hours. Subsequently, 40.3 g of epichlorohydrin is added in the flask, and a solution with 8.7 g of sodium hydroxide dissolved in 150 mol of $H_2O$ is added thereto for 10 minutes at room temperature, followed by stirring for 19 hours. After stirring, THF is removed by using an evaporator, and 400 ml of ethyl acetate is added and worked-up with $H_2O$ to remove inorganic materials. In an organic layer, $MgSO_4$ is added to remove remaining $H_2O$. The organic layer thus obtained is filtered using a celite filter, evaporated and dried to obtain Intermediate Product F11.

(2) Second Step 20 g of the above Intermediate Product F11, 0.17 g of $PtO_2$, 13.5 g of triethoxysilane, and 250 ml of toluene are added in a flask, followed by stirring for 5 minutes at room temperature. Then, the temperature is increased to 80° C., and heating and stirring are performed for 12 hours. Then, the reactant is cooled to room temperature and filtered using a celite filter to remove inorganic materials. By removing toluene through drying by evaporation and complete drying using a vacuum pump, Target Product FI is obtained.

The synthetic reaction of the above Expected Synthetic Example F1 is as follows.

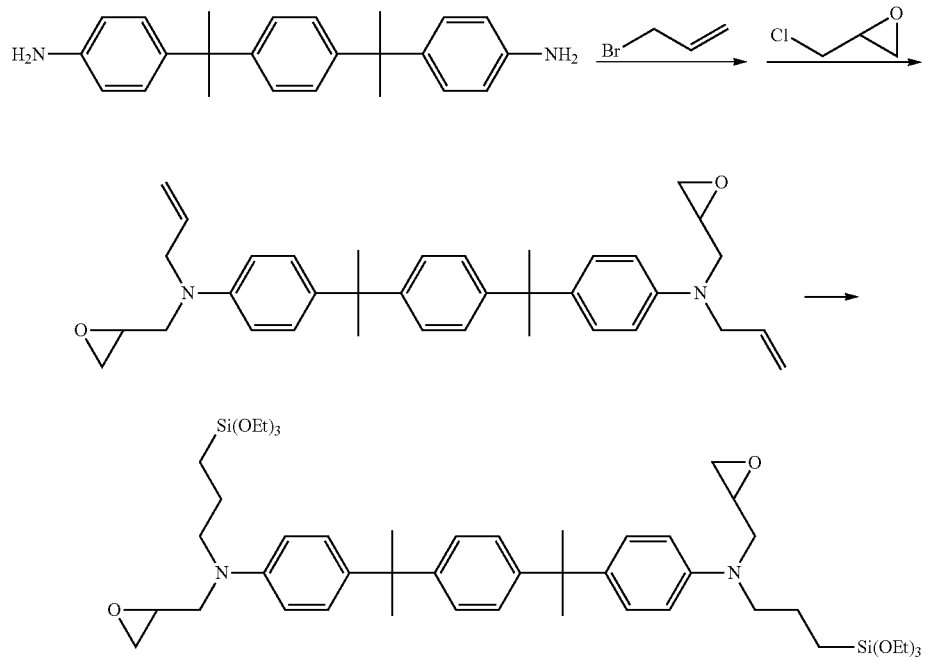

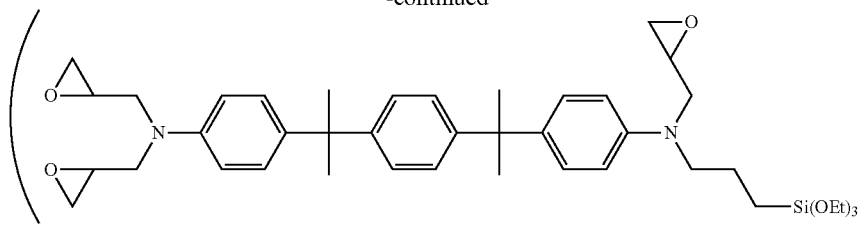

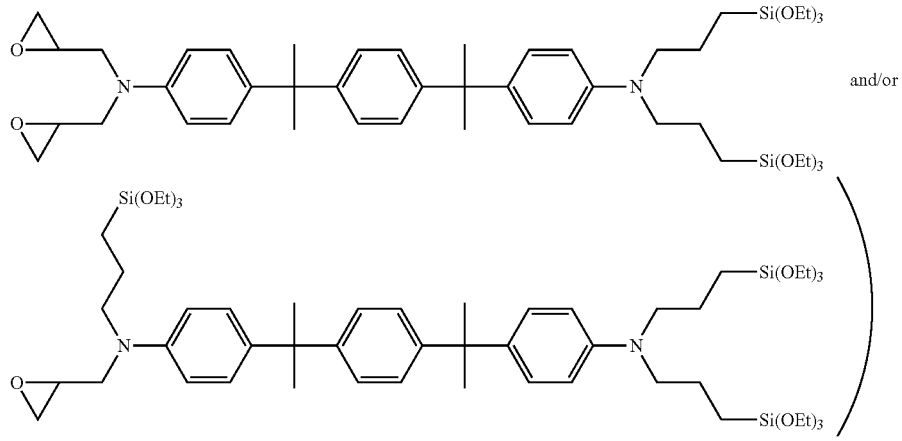

Expected Synthetic Example F2 Synthesis of Phenylenedibenzeneamine-Based Epoxy Having Alkoxysilyl Group (Formula FI) (Method 2)

(1) First Step 25 g of 4,4'-(2,2'-(1,4-phenylene)bis(propane-2,2-diyl) dibenzeneamine, 17.5 g of allyl bromide, and 300 ml of THF are inserted in a two-necked flask at room temperature, followed by stirring. A solution with 7.3 g of sodium hydroxide dissolved in 300 ml of $H_2O$ is slowly added thereto at room temperature for 1 hour, followed by further stirring for 2 hours. After completing the reaction, THF is removed by using an evaporator, and the crude product is worked-up using 400 ml of ethyl acetate and $H_2O$ to remove inorganic materials. $MgSO_4$ is added in an organic layer to remove remaining $H_2O$. The organic layer thus obtained is filtered using a celite filter and evaporated to obtain Intermediate Product F21 having two allyl functional groups.

(2) Second step 10 g of the above Intermediate Product F21 obtained in the first step, 0.94 g of $KHCO_3$, 19.3 g of $CH_3CN$, and 300 ml of methanol are added in a two-necked flask, followed by stirring at room temperature. Subsequently, 13.3 g of a 30 wt % $H_2O_2$ solution is slowly added thereto for 10 minutes and stirred at room temperature for 12 hours. After completing the reaction, $CH_3CN$ and methanol are removed by using an evaporator, and 300 ml of ethyl acetate is added and worked-up with $H_2O$ to remove remaining $H_2O_2$. An organic layer is separated, and $MgSO_4$ is added in the organic layer to remove remaining $H_2O$. The organic layer thus obtained is filtered using a celite filter and evaporated to obtain Intermediate Product F22.

(3) Third Step

In a two-necked flask, 10 g of the above Intermediate Product F22 obtained in the second step, 12.1 g of $K_2CO_3$, and 250 ml of a $CH_3CN$ solvent are added and stirred at room temperature. Then, 13.2 g of allyl bromide is added thereto at room temperature, and the temperature is increased to 80° C., followed by stirring for 5 hours to perform the reaction. After completing the reaction, the reactant is cooled to room temperature and filtered using a celite filter to remove inorganic materials. The $CH_3CN$ solvent is removed by using an evaporator, and the crude product thus obtained is worked-up using ethyl acetate and $H_2O$ three times. An organic layer is separated, and $MgSO_4$ is added in the organic layer to remove remaining $H_2O$. The organic layer thus obtained is filtered and evaporated to obtain Intermediate Product F23 having an allyl group.

(4) Fourth Step 20 g of the above Intermediate Product F23, 0.17 g of $PtO_2$, 13.5 g of triethoxysilane, and 250 ml of toluene are added in a flask, followed by stirring for 5 minutes at room temperature. Then, the reaction temperature is increased to 80° C., and the reaction is performed for 12 hours while heating and stirring. Subsequently, the reactant is cooled to room temperature and filtered using a celite filter to remove inorganic materials. Then, toluene is removed through evaporation and drying, and completely dried using a vacuum pump to obtain Target Product FI.

The synthetic reaction of the above Expected Synthetic Example F2 is as follows.

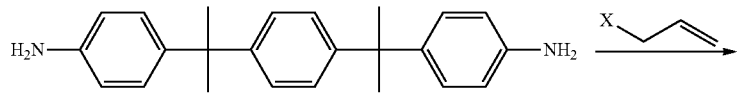

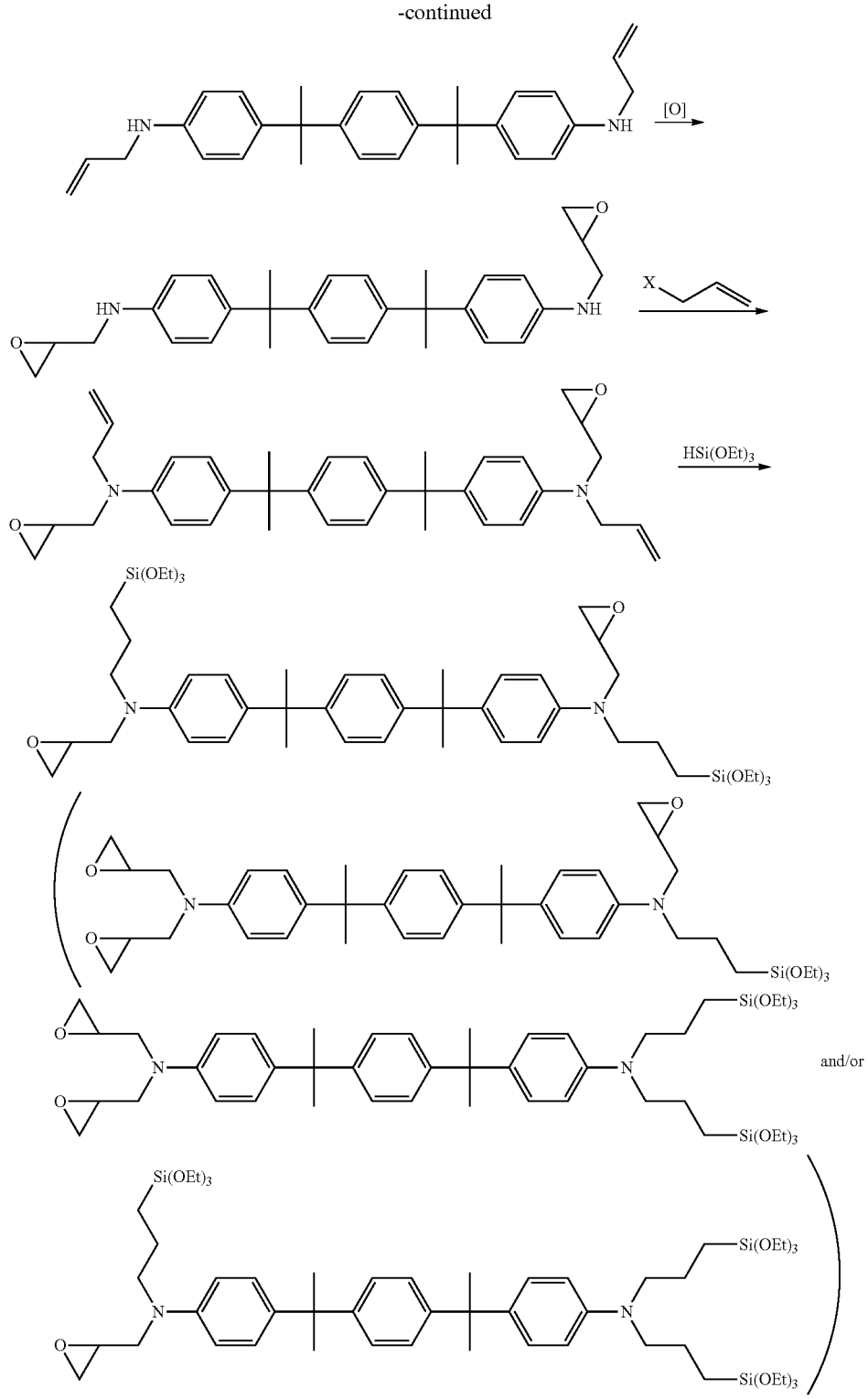

Expected Synthetic Example F3 Synthesis of Phenylenedibenzeneamine-Based Epoxy Having Alkoxysilyl Group (Formula FI) (Method 3)

(1) First Step 20 g of 4,4'-(2,2'-(1,4-phenylene)bis(propane-2,2-diyl))dibenzeneamine, 29.5 g of allyl bromide, and 300 ml of THF are inserted in a two-necked flask, followed by stirring at room temperature. Then, a solution with 11.6 g of sodium hydroxide dissolved in 300 ml of H$_2$O is slowly added thereto for 1 hour at room temperature, followed by further stirring for 4 hours. After completing the reaction, THF is removed by using an evaporator, and 300 ml of ethyl acetate and 400 ml of H$_2$O are added to work-up three times to remove inorganic materials. In an organic layer, MgSO$_4$ is added to remove remaining H$_2$O. The organic layer thus obtained is filtered using a celite filter to obtain Intermediate Product F31.

(2) Second Step 10 g of the above Intermediate Product F31 obtained in the first step, 0.43 g of KHCO$_3$, 4.88 g of CH$_3$CN, and 300 ml of methanol are added in a two-necked flask, followed by stirring at room temperature. Subsequently, 8.98 g of a 30 wt % H$_2$O$_2$ solution is slowly added thereto for 10 minutes and stirred at room temperature for 6 hours to perform the reaction. After completing the reaction, CH$_3$CN and methanol are removed by using an evaporator, and 250 ml of ethyl acetate and 400 ml of H$_2$O are added to work-up to remove remaining H$_2$O$_2$. An organic layer is separated, and MgSO$_4$ is added in the organic layer to remove remaining H$_2$O. The organic layer thus obtained is filtered using a celite filter to obtain Intermediate Product F32.

(3) Third step 20 g of the above Intermediate Product F32 of the second step, 0.17 g of PtO$_2$, 13.5 g of triethoxysilane, and 250 ml of toluene are added in a flask, followed by stirring for 5 minutes at room temperature. Then, the temperature is increased to 80° C., and heating and stirring are performed for 12 hours. After completing the reaction, the reactant is cooled to room temperature and filtered using a celite filter to remove inorganic materials. By removing toluene through evaporation and complete drying using a vacuum pump, Target Product FI is obtained.

The synthetic reaction of the above Expected Synthetic Example F3 is as follows.

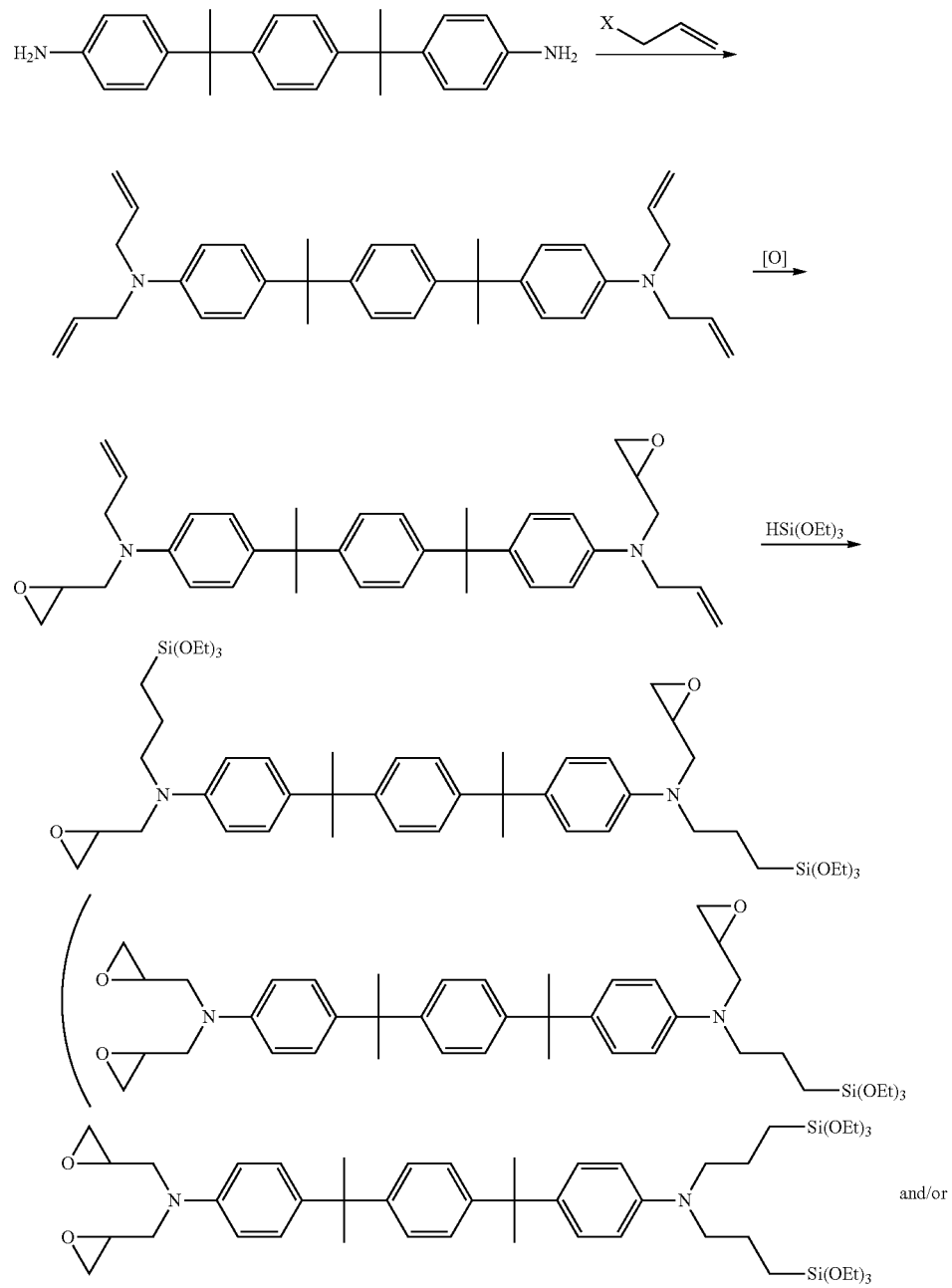

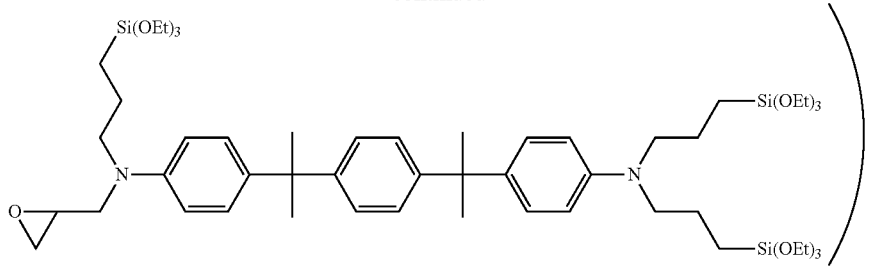

Expected Synthetic Example F4 Synthesis of Phenylenedibenzeneamine-Based Epoxy Having Alkoxysilyl Group (Formula FI) (Method 4)

(1) First Step 10 g of 4,4'-(2,2'-(1,4-phenylene)bis(propane-2,2-diyl)dibenzeneamine, 8.8 g of $K_2CO_3$, and 300 ml of $CH_3CN$ are inserted in a two-necked flask, followed by stirring at room temperature. Then, 5.4 g of epichlorohydrin is added thereto at room temperature, followed by stirring at 80° C. for 5 hours to perform the reaction. After completing the reaction, the reactant is cooled to room temperature, and filtered by using a celite filter to remove inorganic materials. The $CH_3CN$ solvent is removed by using an evaporator. The crude product is worked-up using ethyl acetate and $H_2O$ three times, and an organic layer is separated. In the organic layer, $MgSO_4$ is added to remove remaining $H_2O$. The organic layer thus obtained is filtered and evaporated to obtain Intermediate Product F41.

(2) Second Step and Third Step

By using the above Intermediate Product F41 of the first step and performing the same method as described in the third step and the fourth step of the above Expected Synthetic Example F2, Target Product FI is obtained.

The synthetic reaction of the above Synthetic Example F4 is as follows.

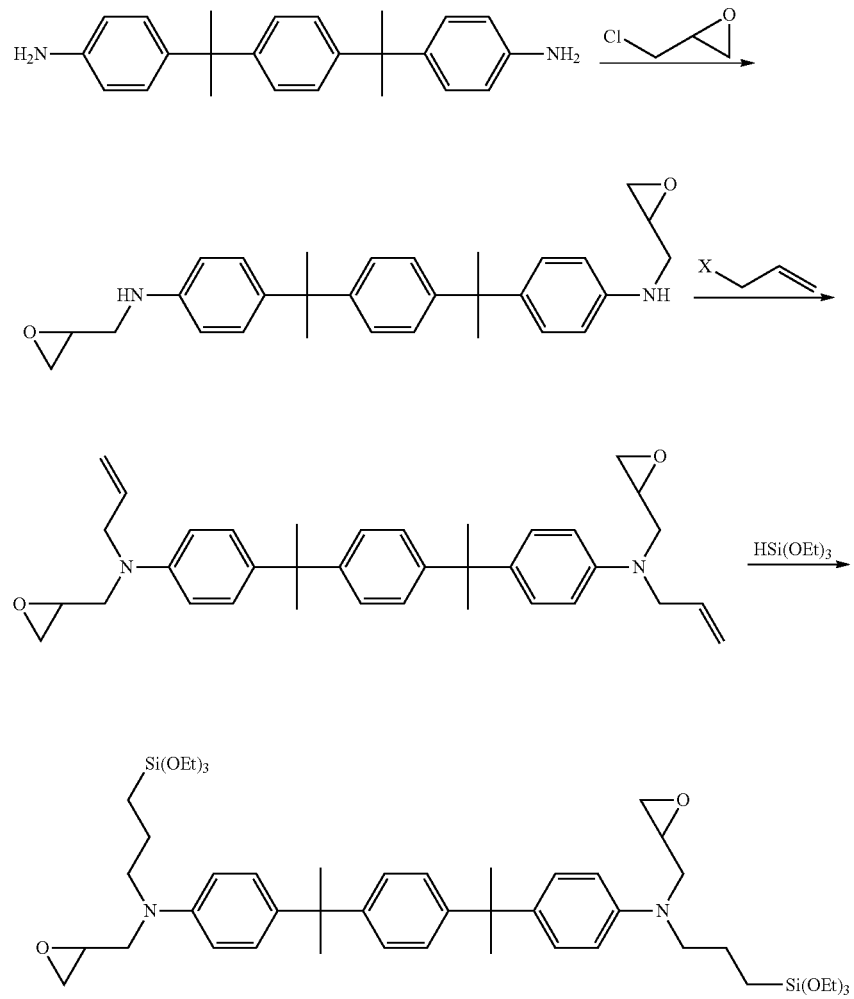

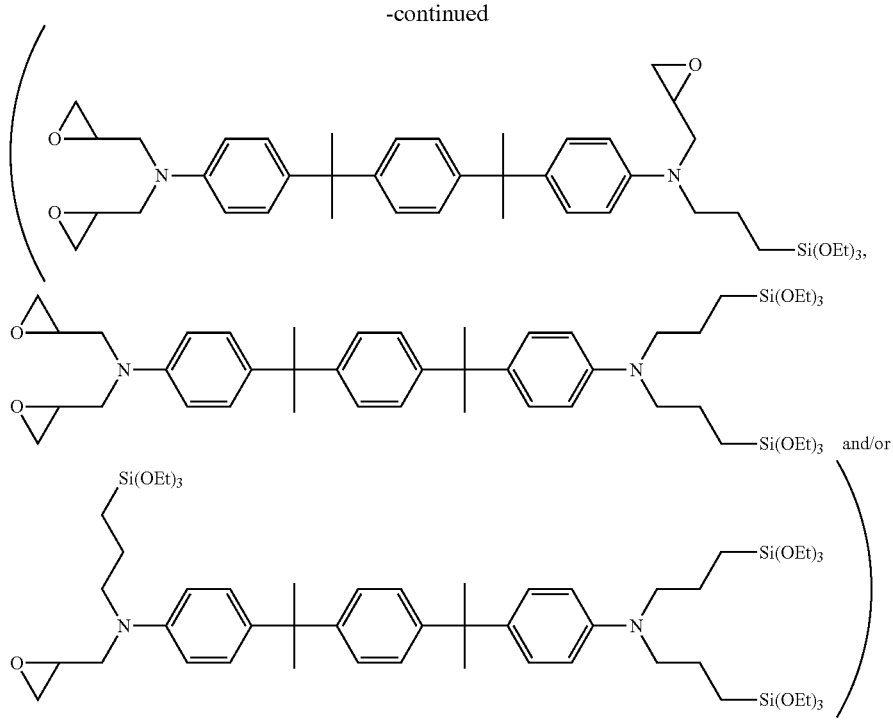

Expected Synthetic Example F5 Synthesis of Phenylenedibenzeneamine-Based Epoxy Having Alkoxysilyl Group (Formula FI) (Method 5)

The same intermediate product as that of the second step of Expected Synthetic Example F2 is obtained by performing the first step and the second step of Expected Synthetic Example F2. Then, as the third step, 10 g of Intermediate Product F22 of the second step of the above Expected Synthetic Example F2, 8.5 g of diisopropylethylamine, and 300 ml of methylene chloride are added in a two-necked flask, followed by stirring at room temperature. Then, 10.8 g of triethoxysilylpropyl isocyanate is added thereto at room temperature, the temperature is increased to 60° C., and the reaction is performed for 12 hours while heating. After completing the reaction, the reactant is cooled to room temperature and worked-up using $H_2O$. An organic layer is separated, and $MgSO_4$ is added in the separated organic layer to remove remaining $H_2O$. The organic layer thus obtained is filtered using a celite filter and evaporated to obtain Target Product FI.

The synthetic reaction of the above Expected Synthetic Example F5 is as follows.

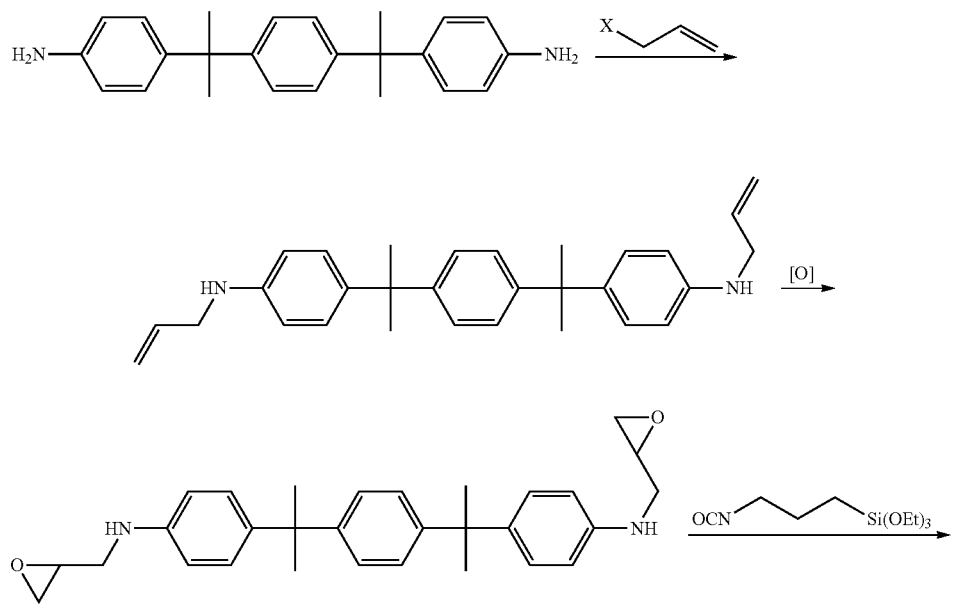

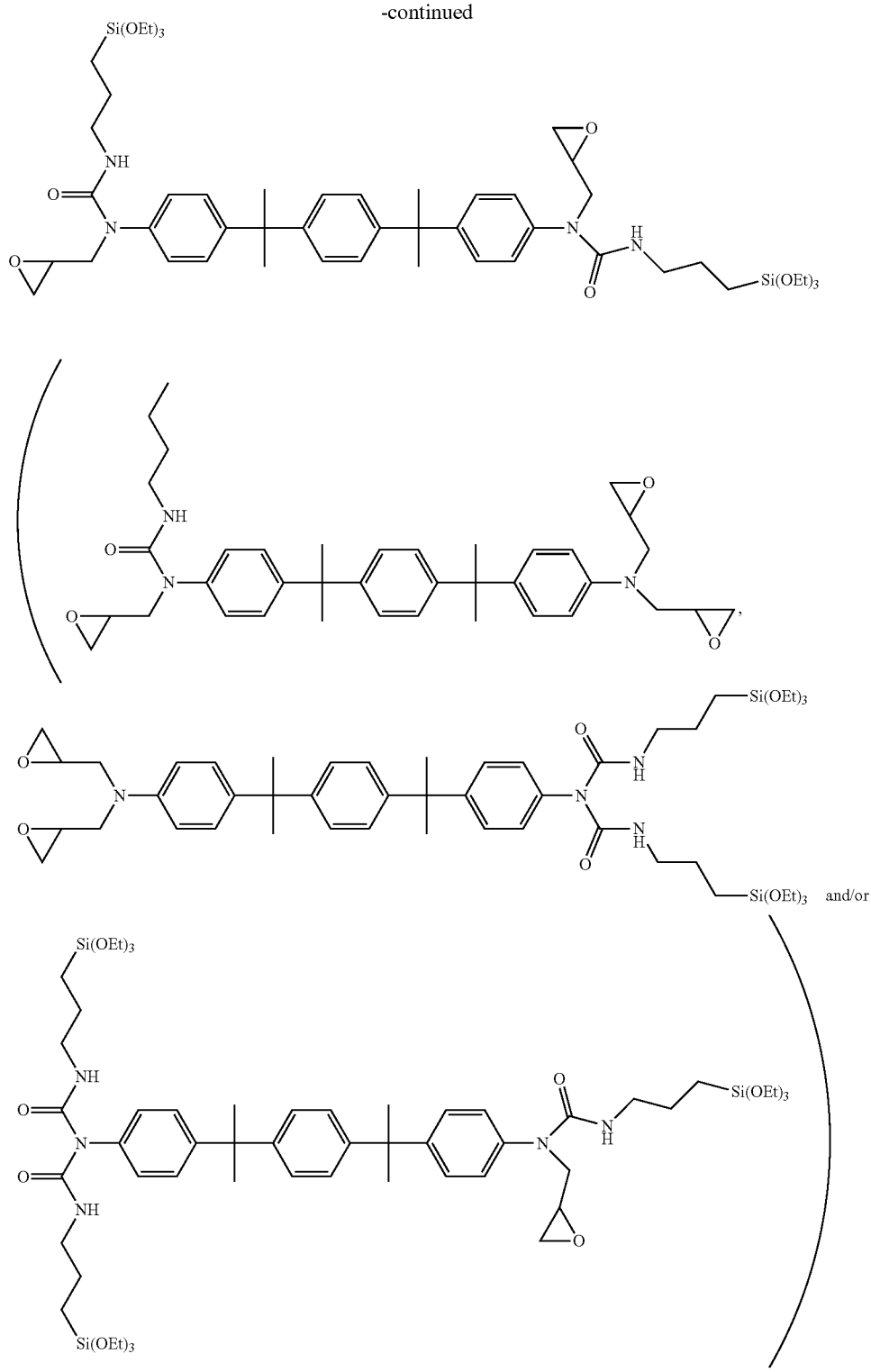

Expected Synthetic Example F6 Synthesis of Phenylenedibenzeneamine-Based Epoxy Having Alkoxysilyl Group (Formula FI) (Method 6)

The same Intermediate Product F41 as that of the first step of Expected Synthetic Example F4 is obtained by performing the same reaction as the first step of Expected Synthetic Example F4. Then, the same reaction as that of the third step of Expected Synthetic Example F5 is performed using the intermediate product to obtain the same Target Product FI as in Expected Synthetic Example F5.

The synthetic reaction of the above Expected Synthetic Example F6 is as follows.

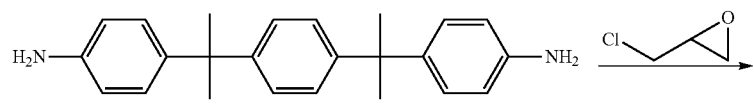
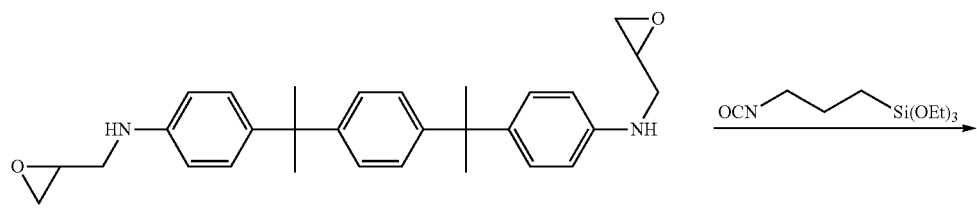
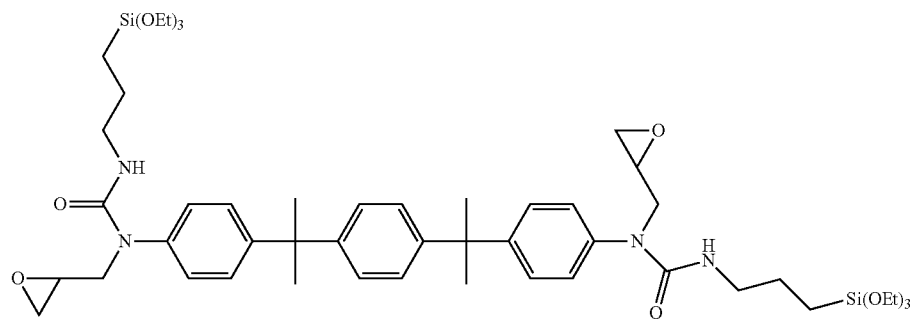
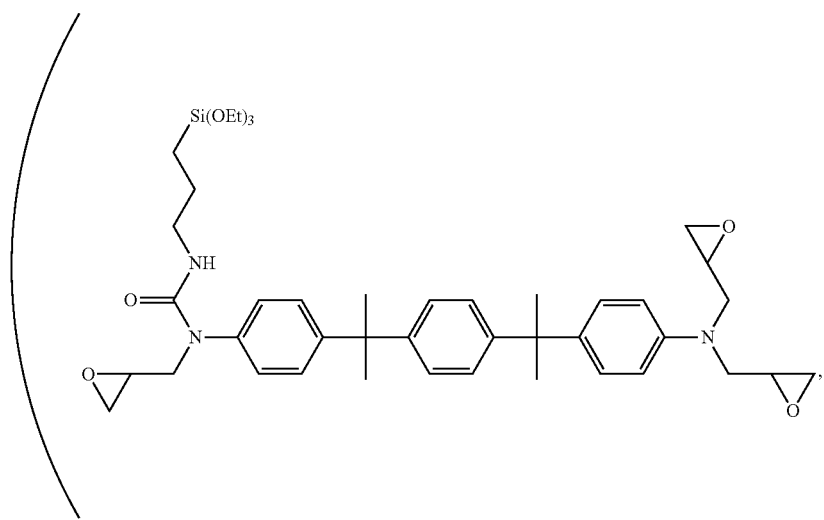
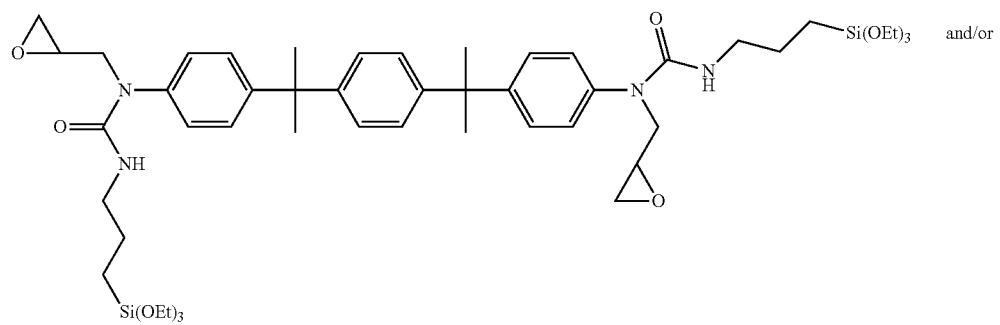

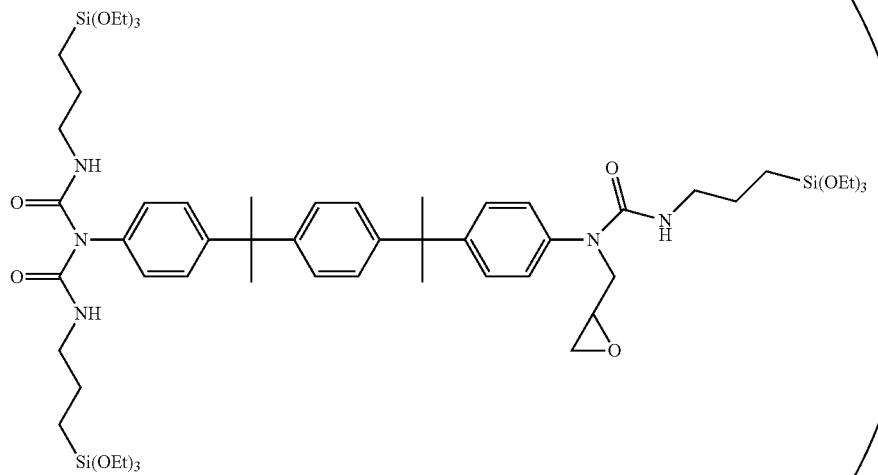

Expected Synthetic Example G1 Synthesis of Phenylenedimethaneamine-Based Epoxy Having Alkoxysilyl Group (Formula GI) (Method 1)

(1) First Step 25 g of 1,3-phenylenedimethaneamine, 44.4 g of allyl bromide, and 300 ml of THF are inserted in a two-necked flask at room temperature, followed by stirring. Then, a solution with 16.4 g of sodium hydroxide dissolved in 150 ml of $H_2O$ is slowly added thereto for 1 hour at room temperature, followed by stirring for 4 hours. 101.9 g of epichlorohydrin is added in the flask, and a solution with 22.0 g of sodium hydroxide dissolved in 150 mol of $H_2O$ is added thereto for 10 minutes at room temperature, followed by stirring for 19 hours. After stirring, THF is removed by using an evaporator, and 400 ml of ethyl acetate is added and worked-up with $H_2O$ to remove inorganic materials. In an organic layer, $MgSO_4$ is added to remove remaining $H_2O$. The organic layer thus obtained is filtered using a celite filter, evaporated and dried to obtain Intermediate Product G11.

(2) Second Step 20 g of the above Intermediate Product G11, 0.28 g of $PtO_2$, 22.0 g of triethoxysilane, and 250 ml of toluene are added in a flask, followed by stirring for 5 minutes at room temperature. Then, the temperature is increased to 80° C., and heating and stirring are performed for 12 hours. Then, the reactant is cooled to room temperature and filtered using a celite filter to remove inorganic materials. By removing toluene through drying by evaporation and complete drying using a vacuum pump, Target Product GI is obtained.

The synthetic reaction of the above Synthetic Example G1 is as follows.

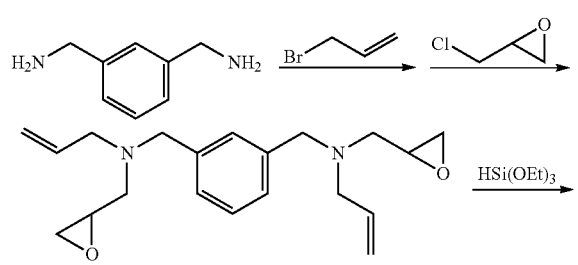

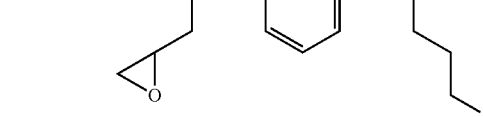

Expected Synthetic Example G2 Synthesis of Phenylenedimethaneamine-Based Epoxy Having Alkoxysilyl Group (Formula GI) (Method 2)

(1) First Step 20 g of 1,3-phenylenedimethaneamine, 35.5 g of allyl bromide, and 300 ml of THF are inserted in a two-necked flask at room temperature, followed by stirring. A solution with 14.7 g of sodium hydroxide dissolved in 300 ml of $H_2O$ is slowly added thereto for 1 hour at room temperature, followed by further stirring for 2 hours. After completing the reaction, THF is removed by using an evaporator, and the crude product is worked-up using 400 ml of ethyl acetate and $H_2O$ to remove inorganic materials. $MgSO_4$ is added in an organic layer to remove remaining $H_2O$. The organic layer thus obtained is filtered using a celite filter and evaporated to obtain Intermediate Product G21.

(2) Second Step 10 g of the above Intermediate Product G21 obtained in the first step, 1.85 g of KHCO₃, 37.9 g of CH₃CN, and 300 ml of methanol are added in a two-necked flask, followed by stirring at room temperature. Subsequently, 23.1 g of a 30 wt % H₂O₂ solution is slowly added thereto for 10 minutes and stirred at room temperature for 12 hours. After completing the reaction, CH₃CN and methanol are removed by using an evaporator, and 300 ml of ethyl acetate is added and worked-up with H₂O to remove remaining H₂O₂. An organic layer is separated, and MgSO₄ is added in the organic layer to remove remaining H₂O. The organic layer thus obtained is filtered using a celite filter and evaporated to obtain Intermediate Product G22.

(3) Third step

In a two-necked flask, 10 g of the above Intermediate Product G22 obtained in the second step, 22.3 g of K₂CO₃, and 250 ml of a CH₃CN solvent are added and stirred at room temperature. 24.4 g of allyl bromide is added thereto at room temperature, and the temperature is increased to 80° C., followed by stirring for 5 hours to perform the reaction. After completing the reaction, the reactant is cooled to room temperature and filtered using a celite filter to remove inorganic materials. The CH₃CN solvent is removed by using an evaporator, and the crude product thus obtained is worked-up using ethyl acetate and H₂O three times. An organic layer is separated, and MgSO₄ is added in the organic layer to remove remaining H₂O. The organic layer thus obtained is filtered and evaporated to obtain Intermediate Product G23 having an allyl group and two functional groups.

(4) Fourth Step 10 g of the above Intermediate Product G23 of the third step, 0.14 g of PtO₂, 11.0 g of triethoxysilane, and 150 ml of toluene are added in a flask, followed by stirring for 5 minutes at room temperature. The reaction temperature is increased to 80° C., and the reaction is performed for 12 hours while heating and stirring. After completing the reaction, the reactant is cooled to room temperature and filtered using a celite filter to remove inorganic materials. Then, toluene is removed through evaporation, and complete drying is performed using a vacuum pump to obtain Target Product GI.

The synthetic reaction of the above Expected Synthetic Example G2 is as follows.

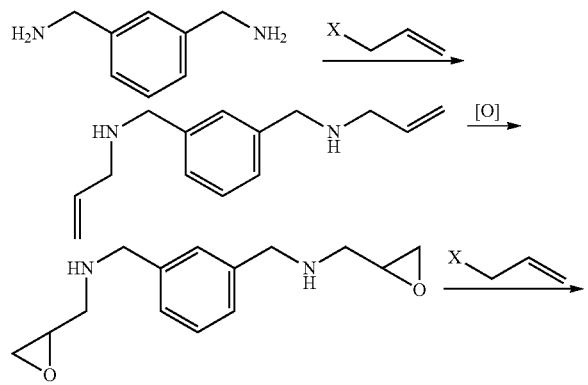

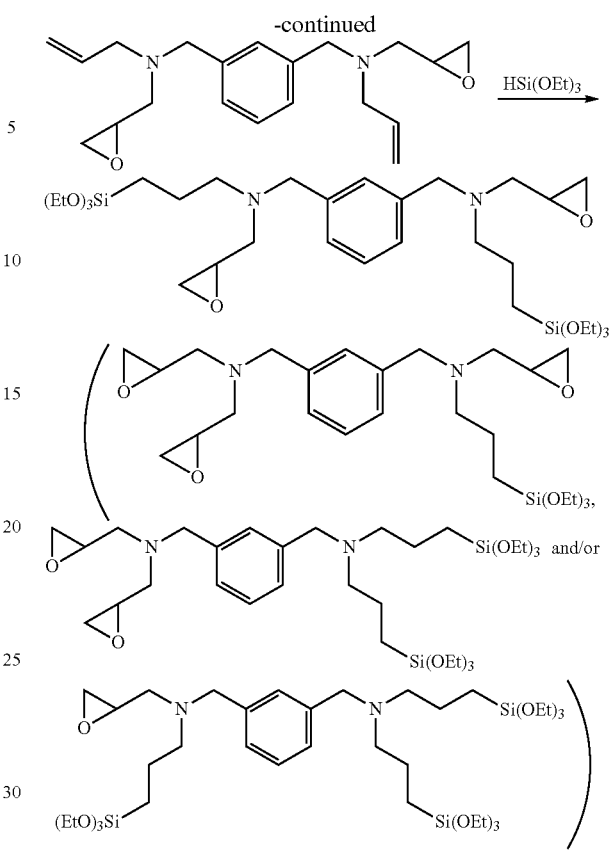

Expected Synthetic Example G3 Synthesis of Phenylenedimethaneamine-Based Epoxy Having Alkoxysilyl Group (Formula GI) (Method 3)

(1) First Step 20 g of 1,3-phenylenedimethaneamine, 74.6 g of allyl bromide, and 300 ml of THF are inserted in a two-necked flask, followed by stirring at room temperature. Then, a solution with 29.4 g of sodium hydroxide dissolved in 300 ml of H₂O is slowly added thereto for 1 hour at room temperature, followed by further stirring for 4 hours. After completing the reaction, THF is removed by using an evaporator, and 300 ml of ethyl acetate and 400 ml of H₂O are added to work-up three times to remove inorganic materials. In an organic layer, MgSO₄ is added to remove remaining H₂O. The organic layer thus obtained is filtered using a celite filter to obtain Intermediate Product G31.

(2) Second Step 10 g of the above Intermediate Product G31 obtained in the first step, 0.74 g of KHCO₃, 8.3 g of CH₃CN, and 300 ml of methanol are added in a two-necked flask, followed by stirring at room temperature. Subsequently, 15.3 g of a 30 wt % H₂O₂ solution is slowly added thereto for 10 minutes and stirred at room temperature for 6 hours to perform the reaction. After completing the reaction, CH₃CN and methanol are removed by using an evaporator, and 250 ml of ethyl acetate and 400 ml of H₂O are added to work-up to remove remaining H₂O₂. An organic layer is separated, and MgSO₄ is added in the organic layer to remove remaining H₂O. The organic layer thus obtained is filtered using a celite filter to obtain Intermediate Product G32.

(3) Third Step 20 g of the above Intermediate Product G32, 0.28 g of PtO$_2$, 22.0 g of triethoxysilane, and 250 ml of toluene are added in a flask, followed by stirring for 5 minutes at room temperature. Then, the temperature is increased to 80° C., and heating and stirring are performed for 12 hours. Then, the reactant is cooled to room temperature and filtered using a celite filter to remove inorganic materials. By removing toluene through evaporation and complete drying using a vacuum pump, Target Product GI is obtained.

The synthetic reaction of the above Expected Synthetic Example G3 is as follows.

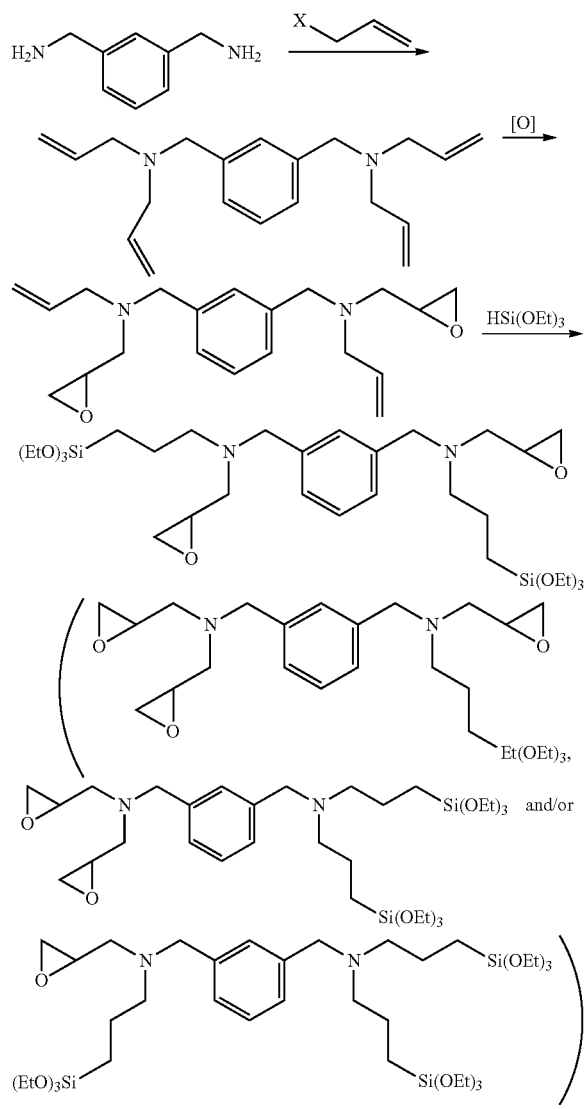

Expected Synthetic Example G4 Synthesis of Phenylenedimethaneamine-Based Epoxy Having Alkoxysilyl Group (Formula GI) (Method 4)

(1) First Step 10 g of 1,3-phenylenedimethaneamine, 22.3 g of K$_2$CO$_3$, and 300 ml of CH$_3$CN are inserted in a two-necked flask, followed by stirring at room temperature. Then, 13.6 g of epichlorohydrin is added thereto at room temperature, followed by stirring at 80° C. for 5 hours to perform the reaction. After completing the reaction, the reactant is cooled to room temperature, and filtered by using a celite filter to remove inorganic materials. The CH$_3$CN solvent is removed by using an evaporator. The crude product is worked-up using ethyl acetate and H$_2$O three times, and an organic layer is separated. In the organic layer, MgSO$_4$ is added to remove remaining H$_2$O. The organic layer thus obtained is filtered and evaporated to obtain Intermediate Product G41.

(2) Second Step and Third Step

By using the above Intermediate Product G41 of the first step and performing the same method as described in the third step and the fourth step of the above Expected Synthetic Example G2, Target Product GI is obtained.

The synthetic reaction of the above Expected Synthetic Example G4 is as follows.

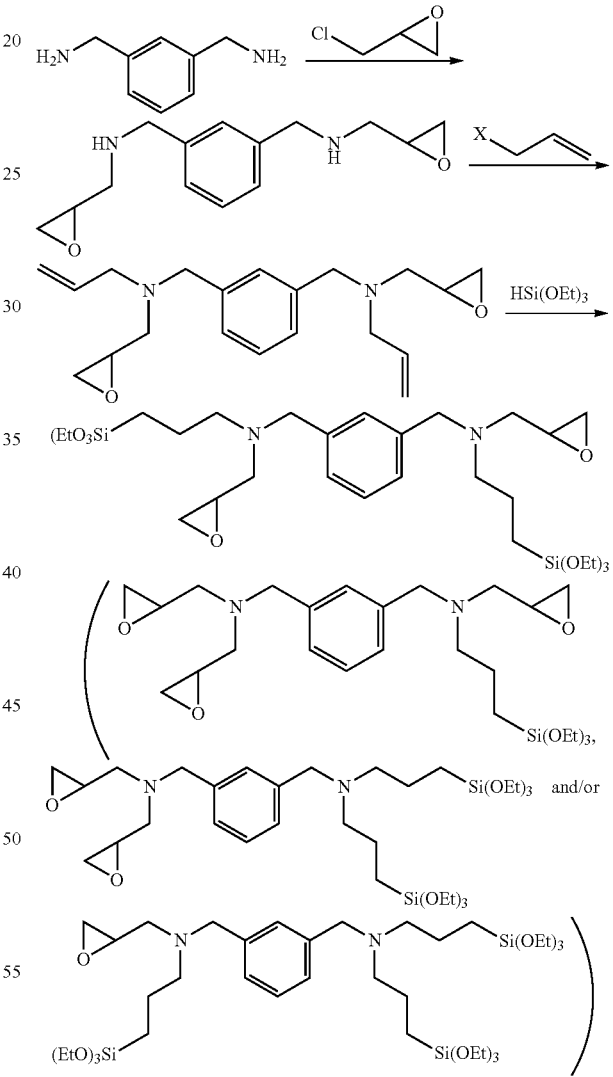

Expected Synthetic Example G5 Synthesis of Phenylenedimethaneamine-Based Epoxy Having Alkoxysilyl Group (Formula GI) (Method 5)

The same Intermediate Product G22 as that of the second step of Expected Synthetic Example G2 is obtained by performing the first step and the second step of Expected Synthetic Example G2. Then, as the third step, 10 g of the above Intermediate Product G22 of the second step, 15.6 g of diisopropylethylamine, and 200 ml of methylene chloride are added in a two-necked flask, followed by stirring at room temperature. Then, 19.9 g of triethoxysilylpropyl isocyanate is added thereto at room temperature, the temperature is increased to 60° C., and the reaction is performed for 12 hours. After completing the reaction, the reactant is cooled to room temperature and worked-up using H₂O. An organic layer is separated, and MgSO₄ is added in the organic layer to remove remaining H₂O. The organic layer thus obtained is filtered using a celite filter and evaporated to obtain Target Product GI.

The synthetic reaction of the above Expected Synthetic Example G5 is as follows.

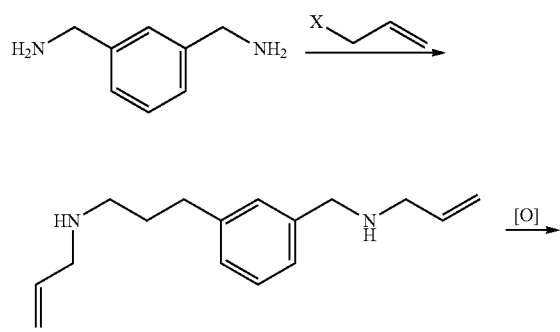

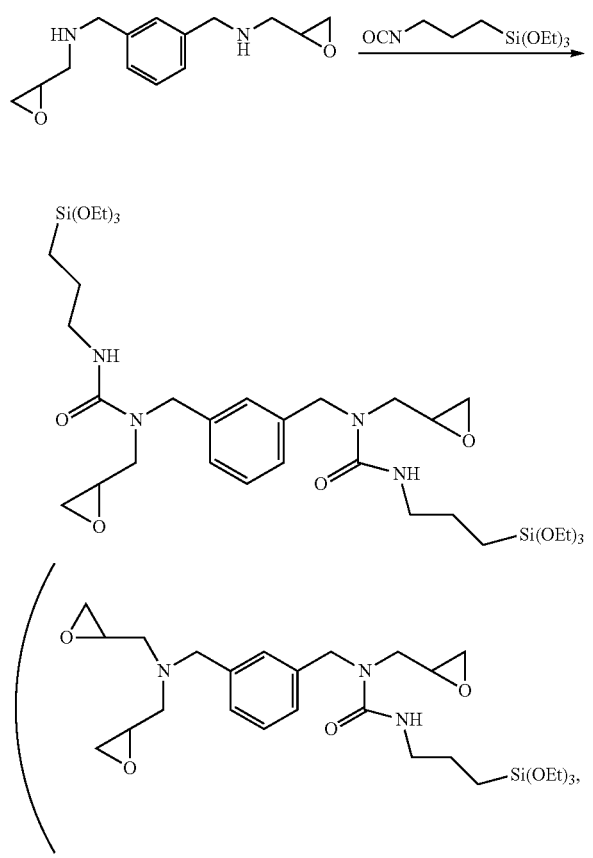

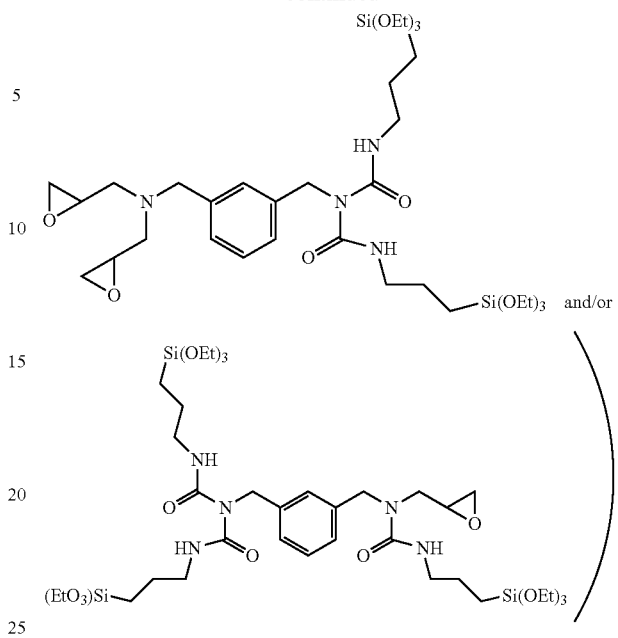

Expected Synthetic Example G6 Synthesis of Phenylenedimethaneamine-Based Epoxy Having Alkoxysilyl Group (Formula GI) (Method 6)

The same Intermediate Product G41 as that of the first step of Expected Synthetic Example G4 is obtained by performing the same reaction as the first step of Expected Synthetic Example F4. Then, the same reaction as that of the third step of Expected Synthetic Example G5 is performed using the intermediate product to obtain the same Target Product GI as that in Expected Synthetic Example G5.

The synthetic reaction of the above Expected Synthetic Example G6 is as follows.

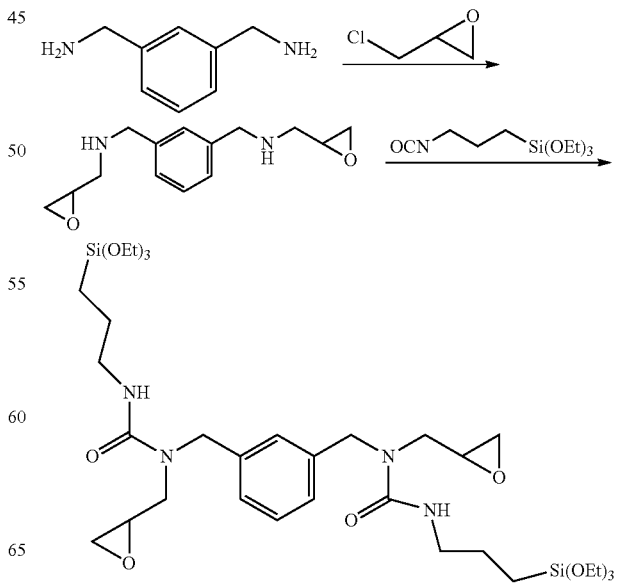

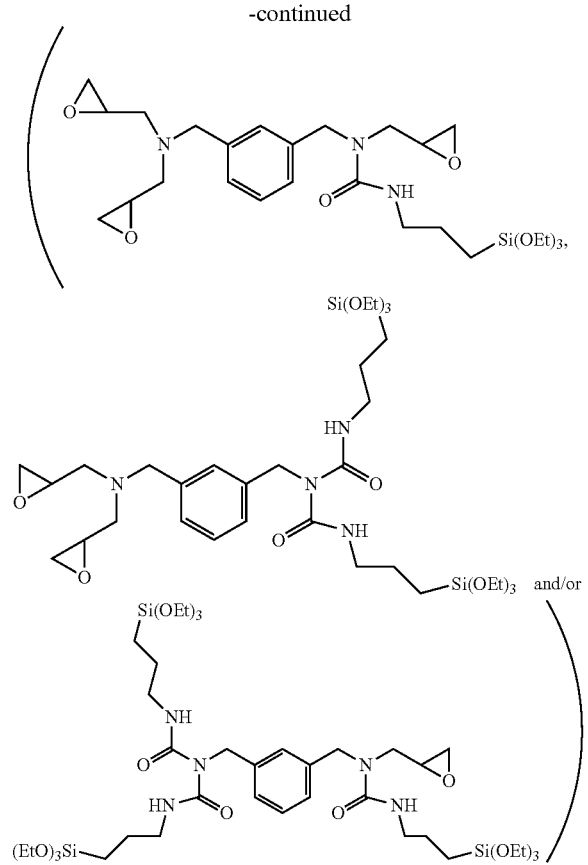

Expected Synthetic Example H1 Synthesis of Cyclohexyl Dimethyldiamine-Based Epoxy Having Alkoxysilyl Group (Formula HI) (Method 1)

(1) First Step 25 g of cyclohexane-1,3-diyldimethaneamine, 42.52 g of allyl bromide, and 300 ml of THF are inserted in a two-necked flask at room temperature, followed by stirring. Then, a solution with 15.5 g of sodium hydroxide dissolved in 150 ml of $H_2O$ is slowly added thereto for 1 hour at room temperature, followed by stirring for 4 hours. 97.6 g of epichlorohydrin is added in the flask, and a solution with 21.1 g of sodium hydroxide dissolved in 150 mol of $H_2O$ is added thereto for 10 minutes at room temperature, followed by stirring for 19 hours. After stirring, THF is removed by using an evaporator, and 400 ml of ethyl acetate is added and worked-up with $H_2O$ to remove inorganic materials. In an organic layer, $MgSO_4$ is added to remove remaining $H_2O$. The organic layer thus obtained is filtered using a celite filter, evaporated and dried to obtain an Intermediate Product H11.

(2) Second Step 20 g of the above Intermediate Product H11, 0.27 g of $PtO_2$, 21.6 g of triethoxysilane, and 250 ml of toluene are added in a flask, followed by stirring for 5 minutes at room temperature. Then, the temperature is increased to 80° C., and heating and stirring are performed for 12 hours. Then, the reactant is cooled to room temperature and filtered using a celite filter to remove inorganic materials. By removing toluene through evaporation and drying, and complete drying using a vacuum pump, Target Product HI is obtained.

The synthetic reaction of the above Expected Synthetic Example H1 is as follows.

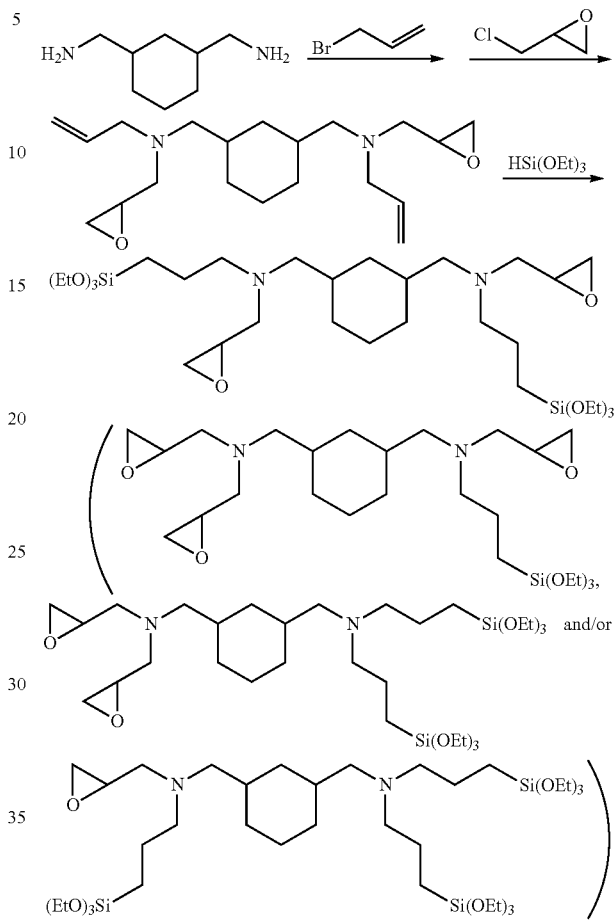

Expected Synthetic Example H2 Synthesis of Cyclohexyl Dimethyldiamine-Based Epoxy Having Alkoxysilyl Group (Formula HI) (Method 2)

(1) First Step 20 g of cyclohexane-1,3-diyldimethaneamine, 34.0 g of allyl bromide, and 300 ml of THF are inserted in a two-necked flask at room temperature, followed by stirring. A solution with 14.1 g of sodium hydroxide dissolved in 300 ml of $H_2O$ is slowly added thereto at room temperature for 1 hour, followed by further stirring for 2 hours. After completing the reaction, THF is removed by using an evaporator, and the crude product is worked-up using 400 ml of ethyl acetate and $H_2O$ to remove inorganic materials. $MgSO_4$ is added in an organic layer to remove remaining $H_2O$. The organic layer thus obtained is filtered using a celite filter and evaporated to obtain Intermediate Product H21 having two alkenyl groups.

(2) Second Step 10 g of the above Intermediate Product H21 obtained in the first step, 1.8 g of $KHCO_3$, 36.9 g of $CH_3CN$, and 300 ml of methanol are added in a two-necked flask, followed by stirring at room temperature. Subsequently, 25.5 g of a 30 wt % $H_2O_2$ solution is slowly added thereto for 10 minutes and stirred at room temperature for 12 hours. After completing the reaction, $CH_3CN$ and methanol are removed by using an evaporator, and 300 ml of ethyl acetate is added and worked-up with H$_2$O. An organic layer is separated, and MgSO$_4$ is added in the organic layer to remove remaining H$_2$O. The organic layer thus obtained is filtered using a celite filter and evaporated to obtain Intermediate Product H23.

(3) Third step

In a two-necked flask, 10 g of the above Intermediate Product H22 obtained in the second step, 21.7 g of K$_2$CO$_3$, and 250 ml of a CH$_3$CN solvent are added and stirred at room temperature. 23.8 g of allyl bromide is added thereto at room temperature, and the temperature is increased to 80° C., followed by stirring for 5 hours to perform the reaction. After completing the reaction, the reactant is cooled to room temperature and filtered using a celite filter to remove inorganic materials. The CH$_3$CN solvent is removed by using an evaporator, and the crude product thus obtained is worked-up using ethyl acetate and H$_2$O three times. An organic layer is separated, and MgSO$_4$ is added in the organic layer to remove remaining H$_2$O. The organic layer thus obtained is filtered and evaporated to obtain epoxy Intermediate Product H23 having an allyl group.

(4) Fourth Step 20 g of the above Intermediate Product H23, 0.27 g of PtO$_2$, 21.6 g of triethoxysilane, and 250 ml of toluene are added in a flask, followed by stirring for 5 minutes at room temperature. The reaction temperature is increased to 80° C., and the reaction is performed for 12 hours while heating and stirring. Then, the reactant is cooled to room temperature and filtered using a celite filter to remove inorganic materials. Subsequently, toluene is removed through evaporation and completely dried using a vacuum pump to obtain Target Product HI.

The synthetic reaction of the above Expected Synthetic Example H2 is as follows.

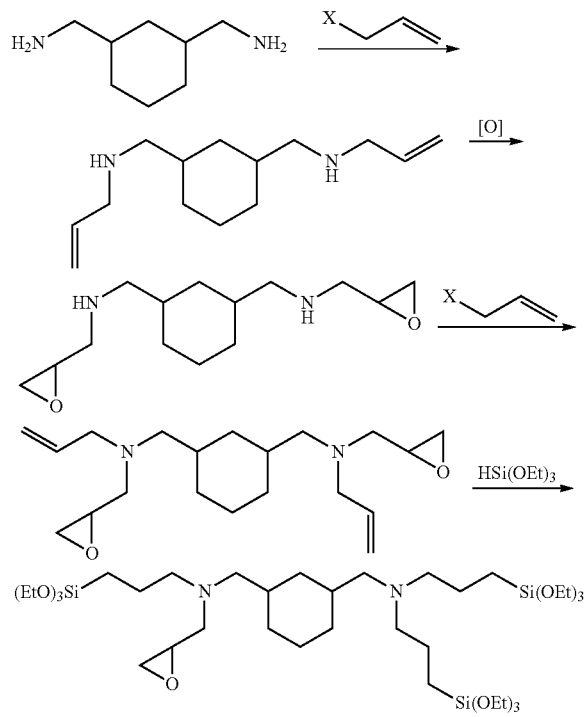

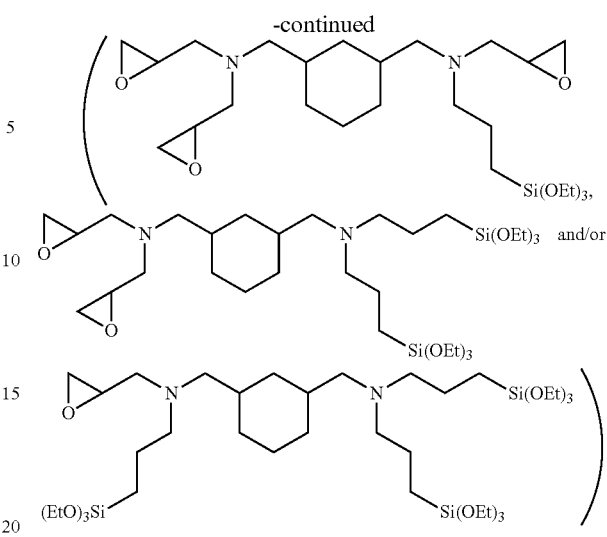

Expected Synthetic Example H3 Synthesis of Cyclohexyl Dimethyldiamine-Based Epoxy Having Alkoxysilyl Group (Formula HI) (Method 3)

(1) First Step 20 g of cyclohexane-1,3-diyldimethaneamine, 71.4 g of allyl bromide, and 300 ml of THF are inserted in a two-necked flask, followed by stirring at room temperature. Then, a solution with 28.1 g of sodium hydroxide dissolved in 300 ml of H$_2$O is slowly added thereto for 1 hour at room temperature, followed by further stirring for 4 hours. After completing the reaction, THF is removed by using an evaporator, and 300 ml of ethyl acetate and 400 ml of H$_2$O are added to work-up three times to remove inorganic materials. In an organic layer, MgSO$_4$ is added to remove remaining H$_2$O. The organic layer thus obtained is filtered using a celite filter to obtain Intermediate Product H31.

(2) Second step 10 g of the above Intermediate Product H31 obtained in the first step, 0.73 g of KHCO$_3$, 8.1 g of CH$_3$CN, and 300 ml of methanol are added in a two-necked flask, followed by stirring at room temperature. Subsequently, 15.0 g of a 30 wt % H$_2$O$_2$ solution is slowly added thereto for 10 minutes and stirred at room temperature for 6 hours to perform the reaction. After completing the reaction, CH$_3$CN and MeOH are removed by using an evaporator, and 250 ml of ethyl acetate and 400 ml of H$_2$O are added to work-up to remove remaining H$_2$O$_2$. An organic layer is separated, and MgSO$_4$ is added in the organic layer to remove remaining H$_2$O. The organic layer thus obtained is filtered using a celite filter to obtain Intermediate Product H32.

(3) Third step 20 g of the above Intermediate Product H32, 0.27 g of PtO$_2$, 21.6 g of triethoxysilane, and 250 ml of toluene are added in a flask, followed by stirring for 5 minutes at room temperature. Then, the temperature is increased to 80° C., and heating and stirring are performed for 12 hours. Then, the reactant is cooled to room temperature and filtered using a celite filter to remove inorganic materials. By removing toluene through evaporation and drying, and complete drying using a vacuum pump, Target Product HI is obtained.

The synthetic reaction of the above Expected Synthetic Example H3 is as follows.

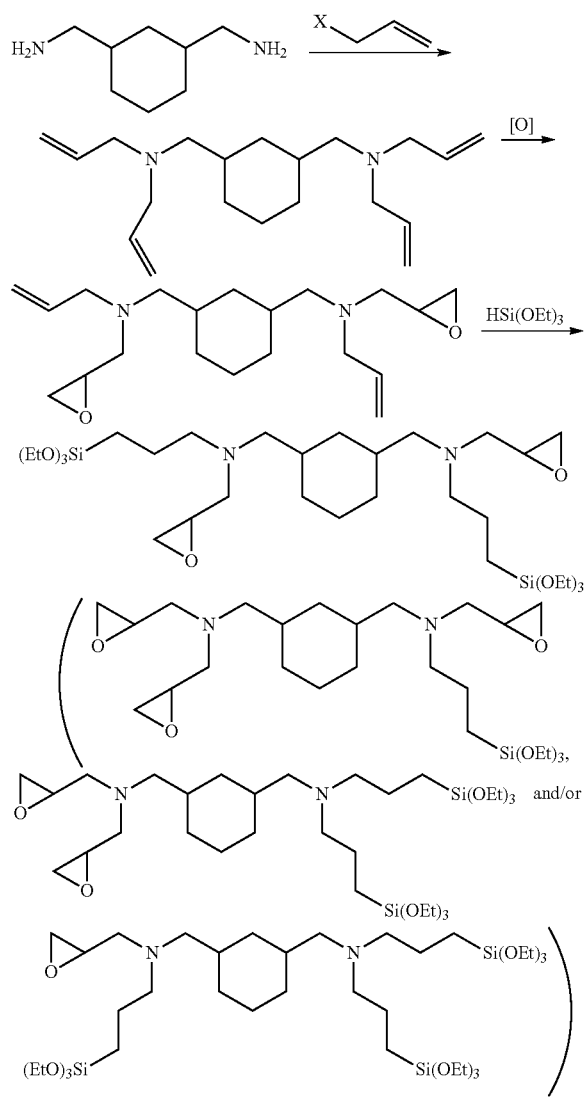

Expected Synthetic Example H4 Synthesis of Cyclohexyl Dimethyldiamine-Based Epoxy Having Alkoxysilyl Group (Formula HI) (Method 4)

(1) First Step 10 g of cyclohexane-1,3-diyldimethaneamine, 21.4 g of $K_2CO_3$, and 300 ml of $CH_3CN$ are inserted in a two-necked flask, followed by stirring at room temperature. Then, 13.0 g of epichlorohydrin is added thereto at room temperature, followed by stirring at 80° C. for 5 hours. After completing the reaction, the reactant is cooled to room temperature, and filtered by using a celite filter to remove inorganic materials. The $CH_3CN$ solvent is removed by using an evaporator. The crude product is worked-up using ethyl acetate and $H_2O$ three times, and an organic layer is separated. In the organic layer, $MgSO_4$ is added to remove remaining $H_2O$. The organic layer thus obtained is filtered and evaporated to obtain Intermediate Product H41.

(2) Second step and third step

By using the above Intermediate Product H41 of the first step and performing the same method as described in the third step and the fourth step of the above Expected Synthetic Example H2, Target Product HI is obtained.

The synthetic reaction of the above Synthetic Example H4 is as follows.

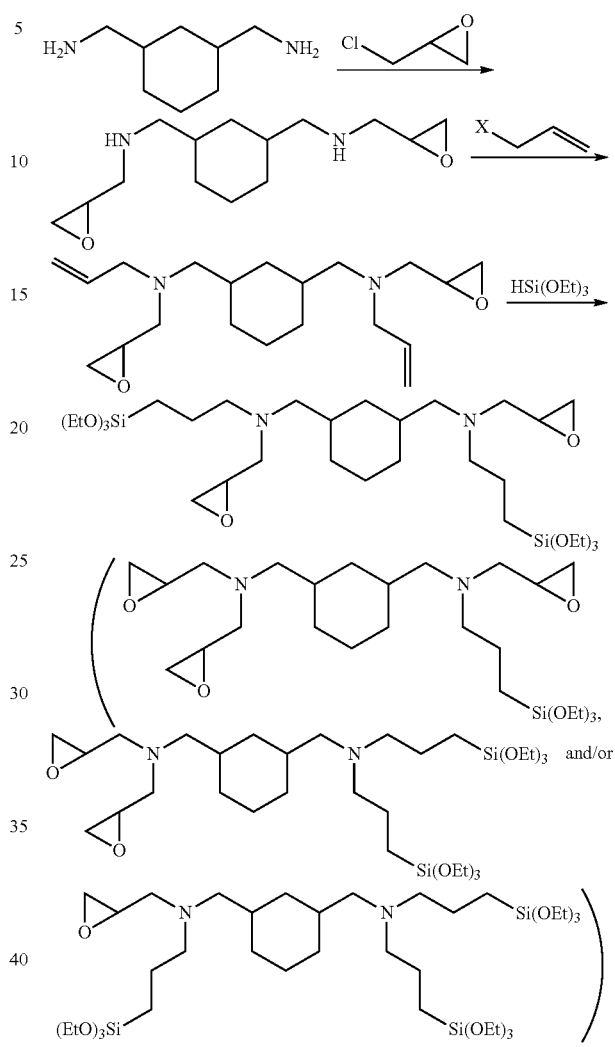

Expected Synthetic Example H5 Synthesis of Cyclohexyl Dimethyldiamine-Based Epoxy Having Alkoxysilyl Group (Formula HI) (Method 5)

The same Intermediate Product H22 as that of the second step of Expected Synthetic Example H2 is obtained by performing the first step and the second step of Expected Synthetic Example H2. Then, as the third step, 10 g of the above Intermediate Product H22 of the second step, 15.24 g of diisopropylethylamine, and 200 ml of methylene chloride are added in a two-necked flask, followed by stirring at room temperature. Then, 19.4 g of triethoxysilylpropyl isocyanate is added thereto at room temperature, the temperature is increased to 60° C., and the reaction is performed for 12 hours. After completing the reaction, the reactant is cooled to room temperature and worked-up using $H_2O$. An organic layer is separated, and $MgSO_4$ is added in the organic layer to remove remaining $H_2O$. The organic layer thus obtained is filtered using a celite filter and evaporated to obtain Target Product HI.

The synthetic reaction of the above Expected Synthetic Example H5 is as follows.

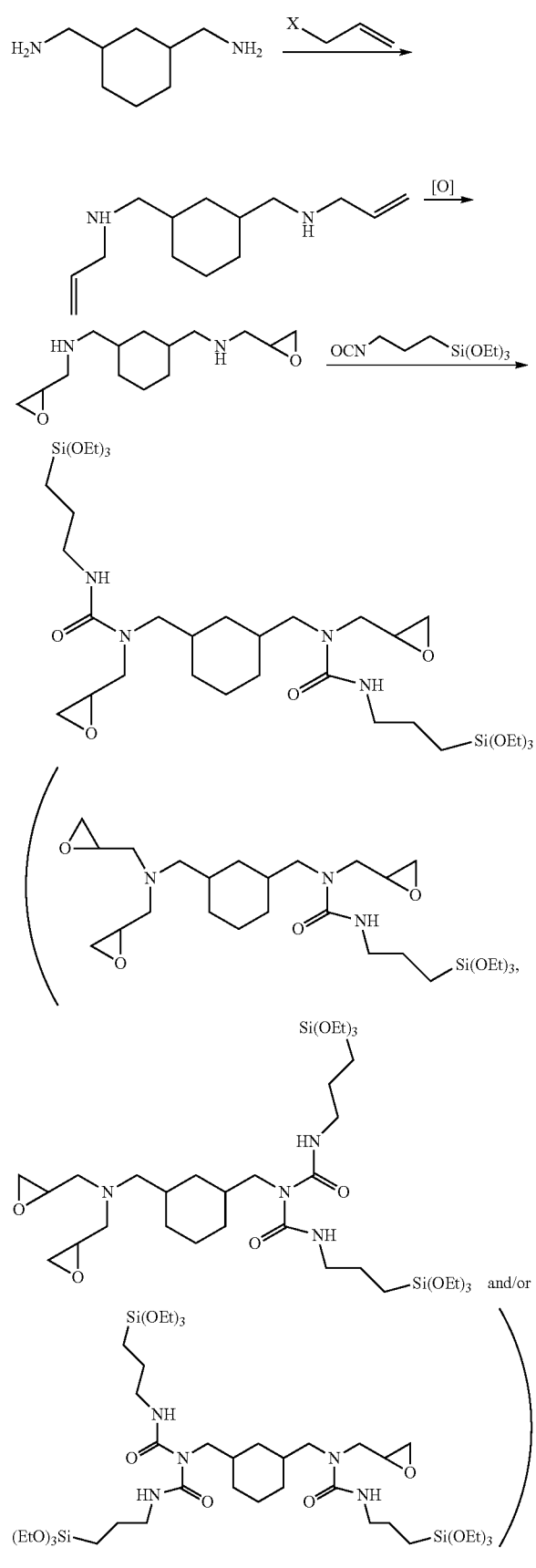

Expected Synthetic Example H6 Synthesis of Cyclohexyl Dimethyldiamine-Based Epoxy Having Alkoxysilyl Group (Formula HI) (Method 6)

The same Intermediate Product H41 as that of the first step of Expected Synthetic Example H4 is obtained by performing the same reaction as that of the first step of Expected Synthetic Example H4. Then, the same reaction as that of the third step of Expected Synthetic Example H5 is performed using the intermediate product to obtain the same Target Product HI as that in Expected Synthetic Example H5.

The synthetic reaction of the above Expected Synthetic Example H6 is as follows.

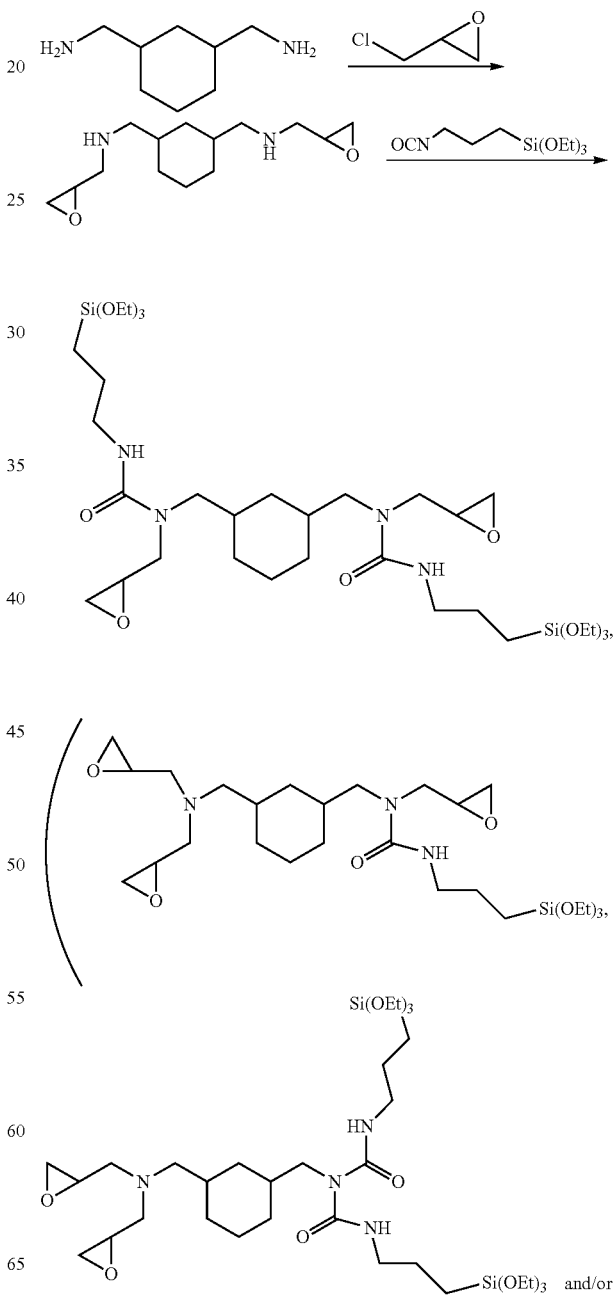

-continued

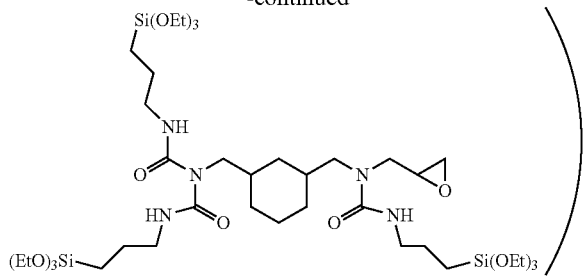

Evaluation of physical properties: Manufacturing of cured product and evaluation of heat resistance properties 1. Manufacturing of epoxy composite (1) Manufacturing of epoxy glass fiber composite (cured product)

A glass fiber composite including an epoxy compound was manufactured by dissolving an epoxy compound, a curing agent, and a curing catalyst in methyl ethyl ketone according to the formulations illustrated in the following Table 1 so that a solid content was 40 wt %, uniformly mixing to obtain a mixture, and immersing a glass fiber (glass fiber fabric by Nittobo Co., E-glass 2116 or T-glass 2116) with the mixture. Then, the composite was inserted into a heated vacuum oven at 100° C. to remove solvents, and was cured in a preheated hot press to 120° C., at 120° C. for 2 hours, at 180° C. for 2 hours and at >200° C. for 2 hours to manufacture a glass fiber composite film (4 mm×16 mm×0.1 mm). While manufacturing the composite film, the resin content of the composite film was controlled according to the pressure of a press and the viscosity of a resin, and the resin content in the composite film is illustrated in the following Table 1.

When a composition for a glass fiber composite includes silica, an epoxy compound, and a silica slurry (70 wt % of solid content, 2-methoxyethanol solvent, 1 μm of silica average size) were dissolved in methyl ethyl ketone according to the formulations illustrated in the following Table 1 so that a solid content was 40 wt %. The mixture thus obtained was mixed in a rate of 1,500 rpm for 1 hour, and a curing agent was added, followed by further mixing for 50 minutes. Finally, a curing accelerator was added and mixed for 10 minutes to obtain an epoxy mixture. A glass fiber composite was manufactured by immersing a glass fiber (glass fiber fabric by Nittobo Co., E-glass 2116 or T-glass 2116) with the epoxy mixture. Then, the same curing process was performed under the same conditions as described above to manufacture a composite film.

(2) Manufacturing of Epoxy Filler Composite (Cured Product)

An epoxy compound, and a silica slurry (70 wt % of solid content, 2-methoxyethanol solvent, 1 μm of silica average size) were dissolved in methyl ethyl ketone according to the formulations illustrated in the following Table 2 so that a solid content was 40 wt %. The mixture thus obtained was mixed in a rate of 1,500 rpm for 1 hour, and a curing agent was added, followed by further mixing for 50 minutes. Finally, a curing accelerator was added and mixed for 10 minutes to obtain an epoxy mixture. Then, the mixture was inserted into a heated vacuum oven to 100° C. to remove solvents, and was cured in a preheated hot press to 120° C., at 120° C. for 2 hours, at 180° C. for 2 hours and at >200° C. for 2 hours to manufacture an epoxy filler (inorganic particle) composite (5 mm×5 mm×3 mm).

2. Evaluation of Heat Resistance Physical Properties

The dimensional changes with respect to the temperature of the cured products obtained in the Examples and Comparative Examples in the following Tables 1 and 2 were evaluated by using a Thermo-mechanical analyzer and are illustrated in the following Tables. The specimens of the epoxy glass fiber composite film were manufactured in a size of 4 mm×16 mm×0.1 mm, and the specimens of the filler composites were manufactured in a size of 5 mm×5 mm×3 mm.

TABLE 1

| | | Epoxy glass fiber composite | | | | | | | | | | |
|---|---|---|---|---|---|---|---|---|---|---|---|---|
| | | Epoxy compound (Synthetic Example No.) | | Example 1 | Example 2 | Example 3 | Example 4 | Example 5 | Example 6 | Example 7 | Example 8 | Example 9 | Example 10 |
| Epoxy formulation (g) | Epoxy | A1(1) | | 5.00 | 4.50 | 4.50 | | | | | | | |
| | | A1(2) | | | | | 5.00 | 5.00 | 5.00 | 5.00 | 5.00 | 5.00 | 5.00 |
| | | A1(3) | | | | | | | | | | | |
| | | A1(4) | | | | | | | | | | | |
| | | A5 | | | | | | | | | | | |
| | | B1(1) | | | | | | | | | | | |
| | | B1(2) | | | | | | | | | | | |
| | | B1(3) | | | | | | | | | | | |
| | | B5 | | | | | | | | | | | |
| | | C1(1) | | | | | | | | | | | |
| | | C1(2) | | | | | | | | | | | |
| | | C1(3) | | | | | | | | | | | |
| | | C5 | | | | | | | | | | | |
| | | D1(1) | | | | | | | | | | | |
| | | D1(2) | | | | | | | | | | | |
| | | D1(3) | | | | | | | | | | | |
| | | D5 | | | | | | | | | | | |
| | | DGEBA[(1)] | | | 0.5 | 0.5 | | | | | | | |
| | | HP-4032D[(2)] | | | | | | | | | | | |
| | | TMTE[(3)] | | | | | | | | | | | |
| | | AP[(4)] | | | | | | | | | | | |

TABLE 1-continued

Epoxy glass fiber composite

| | | | | | | | | | | | | |
|---|---|---|---|---|---|---|---|---|---|---|---|---|
| | | EXA 4700[5] | | | | | | | | | | |
| | | GTR 1800[6] | | | | | | | | | | |
| | | HF-1M[7] | 1.17 | 1.35 | 1.35 | 1.97 | 1.66 | 1.97 | 1.97 | 1.97 | 1.97 | 1.07 |
| | | TPP[8] | | 0.05 | 0.06 | 0.06 | 0.05 | 0.03 | | | 0.03 | |
| | | Tin-OC[9] | | | | | | | | | 0.2 | |
| | | 2E4M[10] | | | | | | 0.04 | 0.05 | | 0.04 | 0.05 |
| | | Silica | 0 | 0 | 1.59 | 0 | 1.67 | 0 | 0 | 0 | 1.74 | 1.75 |
| | | Glass fiber type | E | E | E | E | T | E | E | E | E | E |
| | | Resin content (wt %) | 41 | 40 | 42 | 42 | 41 | 35 | 34 | 40 | 40 | 40 |
| Heat resistance | CTE (ppm/° C.) | $\alpha_1$ (T < Tg) | 8.8 | 8.1 | 7.8 | 7.0 | 1.99 | 6.8 | 4.7 | 8.0 | 6.1 | 7.2 |
| | Tg (° C.) | | 150 | 150 | TGL | 130 | TGL | 130 | TGL | TGL | TGL | TGL |

| | | Epoxy compound (Synthetic Example No.) | Example 11 | Example 12 | Example 13 | Example 14 | Example 15 | Example 16 | Example 17 | Example 18 | Example 19 | Example 20 |
|---|---|---|---|---|---|---|---|---|---|---|---|---|
| Epoxy formulation (g) | Epoxy | A1(1) | | | | | | | | | | |
| | | A1(2) | 2.50 | | | | | | | | | |
| | | A1(3) | | 5.00 | | | | | | | | |
| | | A1(4) | | | 5.00 | 2.5 | | | | | | |
| | | A5 | | | | | 5.00 | 5.00 | 5.00 | 5.00 | | |
| | | B1(1) | | | | | | | | | 5.00 | 4.5 |
| | | B1(2) | | | | | | | | | | |
| | | B1(3) | 2.50 | | | 2.5 | | | | | | |
| | | B5 | | | | | | | | | | |
| | | C1(1) | | | | | | | | | | |
| | | C1(2) | | | | | | | | | | |
| | | C1(3) | | | | | | | | | | |
| | | C5 | | | | | | | | | | |
| | | D1(1) | | | | | | | | | | |
| | | D1(2) | | | | | | | | | | |
| | | D1(3) | | | | | | | | | | |
| | | D5 | | | | | | | | | | |
| | | DGEBA[1] | | | | | | | | | | |
| | | HP-4032D[2] | | | | | | | | | | |
| | | TMTE[3] | | | | | | | | | | |
| | | AP[4] | | | | | | | | | | 0.5 |
| | | EXA 4700[5] | | | | | | | | | | |
| | | GTR 1800[6] | | | | | | | | | | |
| | | HF-1M[7] | 1.45 | 1.97 | 1.96 | 1.43 | 2.35 | 1.97 | 1.97 | 1.97 | 1.50 | 1.91 |
| | | TPP[8] | 0.03 | 0.05 | 0.03 | 0.04 | 0.05 | 0.05 | 0.05 | 0.05 | 0.05 | 0.05 |
| | | Tin-OC[9] | | | | | | | | | | |
| | | 2E4M[10] | | | | | | | | | | |
| | | Silica | 0 | 0 | 0 | 0 | 0 | 0 | 0.5 | 0 | 0 | 0 |
| | | Glass fiber | E | E | E | E | E | E | E | T | E | E |
| | | Resin content (wt %) | 41 | 43 | 43 | 38 | 42 | 37 | 38 | 37 | 40 | 38 |
| Heat resistance | CTE (ppm/° C.) | $\alpha_1$ (T < Tg) | 7.4 | 10.5 | 8.8 | 5.7 | 7.0 | 7.0 | 7.0 | 3.0 | 5.5 | 8.0 |
| | Tg (° C.) | | TGL | TGL | TGL | TGL | TGL | TGL | TGL | TGL | TGL | TGL |

| | | Epoxy compound (Synthetic Example No.) | Example 21 | Example 22 | Example 23 | Example 24 | Example 25 | Example 26 | Example 27 | Example 28 | Example 29 | Example 30 |
|---|---|---|---|---|---|---|---|---|---|---|---|---|
| Epoxy formulation (g) | Epoxy | A1(1) | | | | | | | | | | |
| | | A1(2) | | | | | | | | | | |
| | | A1(3) | | | | | | | | | | |
| | | A1(4) | | | | | | | | | | |
| | | A5 | | | | | | | | | | |
| | | B1(1) | 4.5 | | | | | | | | | |
| | | B1(2) | | 5.00 | | | | | | | | |
| | | B1(3) | | | 4.00 | | | | | | | |
| | | B5 | | | | 5.00 | | | | | | |
| | | C1(1) | | | | | 5.00 | 4.0 | 4.0 | | | |
| | | C1(2) | | | | | | | | | 5.00 | |

TABLE 1-continued

Epoxy glass fiber composite

|  |  |  |  |  |  |  |  |  |  |  |  |
|---|---|---|---|---|---|---|---|---|---|---|---|
|  |  | C1(3) |  |  |  |  |  |  |  |  | 5.00 |
|  |  | C5 |  |  |  |  |  |  |  |  |  | 5.00 |
|  |  | D1(1) |  |  |  |  |  |  |  |  |  |  |
|  |  | D1(2) |  |  |  |  |  |  |  |  |  |  |
|  |  | D1(3) |  |  |  |  |  |  |  |  |  |  |
|  |  | D5 |  |  |  |  |  |  |  |  |  |  |
|  |  | DGEBA[1] |  | 1.00 |  |  |  |  |  |  |  |  |
|  |  | HP-4032D[2] |  |  |  |  | 1.0 | 1.0 |  |  |  |  |
|  |  | TMTE[3] |  |  |  |  |  |  |  |  |  |  |
|  |  | AP[4] | 0.5 |  |  |  |  |  |  |  |  |  |
|  |  | EXA 4700[5] |  |  |  |  |  |  |  |  |  |  |
|  |  | GTR 1800[6] |  |  |  |  |  |  |  |  |  |  |
|  |  | HF-1M[7] | 1.91 | 2.51 | 1.31 | 2.28 | 1.25 | 2.06 | 2.06 | 1.89 | 2.28 | 1.76 |
|  |  | TPP[8] | 0.05 | 0.04 | 0.05 | 0.04 | 0.02 | 0.02 | 0.02 | 0.02 | 0.02 | 0.02 |
|  |  | Tin-OC[9] |  |  |  |  |  |  |  |  |  |  |
|  |  | 2E4M[10] |  |  |  |  |  |  |  |  |  |  |
|  |  | Silica | 1.75 | 1.88 | 0 | 1.83 | 0 | 0 | 1.5 | 0 | 0 | 0 |
|  |  | Glass fiber | E | E | E | E | E | E | E | E | E | E |
|  |  | Resin content (wt %) | 40 | 42 | 40 | 43 | 43 | 39 | 41 | 44 | 45 | 42 |
| Heat resistance | CTE (ppm/° C.) | $\alpha_1$ (T < Tg) | 7.50 | 6.5 | 6.1 | 6.3 | 5.5 | 7.1 | 6.8 | 7.5 | 8.3 | 6.9 |
|  | Tg (° C.) |  | TGL | TGL | TGL | TGL | TGL | TGL | TGL | TGL | PTGL | TGL |

|  |  | Epoxy compound (Synthetic Example No.) | Example 31 | Example 32 | Example 33 | Example 34 | Example 35 | Example 36 | Example 37 | Example 38 | Example 39 | Example 40 |
|---|---|---|---|---|---|---|---|---|---|---|---|---|
| Epoxy formulation (g) | Epoxy | A1(1) |  |  |  |  |  |  |  |  |  |  |
|  |  | A1(2) |  |  |  |  |  |  |  |  |  |  |
|  |  | A1(3) |  |  |  |  |  |  |  |  |  |  |
|  |  | A1(4) |  |  |  |  |  |  |  |  |  |  |
|  |  | A5 |  |  |  |  |  |  |  |  |  |  |
|  |  | B1(1) |  |  |  |  |  |  |  |  |  |  |
|  |  | B1(2) |  |  |  |  |  |  |  |  |  |  |
|  |  | B1(3) |  |  |  |  |  |  |  |  | 2.50 |  |
|  |  | B5 |  |  |  |  |  |  |  |  |  | 1.0 |
|  |  | C1(1) |  |  |  |  |  |  |  |  |  |  |
|  |  | C1(2) |  |  |  |  |  |  |  |  |  |  |
|  |  | C1(3) |  |  |  |  |  |  |  |  |  |  |
|  |  | C5 |  |  |  |  |  |  |  |  |  |  |
|  |  | D1(1) | 5.00 | 5.00 | 5.00 | 4.5 | 4.5 |  |  |  |  |  |
|  |  | D1(2) |  |  |  |  |  | 5.00 |  |  |  |  |
|  |  | D1(3) |  |  |  |  |  |  | 5.00 | 2.50 |  |  |
|  |  | D5 |  |  |  |  |  |  |  |  | 5.0 | 4.0 |
|  |  | DGEBA[1] |  |  |  | 0.5 | 0.5 |  |  |  |  |  |
|  |  | HP-4032D[2] |  |  |  |  |  |  |  |  |  |  |
|  |  | TMTE[3] |  |  |  |  |  |  |  |  |  |  |
|  |  | AP[4] |  |  |  |  |  |  |  |  |  |  |
|  |  | EXA 4700[5] |  |  |  |  |  |  |  |  |  |  |
|  |  | GTR 1800[6] |  |  |  |  |  |  |  |  |  |  |
|  |  | HF-1M[7] | 1.00 | 1.00 | 1.00 | 1.25 | 1.25 | 1.63 | 1.90 | 2.01 | 1.63 | 1.70 |
|  |  | TPP[8] | 0.02 | 0.02 | 0.02 | 0.02 | 0.03 | 0.02 | 0.04 | 0.05 | 0.04 | 0.04 |
|  |  | Tin-OC[9] | 0.2 |  |  |  |  |  |  |  |  |  |
|  |  | 2E4M[10] |  |  |  |  |  |  |  |  |  |  |
|  |  | Silica | 0 | 0 | 0 | 0 | 1.61 | 0 | 0.5 | 0 | 0 | 0 |
|  |  | Glass fiber | E | E | T | E | E | E | E | E | E | E |
|  |  | Resin content (wt %) | 40 | 38 | 38 | 40 | 41 | 40 | 46 | 36 | 38 | 39 |
| Heat resistance | CTE (ppm/° C.) | $\alpha_1$ (T < Tg) | 8.7 | 6.3 | 4.0 | 6.9 | 07.2 | 7.1 | Too fast cure | 6.7 | 7.5 | 7.0 |
|  | Tg (° C.) |  | TGL | TGL | TGL | TGL | TGL | TGL | TGL | TGL | TGL | TGL |

TABLE 1-continued

| | | Epoxy glass fiber composite | | | | |
|---|---|---|---|---|---|---|
| | Epoxy compound (Synthetic Example No.) | | Comparative Example 1 | Comparative Example 2 | Comparative Example 3 | Comparative Example 4 |
| Epoxy formulation (g) | Epoxy | A1(1) | | | | |
| | | A1(2) | | | | |
| | | A1(3) | | | | |
| | | A1(4) | | | | |
| | | A5 | | | | |
| | | B1(1) | | | | |
| | | B1(2) | | | | |
| | | B1(3) | | | | |
| | | B5 | | | | |
| | | C1(1) | | | | |
| | | C1(2) | | | | |
| | | C1(3) | | | | |
| | | C5 | | | | |
| | | D1(1) | | | | |
| | | D1(2) | | | | |
| | | D1(3) | | | | |
| | | D5 | | | | |
| | | DGEBA[1] | | | | 2.00 |
| | | HP-4032D[2] | | | | |
| | | TMTE[3] | 5.00 | | | |
| | | AP[4] | | 5.00 | | |
| | | EXA 4700[5] | | | 5.00 | |
| | | GTR 1800[6] | | | | 3.00 |
| | | HF-1M[7] | 3.48 | 5.30 | 3.32 | 3.00 |
| | | TPP[8] | 0.05 | 0.05 | 0.05 | 0.025 |
| | | Tin-OC[9] | | | | |
| | | 2E4M[10] | | | | |
| | | Silica | 0 | 0 | 0 | 0 |
| | | Glass fiber | E | E | E | E |
| | | Resin content (wt %) | 43 | 41 | 47 | 37 |
| Heat resistance | CTE (ppm/° C.) | $\alpha_1$ (T < Tg) | 15.8 | 17.0 | 16.6 | 13.0 |
| | Tg (° C.) | | 170 | 160 | 200 | 200 |

TABLE 2

| | | Epoxy filler composite | | | | | | | | | |
|---|---|---|---|---|---|---|---|---|---|---|---|
| | Epoxy compound (Synthetic Example No.) | | Example 41 | Example 42 | Example 43 | Example 44 | Example 45 | Example 46 | Example 47 | Example 48 | Example 49 | Example 50 |
| Epoxy formulation (g) | Epoxy | A1(1) | 5.00 | 5.00 | 5.00 | 5.00 | 4.00 | 3.41 | | | | |
| | | A1(2) | | | | | | | 5.00 | 4.5 | | |
| | | B1(1) | | | | | | | | | 4.5 | |
| | | B1(3) | | | | | 0.5 | | | | | 4.00 |
| | | C1(1) | | | | | | | | | | |
| | | C1(2) | | | | | | | | | | |
| | | D1(1) | | | | | | | | | | |
| | | D1(2) | | | | | | | | | | |
| | | DGEBA[1] | | | | | | | | | | |
| | | TGIC[11] | | | | | | 0.40 | | | 0.5 | |
| | | HP-4032D[2] | | | | | | | | 0.5 | | |
| | | EOCN[12] | | | | | | | | | | 1.00 |
| | | Polydis[12] | | | | | 0.5 | 0.92 | | | | |
| | | Polyvinyl butyral | | | | | | 0.70 | | | | |
| | | HF-1M[7] | 1.18 | 1.18 | 1.18 | 1.18 | 1.14 | 1.46 | 1.66 | 1.87 | 1.99 | 1.29 |
| | | TPP[9] | 0.02 | 0.02 | 0.02 | 0.02 | 0.02 | 0.33 | 0.05 | 0.03 | 0.07 | 0.03 |
| | | Silica | 2.65 | 6.20 | 14.4 | 24.2 | 24.2 | 27.6 | 26.8 | 27.5 | 27.9 | 25.2 |
| | | Filler content (wt %) | 30 | 50 | 70 | 80 | 80 | 80 | 80 | 80 | 80 | 80 |
| Heat resistance | CTE (ppm/° C.) | $\alpha_1$ (T < Tg) | 61 | 38 | 11.2 | 6.5 | 7.5 | 7.5 | 6.6 | 9.5 | 7.5 | 4.89 |
| | Tg (° C.) | | TGL | TGL | TGL | TGL | TGL | TGL | TGL | TGL | TGL | TGL |

TABLE 2-continued

| | | | Example 51 | Example 52 | Example 53 | Example 54 | Example 55 | Example 56 | Example 57 | Example 58 | Example 59 | Example 60 |
|---|---|---|---|---|---|---|---|---|---|---|---|---|
| | Epoxy compound (Synthetic Example No.) | | | | | | | | | | | |
| Epoxy formulation (g) | Epoxy | A1(1) | | | | | | | | | | |
| | | A1(2) | | | | | | | | | | |
| | | B1(1) | | | | | | | | | | |
| | | B1(3) | 4.00 | 4.00 | | | | | | | | |
| | | C1(1) | | | 4.00 | 4.00 | | | | | | |
| | | C1(2) | | | | | 4.00 | 4.00 | | | | |
| | | D1(1) | | | | | | | 4.00 | 4.00 | | |
| | | D1(2) | | | | | | | | | 4.00 | 4.00 |
| | | DGEBA[1] | 1.0 | | | | | | | | | |
| | | TGIC[11] | | | 0.44 | | 0.44 | | 0.44 | | 0.44 | |
| | | HP-4032D[2] | | 1.0 | | | | | | | | |
| | | EOCN[12] | | | | 0.44 | | 0.44 | | 0.44 | | 0.44 |
| | | Polydis[12] | | | 1.08 | 1.08 | | | 1.08 | 1.08 | | |
| | | Polyvinyl butyral | | | 0.82 | 0.82 | | | 0.82 | 0.82 | | |
| | | HF-1M[7] | 1.31 | 1.57 | 1.81 | 1.57 | 1.61 | 1.37 | 1.57 | 0.34 | 1.78 | 1.55 |
| | | TPP[9] | 0.05 | 0.05 | 0.03 | 0.03 | 0.03 | 0.03 | 0.02 | 0.02 | 0.02 | 0.02 |
| | | Silica | 25.4 | 27.4 | 32.7 | 31.7 | 24.3 | 23.3 | 31.7 | 26.8 | 24.9 | 24.0 |
| | | Filler content (wt %) | 80 | 80 | 80 | 80 | 80 | 80 | 80 | 80 | 80 | 80 |
| Heat resistance | CTE (ppm/° C.) | $\alpha_1$ (T < Tg) | 6.4 | 5.39 | 6.5 | 7.1 | 8.8 | 9.4 | 7.6 | 8.1 | 9.7 | 10.2 |
| | Tg (° C.) | | TGL | TGL | TGL | TGL | TGL | TGL | TGL | TGL | TGL | TGL |

(TGL: Tg-less (not exhibiting glass transition temperature))

Note: The compounds used in Tables 1 and 2 are as follows.

(1) DGEBA: Bisphenyl A-based epoxy (Aldrich Co.)

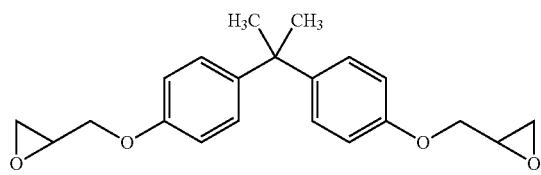 [SMILES: CC(C)(c1ccc(OCC2CO2)cc1)c1ccc(OCC2CO2)cc1]

(2) HP-4032D: Naphthalene epoxy (DIC Inc., Japan)

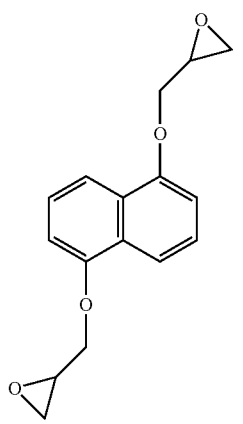 [SMILES: c1cc(OCC2CO2)c2cccc(OCC3CO3)c2c1]

(3) TMTE: Triphenylmethane-based epoxy (Aldrich Co.)

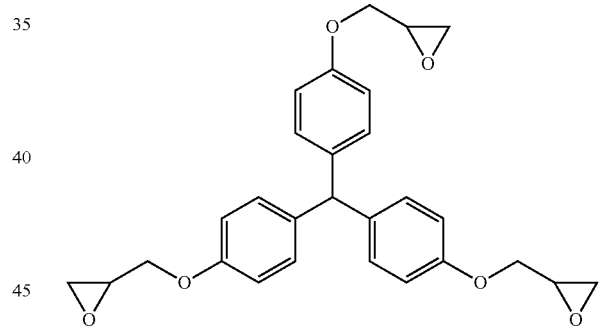

(4) AP: Aminophenol epoxy (Ciba geigy)

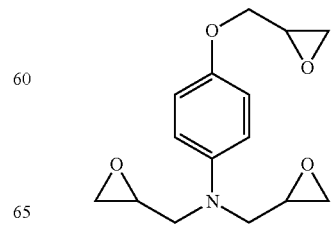

(5) EXA-4700: Binaphthalene-based epoxy (DIC Inc., Japan)

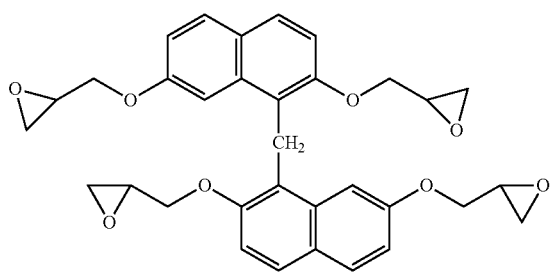 [SMILES: c1cc2ccc(OCC3CO3)c(Cc3c(OCC4CO4)ccc4ccc(OCC5CO5)cc34)c2cc1OCC1CO1]

(6) GTR 1800: Binaphthalene-based epoxy (DIC Inc., Japan)

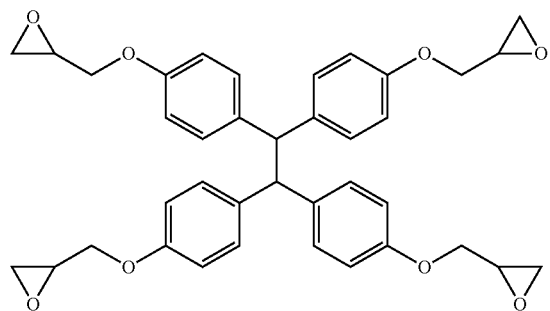 [SMILES: c1cc(C(c2ccc(OCC3CO3)cc2)C(c2ccc(OCC3CO3)cc2)c2ccc(OCC3CO3)cc2)ccc1OCC1CO1]

(7) HF-1M: Phenol novolak-based curing agent (Meiwa Plastic Industries)
(8) TPP: Triphenylphosphine (Aldrich Co.)
(9) Tin-OC: Tin(II) 2-ethylhexanoate (Aldrich Co.)
(10) 2E4M: 2-ethyl-4-methyl imidazole (Aldrich Co.)
(11) TGIC: Triglycidyl isocyanurate (Aldrich Co.)
(12) EOCN: ortho-cresol novolak epoxy
(13) Polydis: rubber modified epoxy (Struktol Co.)

As shown in the above Table 1, the CTE of the alkoxysilylated epoxy composites of Formula AI having a triphenylmethane core according to the present invention (Examples 1 to 18) is 4.7 to 10 ppm/° C. (E-glass), which is relatively very low when compared to CTE=15.8 ppm/° C. (E-glass) of a composite of a triphenylmethane-based epoxy compound excluding an alkoxysilyl group (Comparative Example 1). Particularly, as shown in FIG. 1, the CTE of the epoxy compound having a triphenylmethane-based core manufactured by using E-glass (Example 4) is very small when compared to the CTE of the composite of Comparative Example 1.

Figure 2:
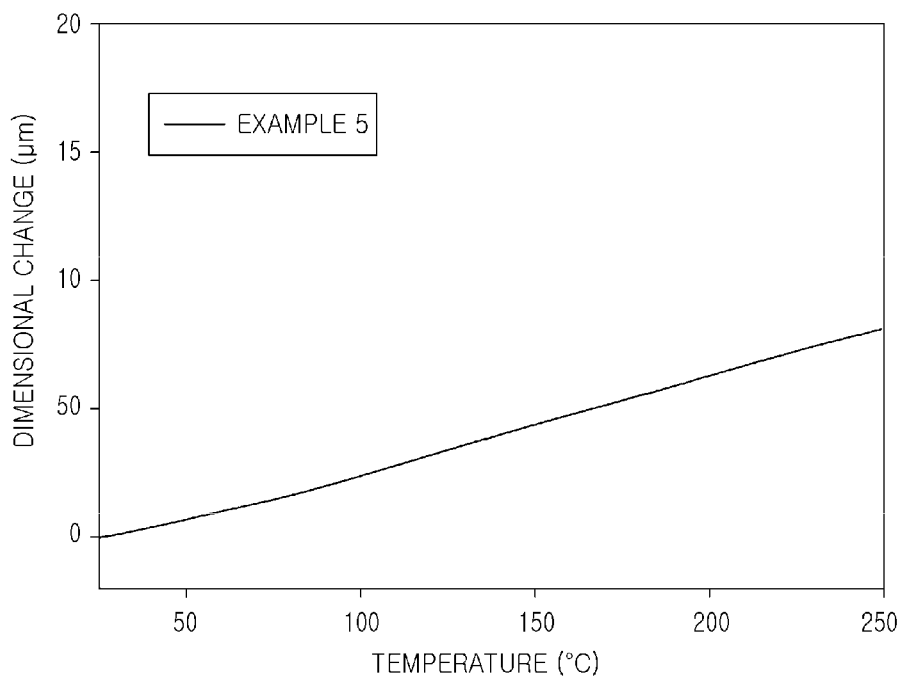
FIG. 2 is a graph illustrating dimensional change with the change of a temperature of composites according to Example 5.
Figure 3:
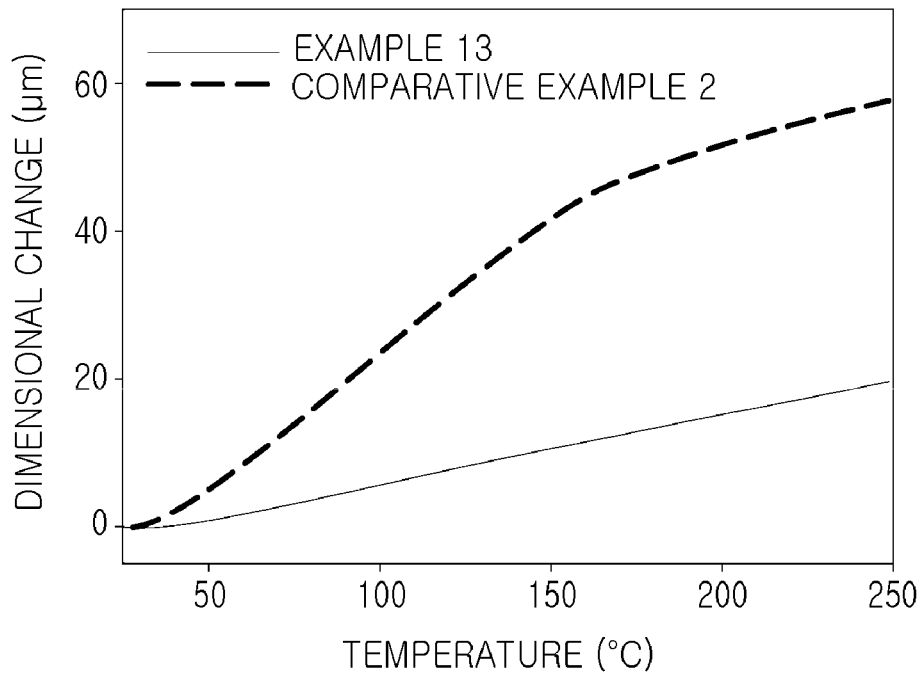
FIG. 3 is a graph illustrating dimensional changes with the change of a temperature of composites according to Example 23 and Comparative Example 2.

In addition, the CTE of the alkoxysilylated epoxy complex of Formula BI having the aminophenol core according to the present invention (Examples 19 to 24) is 6 to 8 ppm/° C., which is relatively very small when compared to CTE=17 ppm/° C. of the composite of the aminophenol-based epoxy compound excluding an alkoxysilyl group (Comparative Example 2). Particularly, when a composite is manufactured by using T-glass, the CTE is about 2 to 3 ppm/° C. as in FIG. 2 and Example 5, and Example 8, which is very small and similar to that of a silicon chip. In addition, as shown in FIG. 3, the CTE of the epoxy compound having the aminophenol-based core manufactured by using E-glass (Example 23) is largely decreased when compared to the CTE of the composite of Comparative Example 2.

Figure 4:
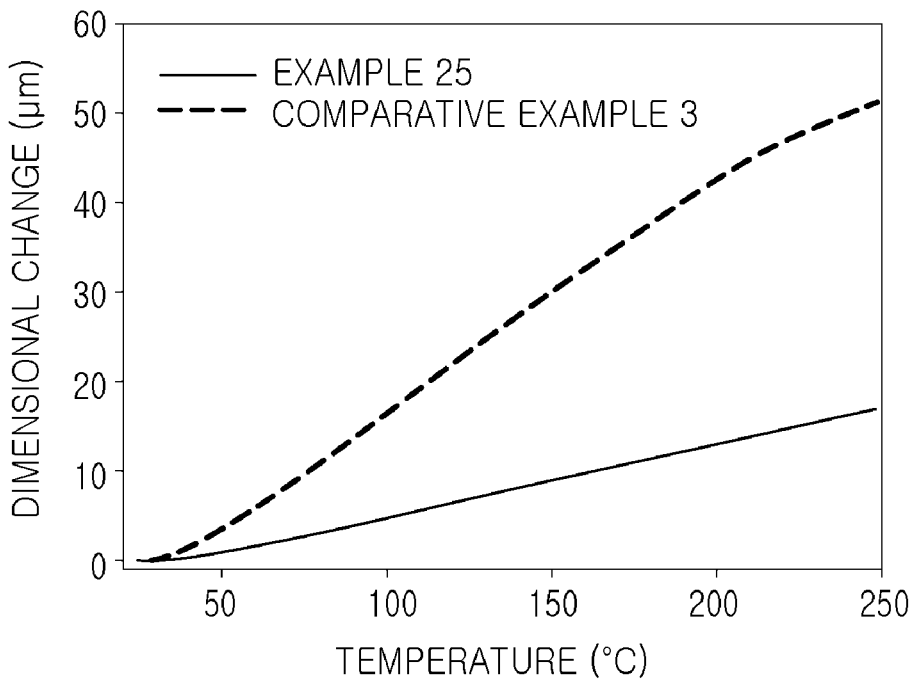
FIG. 4 is a graph illustrating dimensional changes with the change of a temperature of composites according to Example 25 and Comparative Example 3.

The CTE of the alkoxysilylated epoxy composite of Formula CI having the binaphthalene core according to the present invention (Examples 25 to 30) is 5 to 8 ppm/° C., which is very small when compared to CTE=16.6 ppm/° C. of the binaphthalene-based epoxy compound excluding an alkoxysilyl group (Comparative example 3). Particularly, as shown in FIG. 4, the CTE of the epoxy compound having the binaphthalene-based core manufactured by using E-glass (Example 25) is largely decreased when compared to the CTE of the composite of Comparative Example 3.

Figure 5:
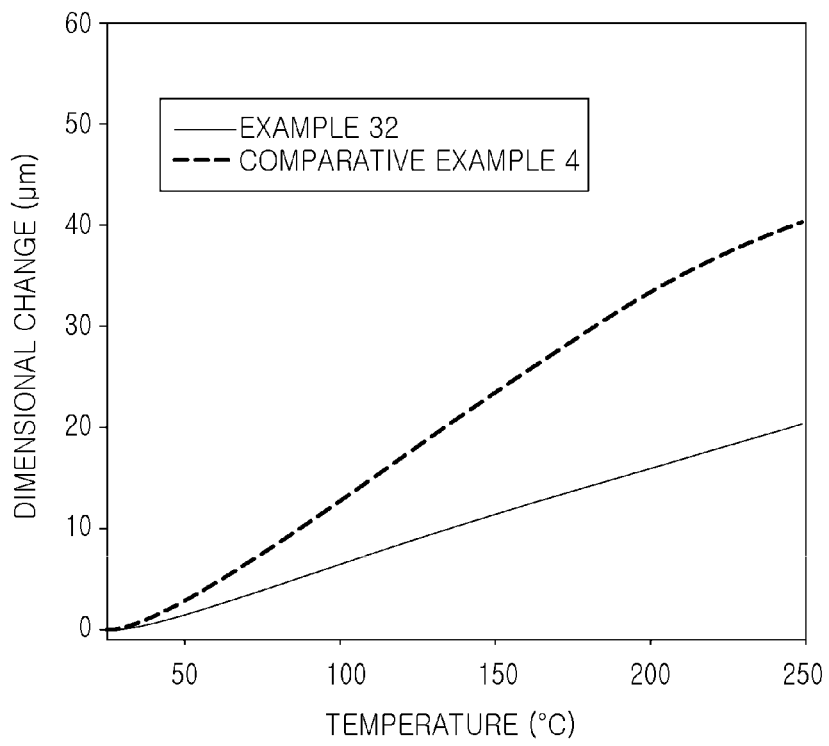
FIG. 5 is a graph illustrating dimensional changes with the change of a temperature of composites according to Example 32 and Comparative Example 4.

The CTE of the alkoxysilylated epoxy composite of Formula DI having the tetraphenylethane-based core according to the present invention (Examples 31 to 40) is 6 to 7.6 ppm/° C., which is very small when compared to CTE=13 ppm/° C. of the tetraphenylethane-based epoxy compound excluding an alkoxysilyl group (Comparative Example 4). Particularly, as shown in FIG. 5, the CTE of the epoxy compound having a tetraphenylethane-based core manufactured by using E-glass (Example 32) is largely decreased when compared to the CTE of the composite of Comparative Example 4.

Figure 6:
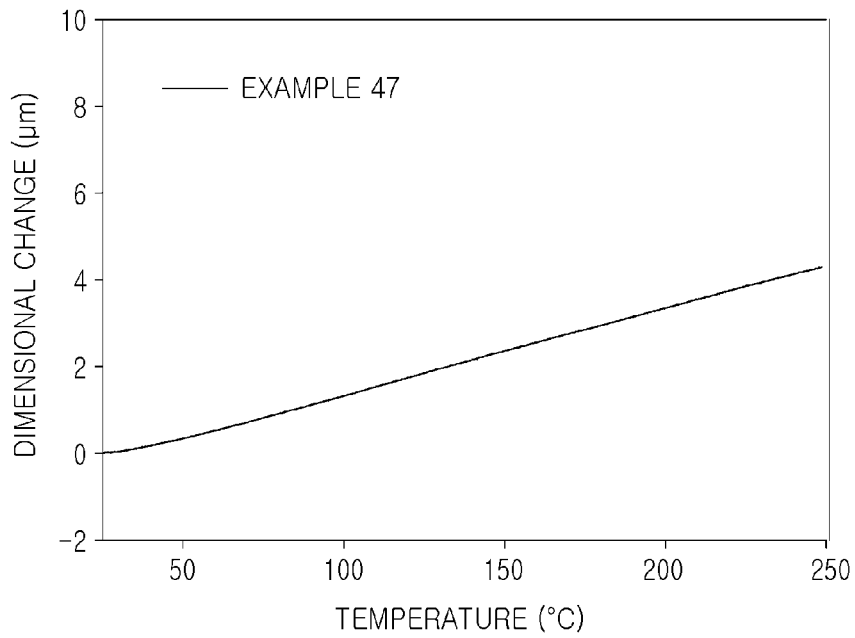
FIG. 6 is a graph illustrating dimensional change with the change of a temperature of composites according to Example 47.

Meanwhile, as shown in Table 2 and FIG. 6, the CTE of a composite of an epoxy compound having an alkoxysilyl group highly filled with inorganic materials (filler composite) is 5 to 10 ppm/° C., and very good CTE properties are obtained. (For reference, an epoxy composite excluding an alkoxysilyl group, however highly filled with inorganic particles was manufactured for the comparison with Examples 44 to 60. In this case, cracks were generated, and physical properties could not be evaluated.)

In addition, most of the composite of the epoxy compounds having the alkoxysilyl group according to the present invention were Tg-less, as shown in Tables 1 and 2, and FIGS. 1 to 6. Thus, good heat resistance properties could be observed when compared to epoxy composite excluding the alkoxysilyl group and having a glass transition temperature between 160 to 200° C.

Good CTE and glass transition temperature properties of the epoxy compound having an alkoxysilyl group observed through the present invention may be considered to be obtained due to the effective formation of bonds between systems of the alkoxysilyl group with a glass fiber and/or filler, and the additional chemical bonds between the alkoxysilyl groups.

3. Evaluation of Flame Retardant Property

Figure 7:
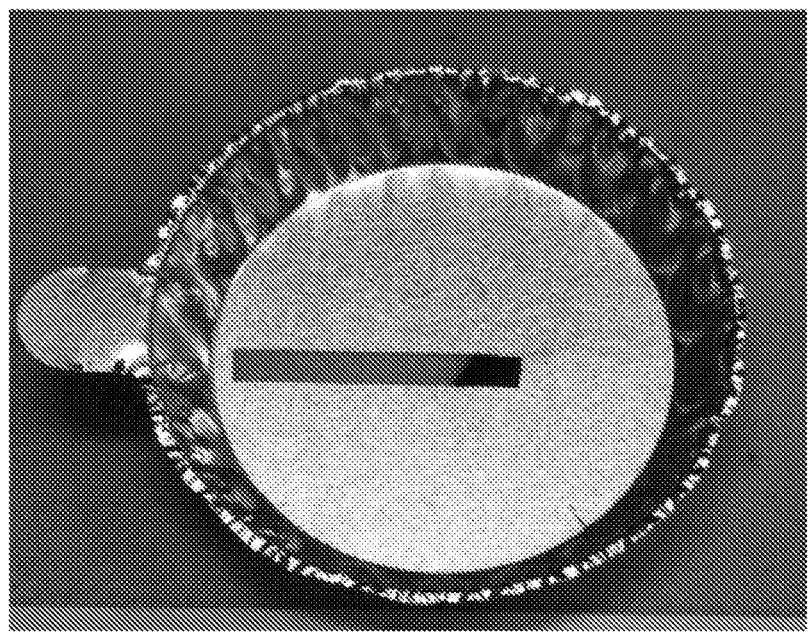
FIG. 7 is a photographic image illustrating flame retardant property according to Example 4.

A strip of the composites according to Example 4 was ignited, and a photographic image of the burned strip is illustrated in FIG. 7. As illustrated in FIG. 7, the strip of the composite according to Example 4 was immediately extinguished after the ignition. Thus, it would be known that the alkoxysilylated epoxy compound according to the present invention has good flame retardant property.

While the present invention has been shown and described in connection with the exemplary embodiments, it will be apparent to those skilled in the art that modifications and variations can be made without departing from the spirit and scope of the invention as defined by the appended claims.

The invention claimed is:
1. An epoxy compound having an alkoxysilyl group selected from the group consisting of following Formulae AI to HI:

AI

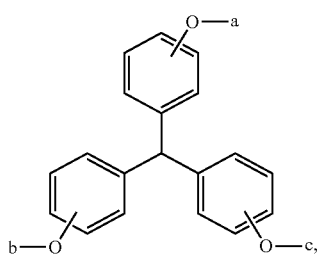

BI

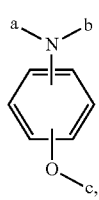

CI

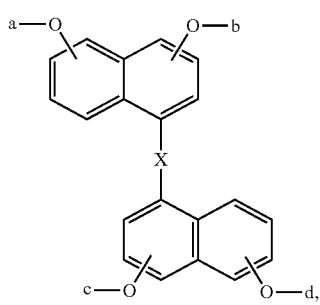

DI

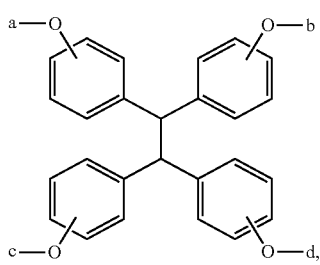

EI

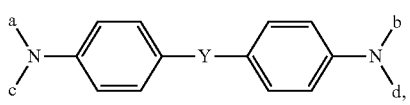

FI

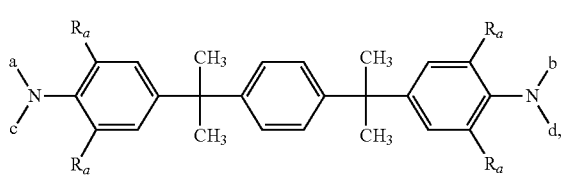

-continued

GI

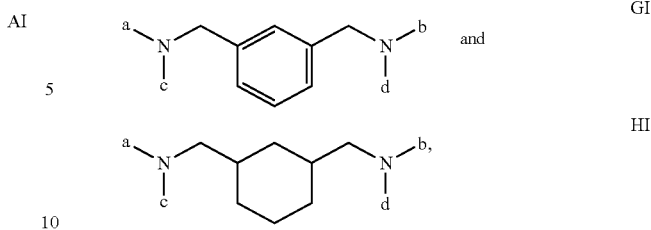

HI and where one or two of substituents a to c in Formula AI or BI have the form of Formula S1, one or two thereof have the form of Formula S2 or S3, and the remainder thereof may be hydrogen or —$(CH_2)_{z-2}$ CH=$CH_2$ where z is an integer from 3 to 10, where one to three of substituents a to d in Formulae CI to HI have the form of Formula S1, one to three thereof have the form of Formula S2 or S3, and the remainder thereof may be hydrogen or —$(CH_2)_{z-2}$ CH=$CH_2$ where z is an integer from 3 to 10, where a meta position of oxygen in Formula BI may be substituted with a linear or branched C1-C10 alkyl group, where X in Formula CI is a direct linkage, —$CH_2$— or

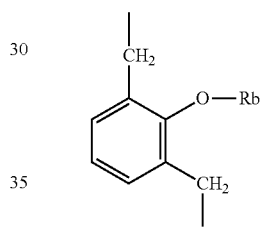

where Rb is H or a C1-C3 alkyl group, where Y in Formula EI is —$CH_2$—, —$C(CH_3)_2$—, —$C(CF_3)_2$—, —S— or —$SO_2$—, and where Ra in Formula FI is H or a C1-C3 alkyl group, wherein Formula S1 is

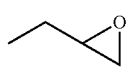

wherein Formula S2 is

—$(CH_2)_z$—$SiR_1R_2R_3$ wherein Formula S3 is

—$CONH(CH_2)_z$—$SiR_1R_2R_3$ in Formulae S2 and S3, at least one of $R_1$ to $R_3$ is an alkoxy group having 1 to 10 carbon atoms, the remainder thereof are alkyl groups having 1 to 10 carbon atoms, the alkyl group and the alkoxy group are a linear chain or a branched chain alkyl group or alkoxy group, and z is an integer from 3 to 10.

2. The epoxy compound having an alkoxysilyl group of claim 1, wherein the epoxy compound having an alkoxysilyl group is selected from the group consisting of following compounds of Formula F:

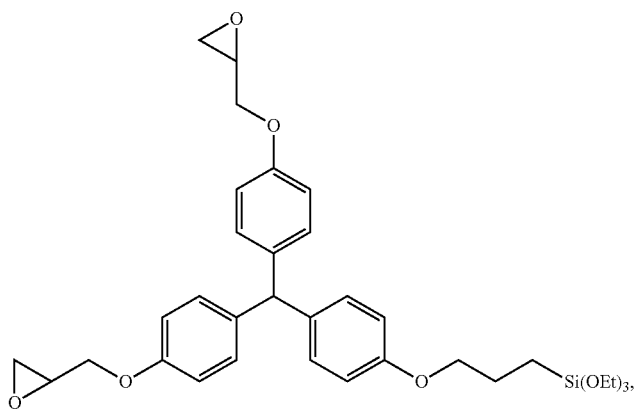
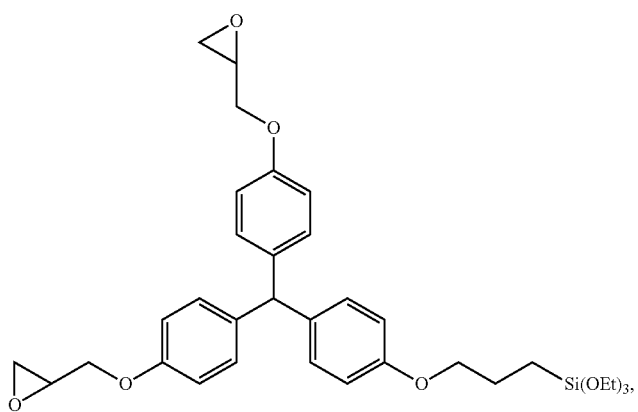
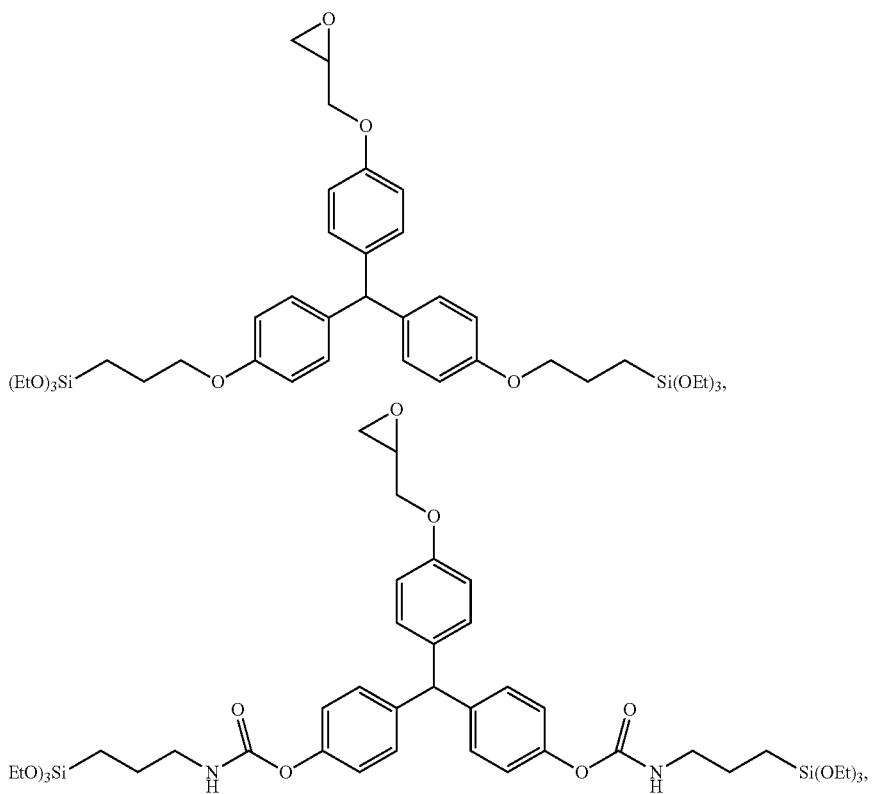

287
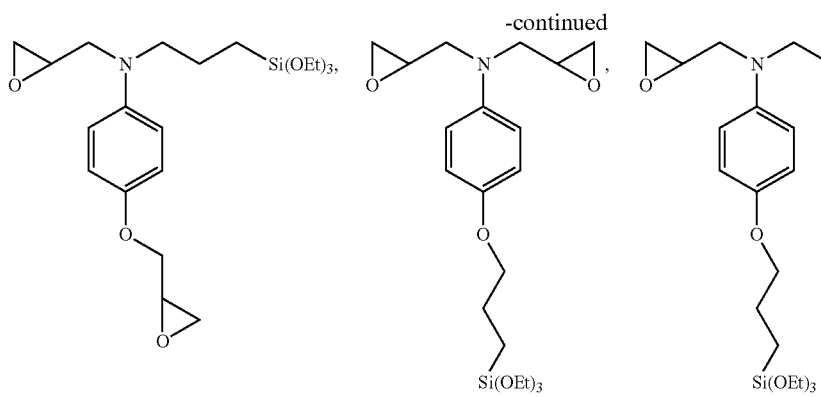
-continued
288
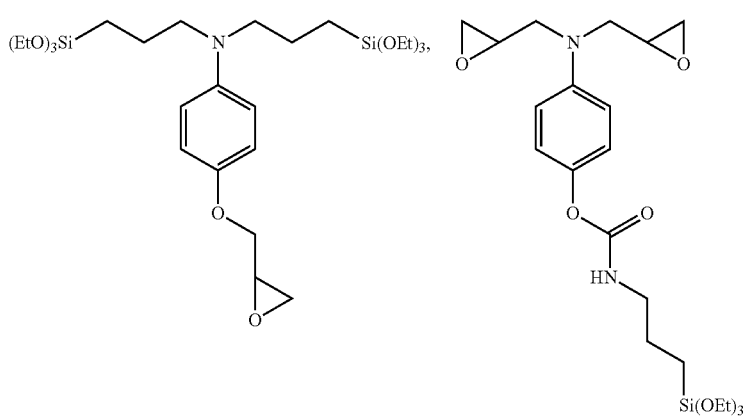
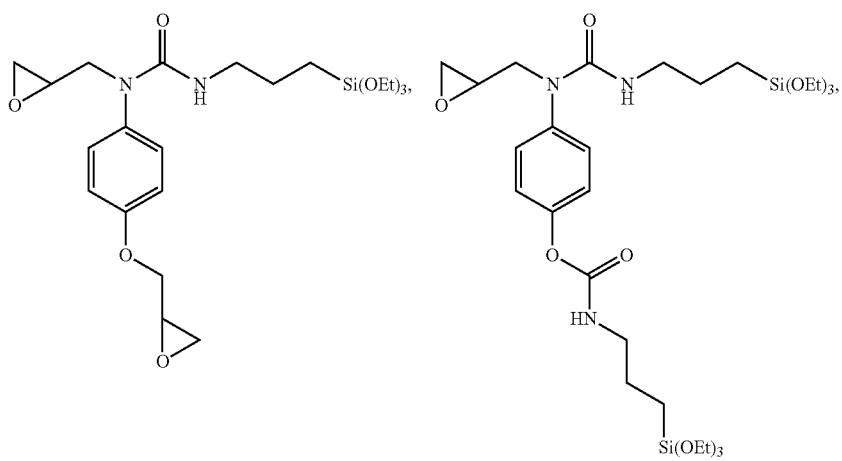
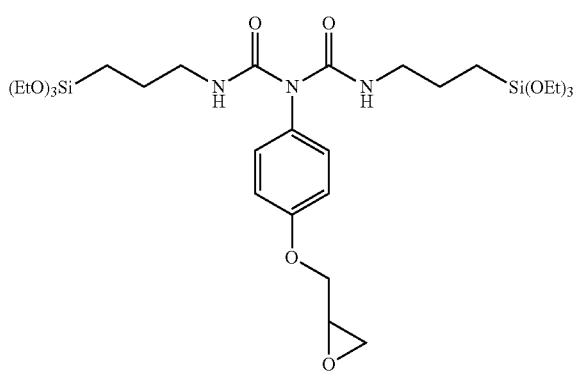

-continued
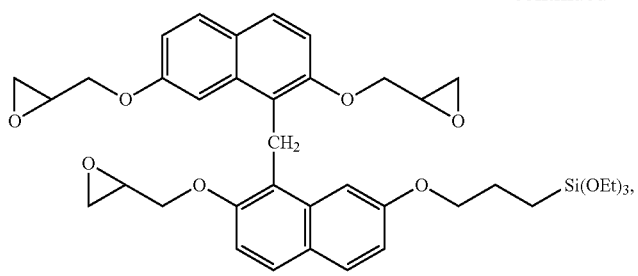
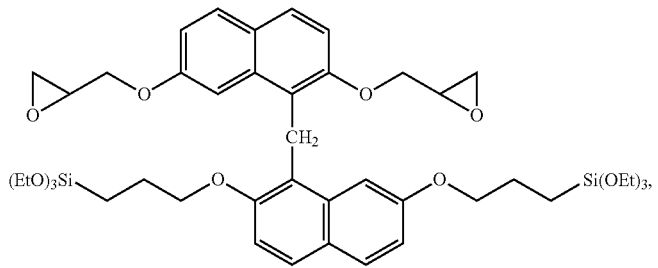
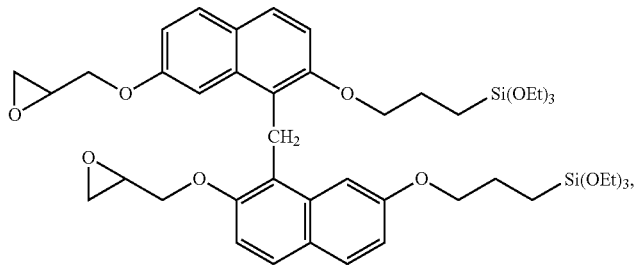
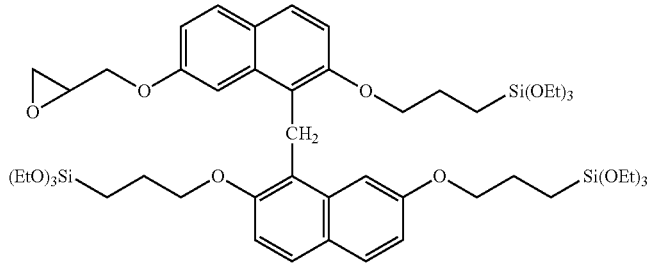
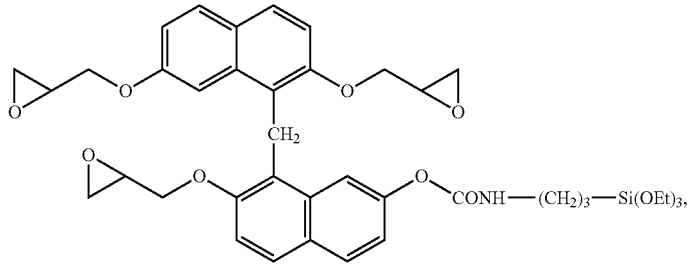
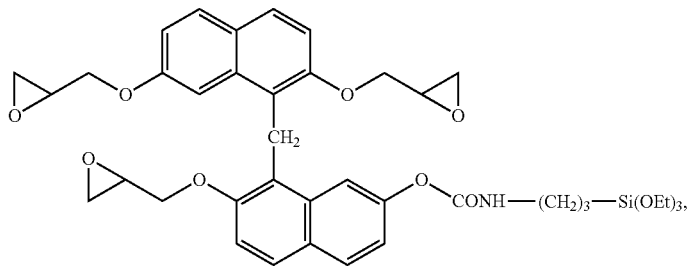

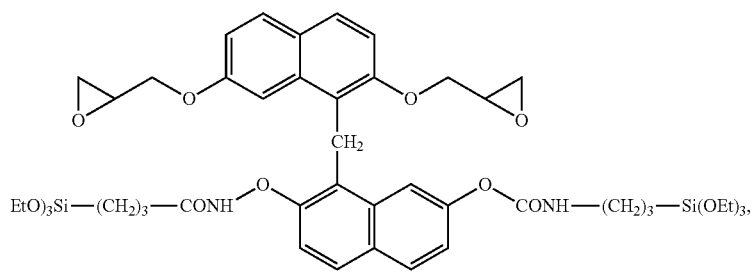
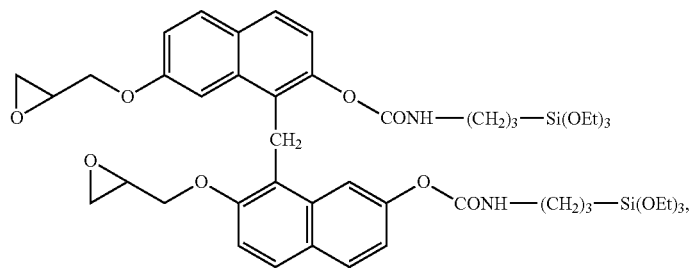
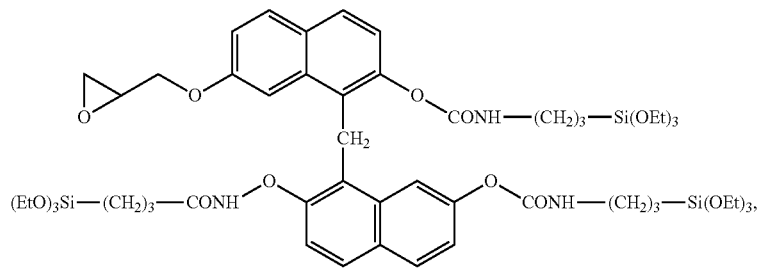
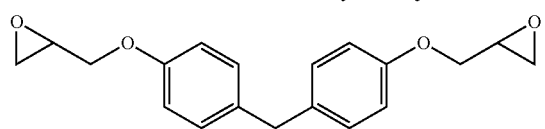
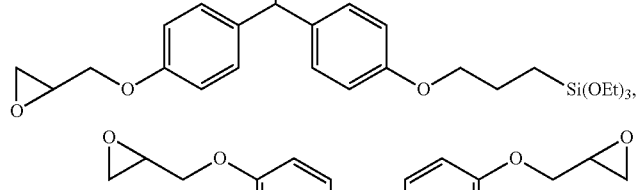
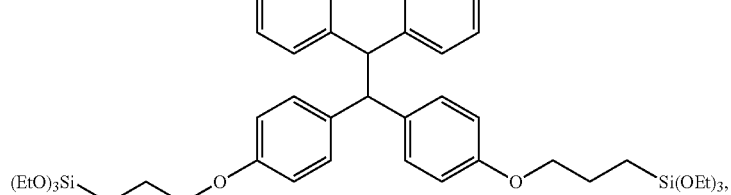
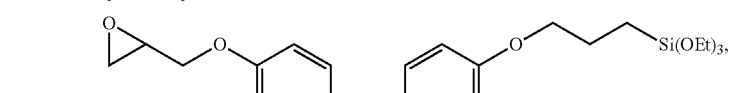
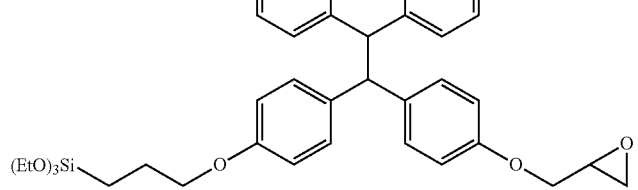

-continued
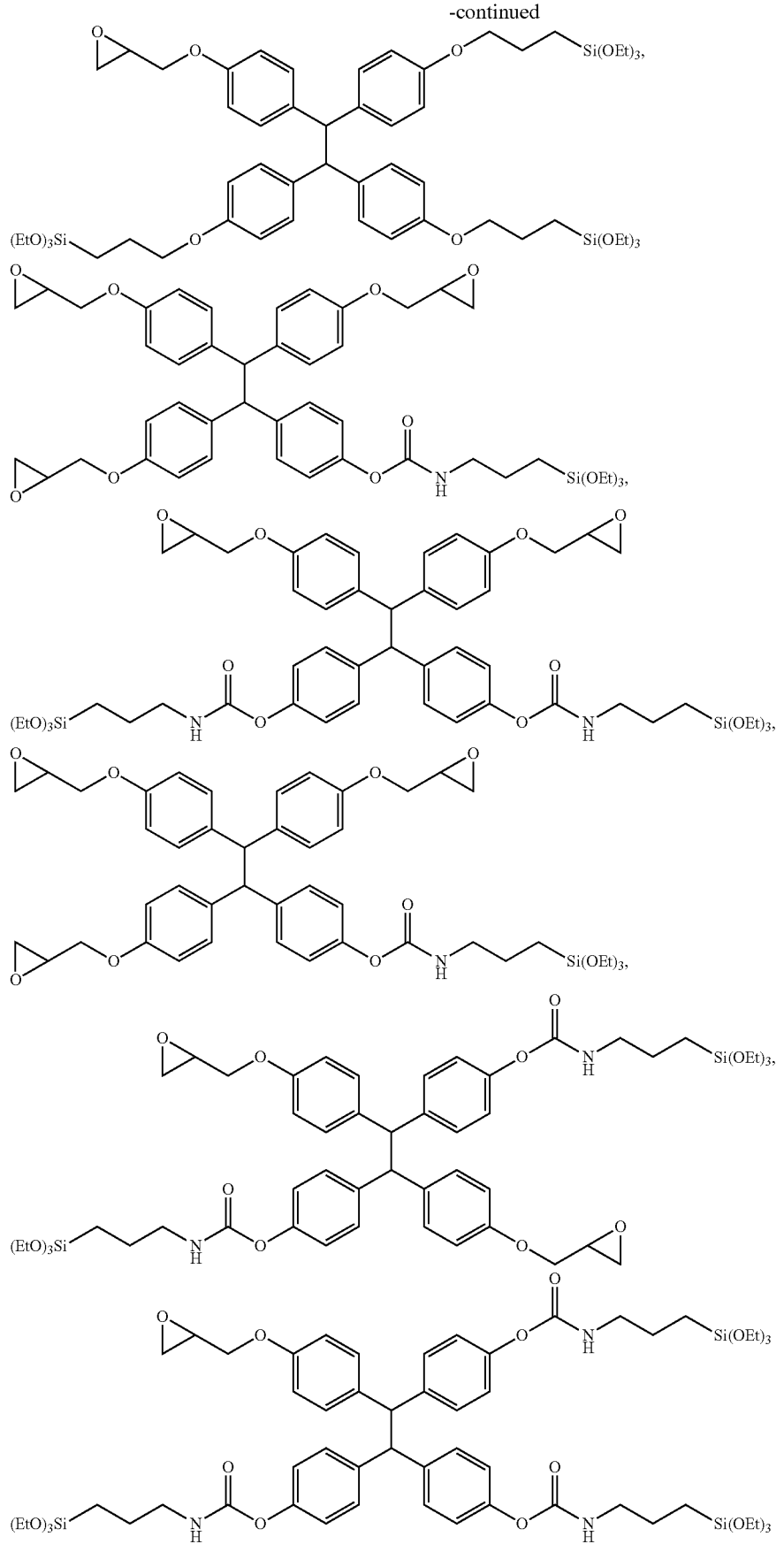

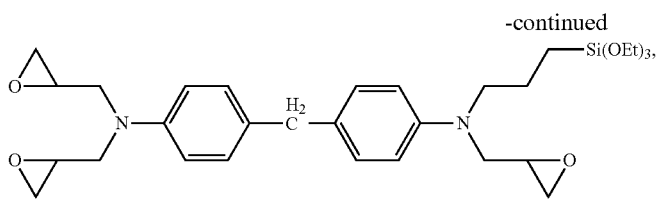
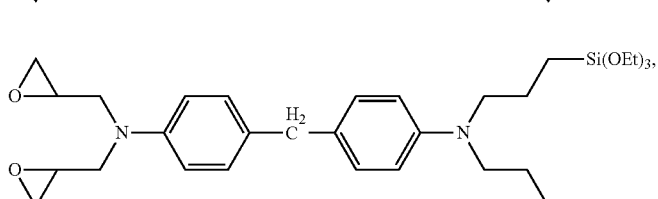
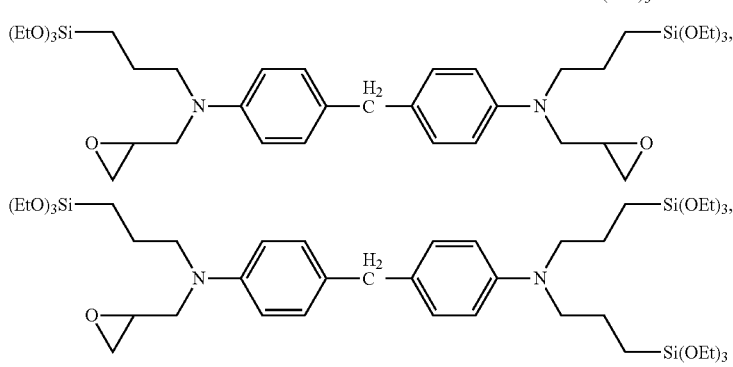
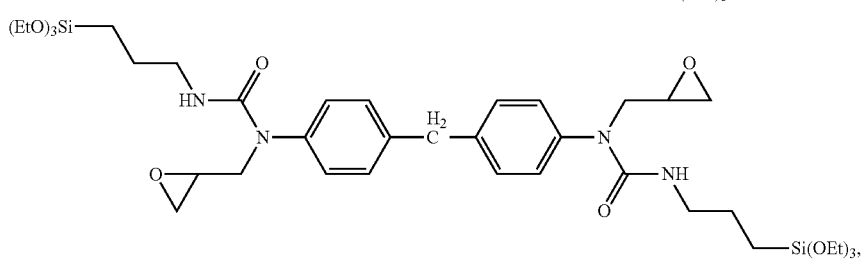
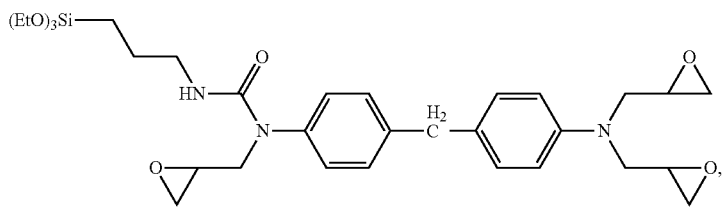
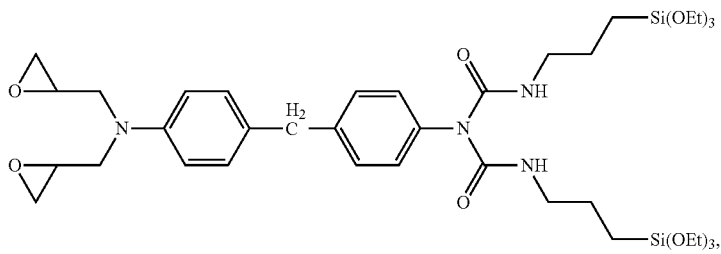
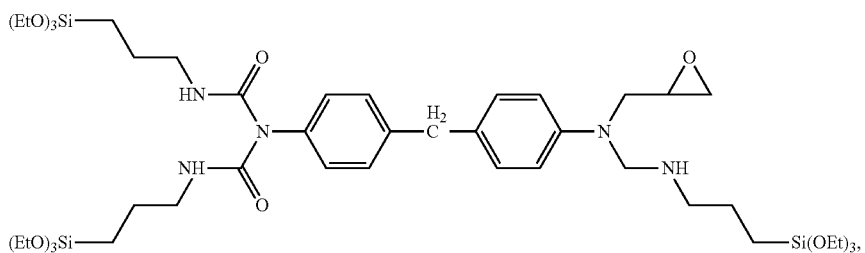

-continued
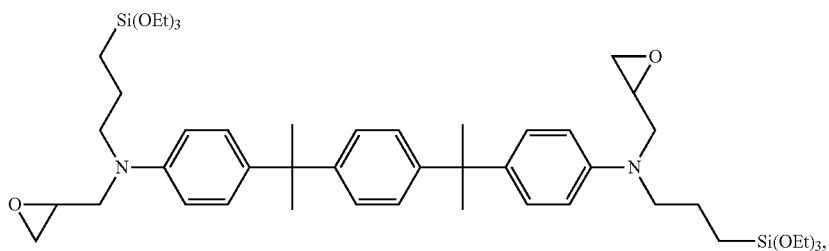
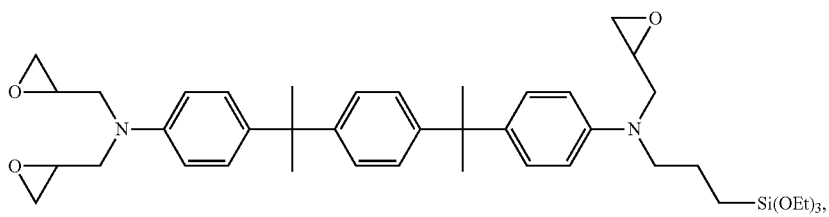
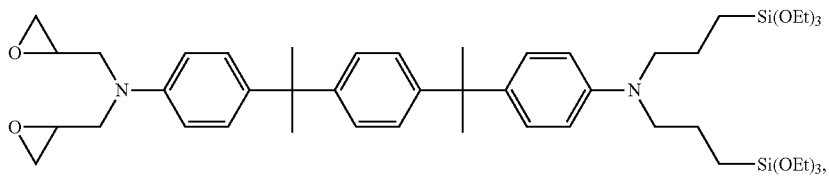
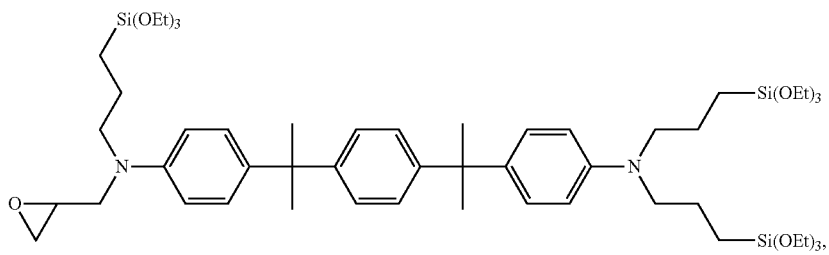
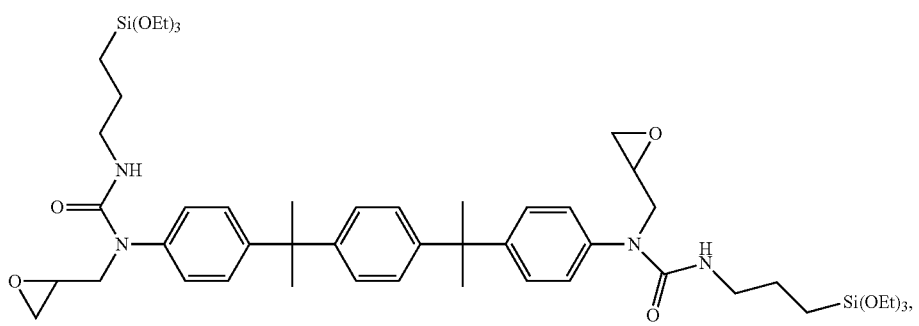
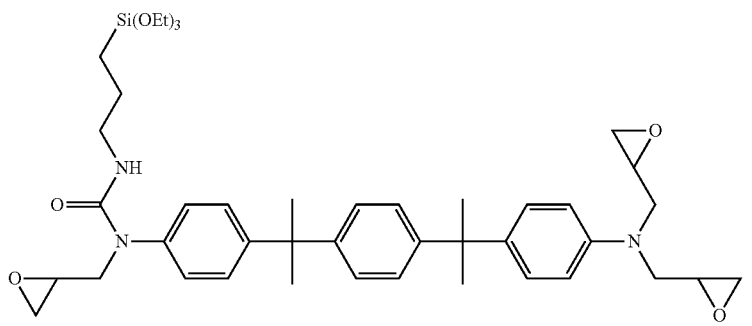

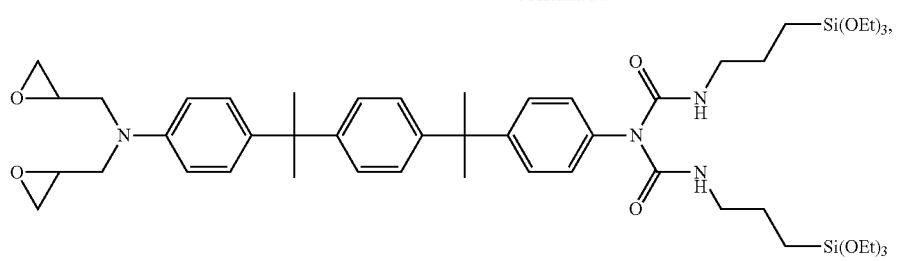
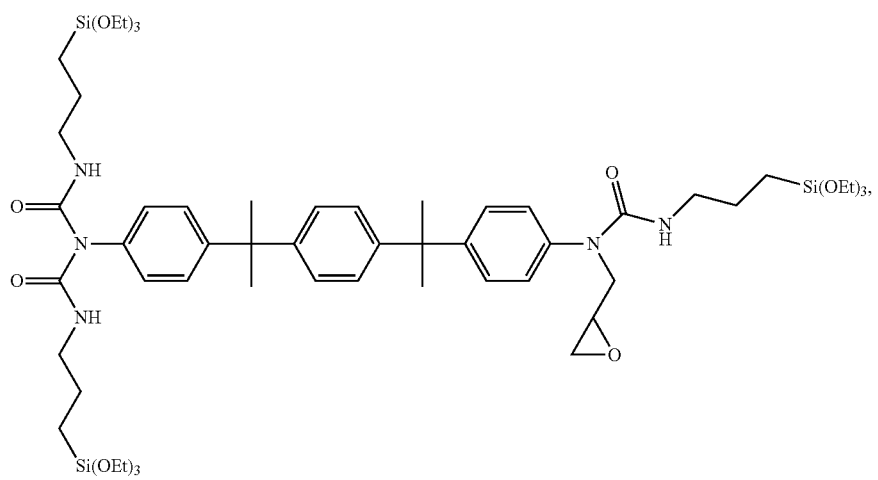
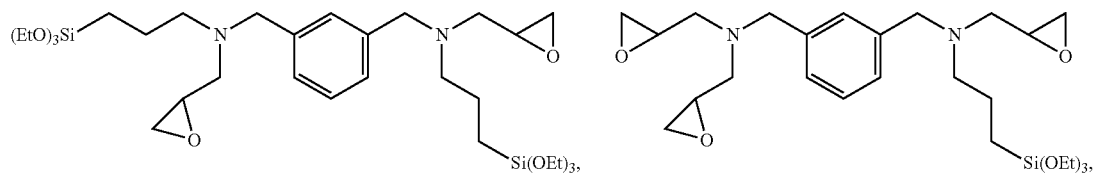
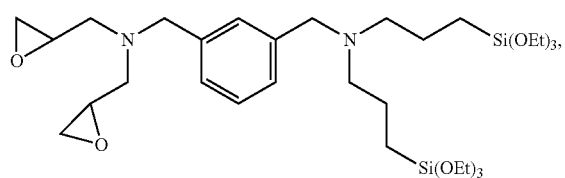
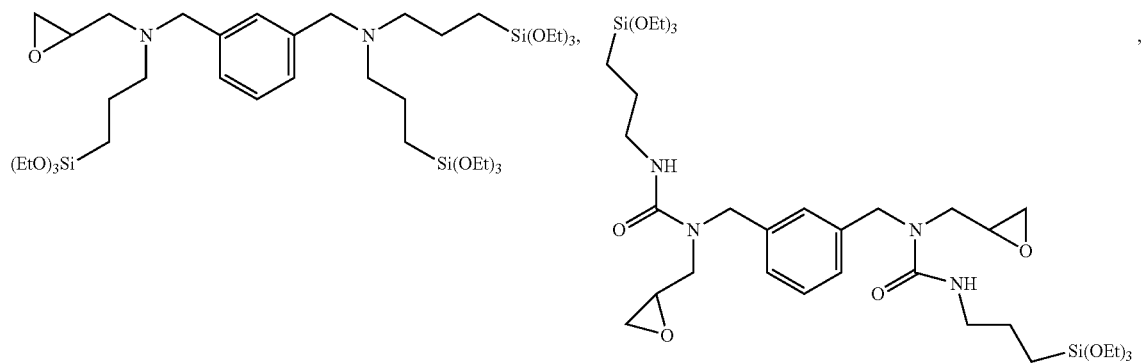

301
302
-continued
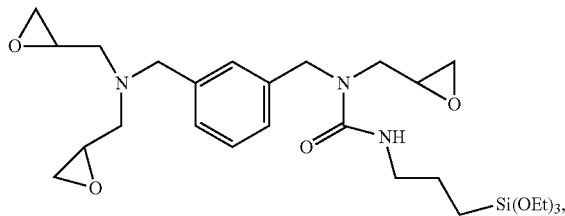
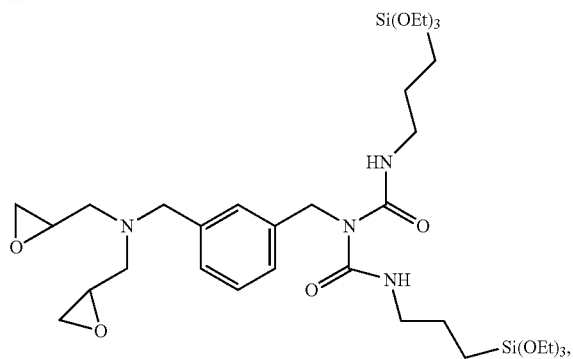
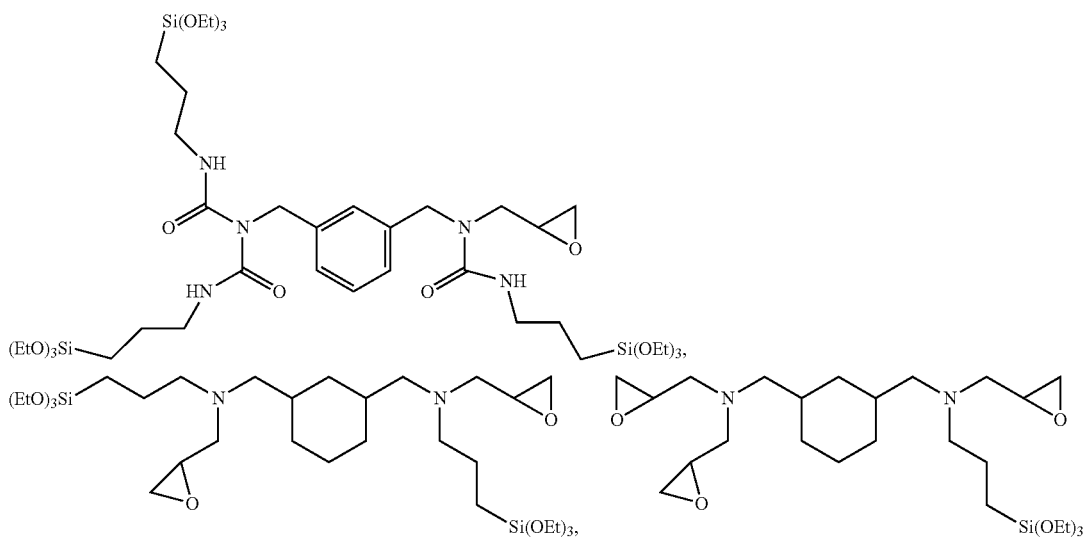
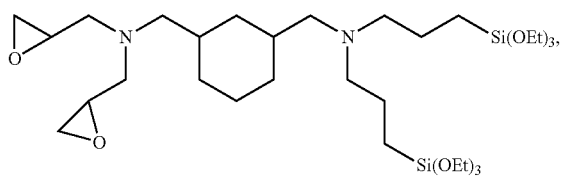
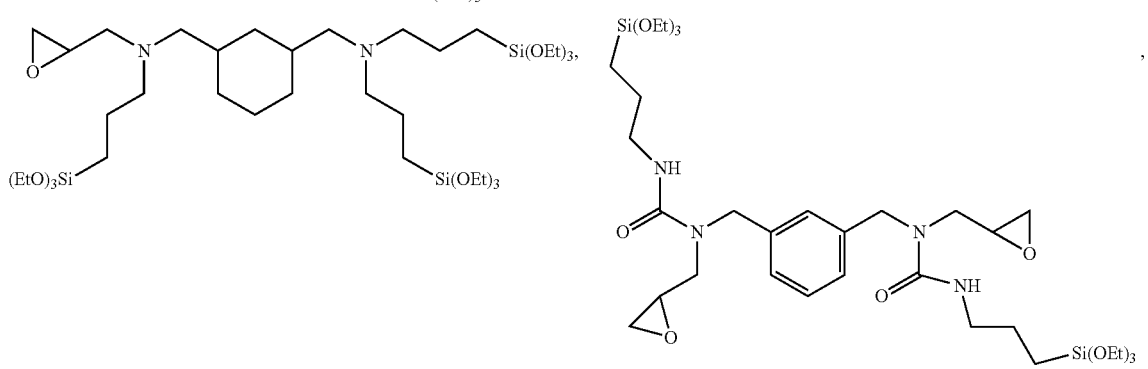
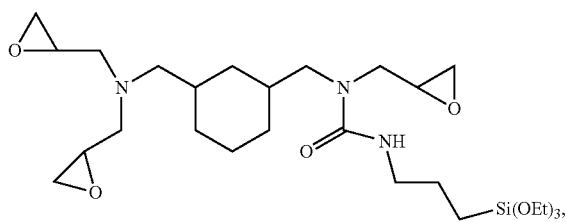

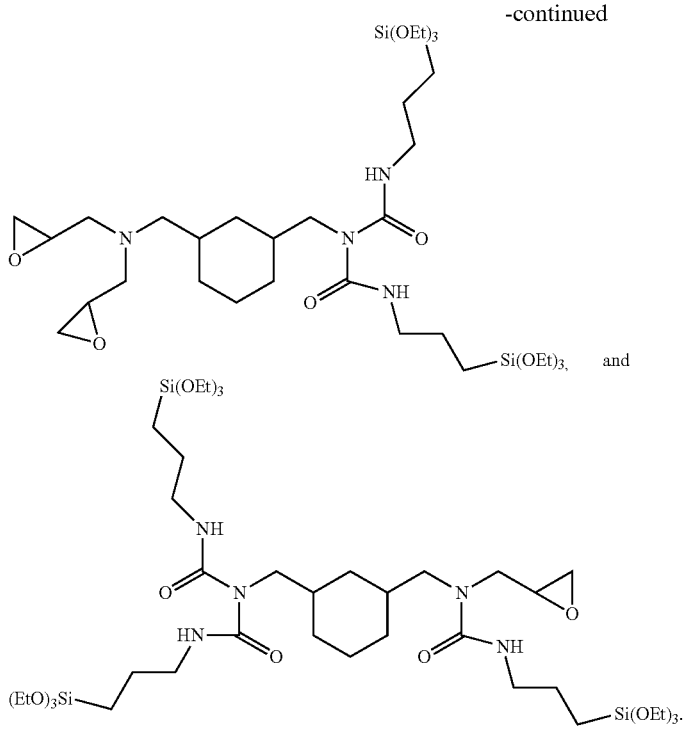
and
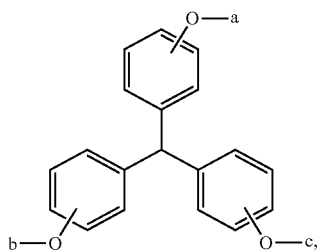
3. An epoxy composition comprising at least one epoxy compound having an alkoxysilyl group selected from following Formulae AI to HI:
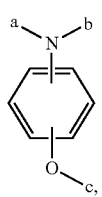
AI
BI
CI
-continued
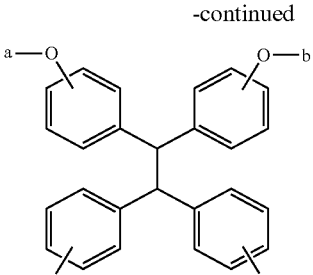
DI
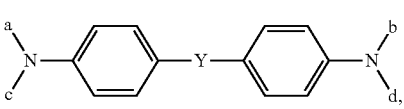
EI
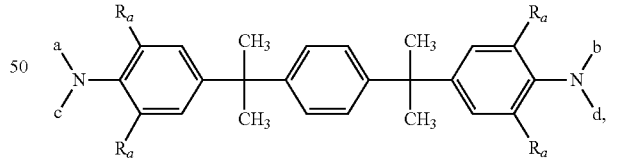
FI
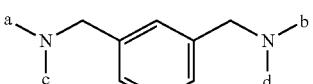
and
GI
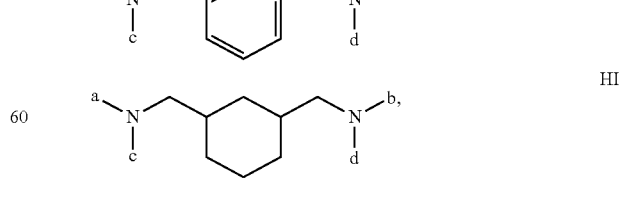
HI
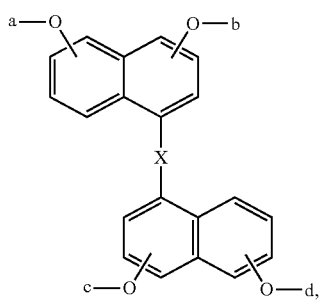
where one or two of substituents a to c in Formula AI or BI have the form of Formula S1, one or two thereof have the form of Formula S2 or S3, and the remainder thereof may be hydrogen or —(CH$_2$)$_{z-2}$ CH=CH$_2$ where z is an integer from 3 to 10, where one to three of substituents a to d in Formulae CI to HI have the form of Formula S1, one to three thereof have the form of Formula S2 or S3, and the remainder thereof may be hydrogen or —(CH$_2$)$_{z-2}$ CH=CH$_2$ where z is an integer from 3 to 10, where a meta position of oxygen in Formula BI may be substituted with a linear or branched C1-C10 alkyl group, where X in Formula CI is a direct linkage, —CH$_2$— or

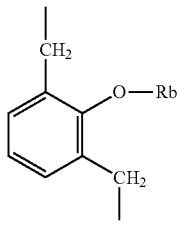

where Rb is H or a C1-C3 alkyl group,
where Y in Formula EI is —CH$_2$—, —C(CH$_3$)$_2$—, —C(CF$_3$)$_2$—, —S— or —SO$_2$—, and
where Ra in Formula FI is H or a C1-C3 alkyl group,
wherein Formula S1 is

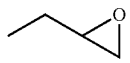

wherein Formula S2 is

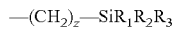

wherein Formula S3 is

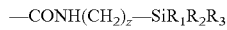

in Formulae S2 and S3, at least one of R$_1$ to R$_3$ is an alkoxy group having 1 to 10 carbon atoms, the remainder thereof are alkyl groups having 1 to 10 carbon atoms, the alkyl group and the alkoxy group are a linear chain or a branched chain alkyl group or alkoxy group, and z is an integer from 3 to 10.

4. The epoxy composition of claim 3, further comprising at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound.

5. The epoxy composition of claim 3, wherein the epoxy composition comprises 10 wt % to 100 wt % of the epoxy compound having an alkoxysilyl group and up to 90 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound, based on a total amount of the epoxy compound.

6. The epoxy composition of claim 3, further comprising at least one kind of filler selected from the group consisting of inorganic particles and a fiber.

7. The epoxy composition of claim 6, wherein the inorganic particle is at least one selected from the group consisting of a metal oxide selected from the group consisting of silica, zirconia, titania, alumina, silicon nitride and aluminum nitride, T-10 type silsesquioxane, ladder type silsesquioxane and cage type silsesquioxane.

8. The epoxy composition of claim 6, wherein an amount of the inorganic particles is 5 wt % to 95 wt % based on a total solid content of the epoxy composition.

9. The epoxy composition of claim 6, wherein the fiber is at least one selected from the group consisting of a glass fiber selected from the group consisting of an E-glass fiber, a T-glass fiber, an S-glass fiber, an NE-glass fiber, a H-glass fiber and quartz, and an organic fiber selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber.

10. The epoxy composition of claim 6, wherein an amount of the fiber is 10 wt % to 90 wt % based on a total solid content of the epoxy composition.

11. The epoxy composition of claim 6, wherein the filler is the inorganic particles.

12. The epoxy composition of claim 3, further comprising a reaction catalyst for the alkoxysilyl group.

13. The epoxy composition of claim 12, wherein the reaction catalyst for the alkoxysilyl group is at least one selected from the group consisting of at least one inorganic acid selected from the group consisting of nitric acid, sulfuric acid, hydrochloric acid, acetic acid and phosphoric acid, ammonia, KOH, NH$_4$OH, amine, a transition metal alkoxide, and a tin compound.

14. A method of preparing an epoxy compound having an alkoxysilyl group, the method comprising:
a first step of preparing one Intermediate Product of following Formulae A11 to H11 by reacting one starting material of following Formulae AS to HS with an alkenyl compound of following Formula M1 in the presence of a base, and an optional solvent, then by reacting with epichlorohydrin in situ; and
a second step of preparing one target product of following Formulae AI to HI by reacting one of the Intermediate Products with an alkoxysilane of following Formula M2 in the presence of a metal catalyst and an optional solvent:
wherein the starting material is one of the following Formulae AS to HS,

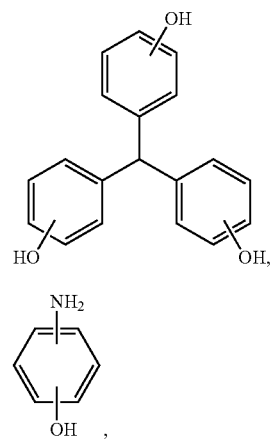

-continued

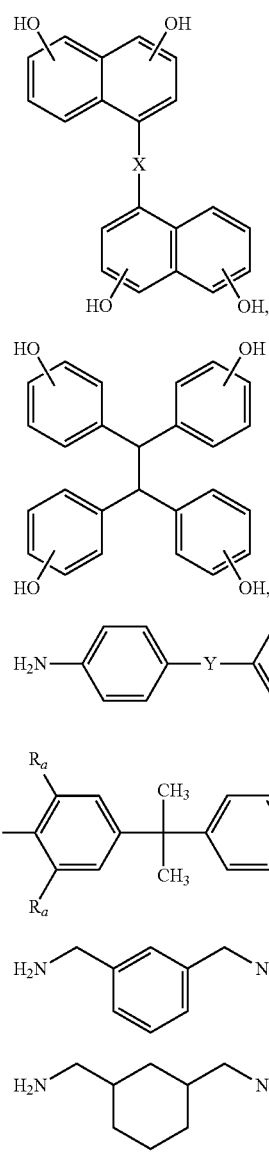

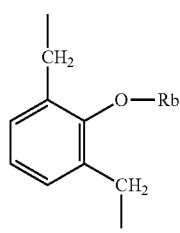

where a meta position of oxygen in Formula BS may be substituted with a linear or branched C1-C10 alkyl group, where X in Formula CS is a direct linkage, —CH₂— or where Rb is H or a C1-C3 alkyl group,
where Y in Formula ES is —CH₂—, —C(CH₃)₂—, —C(CF₃)₂—, —S— or —SO₂—, and
where Ra in Formula FS is H or a C1-C3 alkyl group, wherein Formula M1 is

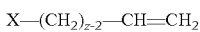

where X is a halide of Cl, Br or I, —O—SO₂—CH₃, —O—SO₂—CF₃, or —O—SO₂—CH₄—CH₃, and z is an integer from 3 to 10, wherein the Intermediate Product is one of the following Formulae A11 to H11

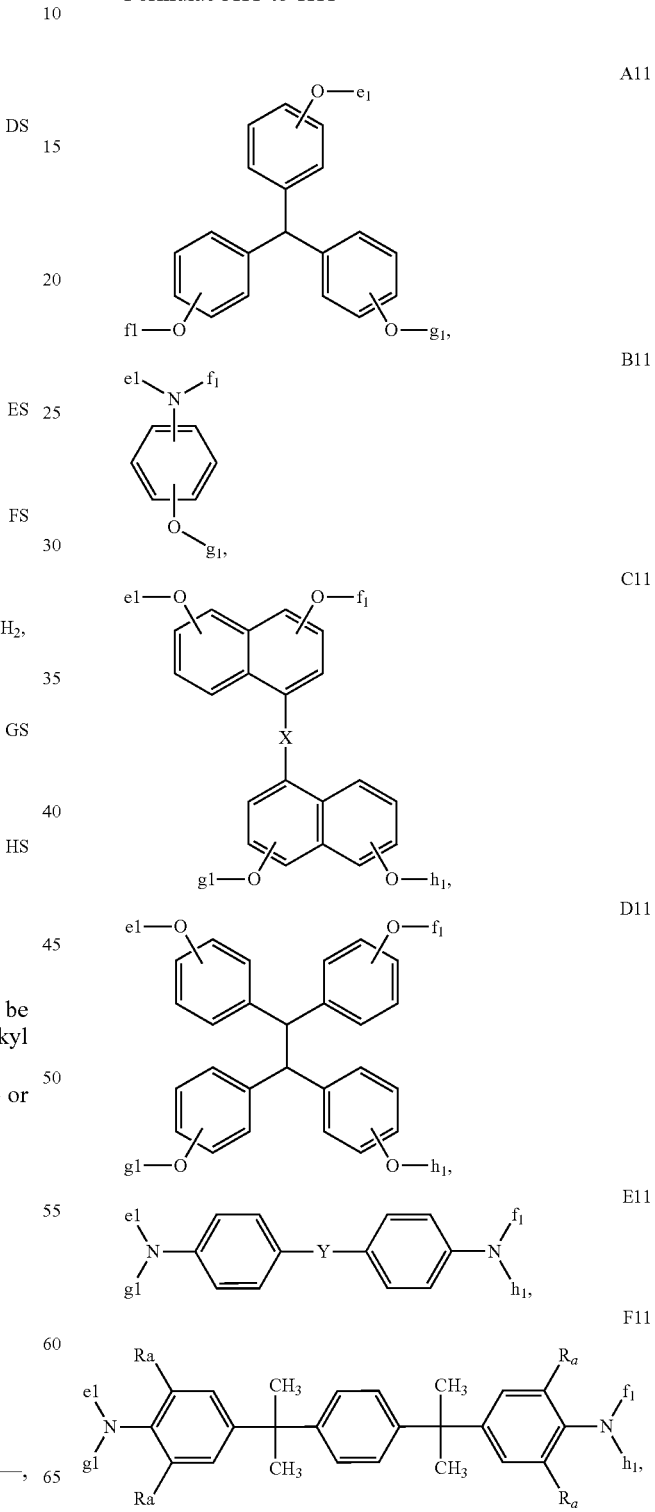

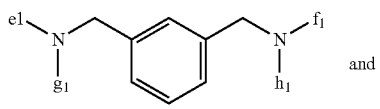
G11 and

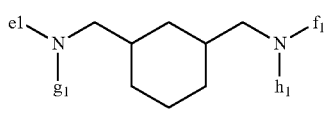
H11 where one or two of substituents e1, f1, and g1 in Formula A11 or B11 have the form of Formula S1, and at least one thereof is —(CH$_2$)$_{z-2}$CH=CH$_2$ where z is an integer from 3 to 10 and may be hydrogen when an unreacted site is present, where one to three of substituents e1, f1, g1, and h1 in Formulae C11 to H11 have the form of Formula S1, and at least one thereof is —(CH$_2$)$_{z-2}$CH=CH$_2$ where z is an integer from 3 to 10 and may be hydrogen when an unreacted site is present, where a meta position of oxygen in Formula B11 may be substituted with a linear or branched C1-C10 alkyl group, where X in Formula C11 is a direct linkage, —CH$_2$— or

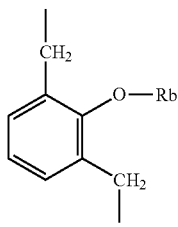

where Rb is H or a C1-C3 alkyl group,
  where Y in Formula E11 is —CH$_2$—, —C(CH$_3$)$_2$—, —C(CF$_3$)$_2$—, —S— or —SO$_2$—, and
  where Ra in Formula F11 is H or a C1-C3 alkyl group,
wherein Formula S1 is

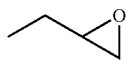

wherein Formula M2 is

HSiR$_1$R$_2$R$_3$ where at least one of R$_1$ to R$_3$ is a C1-C10 alkoxy group, the remainder thereof are C1-C10 alkyl groups, and the alkoxy group and the alkyl group are a linear chain or a branched chain alkoxy group or alkyl group, wherein the Target Product is one of the following Formulae AI to HI,

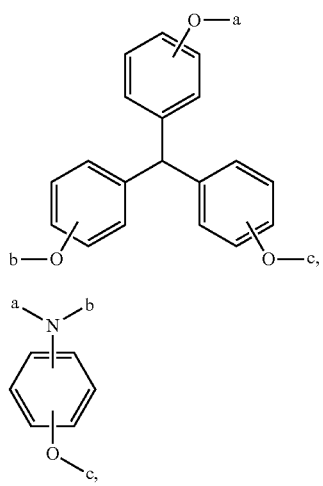
AI

BI

CI

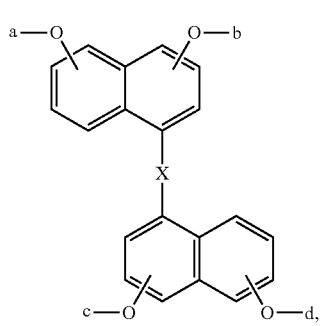
DI

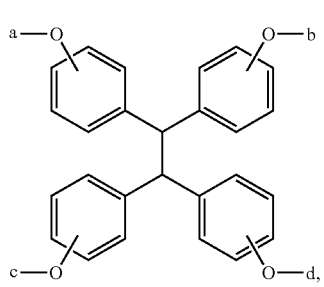
EI

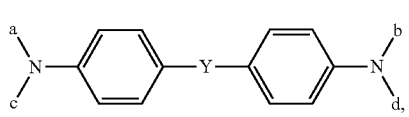
FI

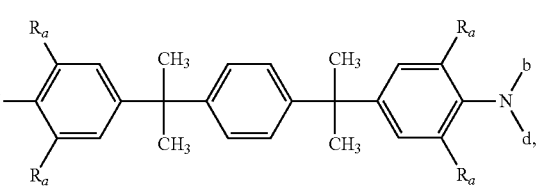
GI

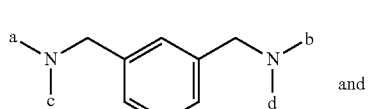
and

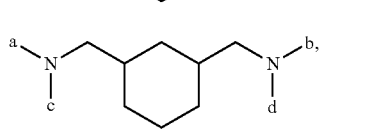
HI where one or two of substituents a to c in Formula AI or BI have the form of Formula S1, one or two thereof have the form of Formula S2, and the remainder thereof may be hydrogen or —(CH$_2$)$_{z-2}$ CH=CH$_2$ where z is an integer from 3 to 10, where one to three of substituents a to d in Formulae CI to HI have the form of Formula S1, one to three thereof have the form of Formula S2, and the remainder thereof may be hydrogen or —(CH$_2$)$_{z-2}$ CH=CH$_2$ where z is an integer from 3 to 10, where a meta position of oxygen in Formula BI may be substituted with a linear or branched C1-C10 alkyl group, where X in Formula CI is a direct linkage, —CH$_2$— or

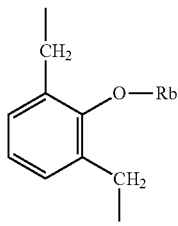

where Rb is H or a C1-C3 alkyl group, where Y in Formula EI is —CH$_2$—, —C(CH$_3$)$_2$—, —C(CF$_3$)$_2$—, —S— or —SO$_2$—, and where Ra in Formula FI is H or a C1-C3 alkyl group, wherein Formula S2 is

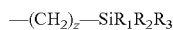

in Formula S2, at least one of R$_1$ to R$_3$ is an alkoxy group having 1 to 10 carbon atoms, the remainder thereof are alkyl groups having 1 to 10 carbon atoms, the alkyl group and the alkoxy group are a linear chain or a branched chain alkyl group or alkoxy group, and z is an integer from 3 to 10.

15. A method of preparing an epoxy compound having an alkoxysilyl group, the method comprising:

a first step of preparing one Intermediate Product 21 of following Formulae A21 to H21 by reacting one starting material of following Formulae AS to HS with an alkenyl compound of following Formula M1 in the presence of a base and an optional solvent;

a second step of preparing one of the above Intermediate Products 22 of following Formulae A22 to H22 by reacting the Intermediate Product 21 with a peroxide in the presence of an optional base and an optional solvent;

a third step of preparing one Intermediate Product 23 of following Formulae A23 to H23 by reacting one of the above Intermediate Product 22 with the alkenyl compound of following Formula M1 in the presence of a base and an optional solvent; and a fourth step of preparing one target product of following Formulae AI to HI by reacting one of the above Intermediate Product 23 with an alkoxysilane of following Formula M2 in the presence of a metal catalyst and an optional solvent:

wherein the starting material is one of the following Formulae AS to HS,

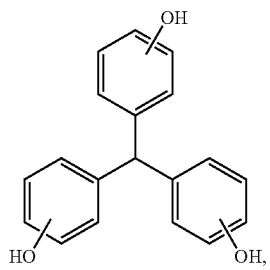
AS

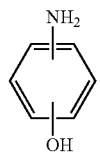
BS

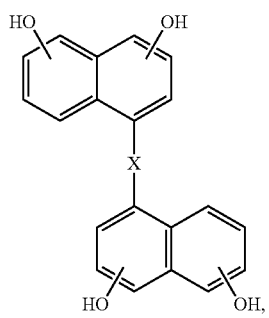
CS

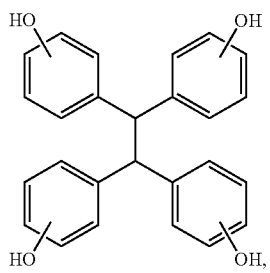
DS

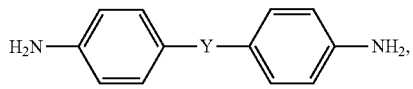
ES

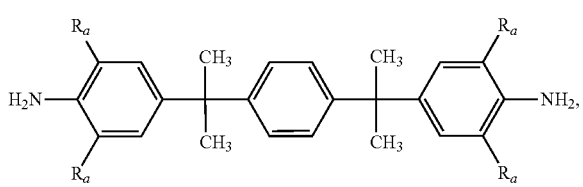
FS

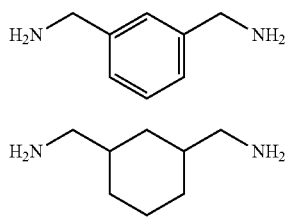
GS and

HS where a meta position of oxygen in Formula BS may be substituted with a linear or branched C1-C10 alkyl group, where X in Formula CS is a direct linkage, —CH₂— or

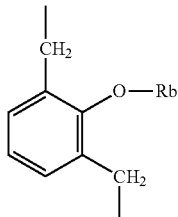

where Rb is H or a C1-C3 alkyl group, where Y in Formula ES is —CH₂—, —C(CH₃)₂—, —C(CF₃)₂—, —S— or —SO₂—, and where Ra in Formula FS is H or a C1-C3 alkyl group, wherein Formula M1 is

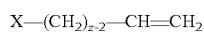

where X is a halide of Cl, Br or I, —O—SO₂—CH₃, —O—SO₂—CF₃, or —O—SO₂—C₆H₄—CH₃, and z is an integer from 3 to 10, wherein the Intermediate Product 21 is one of the following Formulae A21 to H21,

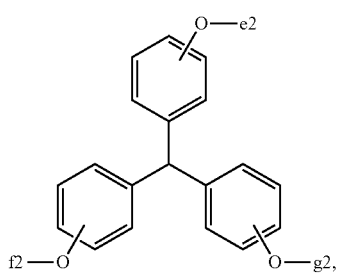
A21

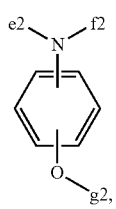
B21

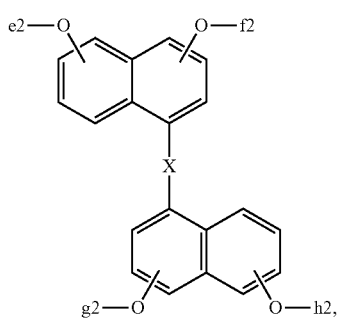
C21

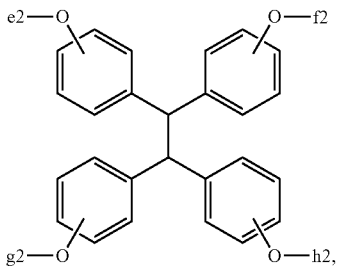
D21

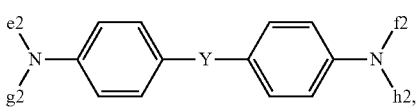
E21

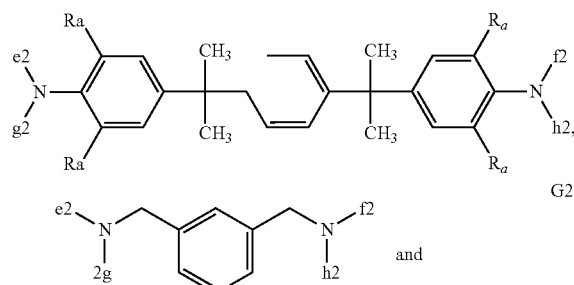
F21

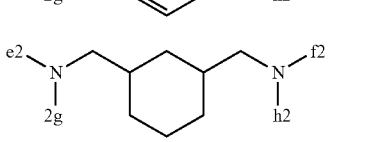
G21 and

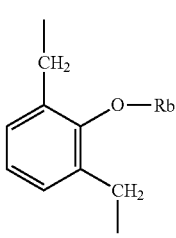
H21 where one or two of substituents e2 to g2 in Formula A21 or B21 are —(CH₂)$_{z-2}$—CH=CH₂ where z is an integer from 3 to 10, and the remainder thereof are hydrogen, where one to three of substituents e2 to h2 in Formulae C21 to H21 are —(CH₂)$_{z-2}$—CH=CH₂ where z is an integer from 3 to 10, and the remainder thereof are hydrogen, where a meta position of oxygen in Formula B21 may be substituted with a linear or branched C1-C10 alkyl group, where X in Formula C21 is a direct linkage, —CH₂— or

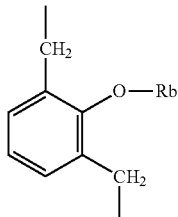

where Rb is H or a C1-C3 alkyl group, where Y in Formula E21 is —CH₂—, —C(CH₃)₂—, —C(CF₃)₂—, —S— or —SO₂—, and where Ra in Formula F21 is H or a C1-C3 alkyl group, wherein the Intermediate Product 22 is one of the following Formulae A22 to H22, A22
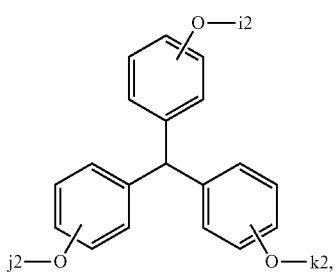

B22
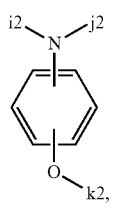

C22
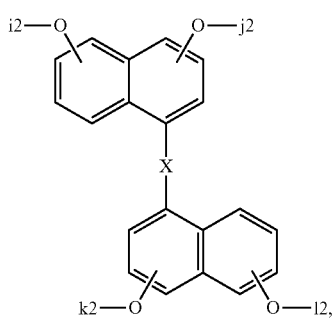

D22
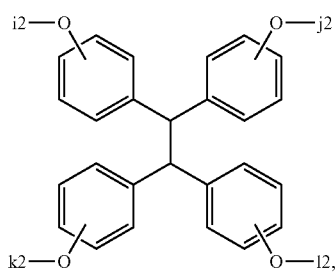

E22
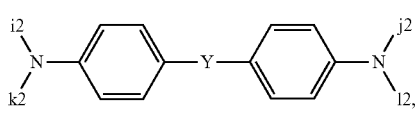

F22
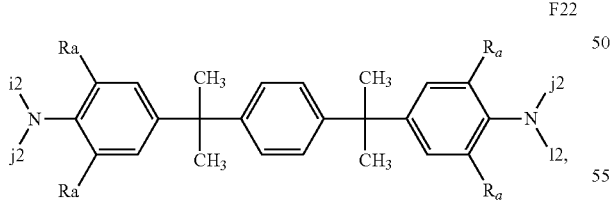

G22
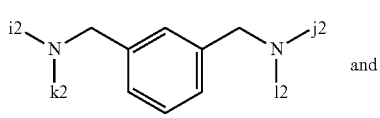

and

H22
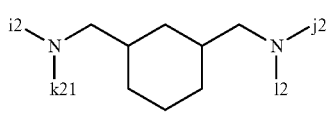

where one or two of substituents i2 to k2 in Formulae A22 to B22 have the form of Formula S1, and at least one is hydrogen and may be —$(CH_2)_{z-2}$—CH=$CH_2$ where z is an integer from 3 to 10, where one to three of substituents i2 to 12 in Formulae C22 to H22 have the form of Formula S1, and at least one is hydrogen and may be —$(CH_2)_{z-2}$—CH=$CH_2$ where z is an integer from 3 to 10, where a meta position of oxygen in Formula B22 may be substituted with a linear or branched C1-C10 alkyl group, where X in Formula C22 is a direct linkage, —$CH_2$— or

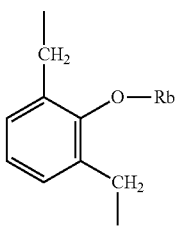

where Rb is H or a C1-C3 alkyl group,
where Y in Formula E22 is —$CH_2$—, —$C(CH_3)_2$—, —$C(CF_3)_2$—, —S— or —$SO_2$—, and
where Ra in Formula F22 is H or a C1-C3 alkyl group, wherein Formula S1 is

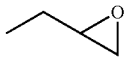

wherein Formula M1 is

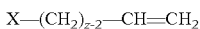

where X is a halide of Cl, Br or I, —O—$SO_2$—$CH_3$, —O—$SO_2$—$CF_3$, or —O—$SO_2$—$C_6H_4$—$CH_3$, and z is an integer from 3 to 10, wherein the Intermediate Product 23 is one of the following Formulae A23 to H23, A23
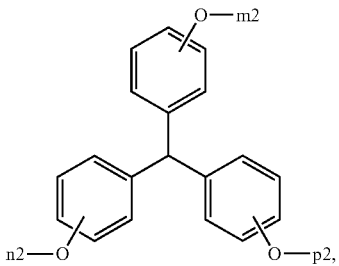

B23
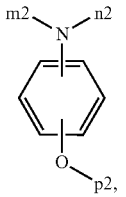

-continued

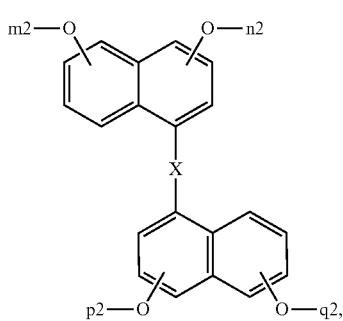
C23

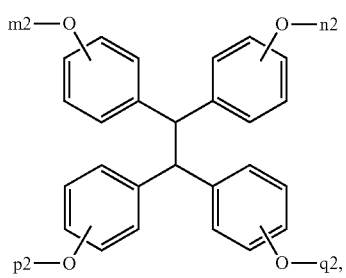
D23

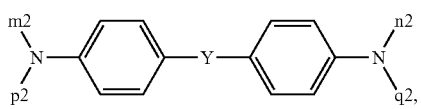
E23

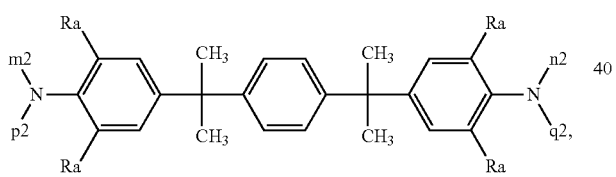
F23

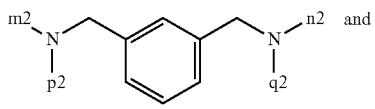
G23

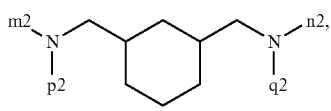
H23 where one or two of substituents m2, n2 and p2 in Formula A23 or B23 are the above Formula S12, and at least one is —(CH$_2$)$_{z-2}$—CH=CH$_2$ where z is an integer from 3 to 10 and may be hydrogen, where one to three among m2, n2, p2 and q2 in Formulae C23 to H23 are the above Formula S2, and at least one is —(CH$_2$)$_{z-2}$—CH=CH$_2$ where z is an integer from 3 to 10 and may be hydrogen, where a meta position of oxygen in Formula B23 may be substituted with a linear or branched C1-C10 alkyl group, where X in Formula C23 is a direct linkage, —CH$_2$— or

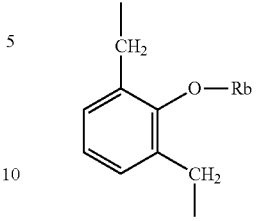

where Rb is H or a C1-C3 alkyl group, where Y in Formula E23 is —CH$_2$—, —C(CH$_3$)$_2$—, —C(CF$_3$)$_2$—, —S— or —SO$_2$—, and where Ra in Formula F23 is H or a C1-C3 alkyl group, wherein Formula M2 is HSiR$_1$R$_2$R$_3$ where at least one of R$_1$ to R$_3$ is a C1-C10 alkoxy group, and the remainder thereof are linear or branched C1-C10 alkyl groups, wherein the Target Product is one of the following Formulae AI to HI,

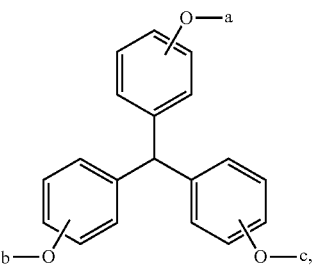
AI

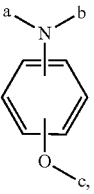
BI

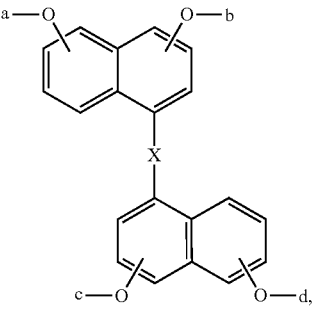
CI

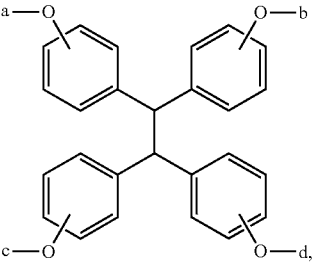
DI

-continued

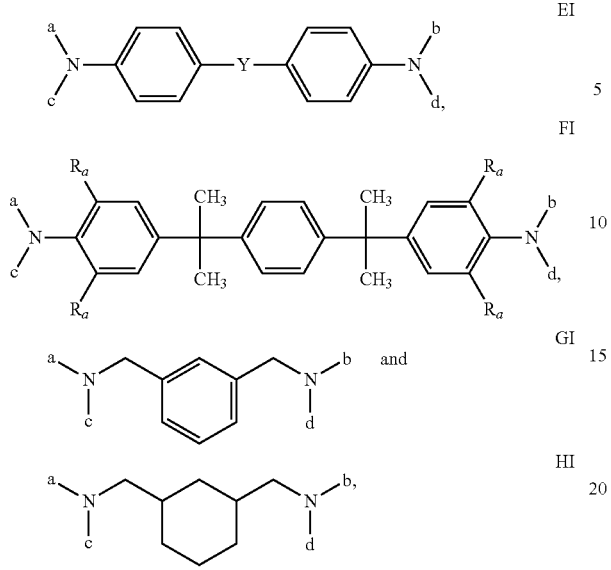

where one or two of substituents a to c in Formula AI or BI are the above Formula S1, one or two thereof have the form of Formula S2, and the remainder thereof may be hydrogen or —(CH$_2$)$_{z-2}$CH=CH$_2$ where z is an integer from 3 to 10, where one to three of substituents a to d in Formulae CI to HI are the above Formula S1, one to three thereof have the form of Formula S2, and the remainder thereof may be hydrogen or —(CH$_2$)$_{z-2}$CH=CH$_2$ where z is an integer from 3 to 10, where a meta position of oxygen in Formula BI may be substituted with a linear or branched C1-C10 alkyl group, where X in Formula CI is a direct linkage, —CH$_2$— or

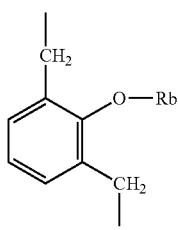

where Rb is H or a C1-C3 alkyl group,
where Y in Formula EI is —CH$_2$—, —C(CH$_3$)$_2$—, —C(CF$_3$)$_2$—, —S— or —SO$_2$—, and
where Ra in Formula FI is H or a C1-C3 alkyl group,
wherein Formula S2 is

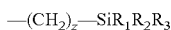

in Formula S2, at least one of R$_1$ to R$_3$ is an alkoxy group having 1 to 10 carbon atoms, the remainder thereof are alkyl groups having 1 to 10 carbon atoms, z is an integer from 3 to 10, and the alkyl group and the alkoxy group are a linear chain or a branched chain alkyl group or alkoxy group.

16. A method of preparing an epoxy compound having an alkoxysilyl group, the method comprising:
a first step of preparing one Intermediate Product 31 of following Formulae A31 to H31 by reacting one starting material of following Formulae AS to HS with an alkenyl compound of following Formula M1 in the presence of a base and an optional solvent;

a second step of preparing one Intermediate Product 32 of following Formulae A32 to H32 by reacting the above Intermediate Product 31 with a peroxide in the presence of an optional base and an optional solvent; and a third step of preparing one target product of following Formulae AI to HI by reacting the above Intermediate Product 32 with alkoxysilane of following Formula M2 in the presence of a metal catalyst and an optional solvent:

wherein the Starting Material is one of the following Formulae AS to HS,

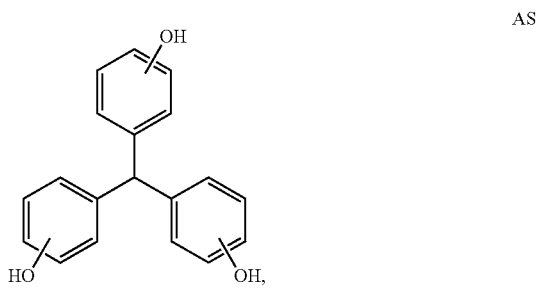
AS

BS

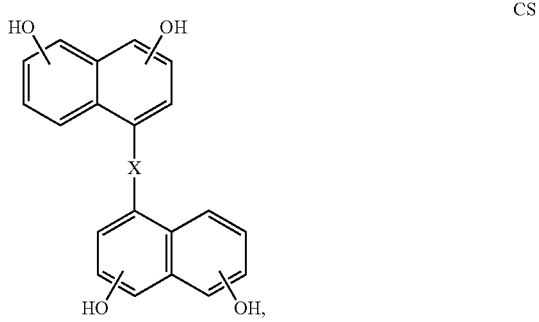
CS

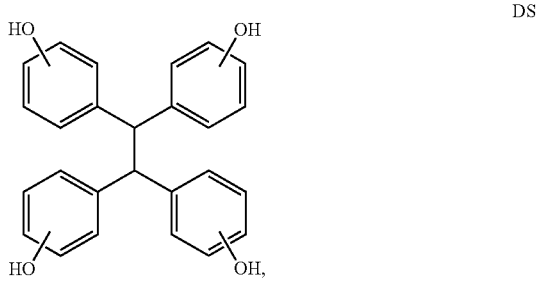
DS

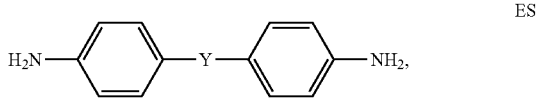
ES

-continued

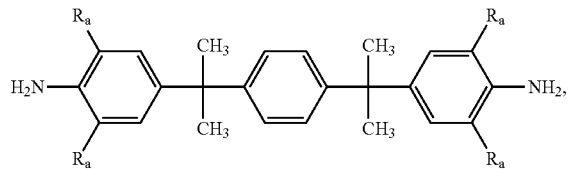
FS

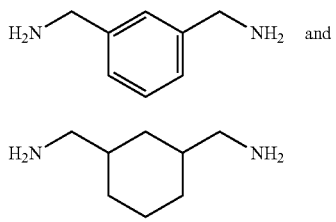
GS and

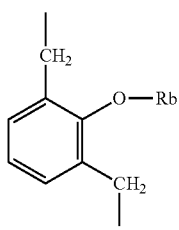
HS where a meta position of oxygen in Formula BS may be substituted with a linear or branched C1-C10 alkyl group, where X in Formula CS is a direct linkage, —CH$_2$— or

where Rb is H or a C1-C3 alkyl group,
  where Y in Formula ES is —CH$_2$—, —C(CH$_3$)$_2$—, —C(CF$_3$)$_2$—, —S— or —SO$_2$—, and
  where Ra in Formula FS is H or a C1-C3 alkyl group,
wherein Formula M1 is X—(CH$_2$)$_{z-2}$—CH=CH$_2$ where X is a halide of Cl, Br or I, —O—SO$_2$—CH$_3$, —O—SO$_2$—CF$_3$, or —O—SO$_2$—C$_6$H$_4$—CH$_3$, and z is an integer from 3 to 10,
wherein Intermediate Product 31 is one of the following Formulae A31 to H31,

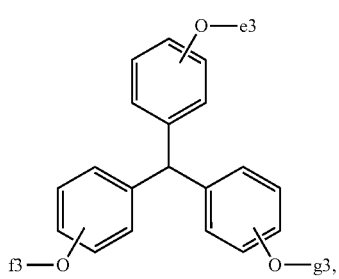
A31

-continued

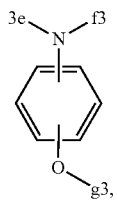
B31

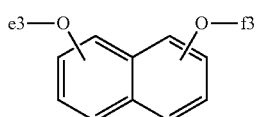
C31

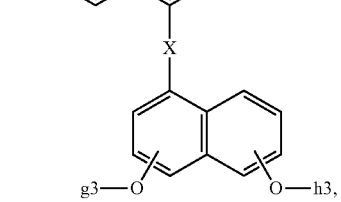
D31

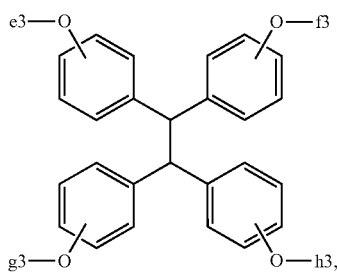
E31

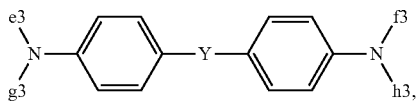
F31

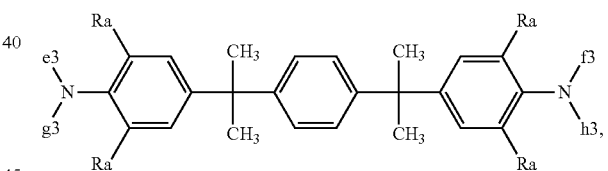
and
G31

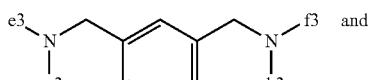
H31 where at least two of substituents e3 to g3 in Formula A31 or B31 is —(CH$_2$)$_{z-2}$—CH=CH$_2$ where z is an integer from 3 to 10, and the remainder thereof may be hydrogen, where at least two of substituents e3 to h3 in Formulae C31 to H31 is —(CH$_2$)$_{z-2}$—CH=CH$_2$ where z is an integer from 3 to 10, and the remainder thereof may be hydrogen, where a meta position of oxygen in Formula B31 may be substituted with a linear or branched C1-C10 alkyl group, where X in Formula C31 is a direct linkage, —CH₂— or

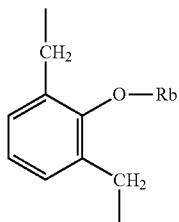

where Rb is H or a C1-C3 alkyl group,
where Y in Formula E31 is —CH₂—, —C(CH₃)₂—, —C(CF₃)₂—, —S— or —SO₂—, and
where Ra in Formula F31 is H or a C1-C3 alkyl group,
wherein Intermediate Product 32 is one of the following Formulae A23 to H32,

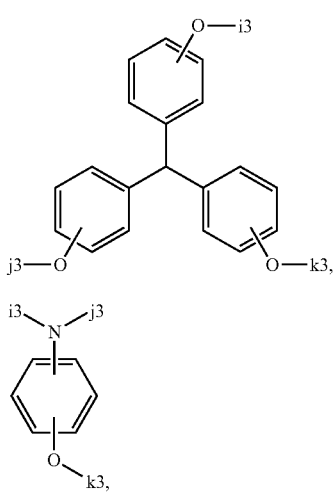
A32

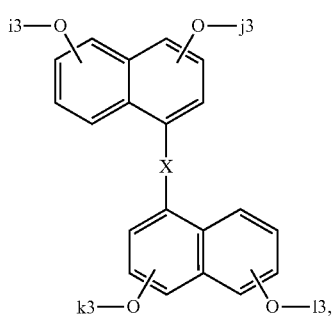
B32

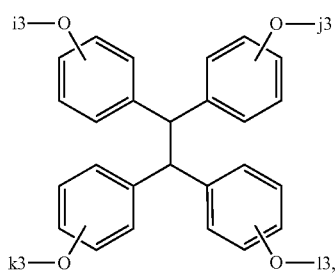
C32

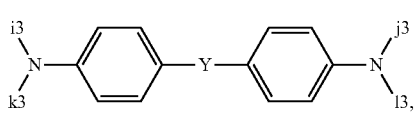
D32

E32

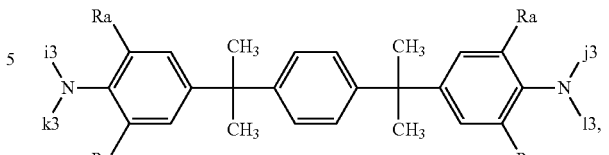
F32

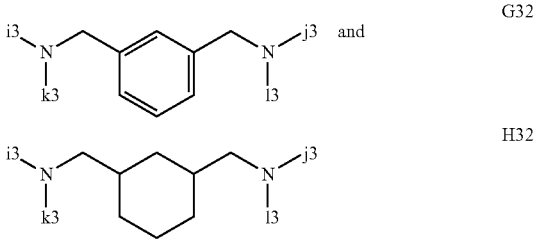
G32 and

H32 where one or two of i3 to k3 in Formulae A32 to B32 have the form of Formula S1, and at least one thereof is —(CH₂)$_{z-2}$—CH=CH₂ where z is an integer from 3 to 10 and may be hydrogen when an unreacted site is present, where one to three of i3 to l3 in Formulae C32 to H32 have the form of Formula S1, and at least one thereof is —(CH₂)$_{z-2}$—CH=CH₂ where z is an integer from 3 to 10 and may be hydrogen when an unreacted site is present, where a meta position of oxygen in Formula B32 may be substituted with a linear or branched C1-C10 alkyl group, where X in Formula C32 is a direct linkage, —CH₂— or

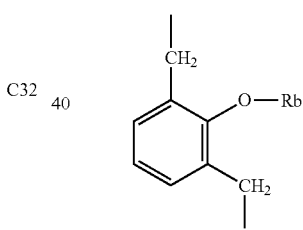

where Rb is H or a C1-C3 alkyl group,
where Y in Formula E32 is —CH₂—, —C(CH₃)₂—, —C(CF₃)₂—, —S— or —SO₂—, and
where Ra in Formula F32 is H or a C1-C3 alkyl group,
wherein Formula S1 is

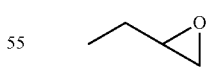

wherein Formula M2 is

where at least one of R₁ to R₃ is a C1-C10 alkoxy group, the remainder thereof are C1-C10 alkyl groups, and the alkoxy group and the alkyl group are a linear chain or a branched chain alkoxy group or alkyl group, wherein the Target product is one of the following Formulae AI to HI, AI
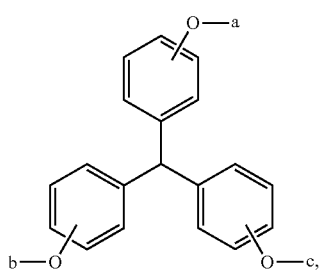

BI
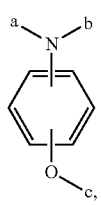

CI
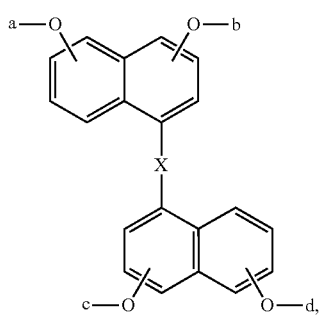

DI
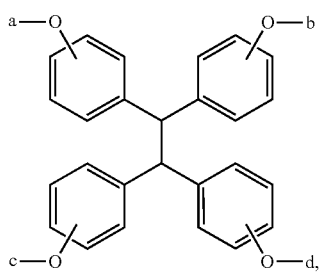

EI
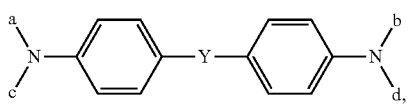

FI
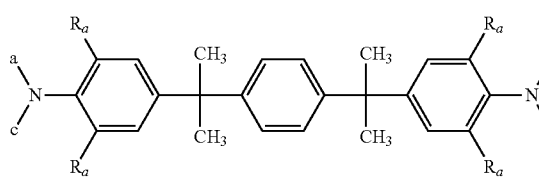

GI
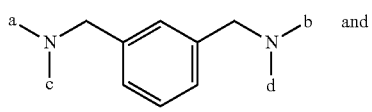

and

-continued

HI
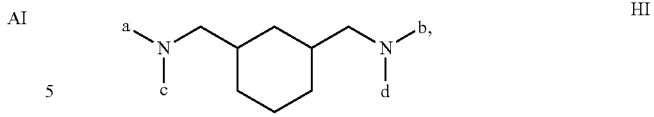

where one or two of substituents a to c in Formula AI or BI are the above Formula S1, one or two thereof have the form of Formula S2, and the remainder thereof may be hydrogen or —(CH$_2$)$_{z-2}$ CH=CH$_2$ where z is an integer from 3 to 10, where one to three of substituents a to d in Formulae CI to HI are the above Formula S1, one to three thereof have the form of Formula S2, and the remainder thereof may be hydrogen or —(CH$_2$)$_{z-2}$ CH=CH$_2$ where z is an integer from 3 to 10, where a meta position of oxygen in Formula BI may be substituted with a linear or branched C1-C10 alkyl group, where X in Formula CI is a direct linkage, —CH$_2$— or

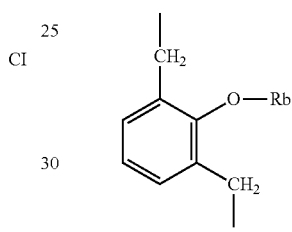

where Rb is H or a C1-C3 alkyl group, where Y in Formula EI is —CH$_2$—, —C(CH$_3$)$_2$—, —C(CF$_3$)$_2$—, —S— or —SO$_2$—, and where Ra in Formula FI is H or a C1-C3 alkyl group, wherein Formula S2 is —(CH$_2$)$_z$—SiR$_1$R$_2$R$_3$ in Formula S2, at least one of R$_1$ to R$_3$ is an alkoxy group having 1 to 10 carbon atoms, the remainder thereof are alkyl groups having 1 to 10 carbon atoms, the alkoxy group and the alkyl group are a side chain or a branched chain alkoxy group or alkyl group, and z is an integer from 3 to 10.

17. A method of preparing an epoxy compound having an alkoxysilyl group, the method comprising:

a first step of preparing one Intermediate Product 41 of following Formulae A41 to H41 by reacting one starting material of following Formulae AS to HS with epichlorohydrin in the presence of a base and an optional solvent;

a second step of preparing one Intermediate Product 42 of following Formulae A42 to H42 by reacting the above Intermediate Product 41 with an alkenyl compound of following Formula M1 in the presence of a base and an optional solvent; and a third step of preparing one target product of following Formulae AI to HI by reacting the above Intermediate Product 42 with alkoxysilane of following Formula M2 in the presence of a metal catalyst and an optional solvent:

wherein the Starting Material is one of the following Formulae AS to HS,

AS
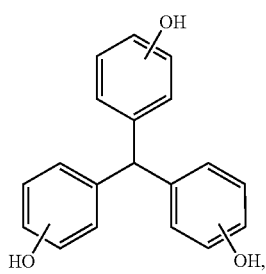

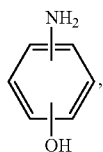,

CS
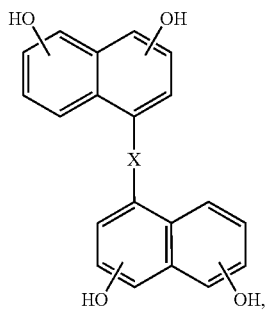

DS
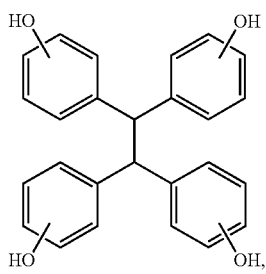

ES
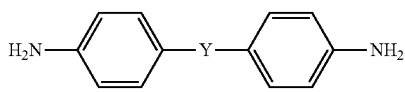

FS
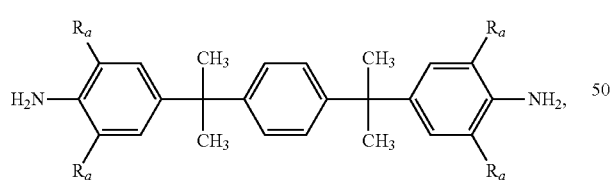

GS
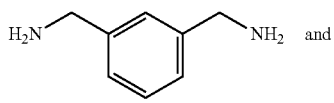 and

HS
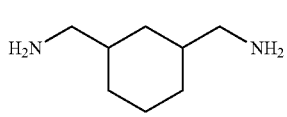

where a meta position of oxygen in Formula BS may be substituted with a linear or branched C1-C10 alkyl group, where X in Formula CS is a direct linkage, —CH₂— or

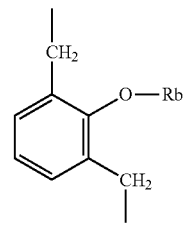

where Rb is H or a C1-C3 alkyl group,
where Y in Formula ES is —CH₂—, —C(CH₃)₂—, —C(CF₃)₂—, —S— or —SO₂—, and
where Ra in Formula FS is H or a C1-C3 alkyl group,
wherein the Intermediate Product 41 is one of the following Formulae A41 to H41, A41
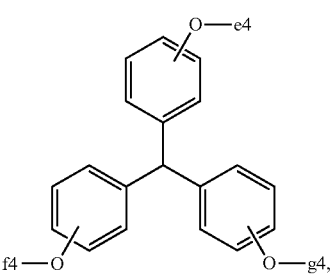

B41
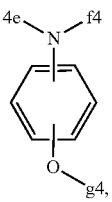

C41
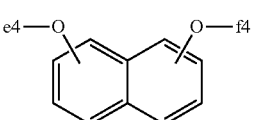

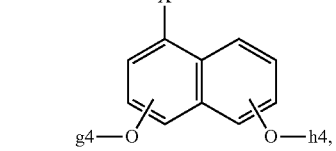

D41
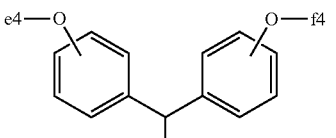

E41
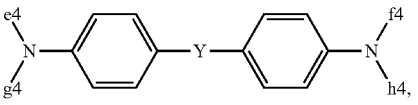

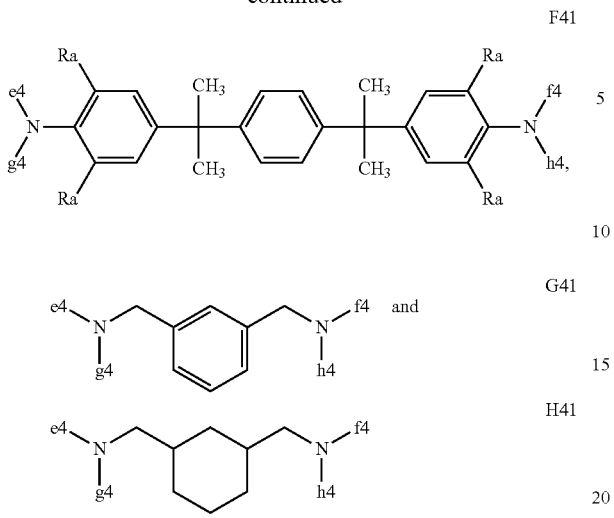
F41

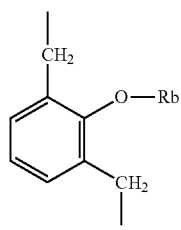
G41 and

H41 where one or two of substituents e4 to g4 in Formulae A41 to B41 have the form of Formula S1, and the remainder thereof are hydrogen, where one to three of substituents e4 to h4 in Formulae C41 to H41 have the form of Formula S1, and the remainder thereof are hydrogen, where a meta position of oxygen in Formula B41 may be substituted with a linear or branched C1-C10 alkyl group, where X in Formula C41 is a direct linkage, —CH$_2$— or

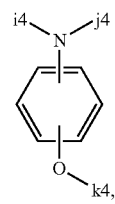

where Rb is H or a C1-C3 alkyl group, where Y in Formula E41 is —CH$_2$—, —C(CH$_3$)$_2$—, —C(CF$_3$)$_2$—, —S— or —SO$_2$—, and where Ra in Formula F41 is H or a C1-C3 alkyl group, wherein Formula S1 is

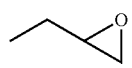

wherein Formula M1 is

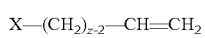

where X is a halide of Cl, Br or I, —O—SO$_2$—CH$_3$, —O—SO$_2$—CF$_3$, or —O—SO$_2$—C$_6$H$_4$—CH$_3$, and z is an integer from 3 to 10, wherein the Intermediate Product 42 is one of the following Formulae A42 to H42,

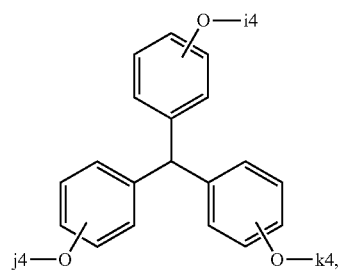
A42

B42

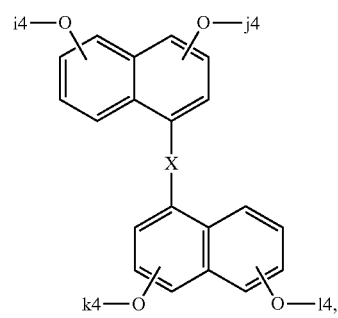
C42

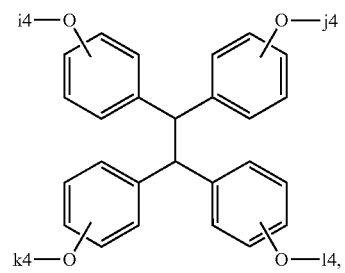
D42

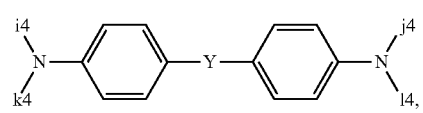
E42

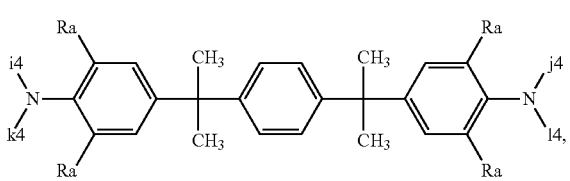
F42

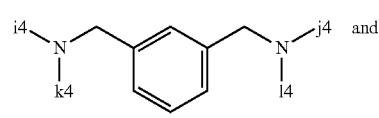
G42 and

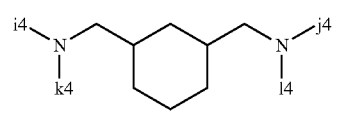
H42 where one or two of substituents i4 to k4 in Formula A42 or B42 are the above Formula S1, and at least one thereof is —(CH$_2$)$_{z-2}$—CH=CH$_2$ where z is an integer from 3 to 10 and may be hydrogen when an unreacted site is present, where one to three of substituents i4 to 14 in Formulae C42 to H42 are the above Formula S1, and at least one thereof is —(CH$_2$)$_{z-2}$—CH=CH$_2$ where z is an integer from 3 to 10 and may be hydrogen when an unreacted site is present, where a meta position of oxygen in Formula B42 may be substituted with a linear or branched C1-C10 alkyl group, where X in Formula C42 is a direct linkage, —CH$_2$— or

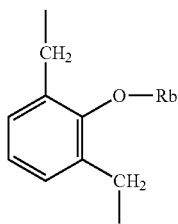

where Rb is H or a C1-C3 alkyl group, where Y in Formula E42 is —CH$_2$—, —C(CH$_3$)$_2$—, —C(CF$_3$)$_2$—, —S— or —SO$_2$—, and where Ra in Formula F42 is H or a C1-C3 alkyl group, wherein Formula M2 is HSiR$_1$R$_2$R$_3$ where at least one of R$_1$ to R$_3$ is a C1-C10 alkoxy group, the remainder thereof are C1-C10 alkyl groups, and the alkoxy group and the alkyl group are a linear chain or a branched chain alkoxy group or alkyl group, wherein the Target Product is one of the following Formulae AI to HI,

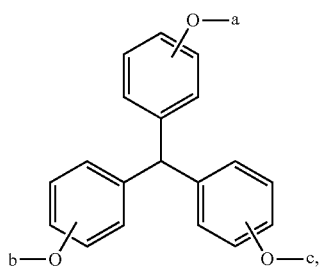
AI

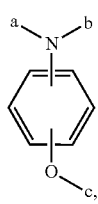
BI

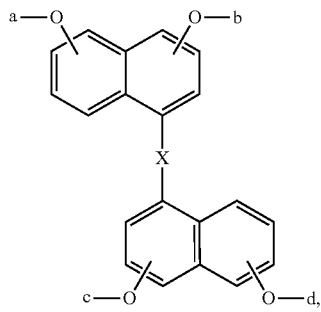
CI

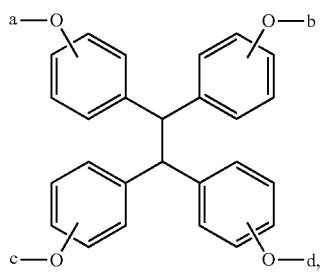
DI

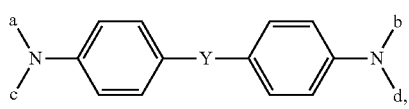
EI

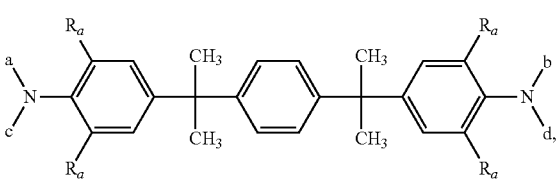
FI

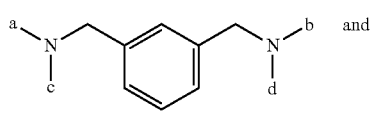
GI and

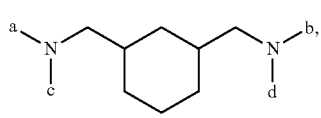
HI where one or two of substituents a to c in Formula AI or BI are the above Formula S1, one or two thereof have the form of Formula S2, and the remainder thereof may be hydrogen or —(CH$_2$)$_{z-2}$ CH=CH$_2$ where z is an integer from 3 to 10, where one to three of substituents a to d in Formulae CI to HI are the above Formula S1, one to three thereof have the form of Formula S2, and the remainder thereof may be hydrogen or —(CH$_2$)$_{z-2}$ CH=CH$_2$ where z is an integer from 3 to 10, where a meta position of oxygen in Formula BI may be substituted with a linear or branched C1-C10 alkyl group, where X in Formula CI is a direct linkage, —CH$_2$— or

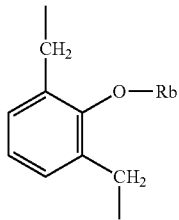

where Rb is H or a C1-C3 alkyl group,
where Y in Formula EI is —CH$_2$—, —C(CH$_3$)$_2$—, —C(CF$_3$)$_2$—, —S— or —SO$_2$—, and
where Ra in Formula FI is H or a C1-C3 alkyl group,
wherein Formula S2 is

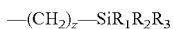

in Formula S2, at least one of R$_1$ to R$_3$ is an alkoxy group having 1 to 10 carbon atoms, the remainder thereof are alkyl groups having 1 to 10 carbon atoms, the alkoxy group and the alkyl group are a side chain or a branched chain alkoxy group or alkyl group, and z is an integer from 3 to 10.

18. A method of preparing an epoxy compound having an alkoxysilyl group, the method comprising:
a first step of preparing one Intermediate Product (51) of following Formulae A51 to H51 by reacting one starting material of following Formulae AS to HS with an alkenyl compound of Formula M1 in the presence of a base and an optional solvent;
a second step of preparing one Intermediate Product (52) of following Formulae A52 to H52 by reacting the above Intermediate Product (51) with a peroxide in the presence of a base and an optional solvent; and
a third step of preparing one target product of following Formulae AI to HI by reacting the above Intermediate Product (52) with isocyanate-based alkoxysilane of following Formula M3 in the presence of an optional base and an optional solvent:
wherein the starting material is one of the following Formulae AS to HS,

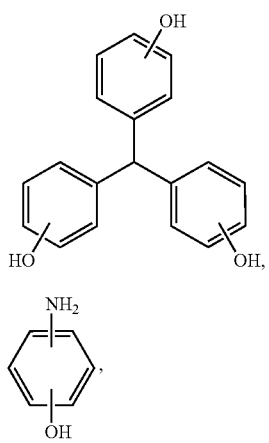

AS

BS

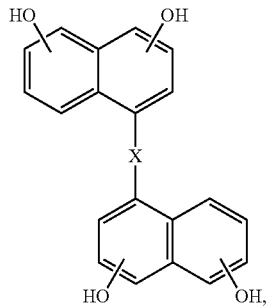

CS

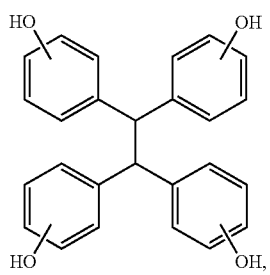

DS

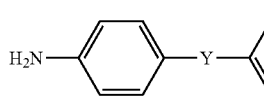

ES

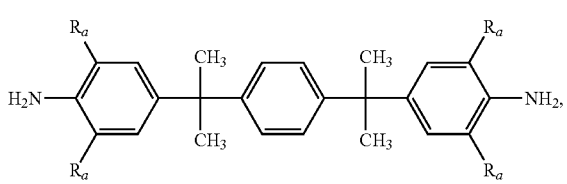

FS

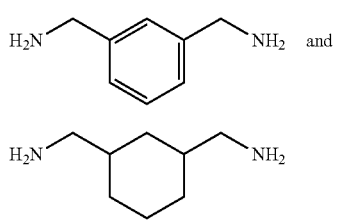

GS

HS or branched C1-C10 alkyl group,
where X in Formula CS is a direct linkage, —CH$_2$— or

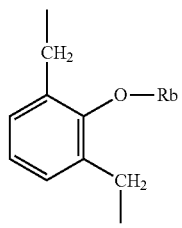

where Rb is H or a C1-C3 alkyl group,
where Y in Formula ES is —CH$_2$—, —C(CH$_3$)$_2$—, —C(CF$_3$)$_2$—, —S— or —SO$_2$—, and
where Ra in Formula FS is H or a C1-C3 alkyl group,
wherein Intermediate Product 51 is one of the following Formulae A51 to H51, A51
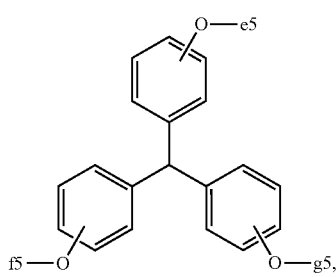

B51
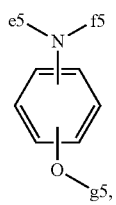

C51
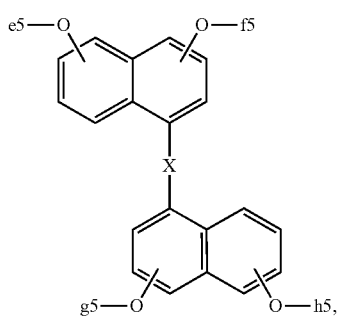

D51
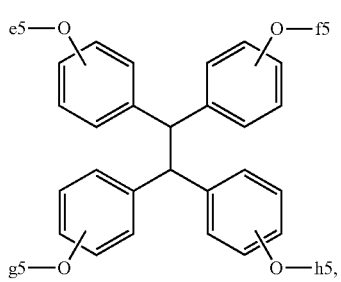

E51
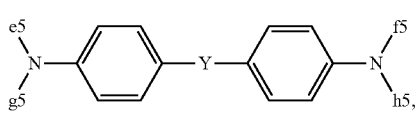

F51
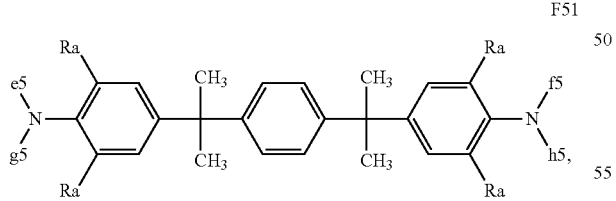

G51
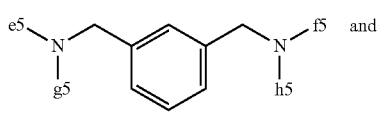

H51
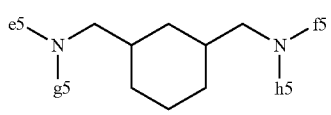

where one or two of substituents e5 to g5 in Formula A51 or B51 have the form of —(CH$_2$)$_{z-2}$CH=CH$_2$ where z is an integer from 3 to 10, and the remainder thereof are hydrogen, where one to three of substituents e5 to h5 in Formulae C51 to H51 are —(CH$_2$)$_{z-2}$CH=CH$_2$ where z is an integer from 3 to 10, and the remainder thereof are hydrogen, where a meta position of oxygen in Formula B51 may be substituted with a linear or branched C1-C10 alkyl group, where X in Formula C51 is a direct linkage, —CH$_2$— or

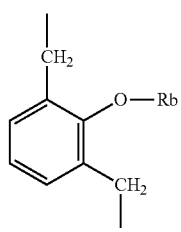

where Rb is H or a C1-C3 alkyl group, where Y in Formula E51 is —CH$_2$—, —C(CH$_3$)$_2$—, —C(CF$_3$)$_2$—, —S— or —SO$_2$—, and where Ra in Formula F51 is H or a C1-C3 alkyl group, wherein Intermediate Product 52 is one of the following Formulae A52 to H52, A52
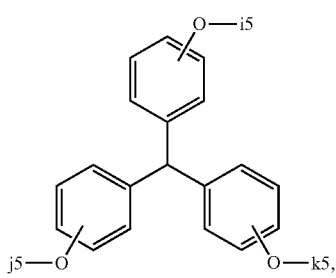

B52
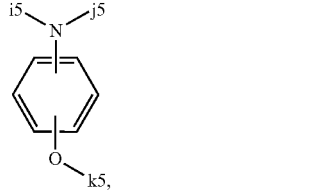

C52
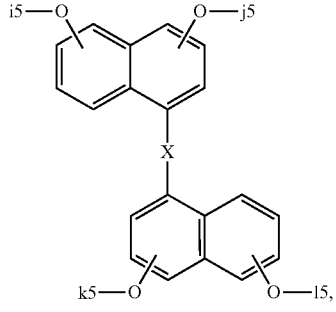

-continued

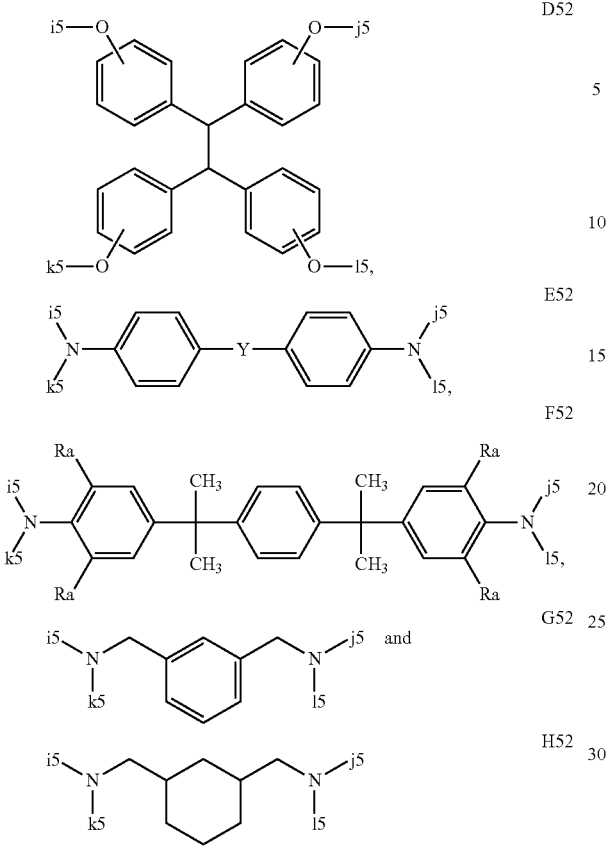

where one or two of substituents i5 to k5 in Formulae A52 to D52 have the form of Formula S1, and at least one thereof is hydrogen and may be —(CH$_2$)$_{Z-2}$ CH=CH$_2$ where z is an integer from 3 to 10 when an unreacted site is present, where one to three of substituents i5 to 15 in Formulae C52 to H52 have the form of Formula S1, and at least one thereof is hydrogen and may be —(CH$_2$)$_{Z-2}$ CH=CH$_2$ where z is an integer from 3 to 10 when an unreacted site is present, where a meta position of oxygen in Formula B52 may be substituted with a linear or branched C1-C10 alkyl group, where X in Formula C52 is a direct linkage, —CH$_2$— or

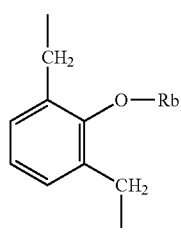

where Rb is H or a C1-C3 alkyl group, where Y in Formula E52 is —CH$_2$—, —C(CH$_3$)$_2$—, —C(CF$_3$)$_2$—, —S— or —SO$_2$—, and where Ra in Formula F52 is H or a C1-C3 alkyl group, wherein Formula S1 is

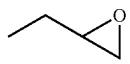

wherein Formula M1 is

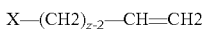

where X is a halide of Cl, Br or I, —O—SO2-CH3, —O—SO2-CF3, or —O—SO2-C6H4-CH3, and z is an integer from 3 to 10, wherein Formula M3 is

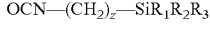

where at least one of R$_1$ to R$_3$ is a C1-C10 alkoxy group, the remainder thereof are linear or branched C1-C10 alkyl groups, the alkoxy group and the alkyl group are a linear chain or a branched chain alkoxy group or alkyl group, and z is an integer from 3 to 100, wherein the Target Product is one of the following Formulae AI to HI,

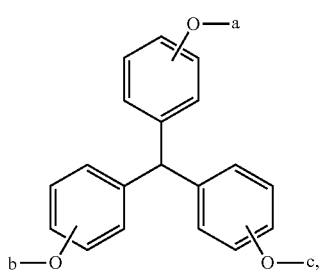

AI

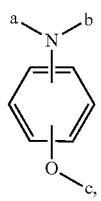

BI

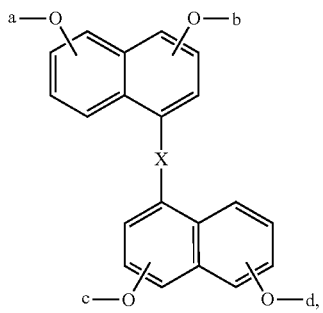

CI

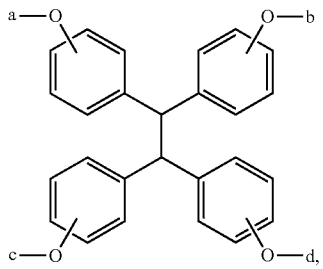

DI

-continued

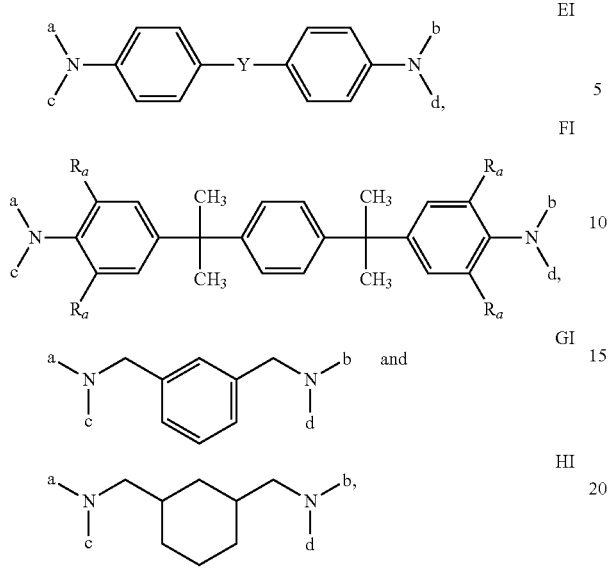

where one or two of substituents a to c in Formula AI or BI are the above Formula S1, one or two thereof have the form of Formula S3, and the remainder thereof may be hydrogen or —(CH$_2$)$_{z-2}$ CH=CH$_2$ where z is an integer from 3 to 10, where one to three of substituents a to d in Formulae CI to HI are the above Formula S1, one to three thereof have the form of Formula S3, and the remainder thereof may be hydrogen or —(CH$_2$)$_{z-2}$ CH=CH$_2$ where z is an integer from 3 to 10, where a meta position of oxygen in Formula BI may be substituted with a linear or branched C1-C10 alkyl group, where X in Formula CI is a direct linkage, —CH$_2$— or

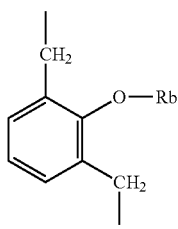

where Rb is H or a C1-C3 alkyl group,
where Y in Formula EI is —CH2-, —C(CH$_3$)$_2$—, —C(CF3)2-, —S— or —SO2-, and
where Ra in Formula FI is H or a C1-C3 alkyl group,
wherein Formula S3 is —CONH(CH$_2$)$_z$—SiR$_1$R$_2$R$_3$ in Formula S3, at least one of R$_1$ to R$_3$ is an alkoxy group having 1 to 10 carbon atoms, the remainder thereof are alkyl groups having 1 to 10 carbon atoms, the alkoxy group and the alkyl group are a linear chain or a branched chain alkoxy group or alkyl group, and z is an integer from 3 to 10.

19. A method of preparing an epoxy compound having an alkoxysilyl group, the method comprising:
a first step of preparing one Intermediate Product (61) of following Formulae A61 to H61 by reacting one starting material of following Formulae AS to HS with epichlorohydrin in the presence of a base and an optional solvent; and
a second step of preparing one target product of following Formulae AI to HI by reacting the above Intermediate Product (61) with isocyanate-based alkoxysilane of Formula M3 in the presence of an optional base and an optional solvent:
wherein the Starting Material is one of the Formulae AS to HS,

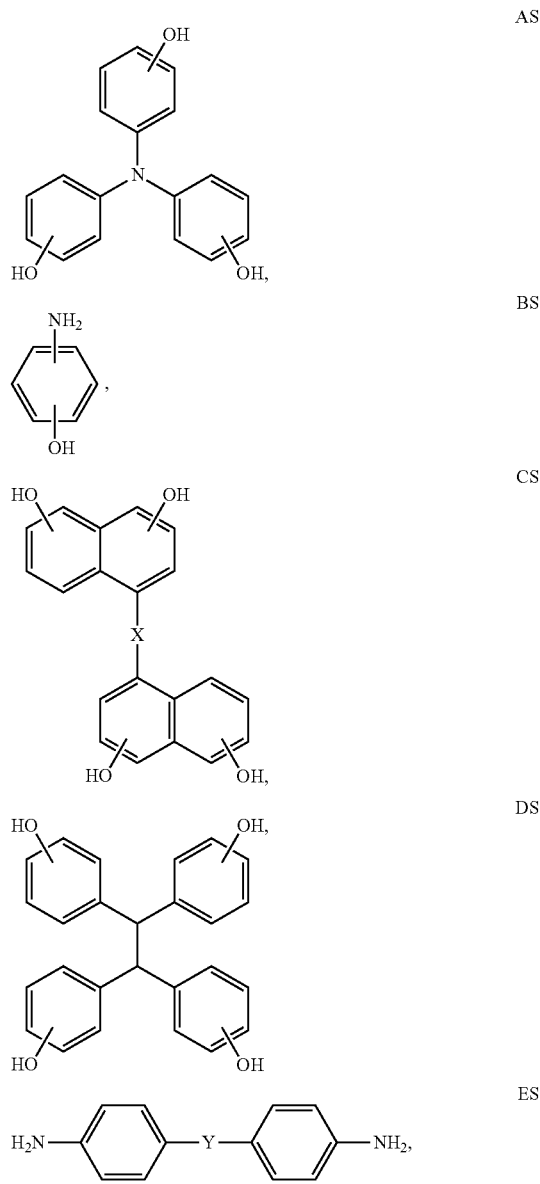

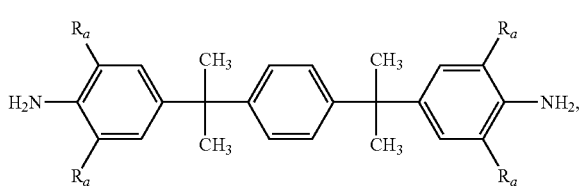

-continued

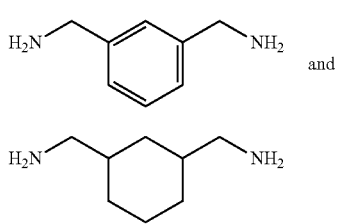
GS

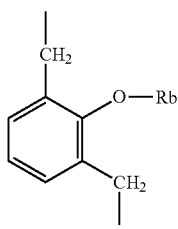
HS where a meta position of oxygen in Formula BS may be substituted with a linear or branched C1-C10 alkyl group,
where X in Formula CS is a direct linkage, —CH$_2$— or

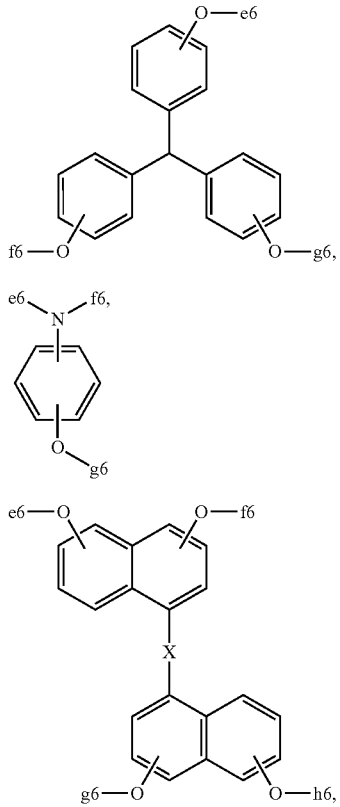

where Rb is H or a C1-C3 alkyl group,
  where Y in Formula ES is —CH$_2$—, —C(CH$_3$)$_2$—, —C(CF$_3$)$_2$—, —S— or —SO$_2$—, and
where Ra in Formula FS is H or a C1-C3 alkyl group,
wherein Intermediate Product (61) is one of the Formulae A61 to H61,

A61

B61

C61

-continued

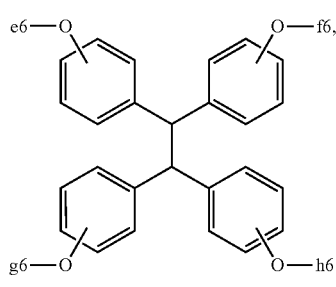
D61

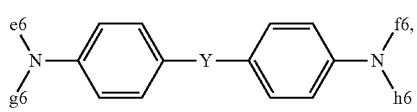
E61

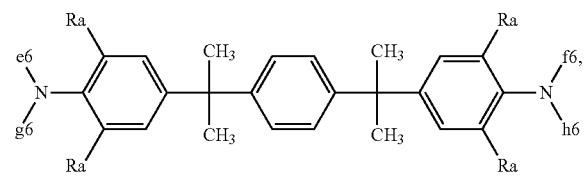
F61

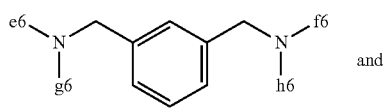
G61
and

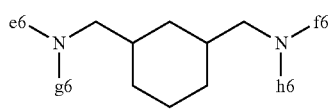
H61 where one or two of substituents e6 to g6 in Formula A61 or B61 have the form of Formula S1, and the remainder thereof are hydrogen,
where one to three of substituents e6 to h6 in Formulae C61 to H61 have the form of Formula S1, and the remainder thereof are hydrogen,
where a meta position of oxygen in Formula B61 may be substituted with a linear or branched a C1-C10 alkyl group,
where X in Formula C61 is a direct linkage, —CH$_2$— or

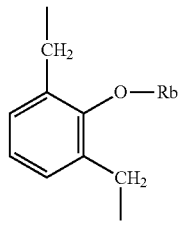

where Rb is H or a C1-C3 alkyl group,
  where Y in Formula E61 is —CH$_2$—, —C(CH$_3$)$_2$—, —C(CF$_3$)$_2$—, —S— or —SO$_2$—, and
where Ra in Formula F61 is H or a C1-C3 alkyl group,
wherein Formula S1 is

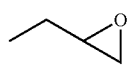

wherein Formula M3 is

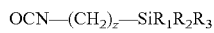

where at least one of $R_1$ to $R_3$ is a C1-C10 alkoxy group, the remainder thereof are linear or branched C1-C10 alkyl groups, the alkoxy group and the alkyl group are a linear chain or a branched chain alkoxy group or alkyl group, and z is an integer from 3 to 10, wherein the Target Product is one of Formulae AI to HI,

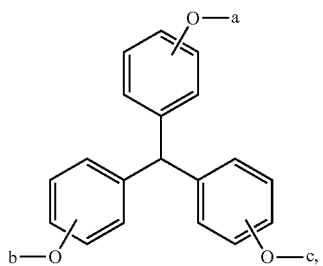

AI

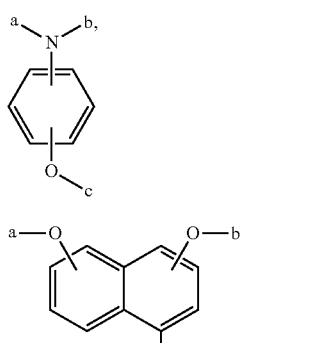

BI

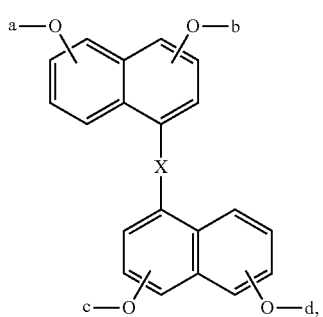

CI

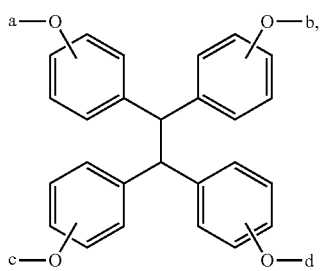

DI

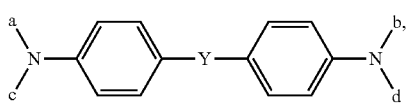

EI

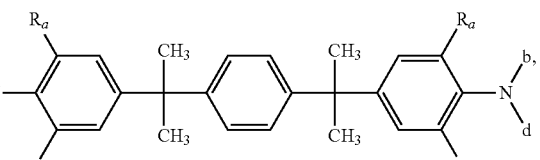

FI

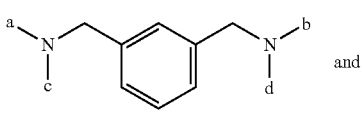

GI and

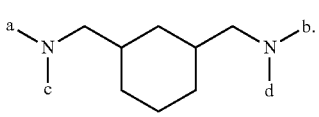

HI where one or two of substituents a to c in Formulae AI to BI are the above Formula S1, one or two thereof have the form of Formula S3, and the remainder thereof may be hydrogen or —(CH$_2$)$_{Z-2}$CH=CH$_2$ where z is an integer from 3 to 10, where one to three of substituents a to d in Formulae CI to HI are the above Formula S1, one to three thereof have the form of Formula S3, and the remainder thereof may be hydrogen or —(CH$_2$)$_{Z-2}$CH=CH$_2$ where z is an integer from 3 to 10, where a meta position of oxygen in Formula BI may be substituted with a linear or branched C1-C10 alkyl group, where X in Formula CI is a direct linkage, —CH$_2$— or

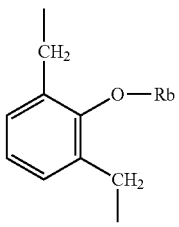

where Rb is H or a C1-C3 alkyl group,
where Y in Formula EI is —CH$_2$—, —C(CH$_3$)$_2$—, —C(CF$_3$)$_2$—, —S— or —SO$_2$—, and
where Ra in Formula FI is H or a C1-C3 alkyl group,
wherein Formula S3 is

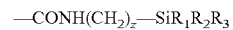

in Formula S3, at least one of $R_1$ to $R_3$ is an alkoxy group having 1 to 10 carbon atoms, the remainder thereof are alkyl groups having 1 to 10 carbon atoms, the alkoxy group and the alkyl group are a linear chain or a branched chain alkoxy group or alkyl group, and z is an integer from 3 to 10.

* * * * *